(12) United States Patent
Pamukcu et al.

(10) Patent No.: US 6,410,584 B1
(45) Date of Patent: Jun. 25, 2002

(54) METHOD FOR INHIBITING NEOPLASTIC CELLS WITH INDOLE DERIVATIVES

(75) Inventors: Rifat Pamukcu, Spring House; Gary A. Piazza, Doylestown, both of PA (US)

(73) Assignee: Cell Pathways, Inc., Horsham, PA (US)

( * ) Notice: Subject to any disclaimer, the term of this patent is extended or adjusted under 35 U.S.C. 154(b) by 0 days.

(21) Appl. No.: 09/199,860

(22) Filed: Nov. 25, 1998

Related U.S. Application Data

(63) Continuation-in-part of application No. 09/007,098, filed on Jan. 14, 1998, now Pat. No. 6,046,199.

(51) Int. Cl.$^7$ .............................................. A61K 31/40
(52) U.S. Cl. ........................ 514/416; 514/414; 514/418; 514/419
(58) Field of Search .............................. 514/416, 418, 514/419, 414

(56) References Cited

U.S. PATENT DOCUMENTS

| | | | |
|---|---|---|---|
| 4,950,680 A | 8/1990 | Taylor et al. | |
| 5,696,159 A | 12/1997 | Gross et al. | |
| 5,874,440 A | * 2/1999 | Pamukcu et al. | ........... 514/269 |
| 6,046,216 A | * 4/2000 | Piazza et al. | ............... 514/340 |
| 6,060,477 A | * 5/2000 | Piazza et al. | ............... 514/258 |

FOREIGN PATENT DOCUMENTS

| WO | WO 95/19978 | 7/1995 |
|---|---|---|
| WO | WO 00/15222 | 3/2000 |

OTHER PUBLICATIONS

Blaya, C. et al., Effect of the protein kinase inhibitors, 1–(5–isoquinolinylsulfonyl)–2–methylpiperazine H–7 and N–(2–[methylamino]ethyl)–5–isoquinoline–sulfonamide H–8 on Lewis lung carcinoma tumor progression, European Journal of Pharmacology, 354, pp. 99–104 (1998).

Chang, W. et al., Sulindac Sulfone Modulates the Expression and Cellular Localization of b–Catenin in Human Colon Carcinoma Cells, Digestive Disease Week, Apr. 1, 1999.

Earnest, D. et al., Piroxicam and Other Cyclooxygenase Inhibitors: Potential for Cancer Chemoprevention, Journal of Cellular Biochemistry, Supplement 161:156–166 (1992).

Easwaran, V. et al., The Ubiquitin–Proteasome Pathway and Serine Kinase Activity Modulate Adenomatous Polyposis Coli Protein–mediated Regulation of β–Catenin–Lymphocyte Enhancer–binding Factor Signaling, The Journal of Biological Chemistry, vol. 274, No. 23, pp. 16641–16645, Jun. 4, 1999.

Jiang, X. et al., Inhibition of calmodulin–dependent phosphodiesterase induces apoptosis in human leukemic cells, Proc. Natl. Acad. Sci. USA, vol. 83, pp. 11236–11241, Oct. 1996.

Korinek, V. et al., Constitutive Transcriptional Activation by a β–Catenin–Tcf Complex in APC$^{-/-}$ Colon Carcinoma, Science, vol. 275, pp. 1784–1786, Mar. 21, 1997.

Mahmoud, N. et al., Apc Gene Mutation is Associated with a Dominant–Negative Effect upon Intestinal Cell Migration, Cancer Research 57, pp. 5045–5050, Nov. 15, 1997.

Mahmoud, N. et al., Genotype–Phenotype Correlation in Murine Apc Mutation: Differences in Enterocyte Migration and Response to Sulindac, Cancer Research 59, pp. 353–359, Jan. 15, 1999.

Morin, P. et al., Activation of β–Catenin–Tcf Signaling in Colon Cancer by Mutations in β–Catenin or APC, Science, vol. 275, pp. 1787–1789, Mar. 21, 1997.

Peifer, M., β–Catenin as Oncogene: The Smoking Gun, Science, vol. 275, pp. 1752–1753, Mar. 21, 1997.

Rubinfeld, B. et al., Stabilization of β–Catenin by Genetic Defects in Melanoma Cell Lines, Science, vol. 275, pp. 1790–1792, Mar. 21, 1997.

* cited by examiner

Primary Examiner—Jerome D. Goldberg
(74) Attorney, Agent, or Firm—Robert W. Stevenson

(57) ABSTRACT

A method for inhibiting neoplastic cells and related conditions by exposing them to substituted indole derivatives.

2 Claims, 29 Drawing Sheets

(30)

(31)

(32)

(33)

(34)

(35)

(36)

(37)

(38)

(39)

(40)

(41)

(42)

(43)

(44)

(45)

(46)

(47)

(48)

(49)

(50)

(51)

(52)

(53)

(54)

(55)

(56)

(57)

(58)

(59)

(60)

(61)

(62)

(63)

(64)

(65)

(66)

(67)

(68)

(69)

(70)

(71)

(72)

(73)

(74)

(75)

(76)

(77)

(78)

(79)

(80)

(81)

(82)

(83)

(84)

(85)

(86)

(87)

(88)

(89)

(90)

(91)

(92)

(93)

(94)

(95)

(96)

(97)

(98)

(99)

(105)

(106)

(107)

(108)

(109)

(110)

(111)

(112)

(113)

(114)

(115)

(116)

(117)

(118)

(119)

(120)

(121)

(122)

(123)

(124)

(125)

(126)

(127)

(128)

(129)

(130)

(131)

(132)

(133)

(134)

(135)

(136)

(137)

(138)

(139)

(140)

(141)

(142)

(143)

(144)

(145)

(146)

(147)

(148)

(149)

(150)

(151)

(152)

(153)

(154)

(155)

(156)

(157)

(158)

(159)

(165)

(166)

(167)

(168)

(169)

(170)

(171)

(172)

(173)

METHOD FOR INHIBITING NEOPLASTIC CELLS WITH INDOLE DERIVATIVES

This invention relates to a method for the selective inhibition of neoplastic cells, for example, for the treatment or prevention of precancerous lesions or other neoplasias in mammals. This application is a continuation-in-part of U.S. patent application Ser. No. 09/007,098 filed Jan. 14, 1998 now U.S. Pat. No. 6,046,199, which is incorporated herein by reference.

TECHNICAL FIELD

BACKGROUND OF THE INVENTION

Each year in the United States alone, untold numbers of people develop precancerous lesions, which is a form of neoplasia, as discussed below. Such lesions exhibit a strong tendency to develop into malignant tumors, or cancer. Such lesions include lesions of the breast (that can develop into breast cancer), lesions of the skin (that can develop into malignant melanoma or basal cell carcinoma), colonic adenomatous polyps (that can develop into colon cancer), and other such neoplasms. Compounds that prevent or induce the remission of existing precancerous or cancerous lesions or carcinomas would greatly reduce illness and death from cancer.

For example, approximately 60,000 people die from colon cancer, and over 150,000 new cases of colon cancer are diagnosed each year. For the American population as a whole, individuals have a six percent lifetime risk of developing colon cancer, making it the second most prevalent form of cancer in the country. Colon cancer is also prevalent in Western Europe. It is believed that increased dietary fat consumption is increasing the risk of colon cancer in Japan.

In addition, the incidence of colon cancer reportedly increases with age, particularly after the age of 40. Since the mean ages of populations in America and Western Europe are increasing, the prevalence of colorectal cancer should increase in the future.

To date, little progress has been made in the prevention and treatment of colorectal cancer, as reflected by the lack of change in the five-year survival rate over the last few decades. The only cure for this cancer is surgery at an extremely early stage. Unfortunately, most of these cancers are discovered too late for surgical cure. In many cases, the patient does not experience symptoms until the cancer has progressed to a malignant stage.

In view of these grim statistics, efforts in recent years have concentrated on colon cancer prevention. Colon cancer usually arises from pre-existing benign neoplastic growths known as polyps. Prevention efforts have emphasized the identification and removal of colonic polyps. Polyps are identified by x-ray and/or colonoscopy, and usually removed by devices associated with the colonoscope. The increased use of colon x-rays and colonoscopies in recent years has detected clinically significant precancerous polyps in four to six times the number of individuals per year that acquire colon cancer. During the past five years alone, an estimated 3.5 to 5.5 million people in the United States have been diagnosed with adenomatous colonic polyps, and it is estimated that many more people have or are susceptible to developing this condition, but are as yet undiagnosed. In fact, there are estimates that 10–12 percent of people over the age of 40 will form clinically significant adenomatous polyps.

Removal of polyps has been accomplished either with surgery or fiber-optic endoscopic polypectomy—procedures that are uncomfortable, costly (the cost of a single polypectomy ranges between $1,000 and $1,500 for endoscopic treatment and more for surgery), and involve a small but significant risk of colon perforation. Overall, about $2.5 billion is spent annually in the United States in colon cancer treatment and prevention.

In the breast, breast cancer is often treated surgically, often by radical mastectomy with its painful aftermath. Such surgery is costly, too.

As indicated above, each lesion carries with it a chance that it will develop into a cancer. The likelihood of cancer is diminished if a precancerous lesion is removed. However, many of these patients demonstrate a propensity for developing additional lesions in the future. They must, therefore, be monitored periodically for the rest of their lives for reoccurrence.

In most cases (i.e. the cases of sporadic lesion formation, e.g. so-called common sporadic polyps), lesion removal will be effective to reduce the risk of cancer. In a small percentage of cases (i.e. cases where numerous lesions form, e.g. the so-called polyposis syndromes), removal of all or part of the effected area (e.g. the colon) is indicated. For example, the difference between common sporadic polyps and polyposis syndromes is dramatic. Common sporadic polyp cases are characterized by relatively few polyps which can usually be removed leaving the colon intact. By contrast, polyposis syndrome cases can be characterized by many (e.g. hundreds or more) of polyps—literally covering the colon in some cases—making safe removal of the polyps impossible short of surgical removal of the colon.

Because each lesion carries with it a palpable risk of cancerous development, patients who form many lesions (e.g. polyposis syndrome patients) invariably develop cancer if left untreated. Surgical removal of the colon is the conventional treatment in polyposis patients. Many polyposis patients have undergone a severe change in lifestyle as a result of the disfiguring surgery. Patients have strict dietary restrictions, and many must wear ostomy appliances to collect their intestinal wastes.

The search for drugs useful for treating and preventing cancer is intensive. Indeed, much of the focus of cancer research today is on the prevention of cancer because chemotherapy for cancer itself is often not effective and has severe side effects. Cancer chemoprevention is important for recovered cancer patients who retain a risk of cancer reoccurrence. Also, cancer prevention is important for people who have not yet had cancer, but have hereditary factors that place them at risk of developing cancer. With the development of new genetic screening technologies, it is easier to identify those patients with high-risk genetic factors, such as the potential for polyposis syndrome, who would greatly benefit from chemopreventative drugs. Therefore, finding such anti-cancer drugs that can be used for prolonged preventive use is of vital interest.

Known chemopreventative and chemotherapeutic drugs are believed to kill cancer cells by inducing apoptosis, sometimes referred to as "programmed cell death." Apoptosis naturally occurs in virtually all tissues of the body, and especially in self-renewing tissues such as bone marrow, immune cells, gut, liver and skin. Apoptosis plays a critical role in tissue homeostasis, that is, it ensures that the number of new cells produced are correspondingly offset by an equal number of cells that die. For example, the cells in the intestinal lining divide so rapidly that the body must eliminate cells after only three days in order to prevent the overgrowth of the intestinal lining.

Recently, scientists have realized that abnormalities of apoptosis can lead to the formation of precancerous lesions and carcinomas. Also, recent research indicates that defects in apoptosis play a major role in other diseases in addition to cancer. Consequently, compounds that modulate apoptosis could be used to prevent or control cancer, as well as used in the treatment of other diseases.

Unfortunately, even though known chemotherapeutic drugs may exhibit such desirable apoptosis effects, most chemotherapeutic drugs have serious side effects that prohibit their long-term use, or use in otherwise healthy individuals with precancerous lesions. These side effects, which are a result of the high levels of cytotoxicity of the drugs, include hair loss, weight loss, vomiting, immune suppression and other toxicities. Therefore, there is a need to identify new drug candidates for therapy that do not have such serious side effects in humans.

In recent years, several non-steroidal anti-inflammatory drugs ("NSAIDs"), originally developed to treat arthritis, have shown effectiveness in inhibiting and eliminating colonic polyps. Polyps virtually disappear when the patients take the drug, particularly when the NSAID sulindac is administered. However, the prophylactic use of currently available NSAIDs, even in polyposis syndrome patients, is marked by severe side reactions that include gastrointestinal irritations, perforations, ulcerations and kidney toxicity. Once NSAID treatment is terminated due to such complications, the polyps return, particularly in polyposis syndrome patients.

Sulindac has been particularly well received among the NSAIDs for polyp treatment. Sulindac is a sulfoxide compound that itself is believed to be inactive as an anti-arthritic agent. The sulfoxide is reportedly converted by liver enzymes to the corresponding sulfide, which is acknowledged to be the active moiety as a prostaglandin synthesis inhibitor. The sulfide, however, is associated with the side effects of conventional NSAIDs. The sulfoxide is also known to be metabolized to a sulfone compound that has been found to be inactive as an inhibitor of prostaglandin synthesis but active as an inhibitor of precancerous lesions.

SUMMARY OF THE INVENTION

This invention includes a method of inhibiting neoplastic cells by exposing those cells to a pharmacologically effective amount of those compounds described below. Such compounds are effective in modulating apoptosis and eliminating and inhibiting the growth of neoplasias such as precancerous lesions, but are not characterized by the severe side reactions of conventional NSAIDs or other chemotherapeutics.

The compounds of that are useful in the methods of this invention include those of formula I

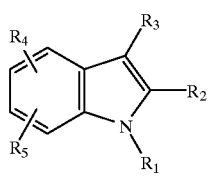

(I)

wherein $R_1$ to $R_3$ are independently selected from the group consisting of;

(1) a hydrogen atom, (2) a lower alkyl group, a lower alkylthio group, or a lower alkoxy-lower alkyl group, or (3) a lower alkyl group, an oxy group, an oxy-lower alkyl group, a lower alkyloxy group, a carbonyl group, a lower alkenyl group, an optionally-substituted imino group, a lower alkylimino group optionally substituted at its nitrogen atom, a thio-lower alkyl group, or a lower alkylthio group; or to each group in (3), bonded is an aryl group or a heterocyclic group, or each group in (3) is substituted by an aryl group or a heterocyclic group; and said aryl or heterocyclic group may be further substituted by a halogen atom, a nitro group, a lower alkylamino group, an acylamino group, a lower alkyl group, a lower alkoxy group, a halo-lower alkyl group, a lower cycloalkyl group, or an aryl, heterocyclic, aryl-lower alkyl, heterocyclic-lower alkyl, aryl-lower alkyloxy, heterocyclic-lower alkyloxy, aryl-lower alkenyl or heterocyclic-lower alkenyl group optionally substituted by any of a halogen atom or a lower alkyl group, with the proviso that $R_1$ to $R_3$ must not be simultaneously all hydrogen atoms;

$R_4$ is selected from the group consisting of a hydrogen atom, or a lower alkyl group;

$R_5$ is selected from the group consisting of a carboxyl group, an esterified carboxyl group, or an amidated carboxyl group.

DETAILED DESCRIPTION OF THE PREFERRED EMBODIMENTS

As indicated above, this invention relates to a method for inhibiting neoplasia, particularly cancerous and precancerous lesions by exposing the affected cells to a compound of Formula I above.

Preferably, such compounds are administered without therapeutic amounts of an NSAID.

The present invention is also a method of treating mammals with precancerous lesions by administering a pharmacologically effective amount of an enterically coated pharmaceutical composition that includes compounds of this invention.

Also, the present invention is a method of inhibiting the growth of neoplastic cells by exposing the cells to an effective amount of compounds of Formula I, wherein $R_1$ through $R_3$ are defined as above.

In still another form, the invention is a method of inducing apoptosis in human cells by exposing those cells to an effective amount of compounds of Formula I to those cells sensitive to such a compound.

As used herein, the term "precancerous lesion" includes syndromes represented by abnormal neoplastic, including dysplastic, changes of tissue.

Examples include adenomatous growths in colonic, breast or lung tissues, or conditions such as dysplastic nevus syndrome, a precursor to malignant melanoma of the skin. Examples also include, in addition to dysplastic nevus syndromes, polyposis syndromes, colonic polyps, precancerous lesions of the cervix (i.e., cervical dysplasia), prostatic dysplasia, bronchial dysplasia, breast, bladder and/or skin and related conditions (e.g., actinic keratosis), whether the lesions are clinically identifiable or not.

As used herein, the term "carcinomas" refers to lesions that are cancerous. Examples include malignant melanomas, breast cancer, and colon cancer.

As used herein, the term "neoplasm" refers to both precancerous and cancerous lesions.

Compounds useful in the methods of this invention may be formulated into compositions together with pharmaceutically acceptable carriers for oral administration in solid or liquid form, or for rectal administration, although carriers for oral administration are most preferred.

Pharmaceutically acceptable carriers for oral administration include capsules, tablets, pills, powders, troches and granules. In such solid dosage forms, the carrier can comprise at least one inert diluent such as sucrose, lactose or starch. Such carriers can also comprise, as is normal practice, additional substances other than diluents, e.g., lubricating agents such as magnesium stearate. In the case of capsules, tablets, troches and pills, the carriers may also comprise buffering agents. Carriers such as tablets, pills and granules can be prepared with enteric coatings on the surfaces of the tablets, pills or granules. Alternatively, the enterically coated compound can be pressed into a tablet, pill, or granule, and the tablet, pill or granules for administration to the patient. Preferred enteric coatings include those that dissolve or disintegrate at colonic pH such as shellac or Eudraget S.

Pharmaceutically acceptable carriers include liquid dosage forms for oral administration, e.g. pharmaceutically acceptable emulsions, solutions, suspensions, syrups and elixirs containing inert diluents commonly used in the art, such as water. Besides such inert diluents, compositions can also include adjuvants such as wetting agents, emulsifying and suspending agents, and sweetening, flavoring and perfuming agents.

Pharmaceutically acceptable carriers for rectal administration are preferably suppositories that may contain, in addition to the compounds of Formula I, excipients such as cocoa butter or a suppository wax.

The pharmaceutically acceptable carrier and compounds of this invention are formulated into unit dosage forms for administration to a patient. The dosage levels of active ingredient (i.e. compounds of this invention) in the unit dosage may be varied so as to obtain an amount of active ingredient effective to achieve lesion-eliminating activity in accordance with the desired method of administration (i.e., oral or rectal). The selected dosage level therefore depends upon the nature of the active compound administered, the route of administration, the desired duration of treatment, and other factors. If desired, the unit dosage may be such that the daily requirement for active compound is in one dose, or divided among multiple doses for administration, e.g., two to four times per day.

The pharmaceutical compositions of this invention are preferably packaged in a container (e.g. a box or bottle, or both) with suitable printed material (e.g. a package insert) containing indications, directions for use, etc.

The amount of the derivative to be used varies, depending on the age and the condition of the patients, on the type and the condition of the diseases, and on the type of the derivative. In general, however, the derivative may be administered in an amount between 1 and 100 mg/kg for oral administration, or between 0.1 and 10 mg/kg for intramuscular or intravenous administration, once to four times a day. In practice, the physician will determine the actual dosing regimen that will be most suitable for an individual patient and it will vary with the age, weight and response of the particular patient. The above dosages are believed to be exemplary of the average case, but there may be individual instances in which higher or lower dosage ranges may be merited, and such are within the scope of this invention.

Methods for producing the indole derivatives useful in this invention are reported in WO 98/145530 (which is incorporated herein by reference), and are set forth below.

As in the reaction formula (a), a compound (1) is processed with a strong base such as sodium hydride, lithium diisopropylamide or the like, and then reacted with a chloride, bromide, iodide, toluenesulfonate or methane sulfonate of $R^{1'a}$ to produce a compound (2). Alternatively, the compound (2) may also be produced, using an inorganic or organic base such as typically potassium carbonate, sodium carbonate, lithium carbonate, sodium hydrogencarbonate, potassium hydrogencarbonate, pyridine or triethylamine. In this case, where $R^{1a}$ in (1) is a hydrogen atom, the compound (1) reacts with the reactant also at its 3-position.

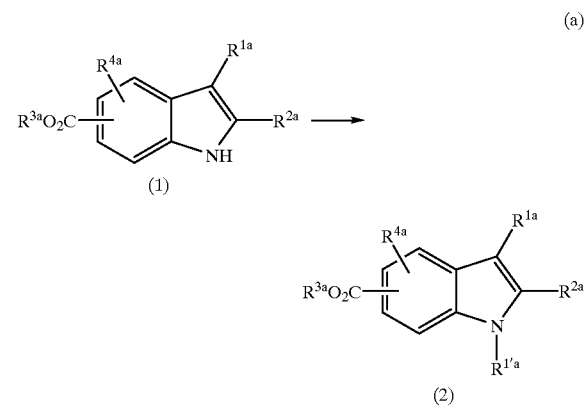

(a)

wherein $R^{1a}$, $R^{1'a}$ and $R^{2a}$ each represent 1) a hydrogen atom, 2) a lower alkyl group, a lower alkylthio group, or a lower alkoxy-lower alkyl group, or 3) a lower alkyl group, an oxy group, an oxy-lower alkyl group, a lower alkyloxy group, a carbonyl group, a lower alkenyl group, an optionally-substituted imino group, a lower alkylimino group optionally substituted at its nitrogen atom, a thio-lower alkyl group, or a lower alkylthio group; to each group in 3), bonded is an aryl group or a heterocyclic group, or each group in 3) is substituted by an aryl group or a heterocyclic group, and said aryl or heterocyclic group may be further substituted by any of a halogen atom, a nitro group, a lower alkylamino group, an acylamino group, a lower alkyl group, a lower alkoxy group, a halo-lower alkyl group, a lower cycloalkyl group, or an aryl, heterocyclic, aryl-lower alkyl, heterocyclic-lower alkyl, aryl-lower alkyloxy, heterocyclic-lower alkyloxy, aryl-lower alkenyl or heterocyclic-lower alkenyl group optionally substituted by any of a halogen atom or a lower alkyl group; but $R^{1a}$ $R^{1'a}$ and $R^{2a}$ must not be all hydrogen atoms at the same time; $R^{3a}$ represents an alkyl group; and $R^{4a}$ represents a hydrogen atom or a lower alkyl group.

The compound (2) is hydrolyzed with a base such as lithium hydroxide, sodium hydroxide, potassium hydroxide or the like to produce a compound (3) (reaction formula (b)).

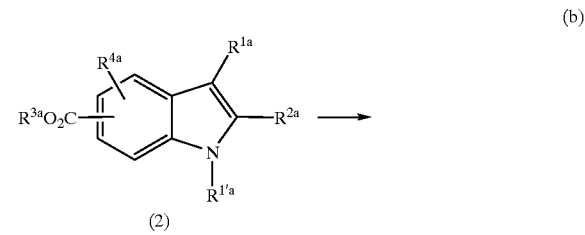

(b)

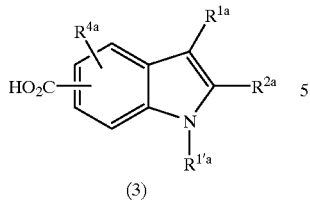

(3)

wherein $R^{1a}$, $R^{1'a}$, $R^{2a}$, $R^{3a}$ and $R^{4a}$ have the same meanings as above.

The compound (3) is processed with a carboxyl activator such as carbonyldiimidazole, 1-(3-(dimethylamino)propyl-3-ethylcarbodiimide, dicyclohexylcarbodiimide or the like, and then reacted with a sulfonamide in the presence of a base to produce a compound (4) (reaction formula (c)). In this case, where the sulfonamide used has a reactive substituent, sultams may be produced through cyclization.

(c)

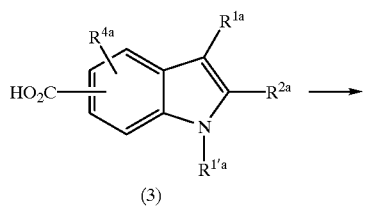

(3)

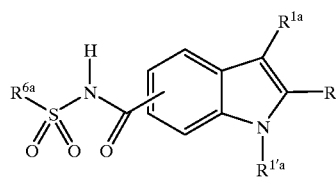

(4)

wherein $R^{1a}$, $R^{1'a}$, $R^{2a}$ and $R^{4a}$ have the same meanings as above; $R^{6a}$ represents an alkyl, alkenyl, lower alkoxy-lower alkyl, aryl, heterocyclic or lower cycloalkyl group, which may be optionally substituted by at least one selected from a halogen atom, a lower alkoxy group, a lower alkyl group, a lower alkenyl group, a lower cycloalkyl group, a nitro group, an aryl group, a heterocyclic group, an arylazo group, a halo-lower alkyl group, a lower alkylaryl group and a lower alkoxyaryl group; and the nitrogen atom of the sulfonamido group in the formula may release the hydrogen atom bonding thereto to form a ring along with $R^{6a}$ As in the reaction formula (a), a compound (6) can be produced from the compound (5) (reaction formula (d)).

(d)

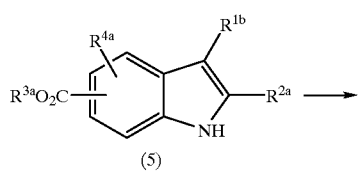

(5)

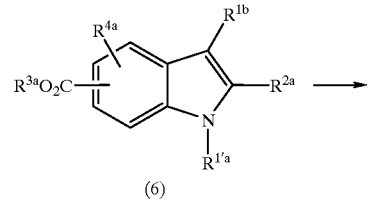

(6)

wherein $R^{1'a}$, $R^{2a}$ and $R^{4a}$ have the same meanings as above; $R^{1b}$ represents a lower alkanoyl group, an arylcarbonyl group, or a heterocyclic-carbonyl group, and said arylcarbonyl or heterocyclic-carbonyl group may be further substituted by any of a halogen atom, a nitro group, a lower alkylamino group, an acylamino group, a lower alkyl group, a lower alkoxy group, a halo-lower alkyl group, a lower cycloalkyl group, or an aryl, heterocyclic, aryl-lower alkyl, heterocyclic-lower alkyl, aryl-lower alkyloxy, heterocyclic-lower alkyloxy, aryl-lower alkenyl or heterocyclic-lower alkenyl group optionally substituted by any of a halogen atom or a lower alkyl group; and $R^{3a}$ represents a lower alkyl group.

In the reaction formula (b), a compound (7) can be produced from the compound (6) (reaction formula (e)).

(e)

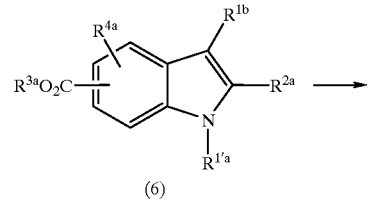

(6)

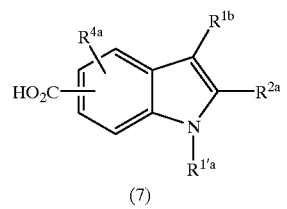

(7)

wherein $R^{1'a}$, $R^{2a}$, $R^{1b}$ and $R^{4a}$ have the same meanings as above; and $R^{3a}$ represents a lower alkyl group.

In the reaction formula (c), a compound (8) can be produced from the compound (7) (reaction formula (f)). In this case, where the sulfonamide used has a reactive substituent, sultams may be produced through cyclization.

(f)

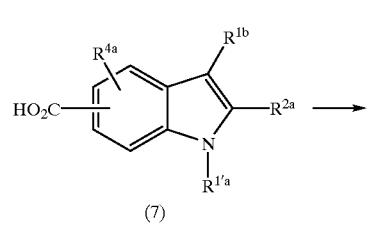

(7)

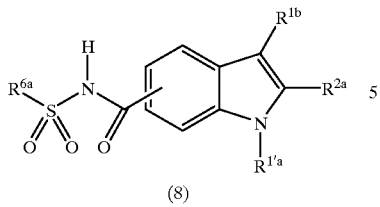

(8)

wherein $R^{1'a}$, $R^{2a}$, $R^{1b}$, $R^{4a}$ and $R^{6a}$ have the same meanings as above.

In the reaction formula (g), a compound (9) is reacted with a chloride, bromide or iodide of $R^{1'a}$ in the presence of silver(I) oxide, whereby the compound (9) is converted into a compound (10). Presence of sodium iodide or potassium iodide in the reaction will improve the result. Alternatively, the compound (9) may be reacted in the same manner as above but in the presence of potassium hydrogentartrate or sodium hydrogentartrate to obtain the compound (10). Presence of sodium iodide or potassium iodide in the reaction will also improve the result. In place of the chloride, bromide or iodide used herein, a corresponding toluenesulfonate or methanesulfonate may also be used to obtain the compound (10).

(g)

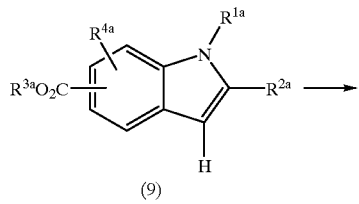

(9)

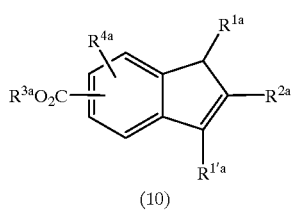

(10)

wherein $R^{1'a}$, $R^{1a}$, $R^{2a}$ and $R^{4a}$ have the same meanings as above; and $R^{3a}$ represents an alkyl group.

In the reaction formula (b), a compound (11) is produced from the compound (10) (reaction formula (h)).

(h)

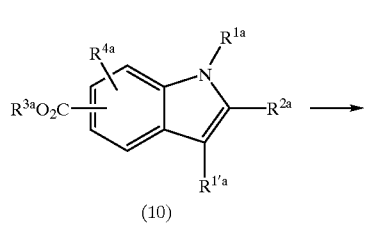

(10)

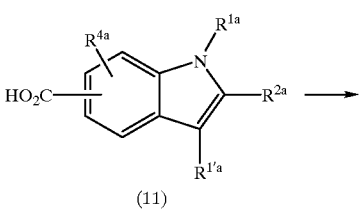

(11)

wherein $R^{1'a}$ $R^{1a}$, $R^{2a}$ and $R^{4a}$ have the same meanings as above; and $R^{3a}$ represents an alkyl group.

In the reaction formula (c), a compound (12) can be produced from the compound (11) (reaction formula (i)). In this case, where the sulfonamide used has a reactive substituent, sultams may be produced through cyclization.

(i)

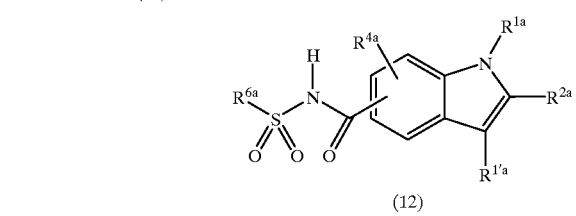

(11)

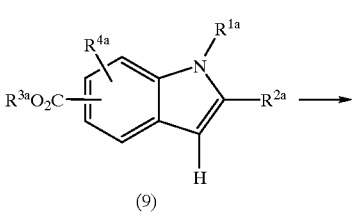

(12)

wherein $R^{1a}$, $R^{1'a}$, $R^{2a}$, $R^{4a}$ and $R^{6a}$ have the same meanings as above.

In the reaction formula (j), the compound (9) is reacted with a lower alkanoyl chloride or bromide, or arylcarbonyl chloride or bromide, or a heterocyclic-carbonyl chloride or bromide (said arylcarbonyl chloride or bromide, or heterocyclic-carbonyl chloride or bromide may be substituted by any of a halogen atom, a nitro group, a lower alkylamino group, an acylamino group, a lower alkyl group, a lower alkoxy group, a halo-lower alkyl group, a lower cycloalkyl group, or an aryl, heterocyclic, aryl-lower alkyl, heterocyclic-lower alkyl, aryl-lower alkyloxy, heterocyclic-lower alkyloxy, aryl-lower alkenyl or heterocyclic-lower alkenyl group optionally substituted by any of a halogen atom or a lower alkyl group), in the presence of a strong Lewis acid such as aluminium chloride, tin(IV) chloride, tin(II) chloride, iron(III) chloride, boron trifluoride, zirconia sulfate or the like, whereby the compound (9) is converted into a compound (13).

(j)

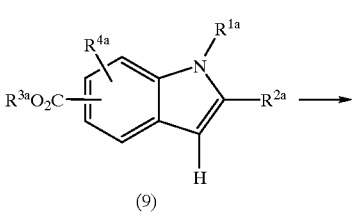

(9)

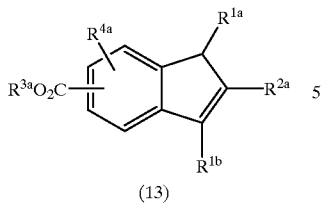

(13)

wherein $R^{1a}$, $R^{2a}$, $R^{1b}$ and $R^{4a}$ have the same meanings as above; and $R^{3a}$ represents an alkyl group.

In the reaction formula (k), the compound (13) is converted into a compound (14), by processing it with a metal hydride such as typically sodium borohydride or borane-tetrahydrofuran complex. The compound (14) is converted into a compound (15), by processing it with sodium borohydride in the presence of trifluoroacetic acid, trifluoromethanesulfonic acid or sulfuric acid. Alternatively, the compound (14) may also be converted into the compound (15), by processing it with a trialkylsilane such as typically triethylsilane in the presence of trifluoroacetic acid. If the compound (13) is processed with a trialkylsilane such as typically triethylsilane in the presence of trifluoroacetic acid, it may be directly converted into the compound (15) in one-step reaction.

(k)

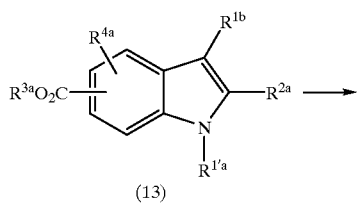

(13)

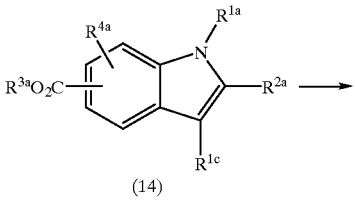

(14)

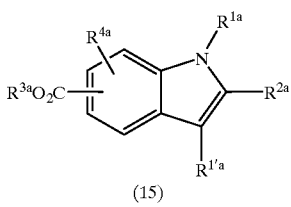

(15)

wherein $R^{1a}$, $R^{1'a}$, $R^{2a}$ and $R^{4a}$ have the same meanings as above; $R^{3a}$ represents an alkyl group; $R^{1c}$ represents a lower alkylhydroxymethyl group, an arylhydroxymethyl group, or a heterocyclic-hydroxymethyl group, and said arylhydroxymethyl group or heterocyclic-hydroxymethyl group may be substituted by any of a halogen atom, a nitro group, a lower alkylamino group, an acylamino group, a lower alkyl group, a lower alkoxy group, a halo-lower alkyl group, a lower cycloalkyl group, or an aryl, heterocyclic, aryl-lower alkyl, heterocyclic-lower alkyl, aryl-lower alkyloxy, heterocyclic-lower alkyloxy, aryl-lower alkenyl or heterocyclic-lower alkenyl group optionally substituted by any of a halogen atom or a lower alkyl group.

In the reaction formula (k), a compound (18) can be produced from a compound (16) via a compound (17) (reaction formula (1)).

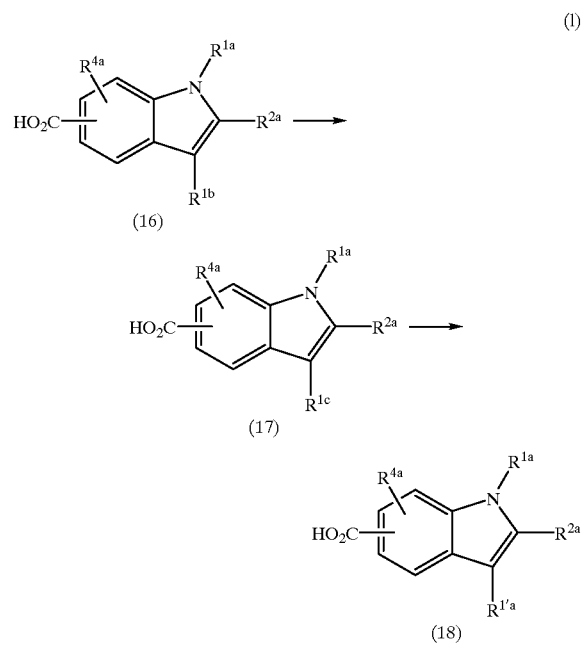

wherein $R^{1a}$, $R^{1'a}$, $R^{1b}$, $R^{1c}$, $R^{2a}$ and $R^{4a}$ have the same meanings as above.

In the reaction formula (k), a compound (21) can be produced from a compound (19) via a compound (20) (reaction formula (m)).

(m)

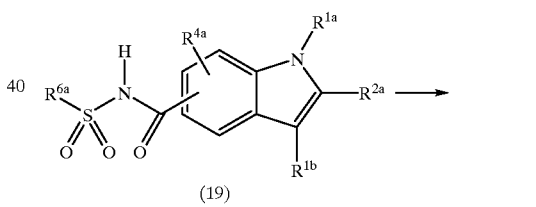

(19)

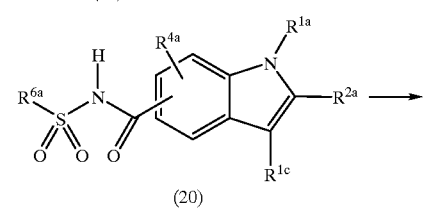

(20)

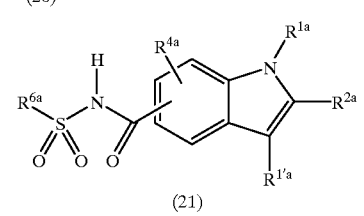

(21)

wherein $R^{1a}$, $R^{1'a}$, $R^{1b}$, $R^{1c}$, $R^{2a}$, $R^{4a}$ and $R^{6a}$ have the same meanings as above.

The compound (13) may be reacted with an aldehyde in the presence of trifluoroacetic acid and a trialkylsilane such as typically triethylsilane, whereby it is converted into the compound (18) via the compound (17). Alternatively, the compound (13) may be reacted with hydrazine and an alkali such as typically sodium hydroxide or potassium hydroxide, whereby it is converted directly into the compound (18).

The compound (1) reportedly can be produced according to the methods described in "Journal of Medicinal Chemistry, 1992, 35, 2419", "U.S. Pat. Nos. 5,212,195", "4,894,386", "EP-0242167". Specifically, a compound (22) is reacted with an N,N-dialkylformamide such as typically N,N-dimethylformamido-dimethyl acetal to produce a compound (23). Where $R^{2a}$ in (23) is 1) a lower alkyl group, a lower alkylthio group, or a lower alkoxy-lower alkyl group, or 2) a lower alkyl group, an oxy group, an oxy-lower alkyl group, a lower alkyloxy group, a carbonyl group, a lower alkenyl group, an optionally-substituted imino group, a lower alkylimino group optionally substituted at its nitrogen atom, a thio-lower alkyl group, or a lower alkylthio group (to each group in 2), bonded is an aryl group or a heterocyclic group, or each group in 2) is substituted by an aryl group or a heterocyclic group, and said aryl or heterocyclic group may be further substituted by any of a halogen atom, a nitro group, a lower alkylamino group, an acylamino group, a lower alkyl group, a lower alkoxy group, a halo-lower alkyl group, a lower cycloalkyl group, or an aryl, heterocyclic, aryl-lower alkyl, heterocyclic-lower alkyl, aryl-lower alkyloxy, heterocyclic-lower alkyloxy, aryl-lower alkenyl or heterocyclic-lower alkenyl group optionally substituted by any of a halogen atom or a lower alkyl group), the compound (23) may be reacted with a lower alkanoyl chloride or bromide to give a compound (24), which is then reduced at its nitro group in the presence of a hydrogenation catalyst such as typically palladium-carbon, in a hydrogen atmosphere, to produce the compound (1) (reaction formula (n)). Apart from this mode, the nitro group may be reduced by any other method of, for example, 1) reduction with reduced iron and zinc, 2) reduction with sodium hydrosulfite, 3) reduction with formic acid or ammonium formate in the presence of a transition metal catalyst such as typically palladium-carbon, or 4) reduction with nickel.

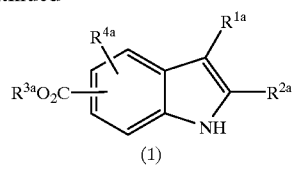

(1)

wherein $R^{1a}$ and $R^{4a}$ have the same meanings as above; $R^{2a}$ represents 1) a lower alkyl group, a lower alkylthio group, or a lower alkoxy-lower alkyl group, or 2) a lower alkyl group, an oxy group, an oxy-lower alkyl group, a lower alkyloxy group, a carbonyl group, a lower alkenyl group, an optionally-substituted imino group, a lower alkylimino group optionally substituted at its nitrogen atom, a thio-lower alkyl group, or a lower alkylthio group, to each group in 2), bonded is an aryl group or a heterocyclic group, or each group in 2) is substituted by an aryl group or a heterocyclic group, and said aryl or heterocyclic group may be further substituted by any of a halogen atom, a nitro group, a lower alkylamino group, an acylamino group, a lower alkyl group, a lower alkoxy group, a halo-lower alkyl group, a lower cycloalkyl group, or an aryl, heterocyclic, aryl-lower alkyl, heterocyclic-lower alkyl, aryl-lower alkyloxy, heterocyclic-lower alkyloxy, aryl-lower alkenyl or heterocyclic-lower alkenyl group optionally substituted by any of a halogen atom or a lower alkyl group; $R^{2a}$ represents an alkyl group; and R' represents a lower alkyl group.

A compound (25) which corresponds to the compound (1) where $R^{3a}$ is a hydrogen atom can be produced by reducing a compound (23) at its nitro group in the presence of a hydrogenation catalyst such as typically palladium-carbon, in a hydrogen atmosphere (reaction formula (o)). Apart from this mode, the nitro group may be reduced by any other method of, for example, 1) reduction with reduced iron and zinc, 2) reduction with sodium hydrosulfite, 3) reduction with formic acid or ammonium formate in the presence of a transition metal catalyst such as typically palladium-carbon, or 4) reduction with nickel.

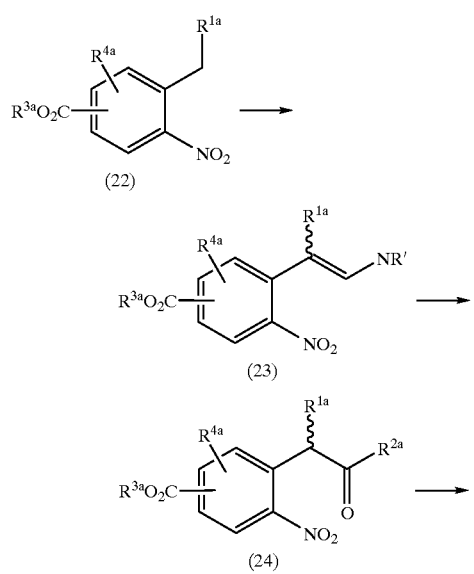

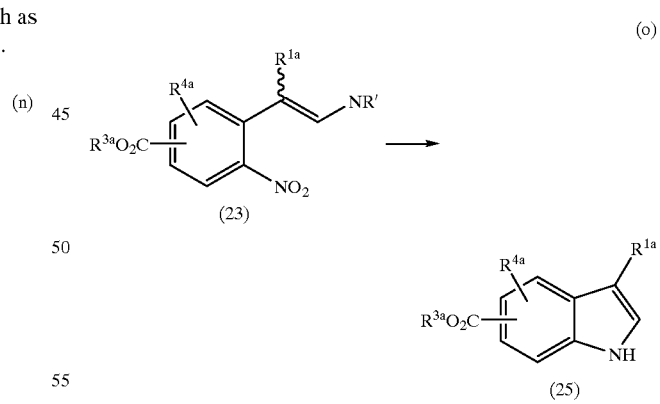

wherein $R^{1a}$, $R^{4a}$ and R' have the same meanings as above; and $R^{3a}$ represents an alkyl group.

In the reaction formula (p), a compound (26), which corresponds to the compound (1) where $R^{1a}$ is a lower alkyl group and $R^{2a}$ is a hydrogen atom, can be converted into a compound (29) which corresponds to the compound (1) where $R^{1a}$ is a lower alkyl group and $R^{2a}$ is a lower alkyl group or an aryl-lower alkyl group (said aryl-lower alkyl group may be substituted by any of a halogen atom, a nitro group, a lower alkylamino group, an acylamino group, a lower alkyl group, a lower alkoxy group, a halo-lower alkyl group, a lower cycloalkyl group, or an aryl, heterocyclic, aryl-lower alkyl, heterocyclic-lower alkyl, aryl-lower alkyloxy, heterocyclic-lower alkyloxy, aryl-lower alkenyl or heterocyclic-lower alkenyl group optionally substituted by any of a halogen atom or a lower alkyl group). Specifically, the compound (26) can be converted into a compound (27), like in the reaction formula (j). The compound (27) can be converted into the compound (29) via a compound (28), like in the reaction formula (k).

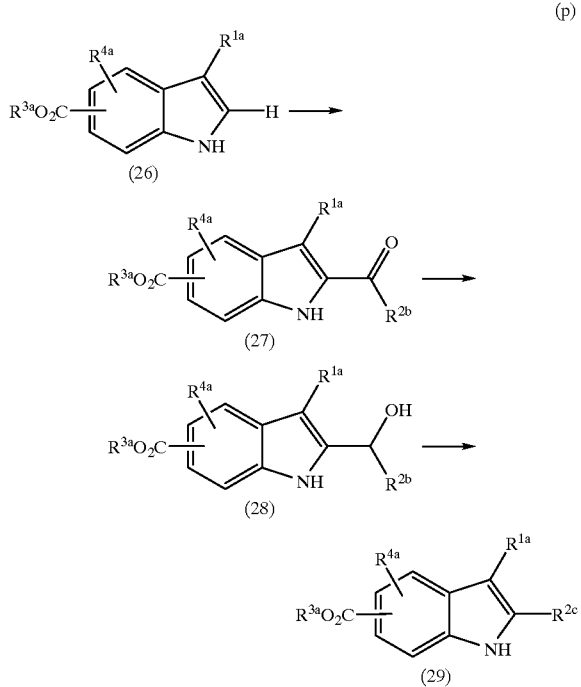

(p)

wherein $R^{1a}$ represents a lower alkyl group; $R^{2b}$ represents a lower alkyl group or an aryl-lower alkyl group (said aryl-lower alkyl group may be substituted by any of a halogen atom, a nitro group, a lower alkylamino group, an acylamino group, a lower alkyl group, a lower alkoxy group, a halo-lower alkyl group, a lower cycloalkyl group, or an aryl, heterocyclic, aryl-lower alkyl, heterocyclic-lower alkyl, aryl-lower alkyloxy, heterocyclic-lower alkyloxy, aryl-lower alkenyl or heterocyclic-lower alkenyl group optionally substituted by any of a halogen atom or a lower alkyl group); $R^{3a}$ represents a lower alkyl group; $R^{2c}$ represents a lower alkyl group or an aryl-lower alkyl group (said aryl-lower alkyl group may be substituted by any of a halogen atom, a nitro group, a lower alkylamino group, an acylamino group, a lower alkyl group, a lower alkoxy group, a halo-lower alkyl group, a lower cycloalkyl group, or an aryl, heterocyclic, aryl-lower alkyl, heterocyclic-lower alkyl, aryl-lower alkyloxy, heterocyclic-lower alkyloxy, aryl-lower alkenyl or heterocyclic-lower alkenyl group optionally substituted by any of a halogen atom or a lower alkyl group); and $R^{4a}$ has the same meaning as above.

The intermediates in each reaction noted above may optionally be purified in any ordinary purification for chemical synthesis, for example, through recrystallization, column chromatography, thin-layer chromatography, high-performance liquid chromatography or the like, prior to the next step where they are processed. The final products of the compounds of the invention may also be purified, if desired, in any ordinary purification for organic chemistry, for example, through recrystallization, column chromatography, thin-layer chromatography, high-performance liquid chromatography or the like. Identification of the compounds may be effected through NMR spectrometric analysis, mass spectrometric analysis, IR spectrometric analysis, elementary analysis, melting point measurement, etc.

Unless otherwise specifically indicated, "lower" is meant to indicate groups having at most 8 carbon atoms.

The alkyl group is meant to have from 1 to 20 carbon atoms. This may be a linear or branched alkyl group, including, for example, a methyl group, an ethyl group, an n-propyl group, an i-propyl group, an n-butyl group, an i-butyl group, a sec-butyl group, a t-butyl group, an n-pentyl group, an i-pentyl group, a sec-pentyl group, a 2,2-dimethylpentyl group, a 2-methylbutyl group, an n-hexyl group, a 1-methylpentyl group, a 2-methylpentyl group, a 3-methylpentyl group, a 4-methylpentyl group, a 1-ethylbutyl group, a 2-ethylbutyl group, a 1,1-dimethylbutyl group, a 2,2-dimethylbutyl group, a 3,3-dimethylbutyl group, a 1-ethyl-1-methylpropyl group, an n-heptyl group, a 1-methylhexyl group, a 2-methylhexyl group, a 3-methylhexyl group, a 4-methylhexyl group, a 5-methylhexyl group, a 1-ethylpentyl group, a 2-ethylpentyl group, a 1,1-dimethylpentyl group, a 2,2-dimethylpentyl group, a 3,3-dimethylpentyl group, an n-octyl group, a 1-methylheptyl group, a 2-methylheptyl group, a 3-methylheptyl group, a 4-methylheptyl group, a 5-methylheptyl group, a 6-methylheptyl group, a 1-ethylhexyl group, a 2-ethylhexyl group, a 1,1-dimethylhexyl group, a 2,2-dimethylhexyl group, a 3,3-dimethylhexyl group, an n-nonyl group, a 1-methyloctyl group, a 2-methyloctyl group, a 3-methyloctyl group, a 4-methyloctyl group, a 5-methyloctyl group, a 6-methyloctyl group, a 7-methyloctyl group, a 1-ethylheptyl group, a 2-ethylheptyl group, a 1,1-dimethylheptyl group, a 2,2-dimethylheptyl group, a 3,3-dimethylheptyl group, an n-decyl group, a 1-methylnonyl group, a 2-methylnonyl group, a 3-methylnonyl group, a 4-methylnonyl group, a 1-ethyloctyl group, a 2-ethyloctyl group, an n-undecyl group, an n-dodecyl group, an n-tridecyl group, an n-tetradecyl group, an n-pentadecyl group, an n-hexadecyl group, an n-octadecyl group, etc. Preferred are alkyl groups each having from 3 to 8 carbon atoms.

The alkenyl group is meant to have from 2 to 20 carbon atoms. This may be a linear or branched alkenyl group, including, for example, a vinyl group, a 1-propenyl group, a 2-propenyl group, a 1-butenyl group, a 2-butenyl group, a 3-butenyl group, a 1-methyl-1-propenyl group, a 2-methyl-1-propenyl group, a 1-methyl-2-propenyl group, a 2-methyl-2-propenyl group, a 1-pentenyl group, a 2-pentenyl group, a 3-pentenyl group, a 4-pentenyl group, a 1-methyl-1-butenyl group, a 2-methyl-1-butenyl group, a 3-methyl-1-butenyl group, a 2-methyl-2-butenyl group, a 3-methyl-2-butenyl group, a 2-methyl-3-butenyl group, a 3-methyl-3-butenyl group, a 1-hexenyl group, a 2-hexenyl group, a 3-hexenyl group, a 4-hexenyl group, a 5-hexenyl group, a 2-methyl-1-pentenyl group, a 3-methyl-1-pentenyl group, a 4-methyl-1-pentenyl group, a 1-heptenyl group, a 1-octenyl group, a 1-nonenyl group, a 1-decenyl group, a 1-undecenyl group, a 1-dodecenyl group, a 1-tridecenyl group, a 1-tetradecenyl group, a 1-pentadecenyl group, a 1-hexadecenyl group, a 1-octadecenyl group, etc. Preferred are alkenyl groups each having from 3 to 8 carbon atoms.

As preferred examples of the alkenyl group, mentioned are linear or branched alkenyl groups including a vinyl group, a 1-propenyl group, a 2-propenyl group, a 1-butenyl group, a 2-butenyl group, a 3-butenyl group, a 1-methyl-1- propenyl group, a 2-methyl-1-propenyl group, a 1-methyl-2-propenyl group, a 2-methyl-2-propenyl group, a 1-pentenyl group, a 2-pentenyl group, a 3-pentenyl group, a 4-pentenyl group, a 1-methyl-1-butenyl group, a 2-methyl-1-butenyl group, a 3-methyl-1-butenyl group, a 2-methyl-2-butenyl group, a 3-methyl-2-butenyl group, a 2-methyl-3-butenyl group, a 3-methyl-3-butenyl group, a 1-hexenyl group, a 2-hexenyl group, a 3-hexenyl group, a 4-hexenyl group, a 5-hexenyl group, a 2-methyl-1-pentenyl group, a 3-methyl-1-pentenyl group, a 4-methyl-1-pentenyl group, etc. More preferred are those each having from 2 to 4 carbon atoms.

The halogen atom includes a fluorine atom, a chlorine atom, a bromine atom, and an iodine atom. Preferred are a fluorine atom, a chlorine atom and a bromine atom.

The halo-lower alkyl group is a linear or branched alkyl group having at most 8 carbon atoms and substituted by any of a fluorine atom, a chlorine atom, a bromine atom and an iodine atom, preferably substituted by any of a fluorine atom, a chlorine atom and a bromine atom and having at most 8 carbon atoms, more preferably having from 1 to 3 carbon atoms. For example, it includes a fluoromethyl group, a difluoromethyl group, a trifluoromethyl group, a chloromethyl group, a dichloromethyl group, a trichloromethyl group, a bromomethyl group, a dibromomethyl group, a tribromomethyl group, a 1-fluoroethyl group, a 1-chloroethyl group, a 1-bromoethyl group, a 2-fluoroethyl group, a 2-chloroethyl group, a 2-bromoethyl group, a 1,2-difluoroethyl group, a 1,2-dichloroethyl group, a 1,2-dibromoethyl group, a 2,2,2-trifluoroethyl group, a heptafluoroethyl group, a 1-fluoropropyl group, a 1-chloropropyl group, a 1-bromopropyl group, a 2-fluoropropyl group, a 2-chloropropyl group, a 2-bromopropyl group, a 3-fluoropropyl group, a 3-chloropropyl group, a 3-bromopropyl group, a 1,2-difluoropropyl group, a 1,2-dichloropropyl group, a 1,2-dibromopropyl group, a 2,3-difluoropropyl group, a 2,3-dichloropropyl group, a 2,3-dibromopropyl group, a 3,3,3-trifluoropropyl group, a 2,2,3,3,3-pentafluoropropyl group, a 2-fluorobutyl group, a 2-chlorobutyl group, a 2-bromobutyl group, a 4-fluorobutyl group, a 4-chlorobutyl group, a 4-bromobutyl group, a 4,4,4-trifluorobutyl group, a 2,2,3,3,4,4,4-heptafluorobutyl group, a perfluorobutyl group, a 2-fluoropentyl group, a 2-chloropentyl group, a 2-bromopentyl group, a 5-fluoropentyl group, a 5-chloropentyl group, a 5-bromopentyl group, a perfluoropentyl group, a 2-fluorohexyl group, a 2-chlorohexyl group, a 2-bromohexyl group, a 6-fluorohexyl group, a 6-chlorohexyl group, a 6-bromohexyl group, a perfluorohexyl group, a 2-fluoroheptyl group, a 2-chloroheptyl group, a 2-bromoheptyl group, a 7-fluoroheptyl group, a 7-chloroheptyl group, a 7-bromoheptyl group, a perfluoroheptyl group, etc.

The lower alkoxy group is a linear or branched alkyloxy group having at most 6 carbon atoms. For example, it includes a methoxy group, an ethoxy group, an n-propyloxy group, an i-propyloxy group, an n-butyloxy group, an i-butyloxy group, a sec-butyloxy group, a t-butyloxy group, an n-pentyloxy group, an i-pentyloxy group, a sec-pentyloxy group, a 2,2-dimethylpropyloxy group, a 2-methylbutoxy group, an n-hexyloxy group, an i-hexyloxy group, a t-hexyloxy group, a sec-hexyloxy group, a 2-methylpentyloxy group, a 3-methylpentyloxy group, a 1-ethylbutyloxy group, a 2-ethylbutyloxy group, a 1,1-dimethylbutyloxy group, a 2,2-dimethylbutyloxy group, a 3,3-dimethylbutyloxy group, a 1-ethyl-1-methylpropyloxy group, etc. Preferred are a methoxy group, an ethoxy group, an n-propyloxy group, an i-propyloxy group, an n-butyloxy group, an i-butyloxy group, a sec-butyloxy group, a t-butyloxy group, etc. More preferred are those each having from 1 to 3 carbon atoms.

The lower alkylthio group is meant to indicate a thio group to which is bonded a lower alkyl group.

The lower alkoxy-lower alkyl group is meant to indicate a lower alkyl group substituted by a lower alkoxy group.

The oxy-lower alkyl group is meant to indicate a lower alkyl group substituted by an oxy group.

The lower alkyloxy group is meant to indicate an oxy group to which is bonded a lower alkyl group.

The optionally-substituted imino group is meant to indicate an imino group which may be optionally substituted by a lower alkyl group or the like.

The lower alkylimino group optionally substituted at its nitrogen atom is meant to indicate an imino group to which is bonded a lower alkyl group and in which the nitrogen atom may be optionally substituted by a lower alkyl group or the like.

The thio-lower alkyl group is meant to indicate a lower alkyl group substituted by a thio group.

The lower alkylthio group is meant to indicate a thio group to which is bonded a lower alkyl group.

The lower cycloalkyl group is a cycloalkyl group having from 3 to 7 carbon atoms. Preferably, it includes a cyclopropyl group, a cyclobutyl group, a cyclopentyl group, a cyclohexyl group, a cycloheptyl group, etc. More preferred are a cyclopropyl group, a cyclobutyl group, a cyclopentyl group, and a cyclohexyl group.

Preferred examples of the "esterified carboxyl group" are mentioned below.

As preferred examples of the ester moiety in the esterified carboxyl group, mentioned are a lower alkyl ester (e.g., methyl ester, ethyl ester, propyl ester, isopropyl ester, butyl ester, isobutyl ester, tert-butyl ester, pentyl ester, hexyl ester, etc.). The lower alkyl ester may have at least one suitable substituent. As its examples, mentioned are a lower alkanoyloxy-(lower) alkyl ester [e.g., acetoxymethyl ester, propionyloxymethyl ester, butyryloxymethyl ester, valeryloxymethyl ester, pivaloyloxymethyl ester, hexanoyloxymethyl ester, 1-(or 2-)acetoxyethyl ester, 1-(or 2- or 3-)acetoxypropyl ester, 1-(or 2-, 3- or 4-)acetoxybutyl ester, 1-(or 2-)propionyloxyethyl ester, 1-(or 2- or 3-)propionyloxypropyl ester, 1-(or 2-) butyryloxyethyl ester, 1-(or 2-)isobutyryloxyethyl ester, 1-(or 2-)pivaloyloxyethyl ester, 1-(or 2-)hexanoyloxyethyl ester, isobutyryloxymethyl ester, 2-ethylbutyryloxymethyl ester, 3,3-dimethylbutyryloxymethyl ester, 1-(or 2-)pentanoyloxyethyl ester, etc.], a lower alkanesulfonyl-(lower) alkyl ester (e.g., 2-mesylethyl ester, etc.), a mono-(or di- or tri-)halo-(lower) alkyl ester (e.g., 2-iodoethyl ester, 2,2,2-trichloroethyl ester, etc.); a lower alkoxycarbonyloxy-(lower) alkyl ester [e.g., methoxycarbonyloxymethyl ester, ethoxycarbonyloxymethyl ester, propoxycarbonyloxymethyl ester, tert-butoxycarbonyloxymethyl ester, 1-(or 2-)methoxycarbonyloxyethyl ester, 1-(or 2-)ethoxycarbonyloxyethyl ester, 1-(or 2-)isopropoxycarbonyloxyethyl ester, etc.], a phthalidylidene-(lower) alkyl ester, or a (5-lower alkyl-2-oxo-1,3-dioxol-4-yl)-(lower) alkyl ester [e.g., (5-methyl-2-oxo-1,3-dioxol-4-yl)methyl ester, (5-ethyl-2-oxo-1,3-dioxol-4-yl)methyl ester, (5-propyl-2-oxo-1,3-dioxol-4-yl) ethyl ester, etc.]; a lower alkenyl ester (e.g., vinyl ester, allyl ester, etc.); a lower alkynyl ester (e.g., ethynyl ester, propynyl ester, etc.); an aryl-(lower) alkyl ester optionally having at least one suitable substituent (e.g., benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-tert-butylbenzyl ester, etc.); an aryl ester optionally having at least one suitable substituent (e.g., phenethyl ester, 4-chlorophenyl ester, tolyl ester, tert-butylphenyl ester, xylyl ester, mesityl ester, cumenyl ester, etc.); a phthalidyl ester, etc.

As preferred examples of the protected, esterified carboxyl group which is defined as above, mentioned are a lower alkoxycarbonyl group, and a phenyl (or nitrophenyl)-($C_{1-4}$) alkoxycarbonyl group. The most preferred are methoxycarbonyl, ethoxycarbonyl and benzyloxycarbonyl groups.

Preferred examples of the "amidated carboxyl group" are mentioned below.

A carbamoyl group;

A mono- or di-lower alkylcarbamoyl group (in which the alkyl group may be any of those mentioned hereinabove) [e.g., methylcarbamoyl, dimethylcarbamoyl, isopropylcarbamoyl, n-butylcarbamoyl, t-butylcarbamoyl, N-methyl-N-(pyridylmethyl)carbamoyl, etc.];

An aryl-lower alkylcarbamoyl group (in which the aryl group and the alkyl group may be any of those mentioned hereinabove) [e.g., benzylcarbamoyl, 3,4-methylenedioxybenzylcarbamoyl, diaminobenzylcarbamoyl, phenethylcarbamoyl];

A cyclo-lower alkylcarbamoyl group having from 3 to 7 carbon atoms (in which the cyclo-lower alkyl group may be any of those mentioned hereinabove) [e.g., cyclopropylcarbamoyl, cyclobutylcarbamoyl, cyclopentylcarbamoyl, cyclohexylcarbamoyl, etc.];

An arylcarbamoyl group (in which the aryl group may be any of those mentioned hereinabove) [e.g., phenylcarbamoyl, naphthylcarbamoyl, etc.];

A heterocyclic carbamoyl group (in which the heterocyclic group may be any of those mentioned hereinabove) [e.g., thiazolylcarbamoyl, thiadiazolylcarbamoyl, pyridylcarbamoyl, triazolylcarbamoyl, tetrazolylcarbamoyl, N-methyl-N-pyridylcarbamoyl, morpholinocarbamoyl, etc.];

A heterocyclic-lower alkylcarbamoyl group (in which the heterocyclic-lower alkyl group may be any of those mentioned hereinabove) [e.g., morpholinoethylcarbamoyl, pyridylmethylcarbamoyl, methylenedioxybenzylcarbamoyl, etc.];

An N-disubstituted carbamoyl group in which the nitrogen atom is one member of atoms constituting a nitrogen-containing hetero-ring (e.g., morpholinocarbonyl, thiomorpholinocarbonyl, 1-perhydroazepinylcarbonyl, 1,1,-dioxothiazolidinecarbonyl, piperidinocarbonyl, 1-piperazinylcarbonyl, 4-(2-hydroxyethyl)-1-piperazinylcarbonyl, 4-methyl-1-piperazinylcarbonyl, carboxypyrrolidinocarbonyl, etc.);

A substituted sulfonylcarbamoyl group, etc.

The substituents for the substituted sulfonylcarbamoyl group include, for example, an alkyl group, an alkenyl group, a halo-lower alkyl group, an aryl-lower alkyl group, a hydroxy-lower alkyl group, a tri-lower alkylsilyl-lower alkyl group, a lower alkoxy-lower alkyl group, a lower alkylthio-lower alkyl group, a heterocyclic group and an aryl group each having at most 20 carbon atoms, such as those mentioned above. The aryl group may optionally be substituted by any of a halogen atom, a lower alkyl group, a halo-lower alkyl group, a lower alkoxy group, a nitro group and the like, such as those mentioned above. As specific examples of the substituted sulfonylcarbonyl group, concretely mentioned are a naphthalenesulfonylcarbamoyl group, a benzenesulfonylcarbamoyl group, a nitrobenzenesulfonylcarbamoyl group, a trihalobenzenesulfonylcarbamoyl group, a lower alkoxybenzenesulfonylcarbamoyl group, a halobenzenesulfonylcarbamoyl group, a mono- or di-lower alkylbenzenesulfonylcarbamoyl group, a $C_{1-20}$ alkanesulfonylcarbamoyl group (e.g., 2,2-dimethylethanesulfonylcarbamoyl, butanesulfonylcarbamoyl, propanesulfonylcarbamoyl, isopropanesulfonylcarbamoyl, ethanesulfonylcarbamoyl, methanesulfonylcarbamoyl, octanesulfonylcarbamoyl, pentanesulfonylcarbamoyl, isopentanesulfonylcarbamoyl, hexanesulfonylcarbamoyl, etc.), a trihalo-(lower) alkanesulfonylcarbamoyl group (e.g., trifluoromethanesulfonylcarbamoyl, etc.), a phenyl-(lower) alkanesulfonylcarbamoyl group, a tri-lower alkanesulfonylcarbamoyl group, a lower alkylthio-lower alkanesulfonylcarbamoyl group, a lower alkoxy-(lower) alkanesulfonylcarbamoyl group, a quinolinesulfonylcarbamoyl group, a hydroxy(lower) alkanesulfonylcarbamoyl group (e.g., 2-hydroxybutanesulfonylcarbamoyl, 3-hydroxybutanesulfonylcarbamoyl, 2-hydroxypentanesulfonylcarbamoyl, etc.), an alkenesulfonylcarbamoyl group (e.g., ethylenesulfonylcarbamoyl, 1-pentenesulfonylcarbamoyl, etc.), a heterocyclicsulfonylcarbamoyl group (e.g., 2-thiophenesulfonylcarbamoyl, 8-quinolinesulfonylcarbamoyl, etc.).

The lower alkanoyl group is a linear or branched alkylcarbonyl group in which the alkyl moiety has at most 6 carbon atoms. For example, it includes a methylcarbonyl group, an ethylcarbonyl group, an n-propylcarbonyl group, an i-propylcarbonyl group, an n-butylcarbonyl group, an i-butylcarbonyl group, a sec-butylcarbonyl group, a t-butylcarbonyl group, an n-pentylcarbonyl group, an i-pentylcarbonyl group, a sec-pentylcarbonyl group, a 2,2-dimethylpropylcarbonyl group, a 2-methylbutylcarbonyl group, an n-hexylcarbonyl group, an i-hexylcarbonyl group, a t-hexylcarbonyl group, a sec-hexylcarbonyl group, a 2-methylpentylcarbonyl group, a 3-methylpentylcarbonyl group, a 1-ethylbutylcarbonyl group, a 2-ethylbutylcarbonyl group, a 1,1-dimethylbutylcarbonyl group, a 2,2-dimethylbutylcarbonyl group, a 3,3-dimethylbutylcarbonyl group, a 1-ethyl-1-methylpropylcarbonyl group, etc. Preferred is a carbonyl group bonded to a $C_{1-4}$ alkyl group, which includes a methylcarbonyl group, an ethylcarbonyl group, an n-propylcarbonyl group, an i-propylcarbonyl group, an n-butylcarbonyl group, an i-butylcarbonyl group, a sec-butylcarbonyl group, a t-butylcarbonyl group, etc.

The aryl group as referred to herein is meant to have from 6 to 10 carbon atoms, including, for example, a phenyl group, a naphthyl group, etc. The naphthyl group includes a 1-naphthyl group, a 2-naphthyl group, etc. On its benzene or naphthalene ring, the aryl group may be substituted by any of a halogen atom, a lower alkyl group, a cyano group, a nitro group, a trifluoromethyl group and the like such as those mentioned above.

The aryl-lower alkyl group is meant to indicate an alkyl group substituted by an aryl group. For the alkyl and aryl moieties in this group, referred to are those mentioned hereinabove. For example, the aryl-lower alkyl group includes a benzyl group, a 1-phenylethyl group, a 2-phenylethyl group, a phenylpropyl group, a phenylbutyl group, a phenylpentyl group, a phenylhexyl group, a naphthylmethyl group, a naphthylethyl group, a naphthylpropyl group, a naphthylbutyl group, a naphthylpentyl group, a naphthylhexyl group, etc.

The aryl-lower alkyloxy group includes, for example, a benzyloxy group, a 1-phenylethyloxy group, a 2-phenylethyloxy group, a phenylpropyloxy group, a phenylbutyloxy group, a phenylpentyloxy group, a phenylhexyloxy group, a naphthylmethyloxy group, a naphthylethyloxy group, a naphthylpropyloxy group, a naphthylbutyloxy group, a naphthylpentyloxy group, etc. On its benzene or naphthalene ring, the aryl-lower alkyloxy group may be substituted.

The aryl-lower alkenyl group is an alkenyl group having at most 6 carbon atoms, to which is bonded an aryl group such as that mentioned above. This includes, for example, a phenylethenyl group, a naphthylethenyl group, etc.

The heterocyclic group is described hereinunder. Concretely, it includes a pyridyl group, a quinolyl group, an isoquinolyl group, a thiazolyl group, a thiadiazolyl group, a benzofuranyl group, a dibenzofuranyl group, a thianaphthalenyl group, a 1H-1,2,3-triazolyl group, a 1,2,4-triazolyl group, a tetrazolyl group, a furyl group, a thienyl group, a pyrrolyl group, an imidazolyl group, a pyrimidinyl group, an indolyl group, a benzimidazolyl group, etc. The heterocyclic group may be optionally substituted by any of a halogen atom, a lower alkyl group or the like mentioned above. For example, the substituted heterocyclic group includes a haloisoquinolyl group, a methylisoquinolyl group, etc.

The pyridyl group as referred to herein is meant to indicate any of a 2-pyridyl group, a 3-pyridyl group or a 4-pyridyl group, in which the bonding position is not specifically defined. The same shall apply to the other heterocyclic groups referred to herein, in which the bonding position is not specifically defined.

Preferably, the "heterocyclic group" indicates a saturated or unsaturated, monocyclic or polycyclic heterocyclic group having at least one hetero atom of oxygen, sulfur and nitrogen atoms and others.

More preferred examples of the heterocyclic group are mentioned below.

A 7- to 12-membered, preferably 9- or 10-membered, unsaturated condensed heterocyclic group (preferably, bicyclic group) having from 1 to 5 nitrogen atoms, for example, an indolyl group, an isoindolyl group, a indolidinyl group, a benzimidazolyl group, a quinolyl group, an isoquinolyl group, an indazolinyl group, a benzotriazolyl group, a tetrazolopyridyl group, a tetrazolopyridazinyl group (e.g., tetrazolo[1,5-b]pyridazinyl, etc.), a dihydrotriazolopyridazinyl group, etc.;

A 7- to 12-membered, preferably 9- or 10-membered, unsaturated condensed heterocyclic group (preferably, bicyclic group) having from 1 to 3 sulfur atoms, or its S,S-dioxide, for example, a dithianaphthalenyl group (e.g., 4H-1,3-dithianaphthalenyl, 1,4-dithianaphthalenyl, etc.), a benzothiophenyl group or its S,S-dioxide (e.g., benzo[a]thiophenyl or its S,S-dioxide, benzo[b]thiophenyl or its S,S-dioxide, etc.), etc.;

A 3- to 8-membered, preferably 5- or 6-membered, unsaturated mono-heterocyclic group having from 1 to 4 nitrogen atoms, for example, a pyrrolyl group, a pyrrolinyl group, an imidazolyl group, a pyrazolyl group, a pyridyl group and its N-oxide, a pyrimidyl group, a pyrazinyl group, a pyridazinyl group, a triazolyl group (e.g., 4H-1,2,4-triazolyl, 1H-1,2,3-triazolyl, 2H-1,2,3-triazolyl, etc.), a tetrazolyl group (e.g., 1H-tetrazolyl, 2H-tetrazolyl, etc.), a dihydrotriazinyl group (e.g., 4,5-dihydro-1,2,4-triazinyl, 2,5-dihydro-1,2,4-triazinyl, etc.), etc.;

A 3- to 8-membered, preferably 5- or 6-membered, saturated mono-heterocyclic group having from 1 to 4 nitrogen atoms, for example, an azetidinyl group, a pyrrolidinyl group, an imidazolidinyl group, a piperidinyl group, a pyrazolidinyl group, a piperazinyl group, etc.;

A 7- to 12-membered, preferably 9- or 10-membered, unsaturated condensed heterocyclic group (preferably, bicyclic group) having 1 or 2 oxygen atoms and from 1 to 3 nitrogen atoms, for example, a benzoxazolyl group, a benzoxadiazolyl group, etc.;

A 3- to 8-membered, preferably 5- or 6-membered, unsaturated mono-heterocyclic group having 1 or 2 oxygen atoms and from 1 to 3 nitrogen atoms, for example, an oxazolyl group, an isoxazolyl group, an oxadiazolyl group (e.g., 1,2,4-oxadiazolyl, 1,3,4-oxadiazolyl, 1,2,5-oxadiazolyl, etc.), etc.;

A 3- to 8-membered, preferably 5- or 6-membered, saturated mono-heterocyclic group having 1 or 2 oxygen atoms and from 1 to 3 nitrogen atoms, for example, a morpholinyl group, etc.;

A 7- to 1 2-membered, preferably 9- or 10-membered, unsaturated condensed heterocyclic group (preferably, bicyclic group) having 1 or 2 sulfur atoms and from 1 to 3 nitrogen atoms, for example, a benzothiazolyl group, a benzothiadiazolyl group, etc.;

A 3- to 8-membered, preferably 5- or 6-membered, unsaturated mono-heterocyclic group having 1 or 2 sulfur atoms and from 1 to 3 nitrogen atoms, for example, a thiazolyl group, a 1,2-thiazolyl group, a thiazolyl group, a thiadiazolyl group (e.g., 1,2,4-thiadiazolyl, 1,3,4-thiadiazolyl, 1,2,5-thiadiazolyl, 1,2,3-thiadiazolyl, etc.), etc.;

A 3- to 8-membered, preferably 5- or 6-membered, saturated mono-heterocyclic group having 1 or 2 sulfur atoms and from 1 to 3 nitrogen atoms, for example, a thiazolidinyl group, etc.;

A 3- to 8-membered, preferably 5- or 6-membered, unsaturated mono-heterocyclic group having one sulfur atom, for example, a thienyl group, etc.

The heterocyclic-lower alkyl group is meant to indicate a lower alkyl group substituted by a heterocyclic group.

The heterocyclic-lower alkyloxy group is meant to indicate an oxy group to which is bonded a heterocyclic-lower alkyl group.

The heterocyclic-lower alkenyl group is meant to indicate a lower alkenyl group substituted by a heterocyclic group.

Preferably, the "acyl group" is an aliphatic acyl group, an aromatic acyl group, a heterocyclic acyl group, or an aromatic group-bonded or heterocyclic group-bonded aliphatic acyl group, which may be derived from carboxylic acids, carbonic acids, sulfonic acids, carbamic acids, etc.

The aliphatic acyl group may be a saturated or unsaturated, acyclic or cyclic one, for example, including an alkanoyl group such as a lower alkanoyl group (e.g., formyl, acetyl, propionyl, butyryl, isobutyryl, valeryl, isovaleryl, pivaloyl, hexanoyl, etc.), an alkylsulfonyl group such as a lower alkylsulfonyl group (e.g., mesyl, ethylsulfonyl, propylsulfonyl, isopropylsulfonyl, butylsulfonyl, isobutylsulfonyl pentylsulfonyl, hexylsulfonyl, etc.), a carbamoyl group, an N-alkylcarbamoyl group (e.g., methylcarbamoyl, ethylcarbamoyl, etc.), an alkoxycarbonyl group such as a lower alkoxycarbonyl group (e.g., methoxycarbonyl, ethoxycarbonyl, propoxycarbonyl, butyoxycarbonyl, tert-butoxycarbonyl, etc.), an alkenyloxycarbonyl group such as a lower alkenyloxycarbonyl group (e.g., vinyloxycarbonyl, allyloxycarbonyl, etc.), an alkenoyl group such as a lower alkenoyl group (e.g., acryloyl, methacryloyl, crotonoyl, etc.), a cycloalkanecarbonyl group such as a cyclo(lower)-alkanecarbonyl group (e.g., cyclopropanecarbonyl, cyclopentanecarbonyl, cyclohexanecarbonyl, etc.), etc.

The aromatic acyl group includes, for example, a $C_{6-10}$ aroyl group (e.g., benzoyl, toluoyl, xyloyl, etc.), an N-($C_{6-10}$) arylcarbamoyl group (e.g., N-phenylcarbamoyl, N-tolylcarbamoyl, N-naphthylcarbamoyl, etc.), a $C_{6-10}$ arenesulfonyl group (e.g., benzenesulfonyl, tosyl, etc.), etc.

The heterocyclic acyl group includes, for example, a heterocyclic carbonyl group, a heterocyclic (lower) alkanoyl group (e.g., heterocyclic acetyl, heterocyclic propanoyl, heterocyclic butanoyl, heterocyclic pentanoyl, heterocyclic hexanoyl, etc.), a heterocyclic (lower) alkenoyl group (e.g., heterocyclic propenoyl, heterocyclic butenoyl, heterocyclic pentenoyl, heterocyclic hexenoyl, etc.), a heterocyclic glyoxyloyl group, a heterocyclic sulfinyl group, a heterocyclic sulfonyl group, etc.

The aromatic group-bonded aliphatic acyl group includes, for example, an aralkoxycarbonyl group such as a phenyl-(lower) alkoxycarbonyl group (e.g., benzyloxycarbonyl, phenethyloxycarbonyl, etc.), etc.

The acyl group may be further substituted by at least one suitable substituent, for example, by a nitro group and the like. As preferred examples of the substituted acyl group, mentioned are a nitroaralkoxycarbonyl group (e.g., nitrobenzyloxycarbonyl, etc.), etc.

Preferred salts of the indole derivatives of the invention are ordinary salts that are not toxic and are acceptable in pharmaceutical use. As their examples, mentioned are salts with bases as well as acid-addition salts, including, for example, salts with inorganic bases such as alkali metal salts with sodium, potassium or the like, alkaline earth metal salts with calcium, magnesium or the like, ammonium salts; organic amine salts with triethylamine, pyridine, picoline, ethanolamine, triethanolamine, dicyclohexylamine, N,N'-dibenzylethyleneamine or the like; inorganic acid salts such as hydrochlorides, hydrobromides, sulfates, phosphates, etc.; organic carboxylates such as formates, acetates, trifluoroacetates, maleates, tartrates, etc.; sulfonic acid-addition salts such as methanesulfonates, benzenesulfonates, p-toluenesulfonates, etc.; salts with basic or acidic amino acids of arginine, aspartic acid, glutamic acid, etc.

The compounds useful in the practice of this invention may have at least one asymmetric center, and therefore they may be in any form of enatiomers or diastereomers. Some alkenyl group-having compounds of the invention may be in any form of cis- or trans-isomers. In any case, the invention shall encompass their mixtures and individual isomers.

The compounds of the invention may be in any form of tautomers. The invention shall encompass their mixtures and individual tautomers.

The compounds and their salts of the invention may be in any form of their solvates, which shall be within the scope of the invention. Preferably, the solvates are hydrates and ethanolates.

Examples of the compounds of the invention are mentioned below. Specific examples of the indole derivatives of formula (III) include 6-(benzensulfonylcarbamoyl)-1-(2-chlorobenzyl)-2-methylindole, 1-(biphenyl-4-ylmethyl)-6-(1-butanesulfonylcarbamoyl)-2-ethylindole, 6-(1-butanesulfonylcarbamoyl)-1-(2,4-dichlorobenzyl)-2-methylindole, 1-(2,4-dichlorobenzyl)-2-methyl-6-(1-pentanesulfonylcarbamoyl)indole, 6-(1-butanesulfonylcarbamoyl)-1-(2,4-dichlorobenzyl)-2-ethylindole, 6-(1-butanesulfonylcarbamoyl)-1-(2,4-dichlorobenzyl)indole, 5-(1-butanesulfonylcarbamoyl)-3-(2,4-dichlorobenzyl)indole, 5-(1-butanesulfonylcarbamoyl)-1-(2,4-dichlorobenzyl)indole, 5-(1-butanesulfonylcarbamoyl)-3-(2,4-dichlorobenzyl)-2-methylindole, 5-butanesulfonylcarbamoyl-3-(2,4-dichlorobenzyl)-1-methylindole, 3-(2,4-dichlorobenzyl)-2-methyl-5-(1-pentansulfonylcarbamoyl)indole, 6-(1-butanesulfonylcarbamoyl)-3-(2,4-dichlorobenzyl)-2-methylindole, 3-(2,4-dichlorobenzyl)-5-(1-pentanesulfonylcarbamoyl)indole, 3-(2,4-dichlorobenzyl)-2-methyl-5-(1-propanesulfonylcarbamoyl)indole, 3-(2,4-dichlorobenzyl)-2-methyl-5-(1-octanesulfonylcarbamoyl)indole, 5-(benzenesulfonylcarbamoyl)-3-(2,4-dichlorobenzyl)-2-methylindole, 3-(2,4-dichlorobenzyl)-5-(1-hexanesulfonylcarbamoyl)-2-methylindole, 3-(biphenyl-4-ylmethyl)-2-methyl-5-(1-pentanesulfonylcarbamoyl)indole, 3-(2-chlorobenzyl)-2-methyl-5-(1-pentanesulfonylcarbamoyl)indole, 5-(1-butanesulfonylcarbamoyl)-3-(2,4-dichlorobenzoyl)-2-methylindole, 3-(2,4-dichlorobenzyl)-2-methyl-5-(3-methyl-1-butanesulfonylcarbamoyl)indole, 3-(2,4-dichlorobenzyl)-5-(2-methoxyethanesulfonylcarbamoyl)-2-methylindole, 3-(4-benzyloxybenzyl)-2-methyl-5-(1-pentanesulfonylcarbamoyl)indole, 3-(2,4-dichlorobenzyl)-5-(1-pentanesulfonylcarbamoyl)-2-propylindole, 3-(2,4-dichlorobenzyl)-2-ethyl-5-(1-pentanesulfonylcarbamoyl)indole, 3-(1-bromonaphthalen-2-ylmethyl)-2-methyl-5-(1-pentanesulfonylcarbamoyl)indole, 3-((3-chloropyridin-4-yl)methyl)-2-methyl-5-(1-pentanesulfonylcarbamoyl)indole, 2-methyl-5-(1-pentanesulfonylcarbamoyl)-3-(4-(2-phenylethenyl)benzyl)indole, 3-(2,4-dichlorobenzyl)-5-(ethanesulfonylcarbamoyl)-2-propylindole, 3-(2,4-dichlorobenzyl)-2-methyl-5-(2-thiophenesulfonylcarbamoyl)indole, 3-(2,4-dichlorobenzyl)-5-((4-methoxybenzene)sulfonylcarbamoyl)-2-methylindole, 5-(benzenesulfonylcarbamoyl)-3-(2,4-dichlorobenzyl)-2-ethylindole, 3-((4-chloroisoquinolin-3-yl)methyl)-2-methyl-5-(1-pentanesulfonylcarbamoyl)indole, 3-((4-bromoisoquinolin-3-yl)methyl)-2-methyl-5-(1-pentanesulfonylcarbamoyl)indole, 3-(2,4-dichlorobenzyl)-2-methyl-5-(1-pent-1-enesulfonylcarbamoyl)indole, 3-(2,4-dichlorobenzyl)-2-methyl-5-(trifluoromethanesulfonylcarbamoyl)indole, 3-(2,4-dichlorobenzyl)-5-(2,2-dimethylpropanesulfonylcarbamoyl)-2-methylindole, 3-(2,4-dichlorobenzyl)-2-methyl-5-(8-quinolinesulfonylcarbamoyl)indole, 3-(2,4-dichlorobenzyl)-2-methyl-5-((2-phenylethane)sulfonylcarbamoyl)indole, 3-(2,4-dichlorobenzyl)-2-methyl-5-(-toluenesulfonylcarbamoyl)indole, 5-cyclohexanesulfonylcarbamoyl-3-(2,4-dichlorobenzyl)-2-methylindole, 5-(3-chloro-1-propanesulfonylcarbamoyl)-3-(2,4-dichlorobenzyl)-2-methylindole, 3-(2,4-dichlorobenzyl)-2-methyl-5-(propanesultam-1-ylcarbonyl)indole, 6-(1-butanesulfonylcarbamoyl)-2-(2,4-dichlorobenzyl)-3-methylindole, 1-(2,4-dichlorobenzyl)-2-methyl-6-(1-pentanesulfonylcarbamoyl)indole, 3-(2,4-dichlorobenzyl)-2-methyl-5-((4-methylbenzene)sulfonylcarbamoyl)indole, 3-(2,4-dichlorobenzyl)-2-methyl-5-((4-nitrobenzene)sulfonylcarbamoyl)indole, 5-((4-chlorobenzene)sulfonylcarbamoyl)-3-(2,4-dichlorobenzyl)-2-methylindole, 5-((3-chlorobenzene)sulfonylcarbamoyl)-3-(2,4-dichlorobenzyl)-2-methylindole, 5-((2-chlorobenzene)sulfonylcarbamoyl)-3-(2,4-dichlorobenzyl)-2-methylindole, 3-(2,4-dichlorobenzyl)-5-((4-fluorobenzene)sulfonylcarbamoyl)-2-methylindole, 3-(2,4-dichlorobenzyl)-2-methyl-5-((2-naphthalene)sulfonylcarbamoyl)indole, 3-(2,4-dichlorobenzyl)-2-methyl-5-((1-naphthalene)sulfonylcarbamoyl)indole, 3-(2,4-dichlorobenzyl)-2-methyl-5-((2-methylbenzene)sulfonylcarbamoyl)indole, 3-(2,4-dichlorobenzyl)-5-(2,6-dimethylbenzene)sulfonylcarbamoyl-2-methylindole, 5-(4-bromobenzene)sulfonylcarbamoyl-3-(2,4-dichlorobenzyl)-2-methylindole, 3-(2,4-dichlorobenzyl)-2-methyl-5-((E)-styrenesulfonylcarbamoyl)indole, 3-(2,4-dichlorobenzyl)-2-methyl-5-((4-vinylbenzene)sulfonylcarbamoyl)indole, 5-((4-phenylazobenzene)sulfonylcarbamoyl)-3-(2,4-dichlorobenzyl)-2-methylindole, 3-(2,4-dichlorobenzyl)-2-methyl-5-((4-trifluoromethylbenzene)sulfonylcarbamoyl)indole, 3-(2,4-dichlorobenzyl)-2-methyl-5-((4-methyl-1-pent-1-ene)sulfonylcarbamoyl)indole, 3-(2,4-dichlorobenzyl)-5-((3,4-dimethoxybenzene)sulfonylcarbamoyl)-2-methylindole, 5-((4-t-butylbenzene)sulfonylcarbamoyl)-3-(2,4-dichlorobenzyl)-2-methylindole, 3-(2,4-dichlorobenzyl)-2-methyl-5-((3-methylbenzene)sulfonylcarbamoyl)indole, 3-(2,4-dichlorobenzyl)-2-methyl-5-(2-octanesulfonylcarbamoyl)indole, 3-(2,4-dichlorobenzyl)-2-methyl-5-((4-phenylbenzene)sulfonylcarbamoyl)indole, 3-((2-chloro-4-phenyl)benzyl)-2-methyl-5-((1-pent-1-ene)sulfonylcarbamoyl)indole, 3-(2-chloro-4-phenylbenzyl)-2-methyl-5-(1-pentanesulfonylcarbamoyl)indole, 5-(benzenesulfonylcarbamoyl)-3-((2-chloro-4-phenyl)benzyl)-2-methylindole, 3-(2,4-dichlorobenzyl)-5-((4-ethylbenzene)sulfonylcarbamoyl)-2-methylindole, 5-((4-n-butylbenzene)sulfonylcarbamoyl)-3-(2,4-dichlorobenzyl)-2-methylindole, 5-((4-n-butoxybenzene)sulfonylcarbamoyl)-3-(2,4-dichlorobenzyl)-2-methylindole, 3-(2,4-dichlorobenzyl)-2-methylthio-5-((1-pent-1-ene)sulfonylcarbamoyl)indole, 5-(benzenesulfonylcarbamoyl)-3-(2,4-dichlorobenzyl)-2-methylthioindole, 3-(2,4-dichlorobenzyl)-2-methylthio-5-(1-pentanesulfonylcarbamoyl)indole, 3-(2,4-dichlorobenzyl)-2-methyl-5-((1-penta-1,3-diene)sulfonylcarbamoyl)indole, 5-((2-cyclopropylethylene)sulfonylcarbamoyl)-3-(2,4-dichlorobenzyl)-2-methylindole, 3-(2,4-dichlorobenzyl)-2-methyl-5-((4-methyl-(E)-styrene)sulfonylcarbamoyl)indole, 3-(2,4-dichlorobenzyl)-5-((4-methoxy-(E)-styrene)sulfonylcarbamoyl)-2-methylindole, 3-(2,4-dichlorobenzyl)-2-methoxymethyl-5-(1-pentanesulfonylcarbamoyl)indole, 3-((1-bromonaphthalen-2-yl)methyl)-2-methyl-5-((E)-styrene)sulfonylcarbamoyl)indole, 3-((1-bromonaphthalen-2-yl )methyl)-2-methyl-5-(4-vinylbenzene)sulfonylcarbamoyl)indole, 3-((1-bromonaphthalen-2-yl)methyl)-2-methyl-5-(p-toluenesulfonylcarbamoyl)indole, 5-(benzenesulfonylcarbamoyl)-3-((1-bromonaphthalen-2-yl)methyl)-2-methylindole, 3-((2-chloro-4-phenyl)benzyl)-2-methyl-5-((E)-styrenesulfonylcarbamoyl)indole, 3-((2-chloro-4-phenyl)benzyl)-2-methyl-5-((4-vinylbenzene)sulfonylcarbamoyl)indole, 3-((1-bromonaphthalen-2-yl)methyl)-2-methyl-5-((1-pent-1-ene)sulfonylcarbamoyl)indole, 3-((2-chloro-4-phenyl)benzyl)-2-methyl-5-(p-toluenesulfonylcarbamoyl)indole, 3-(4-bromo-2-chlorobenzyl)-2-methyl-5-(1-pentanesulfonylcarbamoyl)indole, 3-(4-bromo-2-chlorobenzyl)-2-methyl-5-(2-(5-chlorothienyl)sulfonylcarbamoyl)indole, 3-(2-chloro-4-nitrobenzyl)-2-methyl-5-(1-pentanesulfonylcarbamoyl)indole, 3-(2-chloro-4-(2-phenylethenyl)benzyl)-2-methyl-5-(1-pentanesulfonylcarbamoyl)indole, etc.

Specific examples of the indole derivatives of formula (V) include 1-(2-chlorobenzyl)-6-methoxycarbonyl-2-methylindole, 6-carboxy-1-(2-chlorobenzyl)-2-methylindole, 1-(biphenyl-4-ylmethyl)-2-ethyl-6-methoxycarbonylindole, 1-(biphenyl-4-ylmethyl)-6-carboxy-2-ethylindole, 1-(2,4-dichlorobenzyl)-6-methoxycarbonyl-2-methylindole, 6-carboxy-1-(2,4-dichlorobenzyl)-2-methylindole, 1-(2,4-dichlorobenzyl)-2-ethyl-6-methoxycarbonylindole, 6-carboxy-1-(2,4-dichlorobenzyl)-2-ethylindole, 1-(2,4-dichlorobenzyl)-6-methoxycarbonylindole, 6-carboxy-1-(2,4-dichlorobenzyl)indole, 3-(2,4-dichlorobenzyl)-5-methoxycarbonylindole, 5-carboxy-3-(2,4-dichlorobenzyl)indole, 1-(2,4-dichlorobenzyl)-5-methoxycarbonylindole, 5-carboxy-1-(2,4-dichlorobenzyl)indole, 3-(2,4-dichlorobenzyl)-5-methoxycarbonyl-2-methylindole, 5-carboxy-3-(2,4-dichlorobenzyl)-2-methylindole, 3-(2,4-dichlorobenzyl)-5-methoxycarbonyl-1-methylindole, 5-carboxy-3-(2,4-dichlorobenzyl)-1-methylindole, 3-(2,4-dichlorobenzyl)-6-(methoxycarbonyl)-2-methylindole, 3-(biphenyl-3-ylmethyl)-5-(methoxycarbonyl)-2-methylindole, 3-(2-chlorobenzyl)-5-(methoxycarbonyl)-2-methylindole, 3-(2,4-dichlorobenzoyl)-5-(methoxycarbonyl)-2-methylindole, 3-(4-benzyloxybenzyl)-5-(methoxycarbonyl)-2-methylindole, 3-(2,4-dichlorobenzyl)-5-(methoxycarbonyl)-2-propylindole, 3-(2,4-dichlorobenzyl)-2-ethyl-5-(methoxycarbonyl)indole, 3-(2,4-dichlorobenzyl)-5-(methoxycarbonyl)indole, 3-(1-bromonaphthalen-2-ylmethyl)-5-(methoxycarbonyl)-2-methylindole, 3-((3-chloropyridin-4-yl)methyl)-5-(methoxycarbonyl)-2-methylindole, 5-(methoxycarbonyl)-2-methyl-3-(4-(2-phenylethenyl)benzyl)indole, 3-((4-chloroisoquinolin-3-yl)methyl)-5-(methoxycarbonyl)-2-methylindole, 3-((4-bromoisoquinolin-3-yl)methyl)-5-(methoxycarbonyl)-2-methylindole, 2-(2,4-dichlorobenzoyl)-6-(methoxycarbonyl)-3-methylindole, 1-(2,4-dichlorobenzyl)-6-(methoxycarbonyl)-3-methylindole, 6-carboxy-3-(2,4-dichlorobenzyl)-2-methylindole, 3-(biphenyl-4-ylmethyl)-5-carboxy-2-methylindole, 5-carboxy-3-(2-chlorobenzyl)-2-methylindole, 5-carboxy-3-(2,4-dichlorobenzoyl)-2-methylindole, 3-(4-benzyloxybenzyl)-5-carboxy-2-methylindole, 5-carboxy-3-(2,4-dichlorobenzyl)-2-propylindole, 5-carboxy-3-(2,4-dichlorobenzyl)-2-ethylindole, 5-carboxy-3-(2,4-dichlorobenzyl)indole, 3-(1-bromonaphthalen-2-ylmethyl)-5-carboxy-2-methylindole, 5-carboxy-3-((3-chloropyridin-4-yl)methyl)-2-methylindole, 5-carboxy-2-methyl-3-(4-(2-phenylethenyl)benzyl)indole, 5-carboxy-3-((4-chloroisoquinolin-3-yl)methyl)-2-methylindole, 3-((4-bromoisoquinolin-3-yl)methyl)-5-carboxy-2-methylindole, 6-carboxy-2-(2,4-dichlorobenzyl)-3-methylindole, 6-carboxy-1-(2,4-dichlorobenzyl)-3-methylindole, 3-(2-chloro-4-phenylbenzyl)-5-methoxycarbonyl-2-methylindole, 5-carboxy-3-(2-chloro-4-phenylbenzyl)-2-methylindole, 3-(2,4-dichlorobenzyl)-5-methoxycarbonyl-2-methylthioindole, 5-carboxy-3-(2,4-dichlorobenzyl)-2-methylthioindole, 3-(2,4-dichlorobenzyl)-5-methoxycarbonyl-2-(methoxymethyl)indole, 5-carboxy-3-(2,4-dichlorobenzyl)-2-(methoxymethyl)indole, etc.

Figure 1:
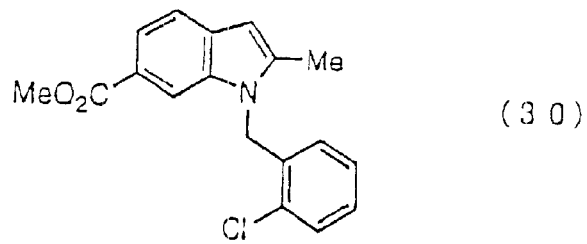
FIG. 1 shows the chemical formulae of compounds (30) to (34).
Figure 1:
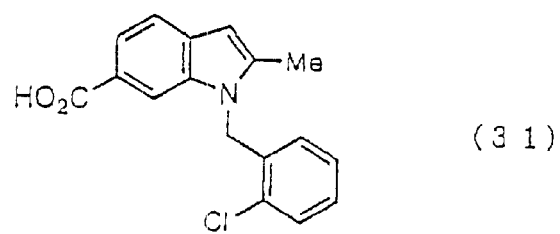
Figure 1:
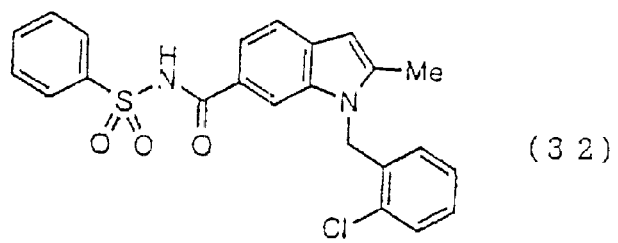
Figure 1:
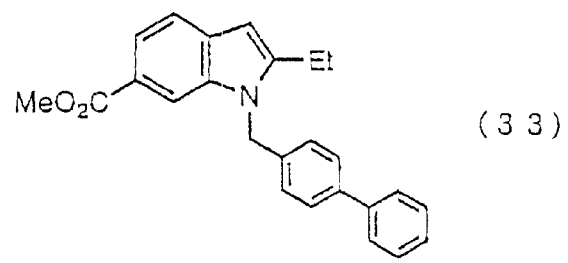
Figure 1:
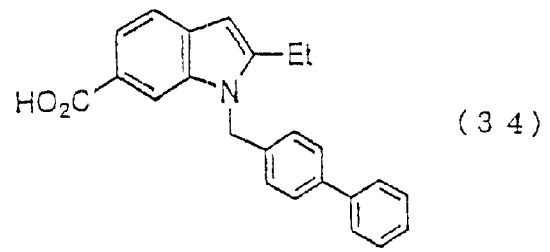
Figure 2:
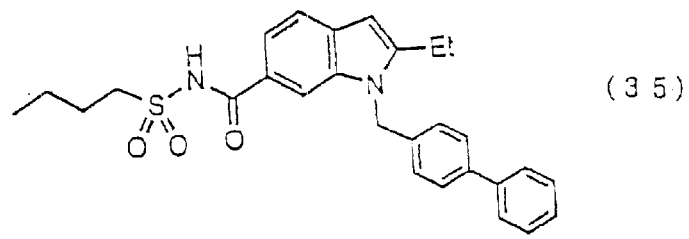
FIG. 2 shows the chemical formulae of compounds (35) to (39).
Figure 2:
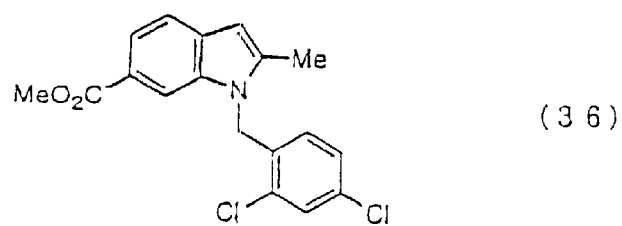
Figure 2:
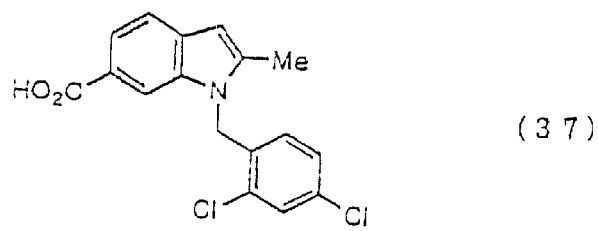
Figure 2:
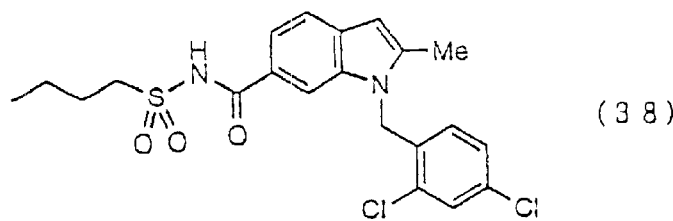
Figure 2:
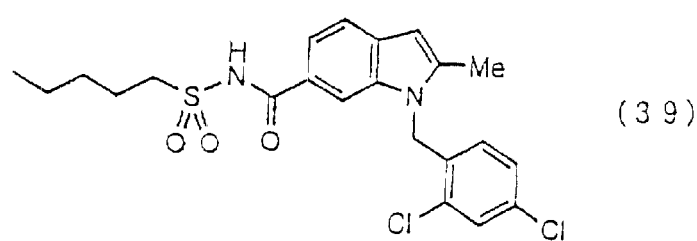
Figure 3:
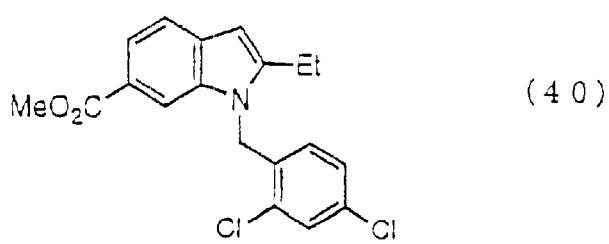
FIG. 3 shows the chemical formulae of compounds (40) to (44).
Figure 3:
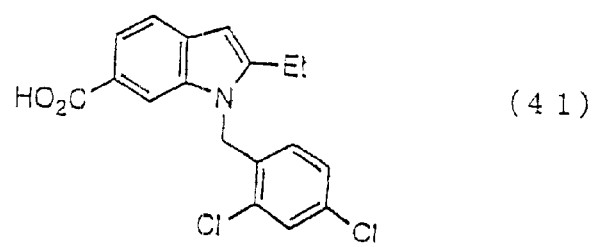
Figure 3:
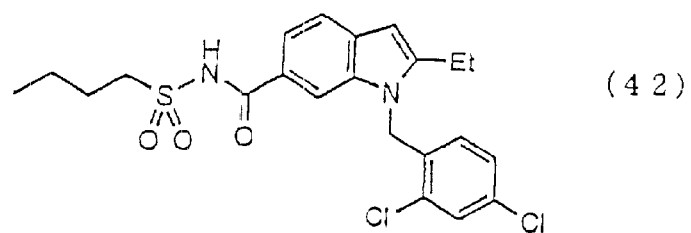
Figure 3:
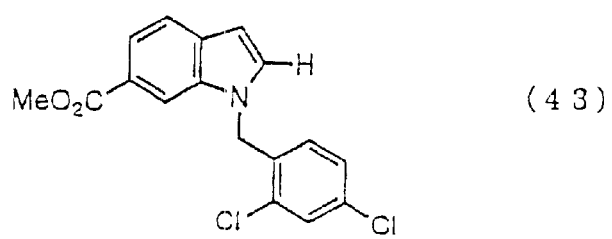
Figure 3:
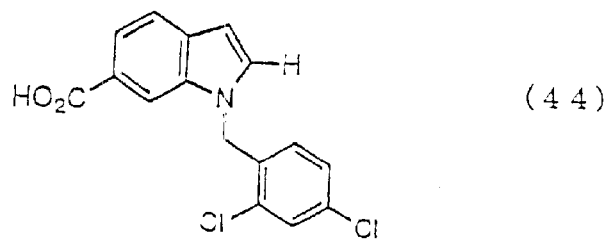
Figure 4:
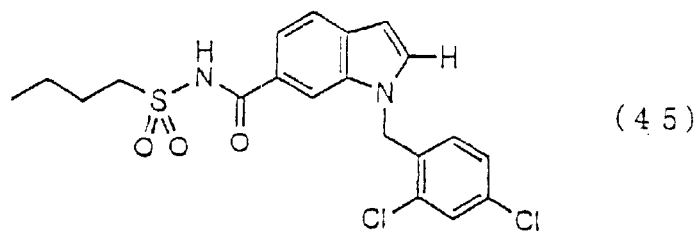
FIG. 4 shows the chemical formulae of compounds (45) to (49).
Figure 4:
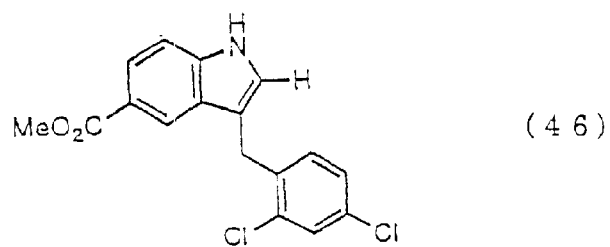
Figure 4:
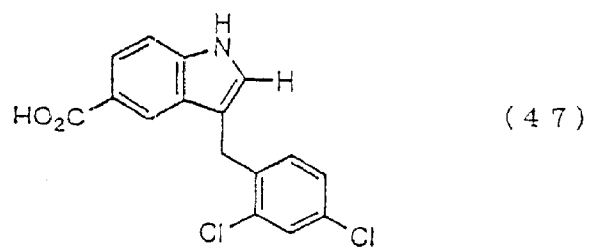
Figure 4:
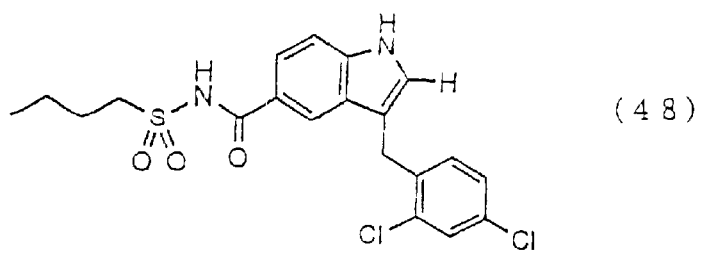
Figure 4:
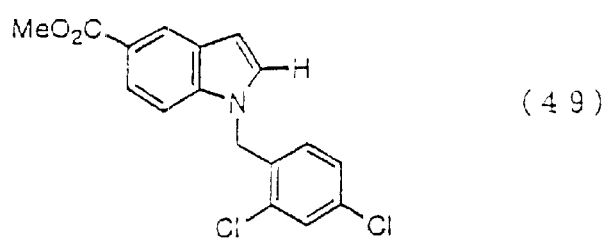
Figure 5:
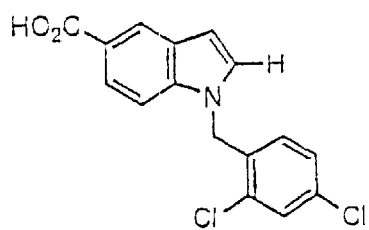
FIG. 5 shows the chemical formulae of compounds (50) to (54).
Figure 5:
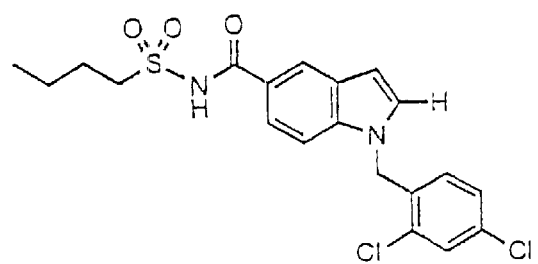
Figure 5:
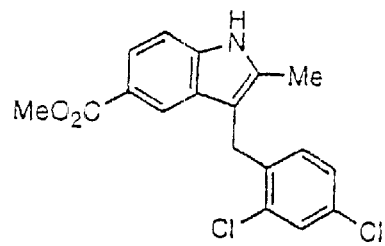
Figure 5:
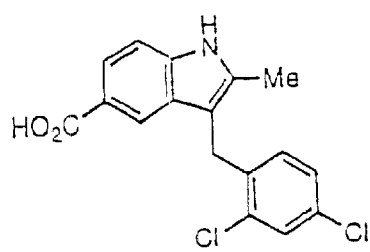
Figure 5:
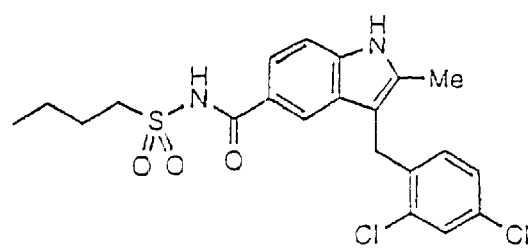
Figure 6:
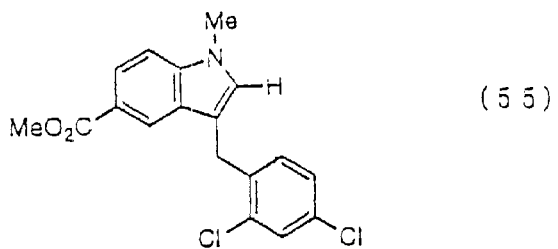
FIG. 6 shows the chemical formulae of compounds (55) to (59).
Figure 6:
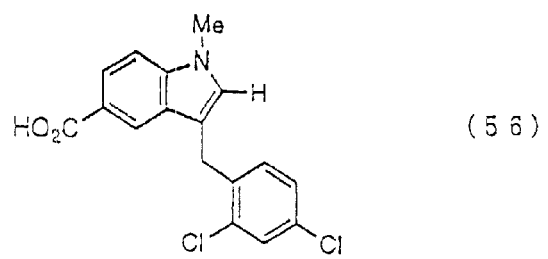
Figure 6:
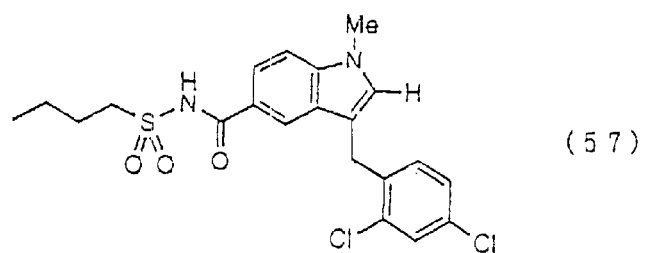
Figure 6:
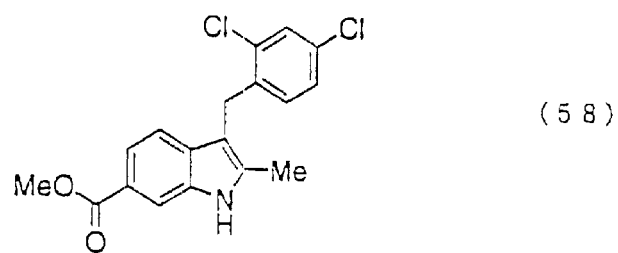
Figure 6:
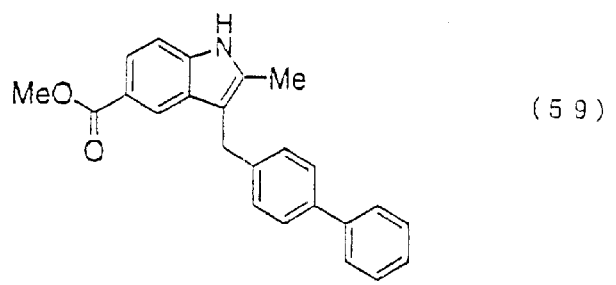
Figure 7:
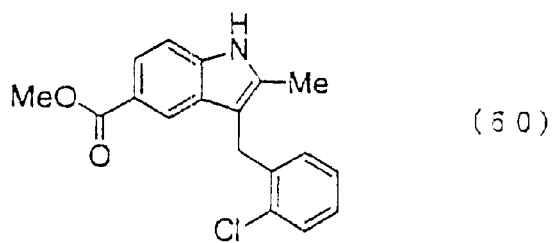
FIG. 7 shows the chemical formulae of compounds (60) to (64).
Figure 7:
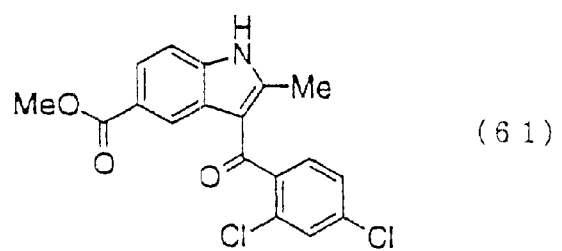
Figure 7:
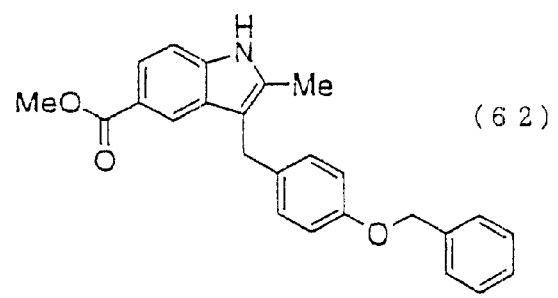
Figure 7:
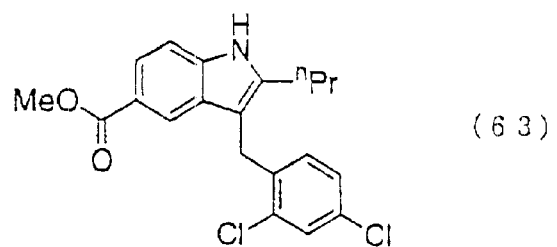
Figure 7:
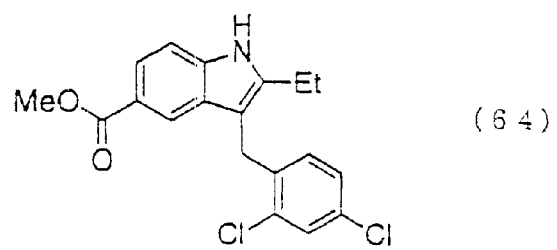
Figure 8:
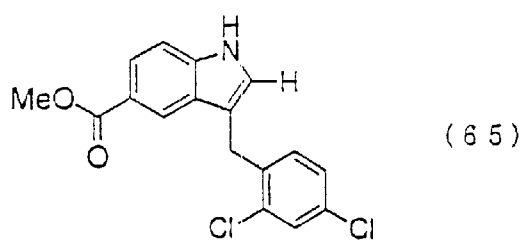
FIG. 8 shows the chemical formulae of compounds (65) to (69).
Figure 8:
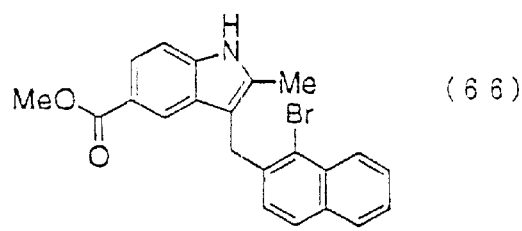
Figure 8:
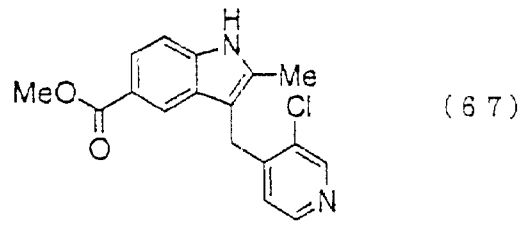
Figure 8:
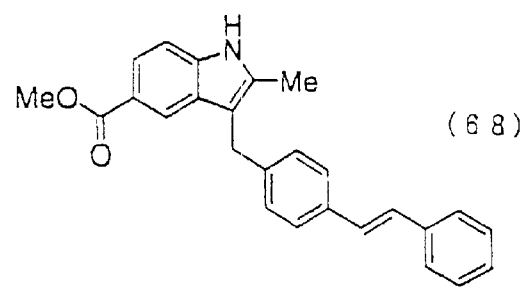
Figure 8:
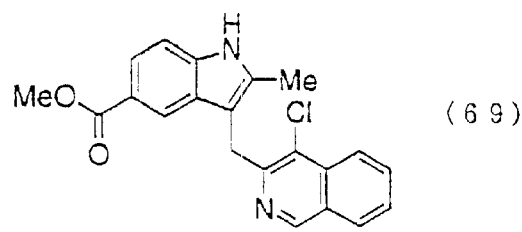
Figure 9:
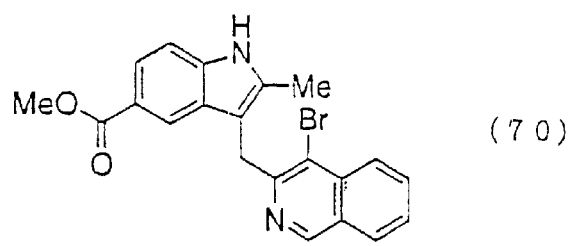
FIG. 9 shows the chemical formulae of compounds (70) to (74).
Figure 9:
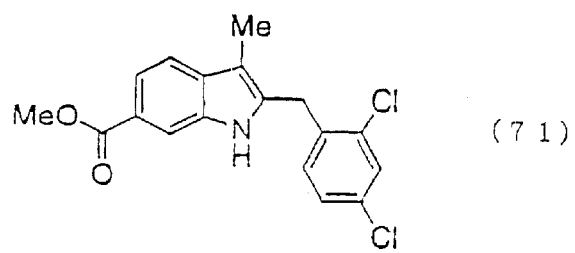
Figure 9:
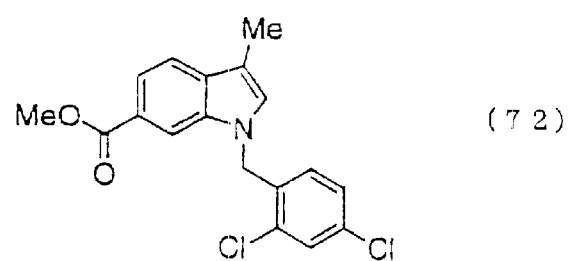
Figure 9:
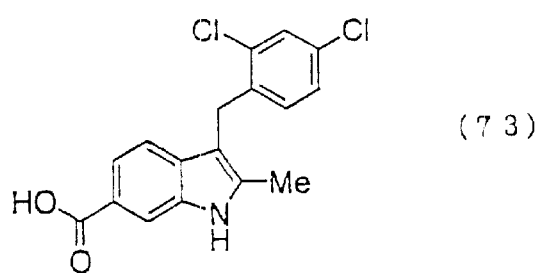
Figure 9:
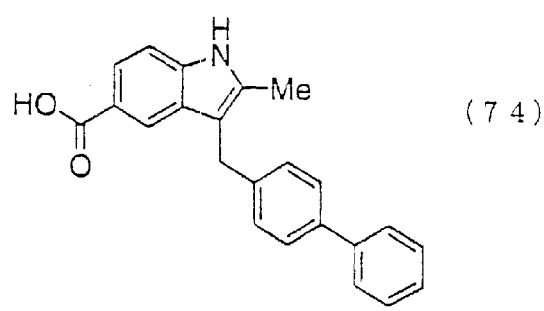
Figure 10:
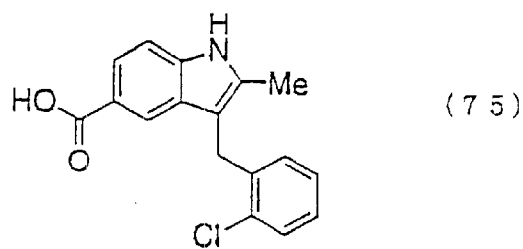
FIG. 10 shows the chemical formulae of compounds (75) to (79).
Figure 10:
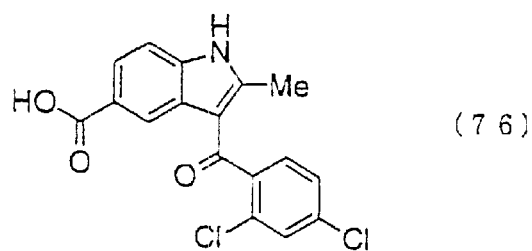
Figure 10:
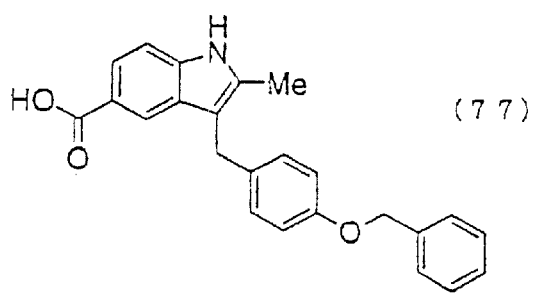
Figure 10:
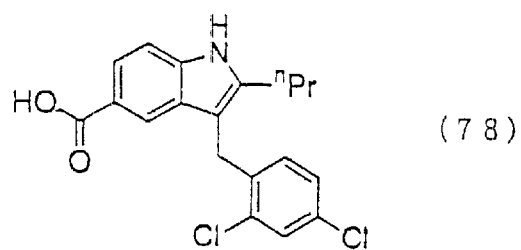
Figure 10:
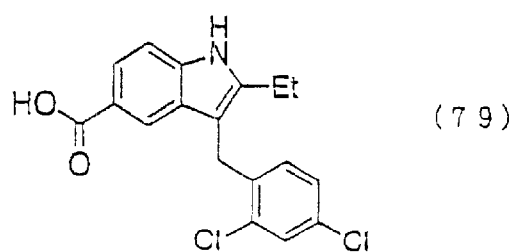
Figure 11:
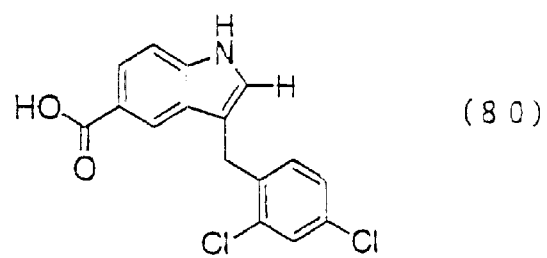
FIG. 11 shows the chemical formulae of compounds (80) to (84).
Figure 11:
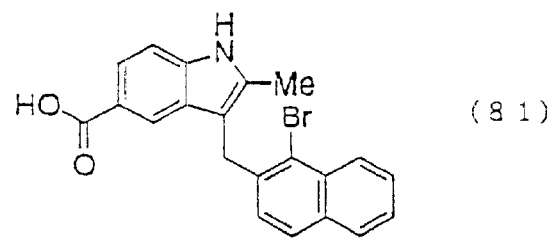
Figure 11:
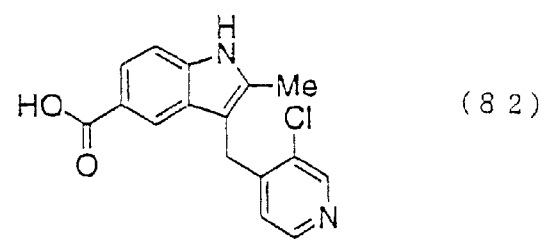
Figure 11:
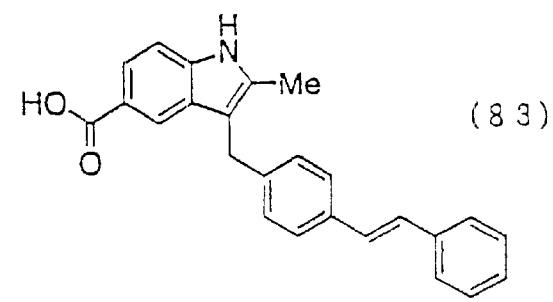
Figure 11:
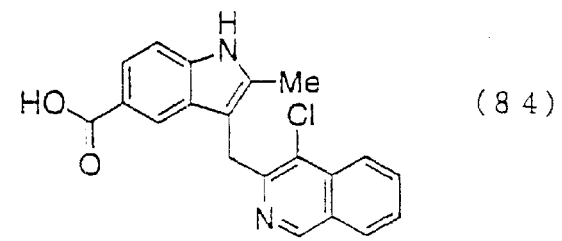
Figure 12:
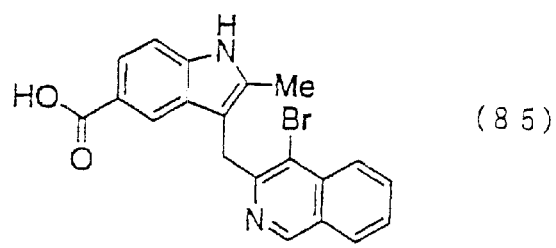
FIG. 12 shows the chemical formulae of compounds (85) to (89).
Figure 12:
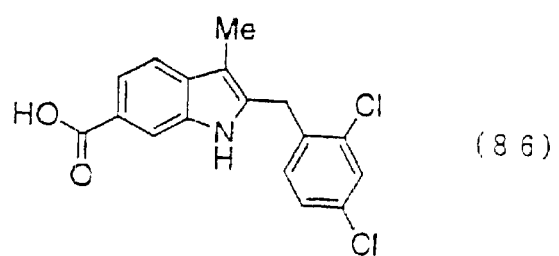
Figure 12:
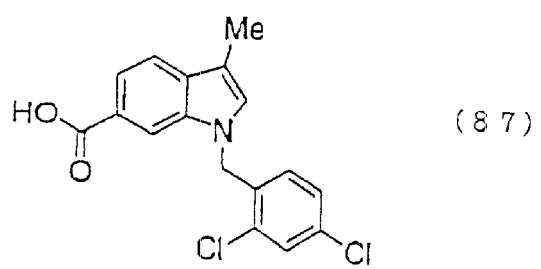
Figure 12:
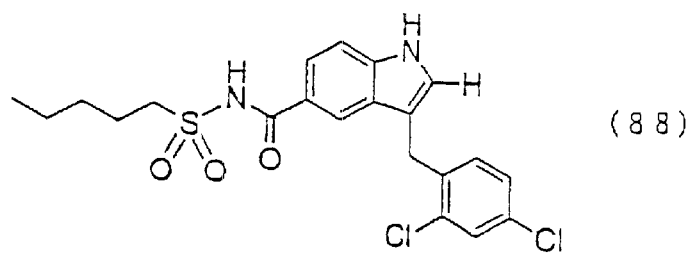
Figure 12:
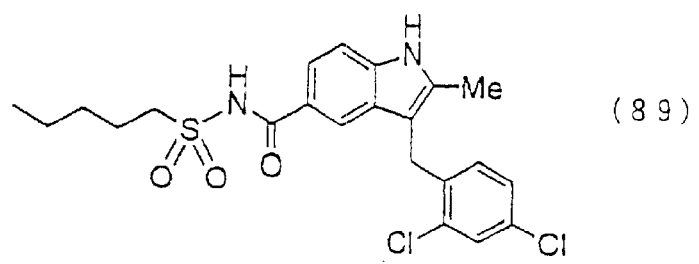
Figure 13:
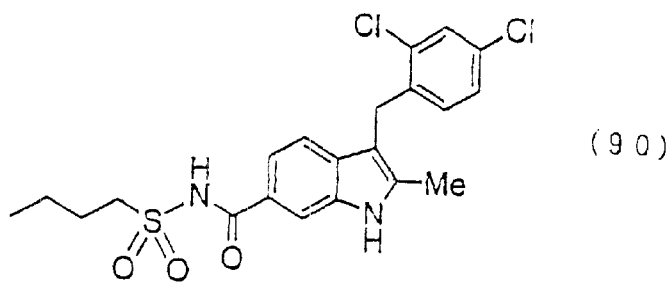
FIG. 13 shows the chemical formulae of compounds (90) to (94).
Figure 13:
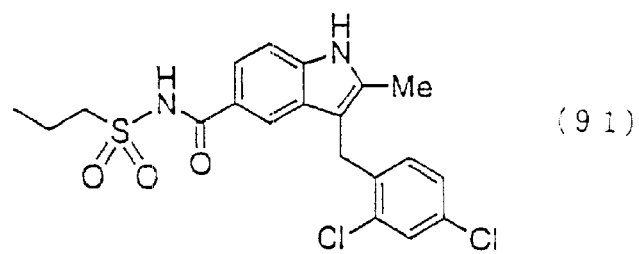
Figure 13:
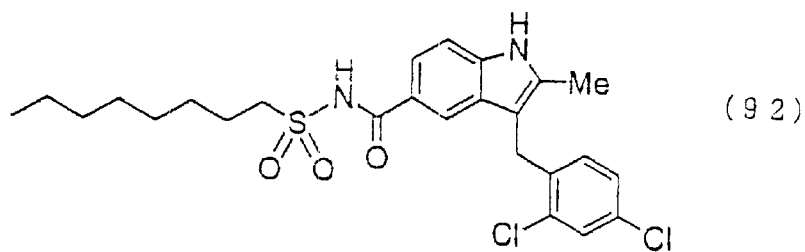
Figure 13:
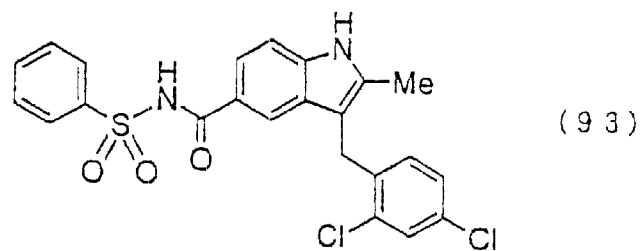
Figure 13:
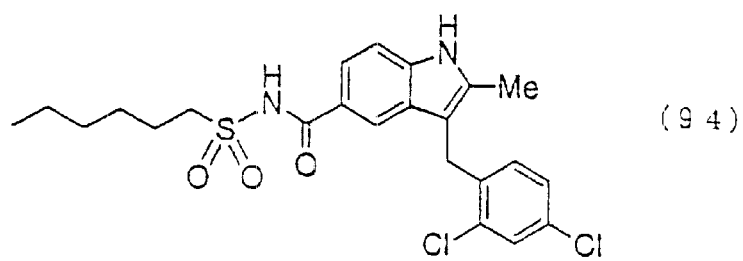
Figure 14:
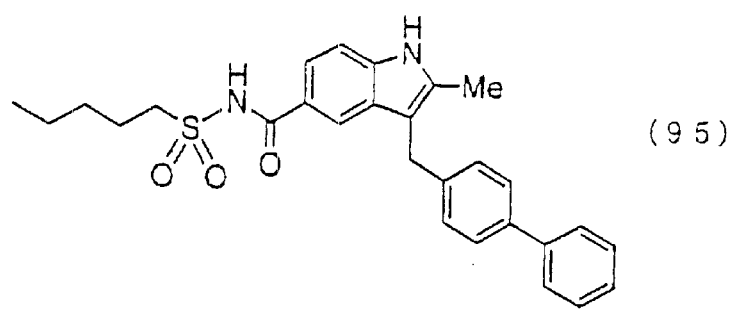
FIG. 14 shows the chemical formulae of compounds (95) to (99).
Figure 14:
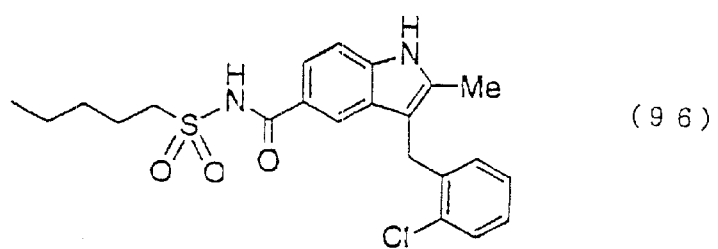
Figure 14:
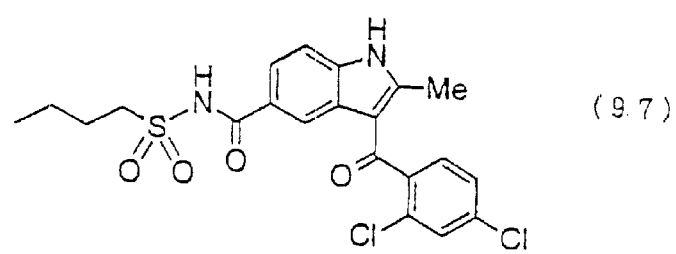
Figure 14:
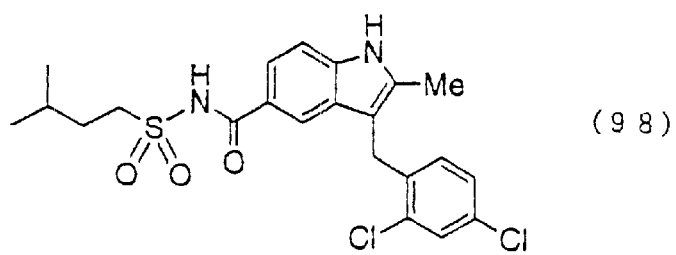
Figure 14:
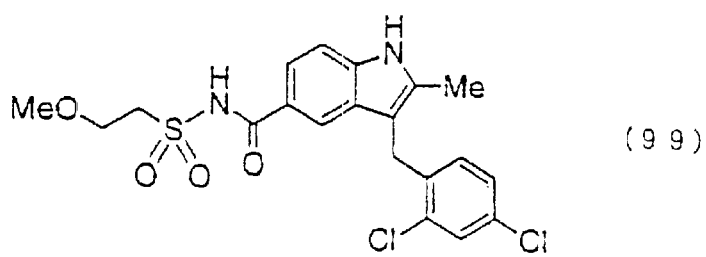
Figure 15:
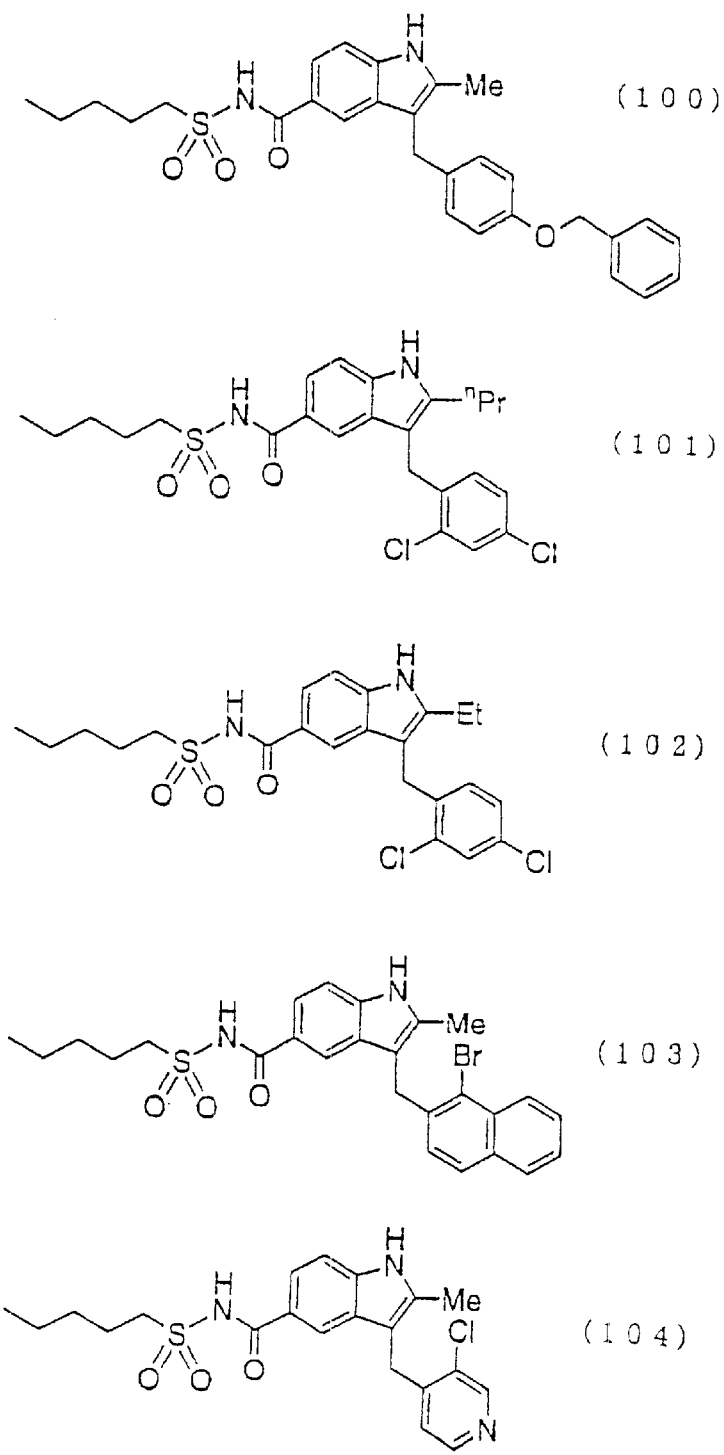
FIG. 15 shows the chemical formulae of compounds (100) to (104).
Figure 16:
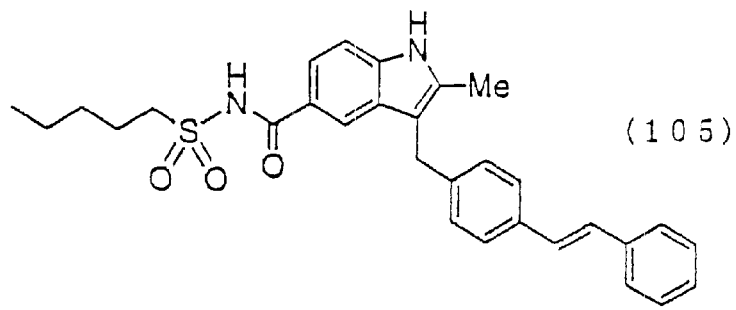
FIG. 16 shows the chemical formulae of compounds (105) to (109).
Figure 16:
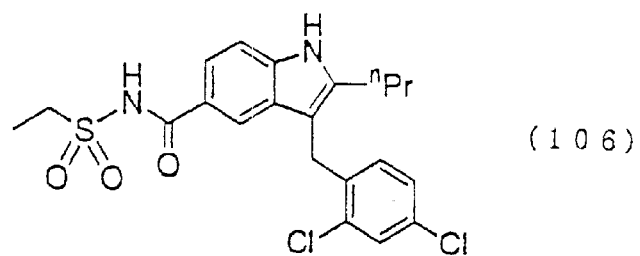
Figure 16:
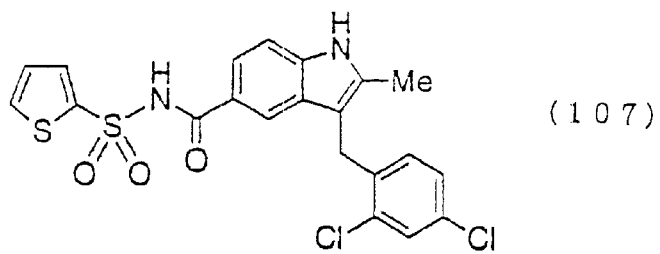
Figure 16:
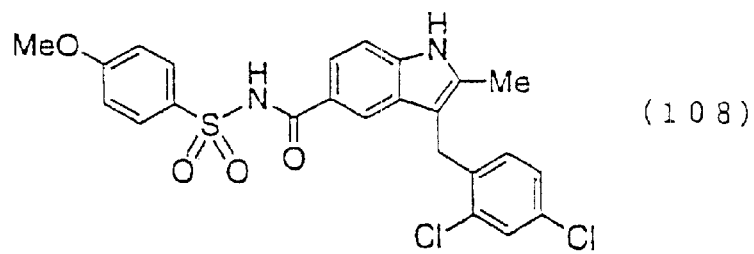
Figure 16:
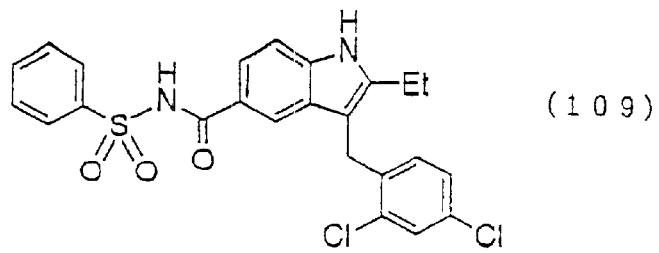
Figure 17:
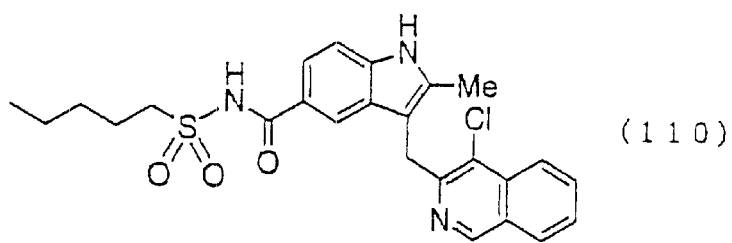
FIG. 17 shows the chemical formulae of compounds (110) to (114).
Figure 17:
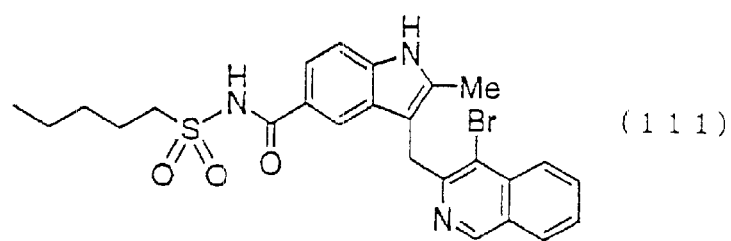
Figure 17:
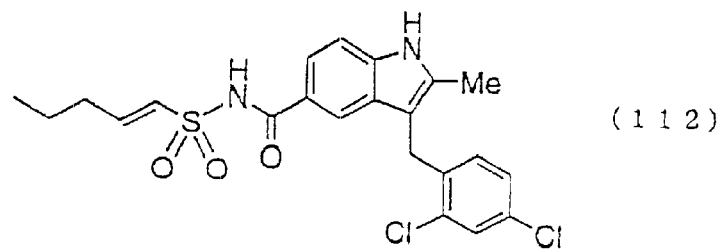
Figure 17:
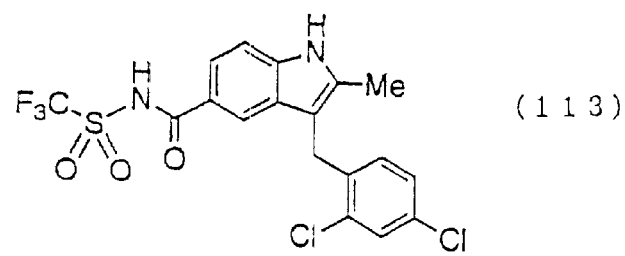
Figure 17:
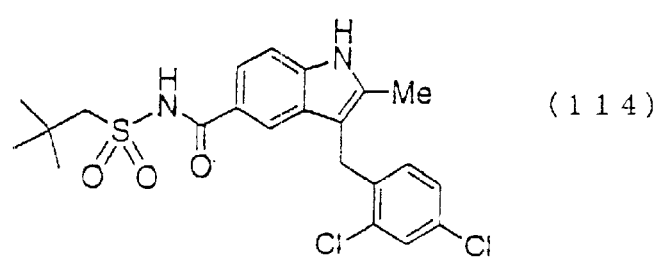
Figure 18:
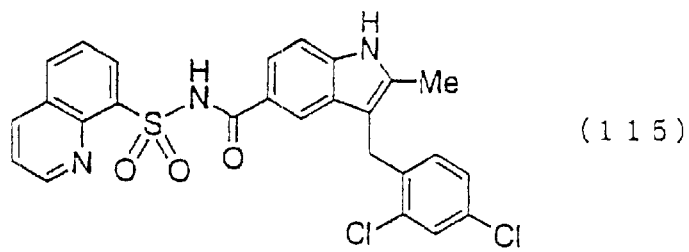
FIG. 18 shows the chemical formulae of compounds (115) to (119).
Figure 18:
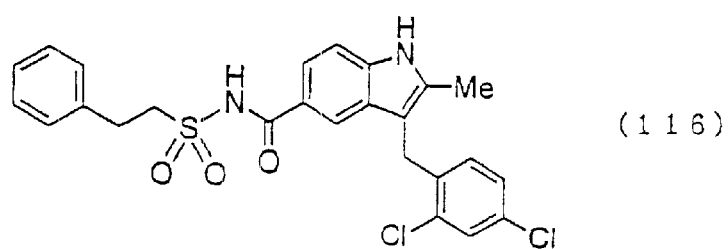
Figure 18:
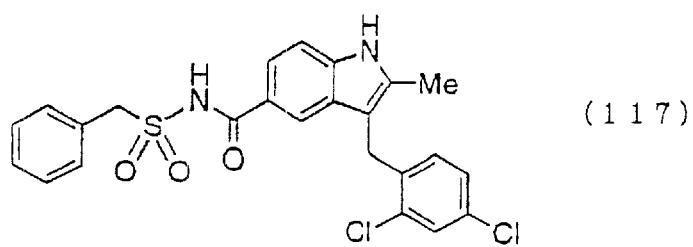
Figure 18:
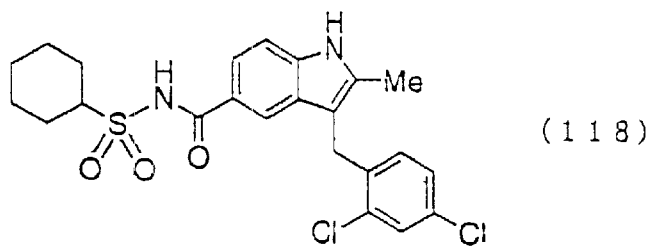
Figure 18:
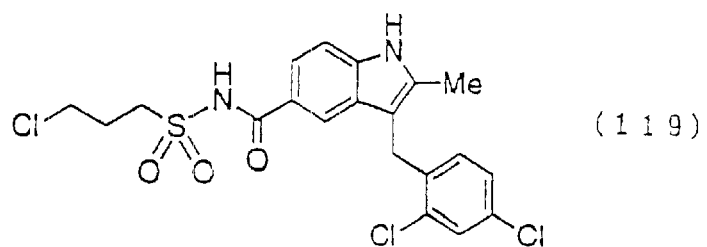
Figure 19:
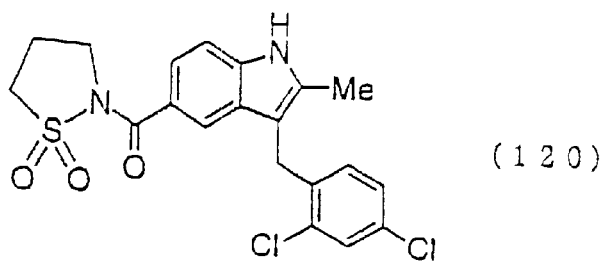
FIG. 19 shows the chemical formulae of compounds (120) to (124).
Figure 19:
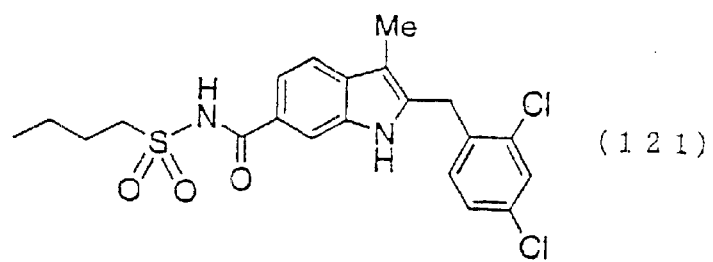
Figure 19:
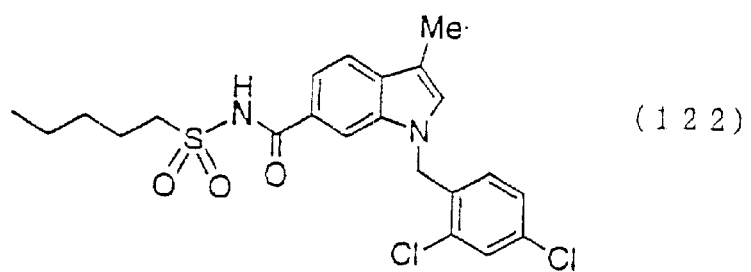
Figure 19:
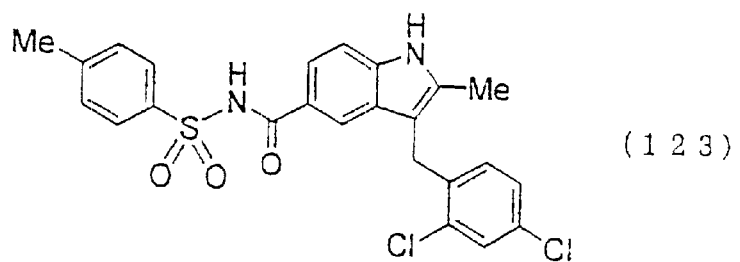
Figure 19:
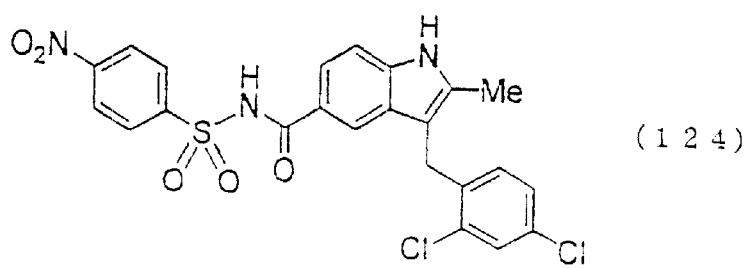
Figure 20:
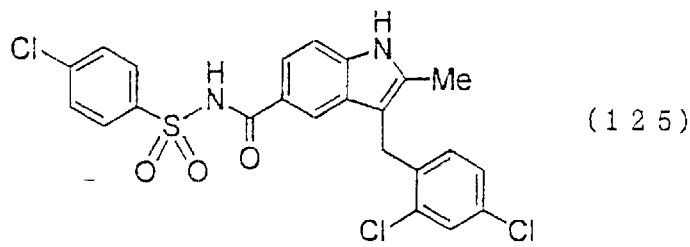
FIG. 20 shows the chemical formulae of compounds (125) to (129).
Figure 20:
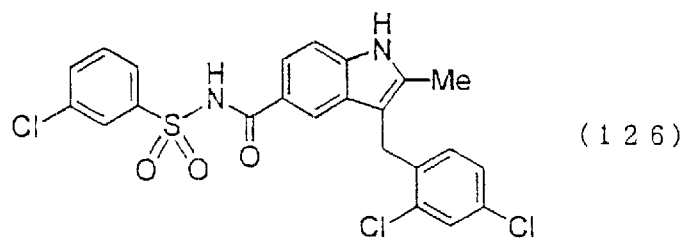
Figure 20:
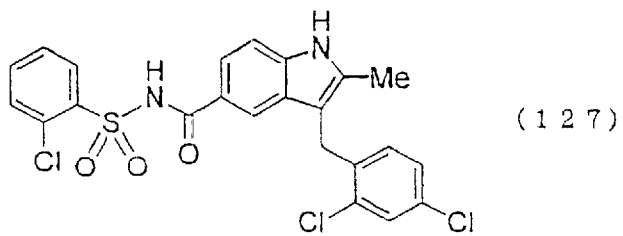
Figure 20:
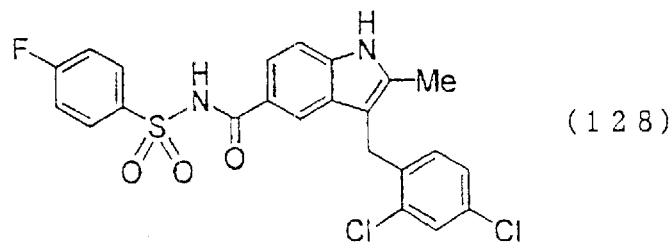
Figure 20:
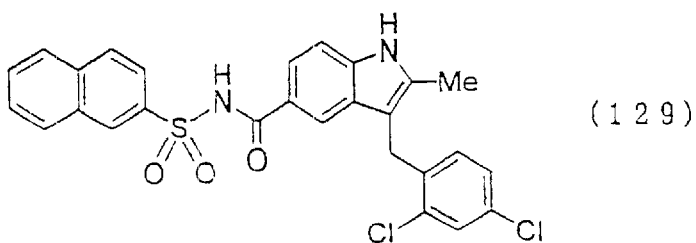
Figure 21:
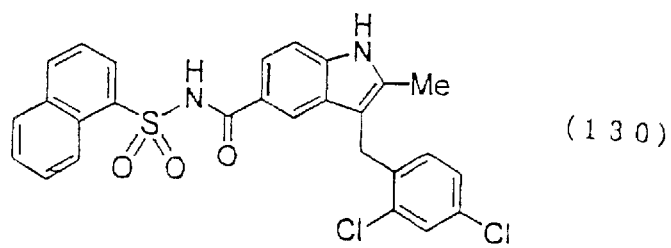
FIG. 21 shows the chemical formulae of compounds (130) to (134).
Figure 21:
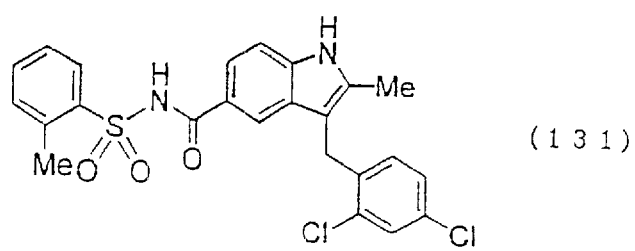
Figure 21:
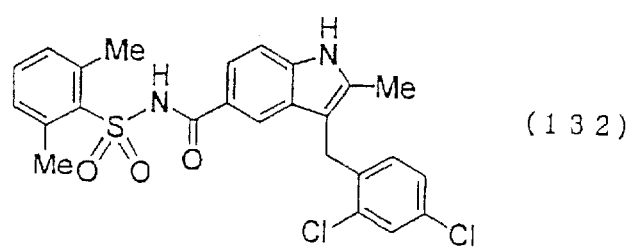
Figure 21:
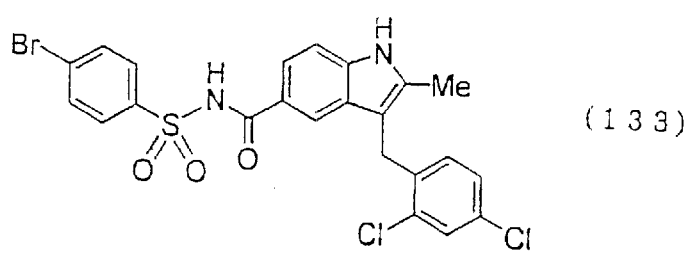
Figure 21:
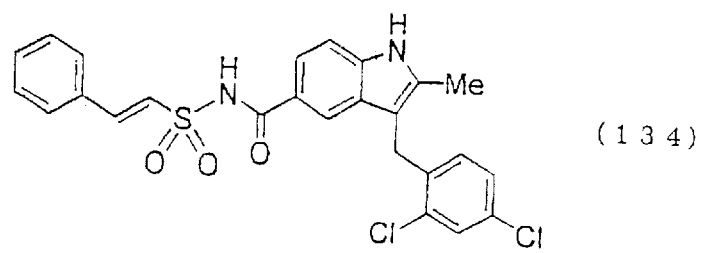
Figure 22:
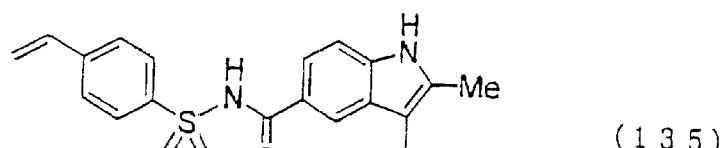
FIG. 22 shows the chemical formulae of compounds (135) to (139).
Figure 22:
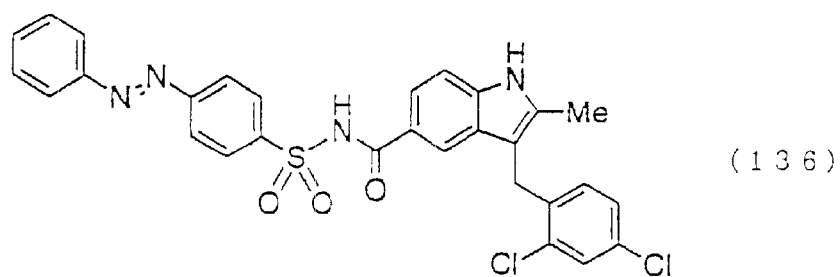
Figure 22:
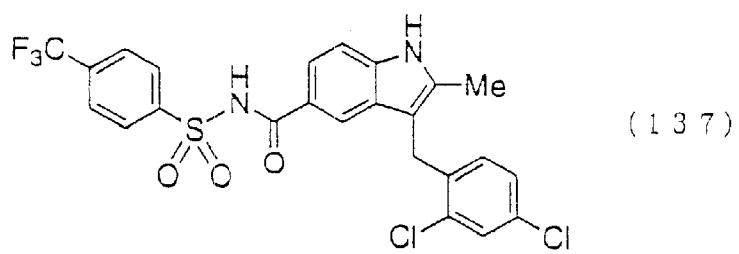
Figure 22:
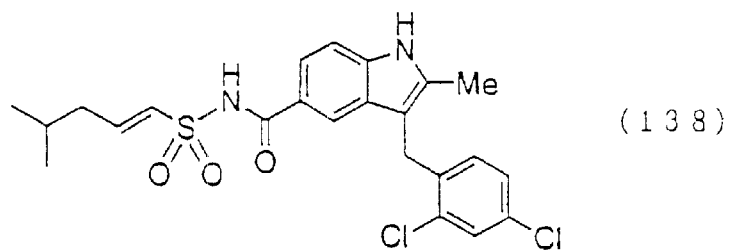
Figure 22:
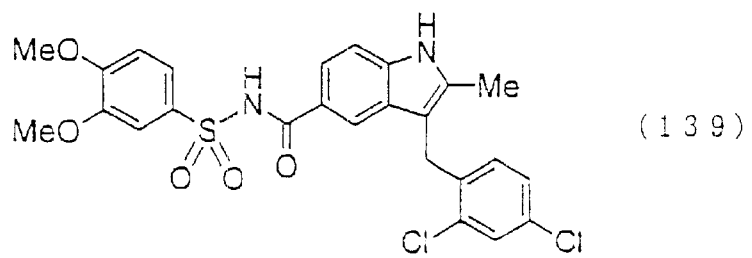
Figure 23:
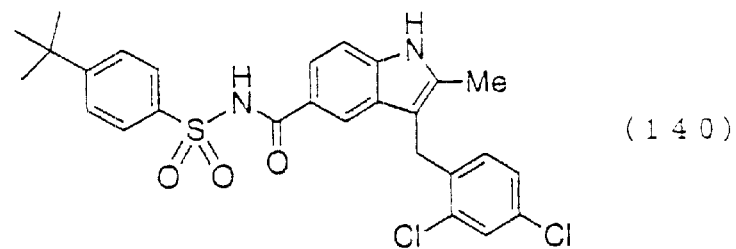
FIG. 23 shows the chemical formulae of compounds (140) to (144).
Figure 23:
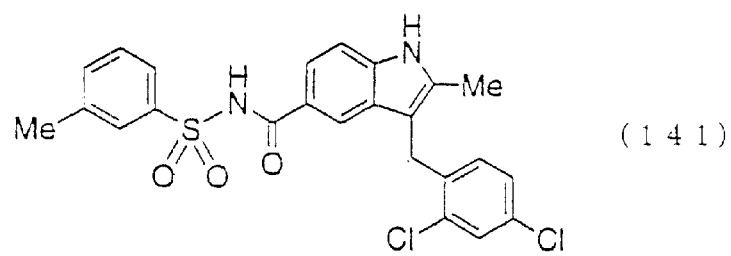
Figure 23:
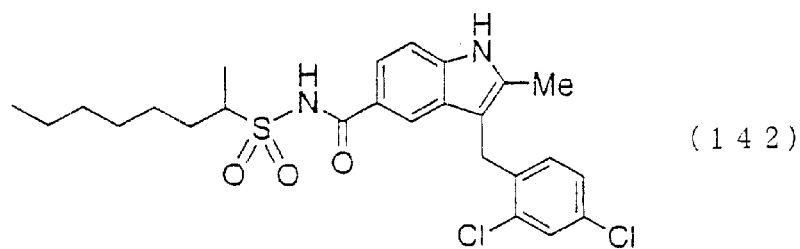
Figure 23:
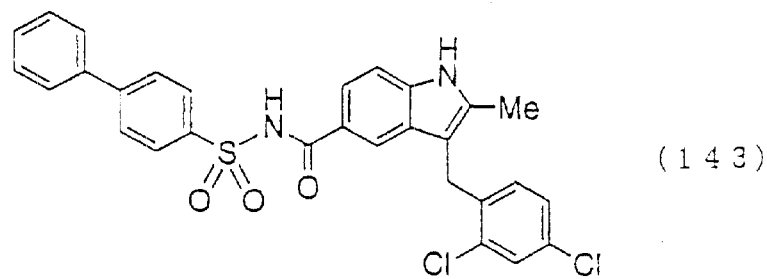
Figure 23:
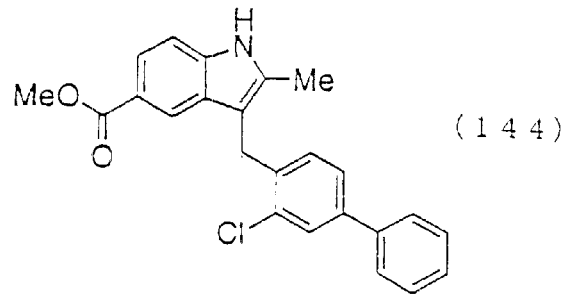
Figure 24:
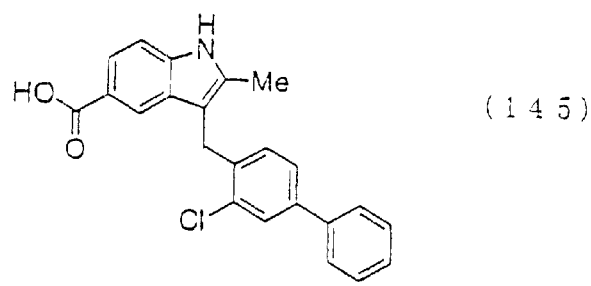
FIG. 24 shows the chemical formulae of compounds (145) to (149).
Figure 24:
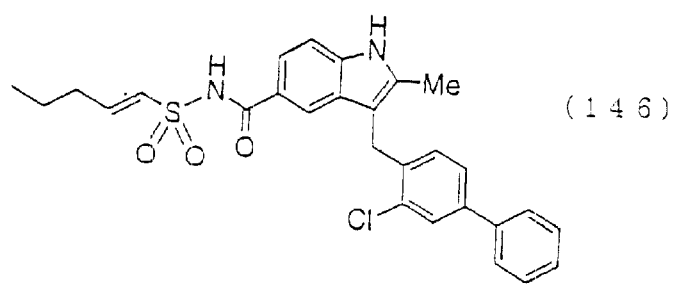
Figure 24:
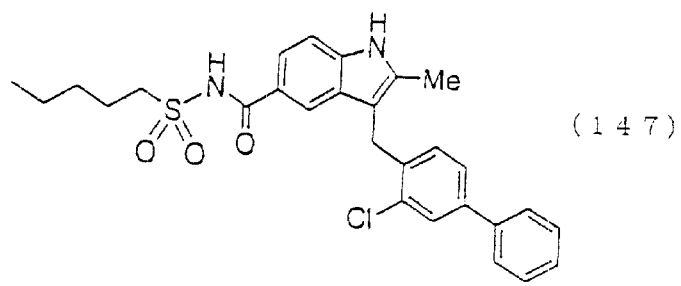
Figure 24:
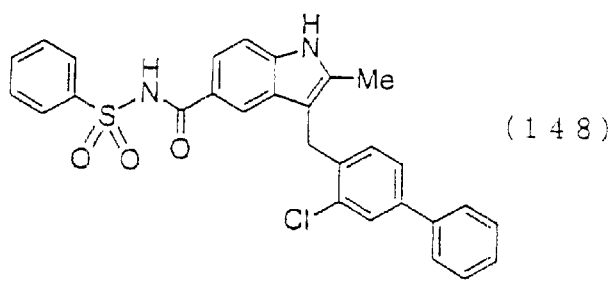
Figure 24:
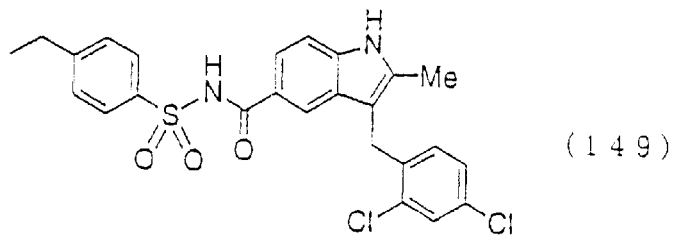
Figure 25:
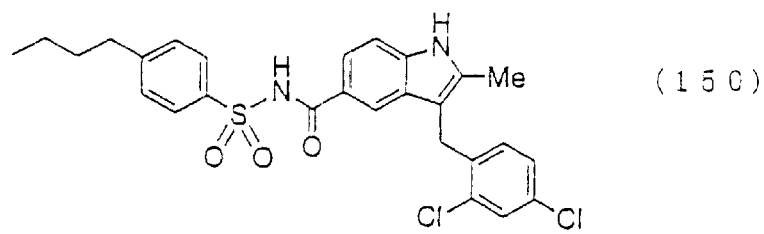
FIG. 25 shows the chemical formulae of compounds (150) to (154).
Figure 25:
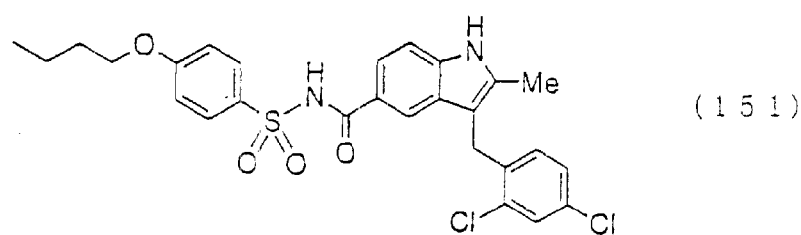
Figure 25:
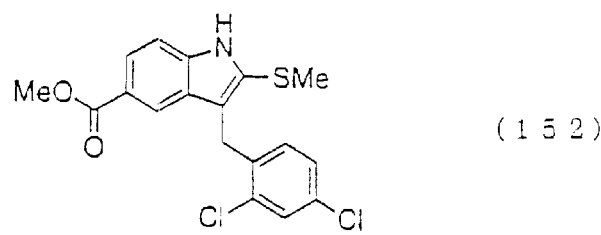
Figure 25:
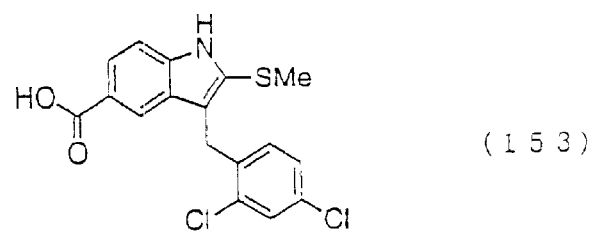
Figure 25:
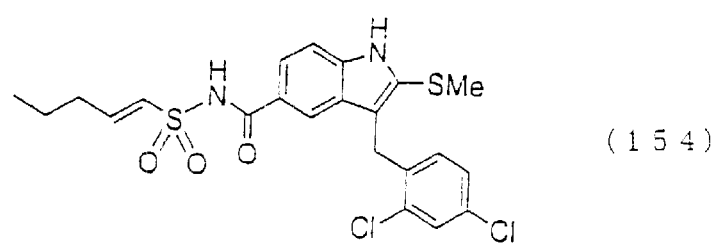
Figure 26:
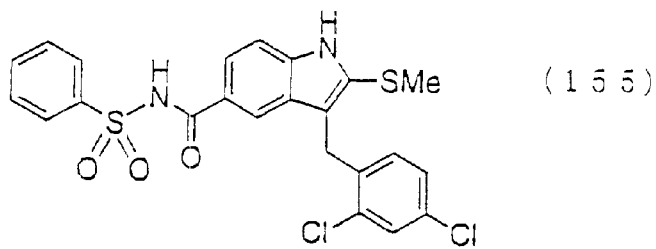
FIG. 26 shows the chemical formulae of compounds (155) to (159).
Figure 26:
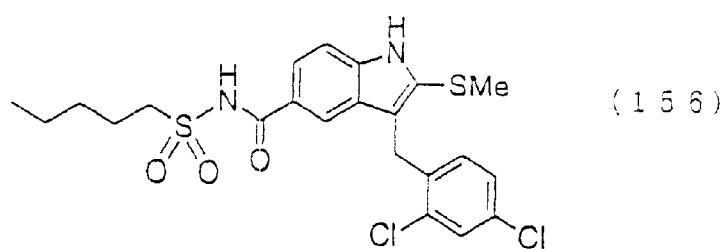
Figure 26:
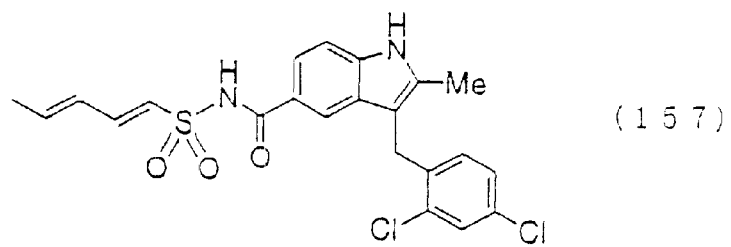
Figure 26:
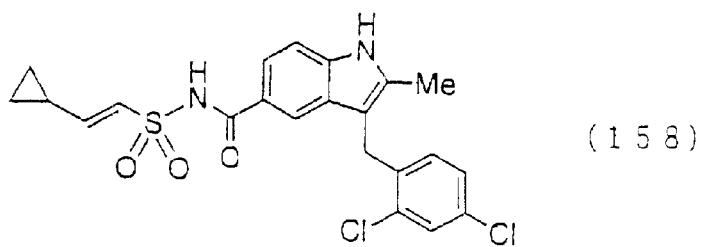
Figure 26:
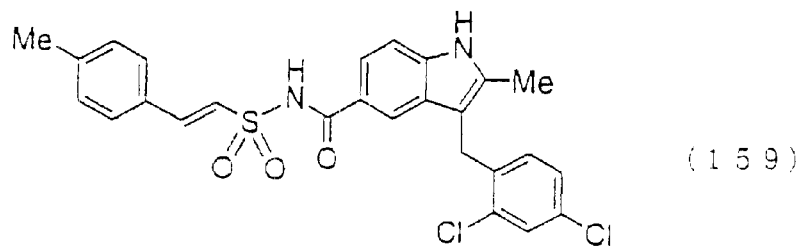
Figure 27:
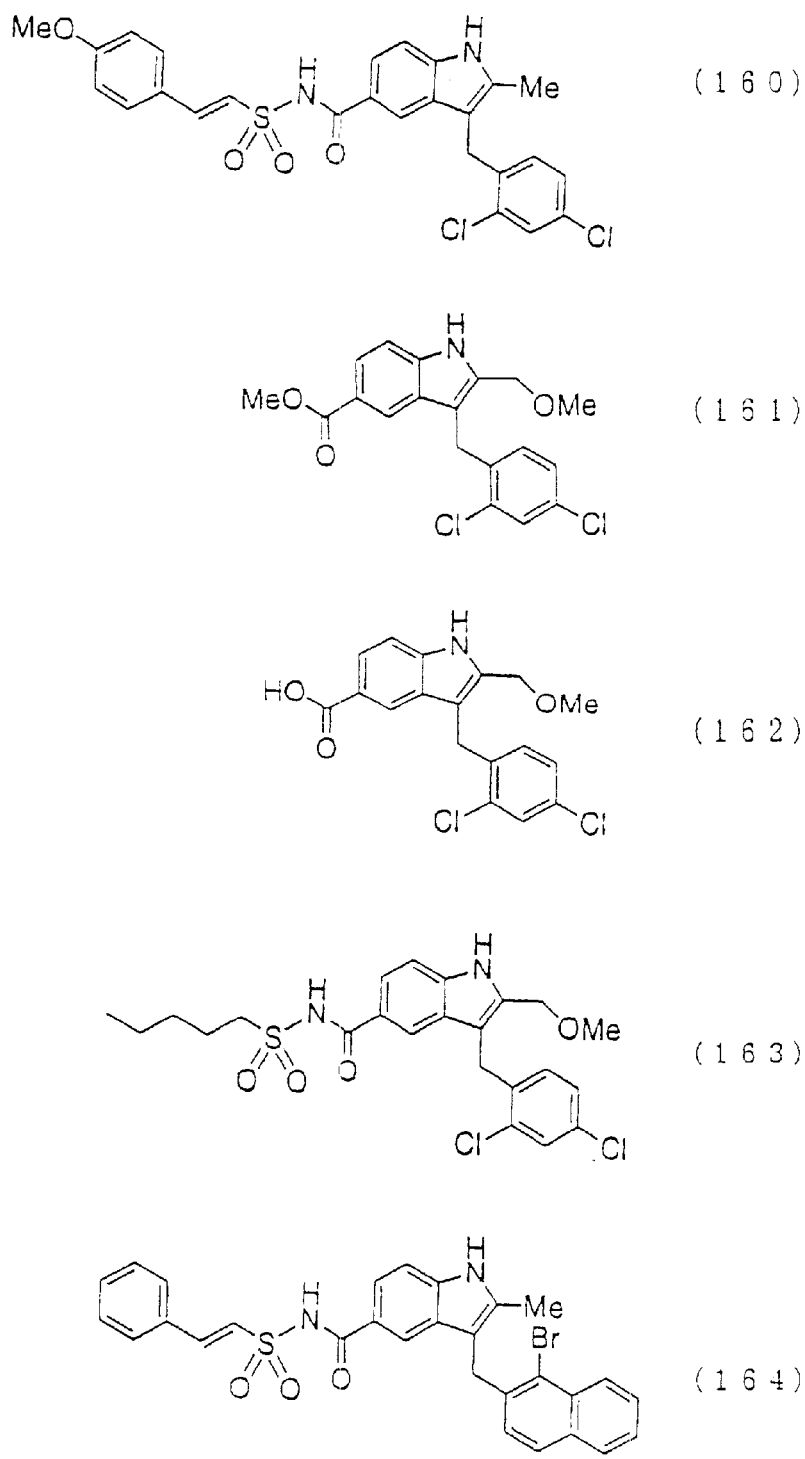
FIG. 27 shows the chemical formulae of compounds (160) to (164).
Figure 28:
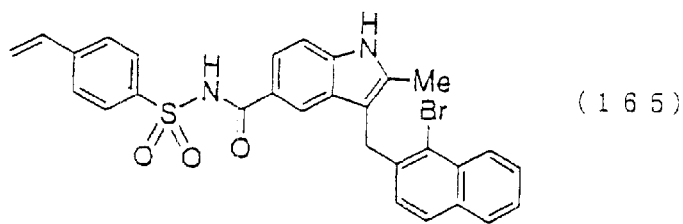
FIG. 28 shows the chemical formulae of compounds (165) to (169).
Figure 28:
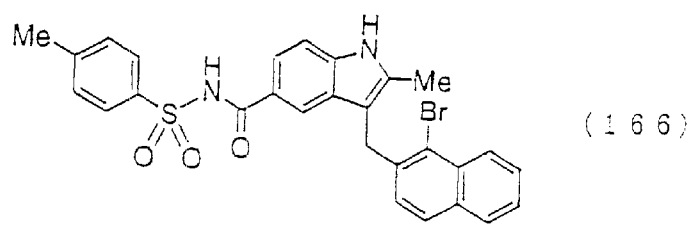
Figure 28:
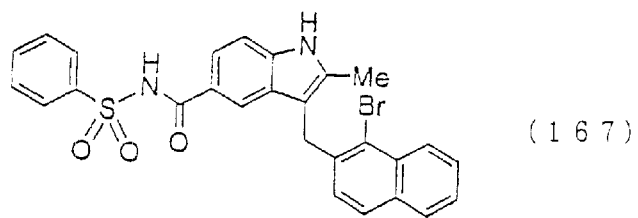
Figure 28:
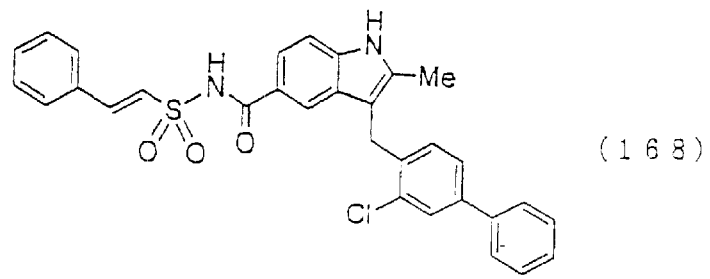
Figure 28:
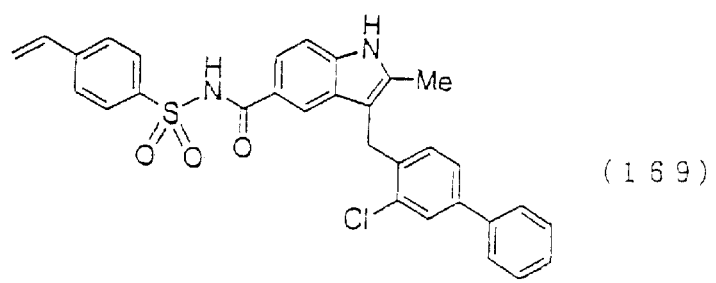
Figure 29:
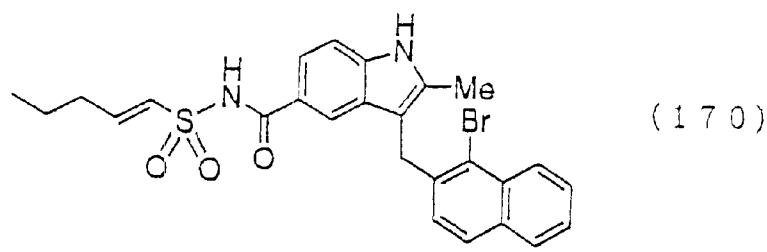
FIG. 29 shows the chemical formulae of compounds (170) to (173).
Figure 29:
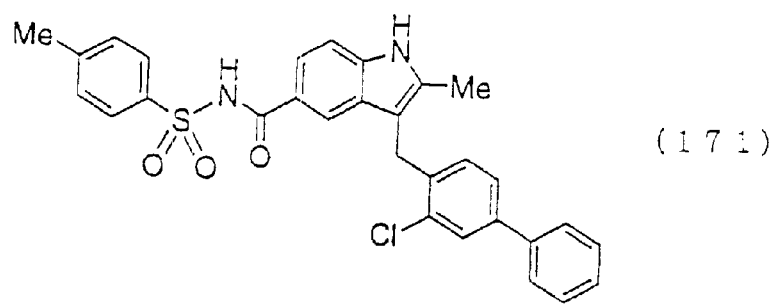
Figure 29:
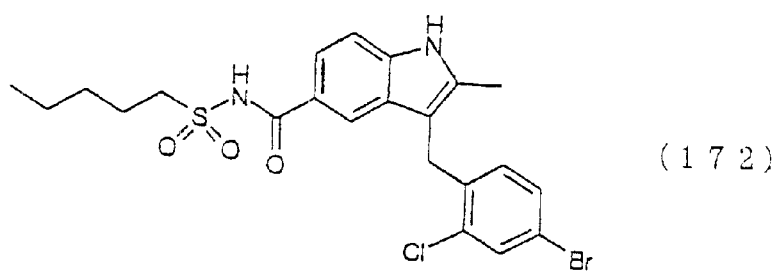
Figure 29:
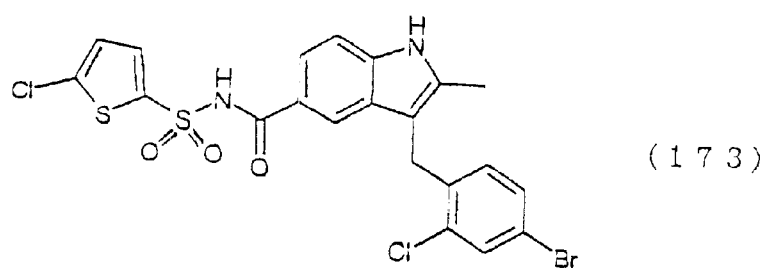

The synthesis of the compounds useful in this invention and of the intermediates for use in making those compounds are illustrated by the following, non-limiting Examples from the above PCT Application WO 98/15530.

Production Example 1
Methyl 4-(2-Oxopropyl)-3-Nitrobenzoate

To a methylene chloride (60 ml) solution of methyl E-4-(2-dimethylaminovinyl)-3-nitrobenzoate (5.0 g) (this is reportedly produced according to the method of U.S. Pat. No. 5,212,195) and pyridine (2.6 ml), added are acetyl chloride (2 ml), and stirred at room temperature for 20 hours. Water is added to this to stop the reaction, and the organic layer is concentrated. To the residue, added is 1,4-dioxane (25 ml) and water (13 ml), and heated under reflux for 16 hours. The solvent is evaporated away under reduced pressure, and the residue is extracted with ethyl acetate and water. The organic layer is washed with a saturated saline solution, then concentrated, and purified through silica gel column chromatography (eluent: hexane/ethyl acetate=2/1) to obtain methyl 4-(2-oxopropyl)-3-nitrobenzoate (4.12 g).
$^1$H-NMR (CDCl$_3$, δ): 2.35 (3H, s), 3.97 (3H, s), 4.19 (2H, s), 7.37 (1H, d, J=7.9 Hz), 8.24 (1H, d, J=7.9 Hz), 8.75 (1H, s).

Production Example 2
6-Methoxycarbonyl-2-Methylindole

A mixed solution of methyl 4-(2-oxopropyl)-3-nitrobenzoate (3.86 g), reduced iron (9.0 g) and acetic acid (40 ml) is stirred at 90° C. for 24 hours. The solid is removed through filtration, and the filtrate is concentrated under reduced pressure. The resulting residue is purified through silica gel column chromatography (eluent: hexane/ethyl acetate=3/1) to obtain 6-methoxycarbonyl-2-methylindole (0.890 g).
[Physical Properties of the Product]
$^1$H-NMR (CDCl$_3$, δ): 2.46 (3H, s), 3.90 (3H, s), 6.25 (1H, s), 7.48 (1H, d, J=8.3 Hz), 7.72 (1H, dd, J=1.4 Hz and 8.3 Hz), 7.97 (1H, s), 8.39 (1H, brs).

EXAMPLE 1
Production of 1-(2-chlorobenzyl)-6-methoxycarbonyl-2-methylindole (30)

A mixture of 6-methoxycarbonyl-2-methylindole (0.89 g), 2-chlorobenzyl bromide (1.45 g), potassium carbonate (0.780 g) and N,N-dimethylformamide (2 ml) is stirred at 80° C. for 18 hours. The solvent is evaporated away under reduced pressure, and the resulting residue is purified through silica gel column chromatography (eluent: hexane/chloroform=3/1) to obtain 1-(2-chlorobenzyl)-6-methoxycarbonyl-2-methylindole (30) (0.660 g).
[Physical Properties of Compound (30)]
$^1$H-NMR (CDCl$_3$, δ): 2.35 (3H, s), 3.88 (3H, s), 5.41 (2H, s), 6.17 (1H, d, J=7.8 Hz), 6.42 (1H, s), 7.02 (1H, t, J=7.6 Hz), 7.18 (1H, t, J=7.1 Hz), 7.42 (1H, d, J=8.0 Hz), 7.58 (1H, d, J=8.3 Hz), 7.80 (1H, dd, J=1.2 and 8.3 Hz).

EXAMPLE 2
Production of 6-carboxy-1-(2-chlorobenzyl)-2-methylindole (31)

A mixture of 1-(2-chlorobenzyl)-6-methoxycarbonyl-2-methylindole (0.630 g), aqueous 10% sodium hydroxide solution (2.7 g), water (1.8 g) and ethanol (7.0 g) is refluxed for 2.5 hours. After cooled, this is processed with 10% HCl to have a pH of 4, and the crystal formed is taken out through filtration and dried to obtain 6-carboxy-1-(2-chlorobenzyl)-2-methylindole (31) (0.480 g).
[Physical Properties of Compound (31)]
$^1$H-NMR (DMSO-d6, δ): 2.35 (3H, s), 5.53 (2H, s), 6.13 (1H, d, J=7.6 Hz), 6.46 (1H, s), 7.15 (1H, t, J=7.6 Hz), 7.28 (1H, t, J=7.6 Hz), 7.54 (2H, t, J=8.3 Hz), 7.62 (1H, d, J=8.3 Hz), 12.49 (1H, brs).

EXAMPLE 3
Production of 6-benzenesulfonylcarbamoyl-1-(2-chlorobenzyl)-2-methylindole (32)

To an N,N-dimethylformamide (10 ml) solution of 6-carboxy-1-(2-chlorobenzyl)-2-methylindole (0.470 g), added is N,N'-carbonyldiimidazole (0.508 g), and stirred at room temperature for 1 hour. Next, benzenesulfonamide (0.493 g) and diazabicycloundecene (0.477 g) are added thereto, and stirred at 100° C. for 72 hours. The solvent is evaporated away under reduced pressure, and the residue is purified through silica gel column chromatography (eluent: chloroform) to obtain 6-(benzenesulfonylcarbamoyl)-1-(2-chlorobenzyl)-2-methylindole. This is dissolved in a small amount of ethyl acetate, to which is added hexane. The crystal formed is taken out through filtration, and dried to obtain 6-(benzenesulfonylcarbamoyl)-1-(2-chlorobenzyl)-2-methylindole (32) (0.440 g).

[Physical Properties of Compound (32)]

$^1$H-NMR (DMSO-d6, δ): 2.30 (3H, s), 5.50 (2H, s), 6.05 (1H, d, J=7.7 Hz), 6.45 (1H, s), 7.14 (1H, t, J=7.6 Hz), 7.29 (1H, t, J=7.7 Hz), 7.48–7.68 (6H, m), 7.89–8.01 (3H, m), 12.22 (1H, brs).

Production Example 3
Methyl 4-(2-oxobutyl)-3-nitrobenzoate

According to the method of Production Example 1, a mixed solution of methyl E-4-(2-dimethylaminovinyl)-3-nitrobenzoate (6.30 g), pyridine (3.2 ml), propionyl chloride (3.26 g) and methylene chloride (60 ml) is heated under reflux for 11 hours, and then heated under reflux with 1,4-dioxane in water for 16 hours to obtain methyl 4-(2-oxobutyl)-3-nitrobenzoate (5.63 g).

[Physical Properties of the Product]

$^1$H-NMR (CDCl$_3$, δ): 1.12 (3H, t, J=7.3 Hz), 2.65 (2H, q, J=7.3 Hz), 3.97 (3H, s), 4.18 (2H, s), 7.37 (1H, d, J=7.9 Hz), 8.22 (1H, dd, J=1.7 and 7.9 Hz), 8.73 (1H, d, J=1.7 Hz).

Production Example 4
2-ethyl-6-methoxycarbonylindole

According to the method of Production Example 2, obtained is 2-ethyl-6-methoxycarbonylindole (2.55 g) from methyl 4-(2-oxobutyl)-3-nitrobenzoate (5.60 g) and reduced iron (13.0 g).

[Physical Properties of the Product]

$^1$H-NMR (CDCl$_3$, δ): 1.37 (3H, t, J=7.6 Hz), 2.83 (2H, q, J=7.6 Hz), 3.92 (3H, s), 6.30 (1H, s), 7.53 (1H, d, J=8.3 Hz), 7.76 (1H, d, J=8.3 Hz), 8.05 (1H, s), 8.20 (1H, brs).

EXAMPLE 4
Production of 1-(biphenyl-4-ylmethyl)-2-ethyl-6-methoxycarbonylindole (33)

According to the method of Example 1, obtained is 1-(biphenyl-4-ylmethyl)-2-ethyl-6-methoxycarbonylindole (33) (2.50 g) from 2-ethyl-6-methoxycarbonylindole (2.55 g), 4-biphenylmethyl bromide (4.00 g) and potassium carbonate (2.07 g). This is directly used in the next reaction.

EXAMPLE 5
Production of 1-(biphenyl-4-ylmethyl)-6-carboxy-2-ethylindole (34)

According to the method of Example 3, obtained is 1-(biphenyl-4-ylmethyl)-6-carboxy-2-ethylindole (34) (1.29 g) from 1-(biphenyl-4-ylmethyl)-2-ethyl-6-methoxycarbonylindole (2.50 g).

[Physical Properties of Compound (34)]

$^1$H-NMR (DMSO-d6, δ): 1.26 (3H, t, =7.5 Hz), 2.76 (2H, q, J=7.5 Hz), 5.30 (2H, s), 6.24 (1H, s), 7.35–7.74 (11H, m), 7.94 (1H, s), 12.57 (1H, brs).

EXAMPLE 6
Production of 1-(biphenyl-4-ylmethyl)-6-(1-butanesulfonylcarbamoyl)-2-ethylindole (35)

According to the method of Example 3, obtained is 1-(biphenyl-4-ylmethyl)-6-(1-butanesulfonylcarbamoyl)-2-ethylindole (35) (0.360 g) from 1-(biphenyl-4-ylmethyl)-6-carboxy-2-ethylindole (0.400 g), N,N'-carbonyldiimidazole (0.365 g), 1-butanesulfonamide (0.309 g) and diazabicycloundecene (0.343 g).

[Physical Properties of Compound (35)]

$^1$H-NMR (DMSO-d6, δ): 0.86 (3H, t, J=7.4 Hz), 1.23 (3H, t, J=7.5 Hz), 1.37 (2H, m), 1.64 (2H, m), 2.70 (2H, q, J=7.4 Hz), 3.28 (2H, m), 5.31 (2H, s), 6.17 (1H, s), 7.39 (1H, t, J=7.4 Hz), 7.43–7.51 (3H, m), 7.59 (2H, d, J=8.2 Hz), 7.66–7.72 (3H, m), 7.75 (2H, d, J=8.2 Hz), 8.11 (1H, d), 11.96 (1H, brs).

IR (Nujol): 1650 cm$^{-1}$.

m.p.: 71–83° C.

EXAMPLE 7
Production of 1-(2,4-dichlorobenzyl)-6-methoxycarbonyl-2-methylindole (36)

According to the method of Example 1, obtained is 1-(2,4-dichlorobenzyl)-6-methoxycarbonyl-2-methylindole (36) (1.71 g) from 6-methoxycarbonyl-2-methylindole (1.59 g), 2,4-dichlorobenzyl chloride (2.14 g), potassium carbonate (1.51 g) and sodium iodide (1.26 g).

hu 1H-NMR (CDCl$_3$, δ): 2.31 (3H, s), 3.94 (3H, s), 5.29 (2H, s), 6.11 (1H, s), 7.26 (1H, dd, J=2.0 and 8.2 Hz), 7.32 (1H, d, J=8.1 Hz), 7.48 (2H, m), 7.76 (1H, d, J=8.3 Hz), 8.02 (1H, s).

EXAMPLE 8
Production of 6-carboxy-1-(2,4-dichlorobenzyl)-2-methylindole (37)

According to the method of Example 1, obtained is 6-carboxy-1-(2,4-dichlorobenzyl)-2-methylindole (37) (1.21 g) from 1-(2,4-dichlorobenzyl)-6-methoxycarbonyl-2-methylindole (1.70 g).

$^1$H-NMR (DMSO-d6, δ): 2.35 (3H, s), 5.35 (2H, s), 6.22 (1H, s), 7.45–7.50 (2H, m), 7.55–7.61 (2H, m), 7.74 (1H, d, J=2.1 Hz), 7.87 (1H, s), 12.57 (1H, brs).

EXAMPLE 9
Production of 6-(1-butanesulfonylcarbamoyl)-1-(2,4-dichlorobenzyl)-2-methylindole (38)

According to the method of Example 3, obtained is 1-(2,4-dichlorobenzyl)-6-(1-butanesulfonylcarbamoyl)-2-methylindole (38) (0.270 g) from 6-carboxy-1-(2,4-dichlorobenzyl)-2-methylindole (0.370 g), N,N'-carbonyldiimidazole (0.269 g), 1-butanesulfonamide (0.228 g) and diazabicycloundecene (0.253 g).

$^1$H-NMR (CDCl$_3$, δ): 0.90 (3H, t), 1.44 (2H, m), 1.82 (2H, m), 3.10 (2H, m), 5.26 (2H, s), 6.11 (1H, s), 7.20–7.30 (2H, m), 7.42–7.49 (2H, m), 7.52–7.59 (1H, m), 7.97 (1H, s).

IR (neat): 1682 cm$^{-1}$.

Oily.

EXAMPLE 10
Production of 1-(2,4-dichlorobenzyl)-2-methyl-6-(1-pentanesulfonylcarbamoyl)indole (39)

According to the method of Example 3, obtained is 1-(2,4-dichlorobenzyl)-2-methyl-6-(1-pentanesulfonylcarbamoyl)indole (39) (0.482 g) from 6-carboxy-1-(2,4-dichlorobenzyl)-2-methylindole (0.668 g), N,N'-carbonyldiimidazole (0.649 g), 1-pentanesulfonamide (0.605 g) and diazabicycloundecene (0.609 g).

$^1$H-NMR (DMSO-d6, δ): 0.85 (3H, t, J=7.3 Hz), 1.30 (2H, m), 1.39 (2H, m), 1.72 (2H, m), 2.28 (3H, s), 3.53 (2H, t, J=7.7 Hz), 5.43 (2H, s), 6.23 (1H, s), 7.51 (1H, dd, J=2.0 and 8.2 Hz), 7.53 (1H, d, J=8.4 Hz), 7.59 (1H, d, J=8.4 Hz), 7.61 (1H, dd, J=2.0 and 8.2 Hz), 7.77 (1H, d, J=2.0 Hz), 8.04 (1H, s), 11.94 (1H, s).

EXAMPLE 11
Production of 1-(2,4-dichlorobenzyl)-2-ethyl-6-methoxycarbonylindole (40)

According to the method of Example 1, obtained is 1-(2,4-dichlorobenzyl)-2-ethyl-6-methoxycarbonylindole (40) (2.70 g) from 2-ethyl-6-methoxycarbonylindole (4.88 g), 2,4-dichlorobenzyl chloride (6.10 g), potassium carbonate (4.31 g) and potassium iodide (3.98 g).

$^1$H-NMR (CDCl$_3$, δ): 1.33 (3H, t, J=7.4 Hz), 2.64 (2H, 1, J=7.4 Hz), 3.89 (3H, s), 5.37 (2H, s), 6.08 (1H, d, J=8.4 Hz), 6.45 (1H, s), 6.99 (1H, dd, J=2.0 and 8.4 Hz), 7.45 (1H, d, J=2.0 Hz), 7.61 (1H, d, J=8.3 Hz), 7.81 (1H, d, J=8.3 Hz), 7.88 (1H, s).

EXAMPLE 12
Production of 6-carboxy-1-(2,4-dichlorobenzyl)-2-ethylindole (41)

According to the method of Example 2, obtained is 6-carboxy-1-(2,4-dichlorobenzyl)-2-ethylindole (41) (0.837 g) from 1-(2,4-dichlorobenzyl)-2-ethyl-6-methoxycarbonylindole (0.959 g).

$^1$H-NMR (DMSO-d6, δ): 1.24 (3H, t, J=7.4 Hz), 2.67 (2H, q, J=7.5 Hz), 5.53 (2H, s), 6.09 (1H, d, J=8.4 Hz), 6.48 (1H, s), 7.26 (1H, d, J=8.4 Hz), 7.59 (1H, d, J=8.3 Hz), 7.64 (1H, d, J=8.3 Hz), 7.72 (1H, d, J=2.0 Hz), 7.88 (1H, s).

EXAMPLE 13
Production of 6-(1-butanesulfonylcarbamoyl)-1-(2,4-dichlorobenzyl)-2-ethylindole (42)

According to the method of Example 3, obtained is 6-(1-butanesulfonylcarbamoyl)-1-(2,4-dichlorobenzyl)-2-ethylindole (42) (0.220 g) from 6-carboxy-1-(2,4-dichlorobenzyl)-2-ethylindole (0.801 g), N,N'-carbonyldiimidazole (0.567 g), 1-butanesulfonamide (0.480 g) and diazabicycloundecene (0.533 g).

$^1$H-NMR (DMSO-d6, δ): 0.84 (3H, t, J=7.3 Hz), 1.22 (3H, t, J–7.4 Hz), 1.38 (2H, m), 1.64 (2H, m), 2.63 (2H, m), 3.48 (2H, m), 5.51 (2H, s), 6.05 (1H, d, J=8.5 Hz), 6.50 (1H, s), 7.26 (1H, dd, J=1.9 and 8.4Hz), 7.63 (2H, m), 7.72 (1H, d, J=2.0 Hz), 8.06 (1H, s), 11.70 (1H, s).

IR (Nujol): 1682 cm$^{-1}$.

m.p.: 162.2–162.7° C.

Production Example 5
6-methoxycarbonylindole

To a mixed solvent of tetrahydrofuran (30 ml), ethanol (30 ml) and water (100 ml), added are methyl E-4-(2-dimethylaminovinyl)-3-nitrobenzoate (10.0 g) and sodium hydrosulfite (104.5 g), and stirred at 70° C. for 1 hours. After this is cooled to room temperature, a saturated saline solution is added thereto. Then, this is extracted with chloroform. The organic layer is dried, and the solvent is evaporated away. The resulting residue is purified through silica gel column chromatography (eluent: hexane/ethyl acetate= 2/1 to 1/1) to obtain 6-methoxycarbonylindole (2.79 g).

$^1$H-NMR (CDCl$_3$, δ): 3.93 (3H, s), 6.60 (1H, s), 7.37 (1H, m), 7.66 (1H, d, J=8.3 Hz), 7.81 (1H, dd, J=1.3 and 8.3 Hz), 8.17 (1H, s), 8.52 (1H, brs).

EXAMPLE 14
Production of 1-(2,4-dichlorobenzyl)-6-methoxycarbonylindole (43)

According to the method of Example 1, obtained is 1-(2,4-dichlorobenzyl)-6-methoxycarbonylindole (43) (1.97 g) from 6-methoxycarbonylindole (2.79 g), 2,4-dichlorobenzyl chloride (4.67 g), potassium carbonate (3.30 g) and potassium iodide (3.96 g).

$^1$H-NMR (CDCl$_3$, δ): 3.91 (3H, s), 5.43 (2H, s), 6.47 (1H, d, J=8.3 Hz), 6.63 (1H, d, J=3.2 Hz), 7.07 (1H, dd, J=1.3 and 8.4 Hz), 7.26 (1H, d, J=1.0 Hz), 7.45 (1H, d, J=1.5Hz), 7.68 (1H, d, J=8.3 Hz), 7.83 (1H, dt, J=1.0 and 8.4 Hz), 8.01 (1H, s).

EXAMPLE 15
Production of 6-carboxy-1-(2,4-dichlorobenzyl)indole (44)

According to the method of Example 2, obtained is 6-carboxy-1-(2,4-dichlorobenzyl)indole (44) (1.55 g) from 1-(2,4-dichlorobenzyl)-6-methoxycarbonylindole (1.67 g).

[Physical Properties of Compound (44)]

$^1$H-NMR (DMSO-d6,): 5.59 (2H, s), 6.61 (2H, m), 7.32 (1H, d, J=8.2 Hz), 7.65 (3H, s), 7.69 (1H, s), 8.00 (1H, s).

EXAMPLE 16
Production of 6-(1-butanesulfonylcarbamoyl)-1-(2,4-dichlorobenzyl)indole (45)

According to the method of Example 3, obtained is 6-(1-butanesulfonylcarbamoyl)-1-(2,4-dichlorobenzyl)indole (45) (0.307 g) from 6-carboxy-1-(2,4-dichlorobenzyl)indole (0.800 g), N,N'-carbonyldiimidazole (0.567 g), 1-butanesulfonamide (0.480 g) and diazabicycloundecene (0.533 g).

$^1$H-NMR (DMSO-d6, δ): 0.84 (3H, m), 1.38 (2H, m), 1.65 (2H, m), 3.47 (2H, m), 5.57 (2H, s), 6.53 (1H, d, J=8.4 Hz), 6.64 (1H, d, J=3.0 Hz), 7.32 (1H, dd, J=2.0 and 8.4 Hz), 7.66 (3H, m), 7.71 (1H, d, J=2.0 Hz), 8.13 (1H, s), 11.79 (1H, s).

IR (neat): 1694 cm$^{-1}$.

Oily.

Production Example 6
2,4-dichlorobenzyl Iodide 2,4-Dichlorobenzyl chloride (23.45 g) and potassium iodide (47.88 g) are stirred in acetone (100 ml) at room temperature for 24 hours. After concentrated, this is extracted with t-butyl methyl ether (300 ml) and water (100 ml). The extract is washed with water, dried and concentrated to obtain 2,4-dichlorobenzyl iodide (34.49 g).

$^1$H-NMR (CDCl$_3$, δ): 4.48 (2H, s), 7.19 (1H, dd, J=2.2 and 8.3 Hz), 7.34 (1H, d, J=8.3 Hz), 7.36 (1H, d, J=2.2 Hz).

EXAMPLE 17
Production of 3-(2,4-dichlorobenzyl)-5-methoxycarbonylindole (46)

Silver oxide (28.09 g) is added to a dioxane (200 ml) solution of 5-methoxycarbonylindole (17.52 g) and 2,4-dichlorobenzyl iodide (34.49 g), and stirred under reflux for 6.5 hours. The insoluble is removed through filtration, and the filtrate is concentrated under reduced pressure. The resulting oily residue is purified through silica gel column chromatography (eluent: hexane/ethyl acetate=4/1), and recrystallized from hexane/ethyl acetate to obtain 3-(2,4-dichlorobenzyl)-5-methoxycarbonylindole (46) (5.49 g).

$^1$H-NMR (CDCl$_3$, δ): 3.92 (3H, s), 4.20 (2H, s), 6.98 (1H, d, J=2.3 Hz), 7.09–7.13 (2H, m), 7.38 (1H, d, J=9.1 Hz), 7.42 (1H, d, J=1.9 Hz), 7.92 (1H, dd, J=1.5 and 8.5 Hz), 8.22 (1H, brs), 8.31 (1H, d, J=1.2 Hz).

EXAMPLE 18
Production of 5-carboxy-3-(2,4-dichlorobenzyl)indole (47)

According to the method of Example 2, obtained is 5-carboxy-3-(2,4-dichlorobenzyl)indole (47) (4.64 g) from 3-(2,4-dichlorobenzyl)-5-methoxycarbonylindole (5.02 g).

$^1$H-NMR (DMSO-d6, δ): 4.15 (2H, s), 7.22–7.24 (2H, m), 7.31 (1H, dd, J=2.0 and 8.3 Hz), 7.41 (1H, d, J=8.7 Hz), 7.59

(1H, d, J=2.0 Hz), 7.71 (1H, dd, J=1.4 and 8.7 Hz), 8.12 (1H, brs), 11.30 (1H, brs), 12.39 (1H, brs).

EXAMPLE 19
Production of 5-(1-butanesulfonylcarbamoyl)-3-(2,4-dichlorobenzyl)indole (48)

According to the method of Example 3, obtained is 5-(1-butanesulfonylcarbamoyl)-3-(2,4-dichlorobenzyl) indole (48) (0.19 g) from 5-carboxy-3-(2,4-dichlorobenzyl) indole (0.96 g), N,N'-carbonyldiimidazole (0.73 g), 1-butanesulfonamide (0.62 g) and diazabicycloundecene (0.69 g).

$^1$H-NMR (DMSO-d6, δ): 0.86 (3H, t, J=7.3 Hz), 1.40 (2H, m), 1.67 (2H, m), 3.51 (2H, t, J=7.7 Hz), 4.16 (2H, s), 7.21 (1H, d, J=2.2 Hz), 7.25 (1H, d, J=8.3 Hz), 7.33 (1H, dd, J=2.1 and 8.3 Hz), 7.44 (1H, d, J=8.6 Hz), 7.60 (1H, d, J=2.1 Hz), 7.71 (1H, dd, J=1.7 and 8.6 Hz), 8.28 (1H, d, J=1.2 Hz), 11.37 (1H, brs), 11.77 (1H, s).

IR (KBr): 1662 cm$^{-1}$.
m.p.: 165.5–166.2° C.
Mass (FD): m/e 438 (M).

EXAMPLE 20
Production of 1-(2,4-dichlorobenzyl)-5-methoxycarbonylindole (49)

2,4-Dichlorobenzyl chloride (8.68 g) is added to a mixture of 5-methoxycarbonylindole (6.49 g), 60% sodium hydride (2.24 g) and N,N-dimethylformamide, while cooled in an ice-water bath. This is stirred at room temperature for 20 minutes, and water is added thereto. Then, this is extracted with ethyl acetate. After washed with water, the organic layer is dried, concentrated, purified through silica gel column chromatography (eluent: hexane/ethyl acetate=6/1), and finally recrystallized from ethyl acetate/hexane to obtain 1-(2,4-dichlorobenzyl)-5-methoxycarbonylindole (49) (6.59 g).

$^1$H-NMR (CDCl$_3$, δ): 3.93 (3H, s), 5.39 (2H, s), 6.49 (1H, d, J=8.4 Hz), 6.69 (1H, d, J=3.2 Hz), 7.08 (1H, dd, J=2.0 and 8.4 Hz), 7.17 (1H, d, J=3.2 Hz), 7.23 (1H, d, J=8.6 Hz), 7.45 (1H, d, J=2.0 Hz), 7.89 (1H, dd, J=1.4 and 8.6 Hz), 8.43 (1H, s).

EXAMPLE 21
Production of 5-carboxy-1-(2,4-dichlorobenzyl)indole (50)

According to the method of Example 2, obtained is 5-carboxy-1-(2,4-dichlorobenzyl)indole (50) (4.52 g) from 1-(2,4-dichlorobenzyl)-5-methoxycarbonylindole (5.02 g).

$^1$H-NMR (DMSO-d6, δ): 5.53 (2H, s), 6.64 (1H, d, J=8.4 Hz), 6.68 (1H, d, J=3.1 Hz), 7.31 (1H, dd, J=2.1 and 8.4Hz), 7.45 (1H, d, J=8.7 Hz), 7.53 (1H, d, J=3.2 Hz), 7.67 (1H, d, J=2.1 Hz), 7.73 (1H, dd, J=1.5 and 8.7 Hz), 8.27 (1H, d, J=1.3 Hz), 12.48 (1H, brs).

EXAMPLE 22
Production of 5-(1-butanesulfonylcarbamoyl)-1-(2,4-dichlorobenzyl)indole (51)

According to the method of Example 3, obtained is 5-(1-butanesulfonylcarbamoyl)-1-(2,4-dichlorobenzyl) indole (51) (0.44 g) from 5-carboxy-1-(2,4-dichlorobenzyl) indole (0.96 g), N,N'-carbonyldiimidazole (0.73 g), 1-butanesulfonamide (0.62 g) and diazabicycloundecene (0.69 g).

$^1$H-NMR (DMSO-d6, δ): 0.86 (3H, t, J=7.4 Hz), 1.40 (2H, m), 1.68 (2H, m), 3.51 (2H, t, J=7.7 Hz), 5.55 (2H, s), 6.64 (1H, d, J=8.4 Hz), 6.70 (1H, d, J=3.2 Hz), 7.32 (1H, dd, J=2.1 and 8.4 Hz), 7.51 (1H, d, J=8.7 Hz), 7.56 (1H, d, J=3.2Hz), 7.68 (1H, d, J=2.1 Hz), 7.72 (1H, dd, J=1.6 and 8.7Hz), 8.31 (1H, d, J=1.5 Hz), 11.83 (1H, s).

IR (KBr): 1646 cm$^{-1}$.
m.p.: 143.8–144.8° C.

Production Example 7
Methyl 3-(2-oxopropyl)-4-nitrobenzoate

According to the method of Production Example 1, a mixed solution of methyl E-3-(2-dimethylaminovinyl)-4-nitrobenzoate (45.05 g), pyridine (23.51 g), acetyl chloride (21.20 g) and methylene chloride (200 ml) is stirred at room temperature for 61 hours, and then heated under reflux with 1,4-dioxane in water for 18 hours to obtain methyl 3-(2-oxopropyl)-4-nitrobenzoate (19.67 g).

$^1$H-NMR (CDCl$_3$, δ): 2.34 (3H, s), 3.96 (3H, s), 4.18 (2H, s), 7.95 (1H, d, J=1.8Hz), 8.10(1H, dd, J=1.8 and 8.5 Hz), 8.15 (1H, d,J=8.5 Hz).

Production Example 8
5-methoxycarbonyl-2-methylindole

According to the method of Production Example 5, obtained is 5-methoxycarbonyl-2-methylindole (8.25 g) from methyl 3-(2-oxopropyl)-4-nitrobenzoate (18.98 g) and sodium hydrosulfite (208.92 g).

[Physical Properties of the Product]
$^1$H-NMR (CDCl$_3$,): 2.46 (3H, s), 3.92 (3H, s), 6.31 (1H, s), 7.28 (1H, d, J=8.5 Hz), 7.83 (1H, dd, J=1.5 and 8.5 Hz), 8.08 (1H, brs), 8.27 (1H, s).

EXAMPLE 23
Production of 3-(2,4-dichlorobenzyl)-5-methoxycarbonyl-2-methylindole (52)

According to the method of Example 17, obtained is 3-(2,4-dichlorobenzyl)-5-methoxycarbonyl-2-methylindole (52) (6.97 g) from 5-methoxycarbonyl-2-methylindole (7.57 g), 2,4-dichlorobenzyl iodide (13.77 g) and silver oxide (11.33 g).

$^1$H-NMR (CDCl$_3$, δ): 2.36 (3H, s), 3.89 (3H, s), 4.11 (2H, s), 6.83 (1H, d, J=8.3 Hz), 7.03 (1H, dd, J=2.1 and 8.3 Hz), 7.31 (1H, d, J=8.6 Hz), 7.41 (1H, d, J=2.1 Hz), 7.85 (1H, dd, J=1.5 and 8.6 Hz), 8.09 (1H, s), 8.11 (1H, brs).

EXAMPLE 24
Production of 5-carboxy-3-(2,4-dichlorobenzyl)-2-methylindole (53)

According to the method of Example 3, obtained is 5-carboxy-3-(2,4-dichlorobenzyl)-2-methylindole (53) (0.77 g) from 3-(2,4-dichlorobenzyl)-5-methoxycarbonyl-2-methylindole (1.74 g).

$^1$H-NMR (DMSO-d6, δ): 2.34 (3H, s), 4.08 (2H, s), 6.98 (1H, d, J=8.4 Hz), 7.26 (1H, dd, J=2.1 and 8.4 Hz), 7.31 (1H, d, J=8.5 Hz), 7.59 (1H, d, J=2.1 Hz), 7.62 (1H, dd, J=1.5 and 8.5 Hz), 7.87 (1H, s), 11.29 (1H, s), 12.32 (1H, s).

EXAMPLE 25
Production of 5-(1-butanesulfonylcarbamoyl)-3-(2,4-dichlorobenzyl)-2-methylindole (54)

According to the method of Example 3, obtained is 5-(1-butanesulfonylcarbamoyl)-3-(2,4-dichlorobenzyl)-2-methylindole (54) (0.49 g) from 5-carboxy-3-(2,4-dichlorobenzyl)-2-methylindole (0.77 g), N,N'-carbonyldiimidazole (0.57 g), 1-butanesulfonamide (0.48 g) and diazabicycloundecene (0.53 g).

$^1$H-NMR (DMSO-d6, δ): 0.84 (3H, t, J=7.4 Hz), 1.38 (2H, m), 1.65 (2H, m), 2.30 (3H, s), 3.48 (2H, t, J=7.7 Hz), 4.08 (2H, s), 6.93 (1H, d, J=8.4 Hz), 7.26 (1H, dd, J=2.2 and 8.4 Hz), 7.35 (1H, d, J=8.5 Hz), 7.60 (1H, d, J=2.2 Hz), 7.63 (1H, dd, J=1.7 and 8.5 Hz), 8.04 (1H, s), 11.39 (1H, s), 11.68 (1H, s).

IR (Nujol): 1673 cm$^{-1}$.
m.p.: 174.9–175.4° C.

EXAMPLE 26
Production of 3-(2,4-dichlorobenzyl)-5-methoxycarbonyl-1-methylindole (55)

60% sodium hydride (0.07 g) and then methyl iodide (0.18 g) are added in that order to an N,N-dimethylformamide solution of 3-(2,4-dichlorobenzyl)-5-methoxycarbonylindole (0.34 g), and stirred at room temperature for 19 hours. After concentrated under reduced pressure, this is extracted with water and ethyl acetate. The resulting extract is washed with water, dried, concentrated, and purified through silica gel column chromatography (eluent: hexane/ethyl acetate=9/1 to 7/1) to obtain 3-(2,4-dichlorobenzyl)-5-methoxycarbonyl-1-methylindole (55) (0.30 g).

[Physical Properties of Compound (55)]
$^1$H-NMR (CDCl$_3$, δ): 3.76 (3H, s), 3.92 (3H, s), 4.17 (2H, s), 6.80 (1H, s), 7.09–7.13 (2H, m), 7.30 (1H, d, J=8.4 Hz), 7.41 (1H, d, J=1.8 Hz), 7.93 (1H, dd, J =1.6 and 8.7 Hz), 8.30 (1H, d, J=1.2 Hz).

EXAMPLE 27
Production of 5-carboxy-3-(2,4-dichlorobenzyl)-1-methylindole (56)

According to the method of Example 3, obtained is 5-carboxy-3-(2,4-dichlorobenzyl)-1-methylindole (56) (0.83 g) from 3-(2,4-dichlorobenzyl)-5-methoxycarbonyl-1-methylindole (0.89 g).

$^1$H-NMR (DMSO-d6, δ): 3.76 (3H, s), 4.14 (2H, s), 7.17 (1H, s), 7.26 (1H, d, J=8.3 Hz), 7.33 (1H, dd, J=2.1 and 8.3 Hz), 7.46 (1H, d, J=8.7 Hz), 7.60 (1H, d, J=2.1 Hz), 7.75 (1H, dd, J=1.5 and 8.7 Hz), 8.13 (1H, d, J=1.1 Hz), 12.45 (1H, brs).

EXAMPLE 28
Production of 5-butanesulfonylcarbamoyl-3-(2,4-dichlorobenzyl)-1-methylindole (57)

According to the method of Example 3, obtained is 5-(1-butanesulfonylcarbomoyl)-3-(2,4-dichlorobenzyl)-1-methylindole (57) (0.80 g) from 5-carboxy-3-(2,4-dichlorobenzyl)-1-methylindole (0.80 g), N,N'-carbonyldiimidazole (0.58 g), 1-butanesulfonamide (0.49 g) and diazabicycloundecene (0.56 g).

$^1$H-NMR (DMSO-d6, δ): 0.86 (3H, t, J=7.4 Hz), 1.40 (2H, m), 1.68 (2H, m), 3.52 (2H, t, J=7.7 Hz), 3.76 (3H, s), 4.15 (2H, s), 7.16 (1H, s), 7.28 (1H, d, J=8.3 Hz), 7.34 (1H, dd, J=2.0 and 8.3 Hz), 7.51 (1H, d, J=8.8 Hz), 7.60 (1H, d, J=2.0 Hz), 7.77 (1H, dd, J=1.4 and 8.8 Hz), 8.30 (1H, d, J=1.1 Hz), 11.80 (1H, s).

IR (Nujol): 1680 cm$^{-1}$.
Foamy.

Production Example 9
6-methoxycarbonyl-2-methylindole

A mixed solution of methyl 4-(2-oxopropyl)-3-nitrobenzoate (3.86 g), reduced iron (9.0 g) and acetic acid (40 ml) is stirred at 90° C. for 24 hours. The solid is taken out through filtration, and the filtrate is concentrated under reduced pressure. The resulting residue is purified through silica gel column chromatography (eluent: hexane/ethyl acetate=3/1) to obtain 6-methoxycarbonyl-2-methylindole (0.890 g).

$^1$H-NMR (CDCl$_3$, δ ppm): 2.46 (3H, s), 3.90 (3H, s), 6.25 (1H, s), 7.48 (1H, d, J=8.3 Hz), 7.72 (1H, dd, J=1.4 and 8.3 Hz), 7.97 (1H, s), 8.39 (1H, brs).

Production Example 10
5-(methoxycarbonyl)-2-methylindole

To an ethanol (10 ml) solution of methyl 4-nitro-3-(oxopropyl)benzoate (13.0 g), added is palladium-carbon (5%, 2.6 g) in a nitrogen atmosphere. This is purged with hydrogen, and further stirred at room temperature for 3 hours and then at 60° C. for 19 hours. The solid is removed through filtration, and the filtrate is concentrated. The resulting oily product is crystallized from toluene. The crystal formed is collected and dried to obtain 5-(methoxycarbonyl)-2-methylindole (8.42 g).

$^1$H-NMR (CDCl$_3$, δ ppm): 2.45 (3H, s), 3.92 (3H, s), 6.30 (1H, d, J=0.7 Hz), 7.27 (1H, d, J=8.3 Hz), 7.83 (1H, dd, J=8.5 and 1.6 Hz), 8.14 (1H, brs), 8.27 (1H, s).

Production Example 11
5-(methoxycarbonyl)-2-propylindole

Methyl 4-nitro-3-(2-oxopentyl)benzoate (5.42 g) is dissolved in a mixed solvent of tetrahydrofuran (20 ml) and methanol (20 ml), to which is added a suspension of sodium hydrosulfite (52.2 g) in water (60 ml). After having been refluxed for 2 hours, this is subjected to liquid-liquid separation by adding ethyl acetate (300 ml) and water (200 ml) thereto. The organic layer is washed with a saline solution, dried and concentrated. The resulting residue is purified through silica gel column chromatography to obtain 5-(methoxycarbonyl)-2-propylindole (3.16 g).

$^1$H-NMR (CDCl$_3$, δ ppm): 1.02 (3H, t, J=7.5 Hz), 1.77 (2H, m), 2.75 (2H, t, J=7.6 Hz), 3.92 (3H, s), 6.33 (1H, dd, J=0.8 and 1.7 Hz), 7.29 (1H, d, J=8.5 Hz), 7.83 (1H, dd, J=1.6 and 8.5 Hz), 8.07 (1H, brs), 8.28 (1H, d, J=1.2 Hz).

Production Example 12
2-ethyl-5-(methoxycarbonyl)indole

According to the method of Production Example 11, obtained is 2-ethyl-5-(methoxycarbonyl)indole (1.88 g) from methyl 4-nitro-3-(2-oxobutyl)benzoate (3.77 g) and sodium hydrosulfite (39.17 g).

$^1$H-NMR (CDCl$_3$, δ ppm): 1.36 (3H, t, J=7.6 Hz), 2.81 (2H, q, J=7.6 Hz), 3.92 (3H, s), 6.33 (1H, d, J=0.8 Hz), 7.29 (1H, d, J=8.5 Hz), 7.83 (1H, dd, J=1.6 and 8.5 Hz), 8.08 (1H, brs), 8.29 (1H, s).

Production Example 13
5-(methoxycarbonyl)indole

A mixture of 5-carboxyindole (16.0 g), sodium hydrogencarbonate (26.68 g), methyl iodide (61.11 g) and N,N-dimethylformamide (30 ml) is stirred at room temperature for 4 days. Water and ethyl acetate are added thereto for liquid-liquid separation. The organic layer is washed with aqueous sodium hydrogencarbonate, dried and concentrated to obtain 5-(methoxycarbonyl)indole (13.74 g).

$^1$H-NMR (CDCl$_3$, δ ppm): 3.93 (3H, s), 6.65 (1H, s), 7.27 (1H, m), 7.40 (1H, d, J=8.6 Hz), 7.91 (1H, dd, J=8.6 and 1.6 Hz), 8.42 (1H, s), 8.46 (1H, brs).

Production Example 14
6-(methoxycarbonyl)-3-methylindole

Methyl 4-ethyl-3-nitrobenzoate (5.0 g), which had been prepared through nitration followed by methyl-esterification of 4-ethylbenzoic acid, is dissolved in N,N-dimethylformamide (50 ml), to which is added N,N-dimethylformamide dimethyl acetal (8.45 g), and stirred under heat at 130° C. for 3 hours. The reaction mixture is concentrated under reduced pressure, and the resulting red oily residue is dissolved in methanol (50 ml), to which is added palladium-carbon (5%, 0.400 g), and stirred in a hydrogen atmosphere at room temperature for 2.5 hours.

Then, this is further stirred at 50° C. for 2 hours and thereafter at room temperature for 3 days. The catalyst is removed through filtration, and the filtrate is concentrated under reduced pressure. The resulting residue is recrystallized from t-butyl methyl ether to obtain a pale yellow crystal of the intended product (2.4 g).

$^1$H-NMR (CDCl$_3$, δ ppm): 8.17 (1H, br), 8.10 (1H, d, J=1.3 Hz), 7.81 (1H, dd, J=1.3 and 8.3 Hz), 7.59 (1H, d, J=8.3 Hz), 7.13 (1H, q, J=0.9 Hz), 3.93(3H, s), 2.34 (3H, d, J=0.9 Hz).

EXAMPLE 29

Production of 3-(2,4-dichlorobenzyl)-6-(methoxycarbonyl)-2-methylindole (58)

6-(Methoxycarbonyl)-2-methylindole (3.03 g), 2,4-dichlorobenzyl chloride (4.69 g) and silver(I) oxide (5.56 g) are suspended in 1,4-dioxane (50 ml), and stirred under heat at 90° C. for 19.5 hours. The solid is separated through filtration, and the filtrate is concentrated. The resulting residue is purified through silica gel column chromatography to obtain 3-(2,4-dichlorobenzyl)-6-(methoxycarbonyl)-2-methylindole (58) (1.15 g).

$^1$H-NMR (CDCl$_3$, δ ppm): 2.40 (3H, s), 3.92 (3H, s), 4.10 (2H, s), 6.84 (1H, d, J=8.3 Hz), 7.04 (1H, dd, J=2.1 and 8.4Hz), 7.31 (1H, d, J=8.3 Hz), 7.40 (1H, d, J=2.1 Hz), 7.73 (1H, dd, J=1.4 and 8.3 Hz), 8.06 (1H, d, J=1.1 Hz), 8.14 (1H, brs).

EXAMPLE 30

Production of 3-(biphenyl-4-ylmethyl)-5-(methoxycarbonyl)-2-methylindole (59)

According to the method of Example 29, obtained is 3-(biphenyl-4-ylmethyl)-5-(methoxycarbonyl)-2-methylindole (59) (0.386 g) from 5-(methoxycarbonyl)-2-methylindole (0.946 g), 4-(bromomethyl)biphenyl (1.73 g) and silver(I) oxide (1.62 g).

$^1$H-NMR (CDCl$_3$, δ ppm): 2.42 (3H, s), 3.89 (3H, s), 4.14 (2H, s), 7.26–7.32 (4H, m), 7.40 (2H, t, J=7.5 Hz), 7.47 (2H, d, J=8.2 Hz), 7.54 (2H, m), 7.84 (1H, dd, J=1.4 and 8.6 Hz), 8.01 (1H, brs), 8.23 (1H, s).

EXAMPLE 31

Production of 3-(2-chlorobenzyl)-5-(methoxycarbonyl)-2-methylindole (60)

According to the method of Example 29, obtained is 3-(2-chlorobenzyl)-5-(methoxycarbonyl)-2-methylindole (60) (0.18 g) from 5-(methoxycarbonyl)-2-methylindole (0.946 g), 2-chlorobenzyl bromide (1.43 g) and silver(I) oxide (1.62 g).

$^1$H-NMR (CDCl$_3$, δ ppm): 2.36 (3H, s), 3.88 (3H, s), 4.17 (2H, s), 6.93 (1H, d, J=7.8 Hz), 7.06 (1H, dt, J=1.3 and 7.5 Hz), 7.12 (1H, dt, J=1.5 and 7.6 Hz), 7.30 (1H, d, J=8.4 Hz), 7.39 (1H, dd, J=1.3 and 7.9 Hz), 7.84 (1H, dd, J=1.5 and 8.4 Hz), 8.06 (1H, brs), 8.13 (1H, s).

EXAMPLE 32

Production of 3-(2,4-dichlorobenzoyl)-5-(methoxycarbonyl)-2-methylindole (61)

Aluminium chloride (0.86 g) is suspended in methylene chloride (30 ml), to which are added 2,4-dichlorobenzoyl chloride (0.67 g) and then 5-(methoxycarbonyl)-2-methylindole (0.50 g), and stirred at 50° C. for 3 hours and then at room temperature for 41 hours. The reaction mixture is poured into water with ice, and extracted twice with ethyl acetate. The organic layer is washed twice with a saturated aqueous sodium hydrogencarbonate solution and then with a saturated saline solution, and thereafter dried with anhydrous sodium sulfate. The drying agent is removed through filtration, and the filtrate is concentrated under reduced pressure. The resulting crystal is washed with t-butyl methyl ether, and dried to obtain a crystal of 3-(2,4-dichlorobenzoyl)-5-(methoxycarbonyl)-2-methylindole (61) (0.60 g).

$^1$H-NMR (DMSO-d6, δ ppm): 12.45 (1H, br), 8.20 (1H, s), 7.81 (1H, d, J=1.9 Hz), 7.79 (1H, dd, J=1.7 and 8.4Hz), 7.60 (1H, dd, J=1.9 and 8.3 Hz), 7.48 (1H, d, J=8.1 Hz), 7.47 (1H, d, J=8.3 Hz), 3.81 (3H, s), 2.23 (3H, s).

EXAMPLE 33

Production of 3-(4-benzyloxybenzyl)-5-(methoxycarbonyl)-2-methylindole (62)

A methylene chloride (15 ml) solution of 5-(methoxycarbonyl)-2-methylindole (0.567 g) and 4-benzyloxybenzaldehyde (0.700 g) is dropwise added to a methylene chloride (15 ml) solution of trifluoroacetic acid (0.513 g) and triethylsilane (1.047 g) in an ice-water bath, over a period of 15 minutes. This is stirred for 30 minutes in the ice-water bath, and an aqueous solution of 2 M sodium hydroxide is added thereto to stop the reaction. The organic layer is washed with a saturated saline solution, dried and concentrated. The resulting residue is purified through silica gel column chromatography (eluent: ethyl acetate/hexane=3/7) to obtain 3-(4-benzyloxybenzyl)-5-(methoxycarbonyl)-2-methylindole (62) (0.510 g).

$^1$H-NMR (CDCl$_3$, δ ppm): 2.34 (3H, s), 3.88 (3H, s), 4.01 (2H, s), 4.98 (2H, s), 6.84 (2H, d, J=8.6 Hz), 7.09 (2H, d, J=8.6 Hz), 7.23 (1H, d, J=8.3 Hz), 7.30 (1H, d, J=7.2 Hz), 7.35 (2H, m), 7.39 (2H, m), 7.81 (1H, dd, J=1.5 and 8.4 Hz), 8.12 (1H, brs), 8.19 (1H, s).

EXAMPLE 34

Production of 3-(2,4-dichlorobenzyl)-5-(methoxycarbonyl)-2-propylindole (63)

According to the method of Example 33, obtained is 3-(2,4-dichlorobenzyl)-5-(methoxycarbonyl)-2-propylindole (63) (0.617 g) from 5-(methoxycarbonyl)-2-propylindole (0.652 g), 2,4-dichlorobenzaldehyde (0.578 g), trifluoroacetic acid (0.513 g) and triethylsilane (1.047 g).

$^1$H-NMR (CDCl$_3$, δ ppm): 0.93 (3H, t, J=7.4 Hz), 1.64 (2H, m), 2.68 (2H, t, J=7.7 Hz), 3.88 (3H, s), 4.12 (2H, s), 6.79 (1H, d, J=8.3 Hz), 7.01 (1H, dd, J=2.0 and 8.4 Hz), 7.32 (1H, d, J=8.5 Hz), 7.41 (1H, d, J=2.0 Hz), 7.86 (1H, d, J=8.3 Hz), 8.07 (1H, s), 8.10 (1H, brs).

EXAMPLE 35

Production of 3-(2,4-dichlorobenzyl)-2-ethyl-5-(methoxycarbonyl)indole (64)

According to the method of Example 33, obtained is 3-(2,4-dichlorobenzyl)-2-ethyl-5-(methoxycarbonyl)indole (64) (0.420 g) from 2-ethyl-5-(methoxycarbonyl)indole (0.610 g), 2,4-dichlorobenzaldehyde (0.578 g), trifluoroacetic acid (0.513 g) and triethylsilane (1.047 g).

$^1$H-NMR (CDCl$_3$, δ ppm): 1.24 (3H, t, J=7.6 Hz), 2.73 (2H, q, J=7.6 Hz), 3.89 (3H, s), 4.17 (2H, s), 6.80 (1H, d, J=8.4 Hz), 7.01 (1H, dd, J=2.1 and 8.4 Hz), 7.33 (1H, d, J=8.5 Hz), 7.41 (1H, d, J=2.1 Hz), 7.86 (1H, dd, J=1.5 and 8.5 Hz), 8.08 (1H, s), 8.14 (1H, brs).

EXAMPLE 36

Production of 3-(2,4-dichlorobenzyl)-5-(methoxycarbonyl)indole (65)

From (5-methoxycarbonyl)indole (17.52 g), 2,4-dichlorobenzyl iodide (34.49 g) and silver oxide (28.09 g), obtained is 3-(2,4-dichlorobenzyl)-5-(methoxycarbonyl)indole (65) (5.49 g).

$^1$H-NMR (CDCl$_3$, δ ppm): 3.92 (3H, s), 4.20 (2H, s), 6.98 (1H, d, J=2.3 Hz), 7.09–7.13 (2H, m), 7.38 (1H, d, J=9.1

Hz), 7.42 (1H, d, J=1.9 Hz), 7.92 dd, J=1.5 and 8.5 Hz), 8.22 (1H, brs), 8.31 (1H, d, J=1.2 Hz).

EXAMPLE 37

Production of 3-(1-bromonaphthalen-2-ylmethyl)-5-(methoxycarbonyl)-2-methylindole (66)

According to the method of Example 33, obtained is 3-(1-bromonaphthalen-2-ylmethyl)-5-(methoxycarbonyl)-2-methylindole (66) (0.339 g) from 5-(methoxycarbonyl)-2-methylindole (0.73 g), 1-bromo-2-naphthaldehyde (1.00 g), trifluoroacetic acid (0.662 g) and triethylsilane (1.35 g).

$^1$H-NMR (CDCl$_3$, δ ppm): 2.36 (3H, s), 3.86 (3H, s), 4.43 (2H, s), 7.08 (1H, d, J=8.5 Hz), 7.31 (1H, d, J=8.4 Hz), 7.47 (1H, t, J=8.1 Hz), 7.58–7.61 (2H, m), 7.75 (1H, d, J=8.5 Hz), 7.85 (1H, dd, J=8.5 and 1.6 Hz), 8.05 (1H, brs), 8.1 (1H, s), 8.38 (1H, d, J=8.6 Hz).

EXAMPLE 38

Production of 3-((3-chloropyridin-4-yl)methyl)-5-(methoxycarbonyl)-2-methylindole (67)

According to the method of Example 33, obtained is 3-((3-chloropyridin-4-yl)methyl)-5-(methoxycarbonyl)-2-methylindole (67) (0.355 g) from 5-(methoxycarbonyl)-2-methylindole (0.486 g), 3-chloropyridine-4-carboxyaldehyde (0.40 g), triethylsilane (0.896 g) and trifluoroacetic acid (0.439 g).

$^1$H-NMR (CDCl$_3$, δ ppm): 2.38 (3H, s), 3.89 (3H, s), 4.16 (2H, s), 6.82 (1H, d, J=5.0 Hz), 7.33 (1H, d, J=8.5 Hz), 7.87 (1H, d, J=8.7 Hz), 8.08 (1H, s), 8.20 (1H, brs), 8.25 (1H, d, J=5.0 Hz), 8.57 (1H, s).

EXAMPLE 39

Production of 5-(methoxycarbonyl)-2-methyl-3-(4-(2-phenylethenyl)benzyl)indole (68)

According to the method of Example 33, obtained is 5-(methoxycarbonyl)-2-methyl-3-(4-(2-phenylethenyl)benzyl)indole (68) (0.16 g) from 5-(methoxycarbonyl)-2-methylindole (0.567 g), 4-stilbenecarboxyaldehyde (0.687 g), trifluoroacetic acid (0.513 g) and triethylsilane (1.047 g).

$^1$H-NMR (CDCl$_3$, δ ppm): 2.40 (3H, s), 3.89 (3H, s), 4.10 (2H, s), 7.05 (2H, d, J=4.5 Hz), 7.19 (2H, d, J=8.2 Hz), 7.23 (1H, tt, J=1.0 and 7.4Hz), 7.29 (1H, d, J=8.9 Hz), 7.34 (2H, t, J=7.7 Hz), 7.40 (2H, d, J=8.2 Hz), 7.48 (2H, m), 7.84 (1H, dd, J=1.6 and 8.4Hz), 7.99 (1H, brs), 8.20 (1H, s).

EXAMPLE 40

Production of 3-((4-chloroisoquinolin-3-yl)methyl)-5-(methoxycarbonyl)-2-methylindole (69)

To a mixture of L-tartaric acid (0.600 g), sodium hydroxide (0.160 g), 1,4-dioxane (4 ml) and water (4 ml), added are sodium iodide (0.15 g) and 5-(methoxycarbonyl)-2-methylindole (0.378 g). Then, a 1,4-dioxane (2 ml) solution of 4-chloro-3-(chloromethyl)isoquinoline (0.50 g) is added thereto, and stirred at 100° C. for 56 hours. The reaction mixture is concentrated, and water is added to the residue, which is then extracted with ethyl acetate. The organic layer is dried and concentrated, and the resulting residue is purified through silica gel column chromatography to obtain 3-((4-chloroisoquinolin-3-yl)methyl)-5-(methoxycarbonyl)-2-methylindole (69) (0.14 g).

$^1$H-NMR (CDCl$_3$, δ ppm): 2.50 (3H, s), 3.89 (3H, s), 4.58 (2H, s), 7.22 (1H, d, J=8.4 Hz), 7.59 (1H, m), 7.75–7.79 (2H, m), 7.93 (1H, d, J=8.1 Hz), 7.98 brs), 8.22 (1H, d, J=8.4 Hz), 8.45 (1H, s), 9.11 (1H, s).

EXAMPLE 41

Production of 3-((4-bromoisoquinolin-3-yl)methyl)-5-(methoxycarbonyl)-2-methylindole (70)

According to the method of Example 40, obtained is 3-((4-bromoisoquinolin-3-yl)methyl)-5-(methoxycarbonyl)-2-methylindole (70) (0.178 g) from 5-(methoxycarbonyl)-2-methylindole (0.687 g), 4-bromo-3-(bromomethyl)isoquinoline (1.31 g), L-tartaric acid (1.088 g), sodium hydroxide (0.290 g) and sodium iodide (0.217 g).

$^1$H-NMR (CDCl$_3$, δ ppm): 2.32 (3H, s), 3.86 (3H, s), 4.60 (2H, s), 7.07 (1H, d, J=8.4Hz), 7.54 (1H, t, J=7.6 Hz), 7.72 (2H, m), 7.82 (1H, d, J=8.2 Hz), 8.19 (1H, d, J=8.5 Hz), 8.37 (1H, s), 8.51 (1H, brs), 9.03 (1H, s).

EXAMPLE 42

Production of 2-(2,4-dichlorobenzoyl)-6-(methoxycarbonyl)-3-methylindole (71)

Aluminium chloride (1.72 g) is suspended in methylene chloride (50 ml), to which are added 2,4-dichlorobenzoyl chloride (1.35 g) and then 6-(methoxycarbonyl)-3-methylindole (1.00 g), and stirred at room temperature for 16 hours and then at 40° C. for 2.5 hours. The reaction mixture is poured into water with ice, and then extracted with ethyl acetate (150 ml). The organic layer is washed three times with a saturated aqueous sodium hydrogencarbonate solution (50 ml) and then with a saturated saline solution, and thereafter dried with anhydrous sodium sulfate. The drying agent is removed through filtration, and the filtrate is concentrated under reduced pressure. The resulting crystal is washed with methyl t-butyl ether and dried to obtain 2-(2,4-dichlorobenzoyl)-6-(methoxycarbonyl)-3-methylindole (71) (1.48 g).

$^1$H-NMR (CDCl$_3$, δ ppm): 2.07 (3H, s), 3.96 (3H, s), 7.36 (1H, d, J=8.2 Hz), 7.42 (1H, dd, J=1.9 and 8.3 Hz), 7.54 (1H, d, J=1.8 Hz), 7.69 (1H, d, J=8.7 Hz), 7.81 (1H, dd, J=1.4 and 8.6 Hz), 8.15 (1H, s), 9.12 (1H, brs).

EXAMPLE 43

Production of 1-(2,4-dichlorobenzyl)-6-methoxycarbonyl)-3-methylindole (72)

6-(Methoxycarbonyl)-3-methylindole (0.57 g) is dissolved in N,N-dimethylformamide (10 ml), to which is added sodium hydride (60% oily, 0.145 g) with cooling with ice. Then, 2,4-dichlorobenzyl chloride (0.707 g) is added thereto, and stirred at room temperature for 1.5 hours. Water is added to the reaction mixture, which is then extracted with ethyl acetate. The organic layer is washed with a saturated saline solution, and dried with anhydrous magnesium sulfate. The drying agent is removed through filtration, and the filtrate is concentrated under reduced pressure. The resulting residue is purified through silica gel column chromatography (eluent: hexane/ethyl acetate=9/1) to obtain 1-(2,4-dichlorobenzyl)-6-(methoxycarbonyl)-3-methylindole (72) (0.83 g).

$^1$H-NMR (CDCl$_3$, δ ppm): 2.35 (3H, d, J=0.7 Hz), 3.91 (3H, s), 5.36 (2H, s), 6.48 (1H, d, J=8.3 Hz), 7.01 (1H, d, J=0.8 Hz), 7.05 (1H, dd, J=2.1 and 8.3 Hz), 7.43 (1H, d, J=2.0 Hz), 7.61 (1H, d, J=8.3 Hz), 7.82 (1H, dd, J=1.3 and 8.3 Hz), 7.96 (1H, s).

EXAMPLE 44

Production of 6-carboxy-3-(2,4-dichlorobenzyl)-2-methylindole (73)

A mixture of 3-(2,4-dichlorobenzyl)-6-(methoxycarbonyl)-2-methylindole (0.330 g), ethanol (15 ml) and 10% aqueous sodium hydroxide (10 ml) is heated under reflux for 1.5 hours. This is processed with hydrochloric acid to have a pH of 3, and the crystal formed is taken out through filtration. This is dried to obtain 6-carboxy-3-(2,4-dichlorobenzyl)-2-methylindole (73) (0.305 g).
[Physical Properties of Compound (73)]
¹H-NMR (DMSO-d6, ppm): 2.35 (3H, s), 4.06 (2H, s), 7.01 (1H, d, J=8.4 Hz), 7.26 (2H, m), 7.49 (1H, d, J=8.3 Hz), 7.57 (1H, d, J=2.0 Hz), 7.89 (1H, s), 11.38 (1H, s).

EXAMPLE 45

Production of 3-(biphenyl-4-ylmethyl)-5-carboxy-2-methylindole (74)

According to the method of Example 44, obtained is 3-(biphenyl-4-ylmethyl)-5-carboxy-2-methylindole (74) (0.359 g) from 3-(biphenyl-4-ylmethyl)-5-(methoxycarbonyl)-2-methylindole (0.381 g).

¹H-NMR (DMSO-d6, δ ppm): 2.37 (3H, s), 4.06 (2H, s), 7.26 (2H, d, J=8.1 Hz), 7.30 (2H, m), 7.41 (2H, t, J=7.6 Hz), 7.52 (2H, d, J=8.1 Hz), 7.58 (2H, d, J=7.7 Hz), 7.61 (1H, dd, J=1.5 and 8.5 Hz), 8.01 (1H, s), 11.24 (1H, s), 12.29 (1H, brs).

EXAMPLE 46

Production of 5-carboxy-3-(2-chlorobenzyl)-2-methylindole (75)

According to the method of Example 44, obtained is 5-carboxy-3-(2-chlorobenzyl)-2-methylindole (75) (0.164 g) from 3-(2-chlorobenzyl)-5-(methoxycarbonyl)-2-methylindole (0.179 g).

¹H-NMR (DMSO-d6, δ ppm): 2.34 (3H, s), 4.10 (2H, s), 7.00 (1H, dd, J=2.0 and 7.6 Hz), 7.18 (2H, m), 7.30 (1H, d, J=8.4 Hz), 7.43 (1H, dd, J=1.6 and 7.5 Hz), 7.61 (1H, dd, J=1.5 and 8.4 Hz), 7.89 (1H, s), 11.25 (1H, s), 12.22 (1H, brs).

EXAMPLE 47

Production of 5-carboxy-3-(2,4-dichlorobenzoyl)-2-methylindole (76)

3-(2,4-Dichlorobenzoyl)-5-(methoxycarbonyl)-2-methylindole (0.60 g) is suspended in ethanol (10 ml), to which is added an aqueous solution of 1.5 M sodium hydroxide (5 ml), and heated under reflux for 3 hours. The reaction mixture is concentrated under reduced pressure, and the residue is made acidic with water and 3 M HCl added thereto. The crystal formed is taken out through filtration, then suspended in ethanol-toluene, and concentrated under reduced pressure for azeotropic dehydration. Next, this is dried on calcium chloride in a vacuum desiccator to obtain a crystal of 5-carboxy-3-(2,4-dichlorobenzoyl)-2-methylindole (76) (0.56 g).

¹H-NMR (DMSO-d6, δ ppm): 2.22 (3H, s), 7.45 (1H, d, J=8.4 Hz), 7.48 (1H, d, J=8.2 Hz), 7.58 (1H, dd, J=1.9 and 8.0 Hz), 7.78 (1H, dd, J=1.5 and 8.4 Hz), 7.80 (1H, d, J=1.9 Hz), 8.24 (1H, brs), 12.43 (1H, brs).

EXAMPLE 48

Production of 3-(4-benzyloxybenzyl)-5-carboxy-2-methylindole (77)

From 3-(4-benzyloxybenzyl)-5-(methoxycarbonyl)-2-methylindole (0.500 g), obtained is 3-(4-benzyloxybenzyl)-5-carboxy-2-methylindole (77) (0.465 g).
[Physical Properties of Compound (77)]
¹H-NMR (DMSO-d6, ppm): 2.37 (3H, s), 3.94 (2H, s), 5.01 (2H, s), 6.87 (2H, d, J=8.6 Hz), 7.08 (2H, d, J=8.6 Hz), 7.27 (1H, d, J=8.5 Hz), 7.30 (1H, d, J=7.3 Hz), 7.34–7.40 (4H, m), 7.60 (1H, dd, J=1.5 and 8.5 Hz), 7.95 (1H, s), 11.15 (1H, s), 12.26 (1H, s).

EXAMPLE 49

Production of 5-carboxy-3-(2,4-dichlorobenzyl)-2-propylindole (78)

According to the method of Example 44, obtained is 5-carboxy-3-(2,4-dichlorobenzyl)-2-propylindole (78) (0.188 g) from 3-(2,4-dichlorobenzyl)-5-(methoxycarbonyl)-2-propylindole (0.610 g).

¹H-NMR (DMSO-d6, δ ppm): 0.85 (3H, t, J=7.3 Hz), 1.60 (2H, m), 2.67 (2H, t, J=7.4 Hz), 4.09 (2H, s), 6.91 (1H, d, J=8.4 Hz), 7.25 (1H, dd, J=2.3 and 8.4 Hz), 7.32 (1H, d, J=8.4 Hz), 7.61 (1H, d, J=2.1 Hz), 7.63 (1H, dd, J=1.5 and 8.4 Hz), 7.86 (1H, s), 11.28 (1H, brs), 12.30 (1H, brs).

EXAMPLE 50

Production of 5-carboxy-3-(2,4-dichlorobenzyl)-2-ethylindole (79)

According to the method of Example 44, obtained is 5-carboxy-3-(2,4-dichlorobenzyl)-2-ethylindole (79) (0.373 g) from 3-(2,4-dichlorobenzyl)-2-ethyl-5-(methoxycarbonyl)indole (0.410 g).

¹H-NMR (DMSO-d6, δ ppm): 1.17 (3H, t, J=7.5 Hz), 2.71 (2H, q, J=7.6 Hz), 4.09 (2H, s), 6.92 (1H, d, J=8.4 Hz), 7.26 (1H, dd, J=2.2 and 8.3 Hz), 7.33 (1H, d, J=8.5 Hz), 7.60 (1H, d, J=2.1 Hz), 7.63 (1H, dd, J=1.5 and 8.4 Hz), 7,87 (1H, d, J=1.0 Hz), 11.33 (1H, brs), 12.29 (1H, brs).

EXAMPLE 51

Production of 5-carboxy-3-(2,4-dichlorobenzyl)indole (80)

According to the method of Example 44, obtained is 5-carboxy-3-(2,4-dichlorobenzyl)indole (80) (4.64 g) from 3-(2,4-dichlorobenzyl)-5-(methoxycarbonyl)indole (5.02 g).

¹H-NMR (DMSO-d6, δ ppm): 4.15 (2H, s), 7.22–7.24 (2H, m), 7.31 (1H, dd, J=2.0 and 8.3 Hz), 7.41 (1H, d, J=8.7 Hz), 7.59 (1H, d, J=2.0 Hz), 7.71 (1H, dd, J=1.4 and 8.7 Hz), 8.12 (1H, brs), 11.30 (1H, brs), 12.39 (1H, brs).

EXAMPLE 52

Production of 3-(1-bromonaphthalen-2-ylmethyl)-5-carboxy-2-methylindole (81)

According to the method of Example 44, obtained is 3-(1-bromonaphthalen-2-ylmethyl)-5-carboxy-2-methylindole (81) (0.300 g) from 3-(1-bromonaphthalen-2-ylmethyl)-5-(methoxycarbonyl)-2-methylindole (0.325 g).

¹H-NMR (DMSO-d6, δ ppm): 2.35 (3H, s), 4.34 (2H, s), 7.13 (1H, d, J=8.5 Hz), 7.15 (1H, d, J=8.5 Hz), 7.54 (1H, t, J=7.1 Hz), 7.63–7.69 (2H, m), 7.75 (1H, d, J=8.5 Hz), 7.88 (2H, m), 8.27 (1H, d, J=7.7 Hz), 10.99 (1H, s).

EXAMPLE 53

Production of 5-carboxy-3-((3-chloropyridin-4-yl)methyl)-2-methylindole (82)

According to the method of Example 44, obtained is 5-carboxy-3-((3-chloropyridin-4-yl)methyl)-2-methylindole (82) (0.380 g) from 3-((3-chloropyridin-4-yl)methyl)-5-(methoxycarbonyl)-2-methylindole (0.431 g).

¹H-NMR (DMSO-d6, δ ppm): 2.36 (3H, s), 4.15 (2H, s), 6.99 (1H, d, J=5.0 Hz), 7.32 (1H, d, J=8.4 Hz), 7.64 (1H, d, J=8.5 Hz), 7.90 (1H, s), 8.33 (1H, d, J=4.9 Hz), 8.59 (1H, s), 11.34 (1H, s), 12.31 (1H, brs).

EXAMPLE 54

Production of 5-carboxy-2-methyl-3-(4-(2-phenylethenyl)benzyl)indole (83)

According to the method of Example 44, obtained is 5-carboxy-2-methyl-3-(4-(2-phenylethenyl)benzyl)indole (83) (0.095 g) from 5-(methoxycarbonyl)-2-methyl-3-(4-(2-phenylethenyl)benzyl)indole (0.16 g).

¹H-NMR (DMSO-d6, δ ppm): 2.39 (3H, s), 4.03 (2H, s), 7.16 (2H, d, J=7.5 Hz), 7.19 (2H, d, J=8.1 Hz), 7.23 (1H, t, J=7.4 Hz), 7.29 (1H, d, J=8.4 Hz), 7.34 (2H, t, J=7.6 Hz), 7.47 (2H, d, J=8.0 Hz), 7.55 (2H, d, J=7.9 Hz), 7.61 (1H, d, J=8.4 Hz), 7.98 (1H, s), 11.22 (1H, s), 12.27 (1H, s).

EXAMPLE 55
Production of 5-carboxy-3-((4-chloroisoquinolin-3-yl)methyl)-2-methylindole (84)

From 3-((4-chloroisoquinolin-3-yl)methyl)-5-(methoxycarbonyl)-2-methylindole (0.140 g), obtained is 5-carboxy-3-((4-chloroisoquinolin-3-yl)methyl)-2-methylindole (84) (0.112 g). This is directly used in the next reaction.

EXAMPLE 56
Production of 3-((4-bromoisoquinolin-3-yl)methyl)-5-carboxy-2-methylindole (85)

According to the method of Example 44, obtained is 3-((4-bromoisoquinolin-3-yl)methyl)-5-carboxy-2-methylindole (85) (0.123 g) from 3-((4-bromoisoquinolin-3-yl)methyl)-5-(methoxycarbonyl)-2-methylindole (0.178 g).

$^1$H-NMR (DMSO-d6, δ ppm): 2.38 (3H, s), 4.49 (2H, s), 7.04 (1H, d, J=8.2 Hz), 7.59 (1H, d, J=8.3 Hz), 7.70 (1H, t, J=7.5 Hz), 7.89 (1H, t, J=7.6 Hz), 8.07 (1H, s), 8.11 (1H, d, J=8.3Hz), 8.14 (1H, d, J=8.7Hz), 9.19 (1H, s), 10.74 (1H, s).

EXAMPLE 57
Production of 6-carboxy-2-(2,4-dichlorobenzyl)-3-methylindole (86)

2-(2,4-Dichlorobenzoyl)-6-(methoxycarbonyl)-3-methylindole (1.00 g) is suspended in ethylene glycol (10 ml), to which is added hydrazine monohydrate (0.83 g), and stirred under heat at 160° C. for 3 hours. After this is once cooled, potassium hydroxide (1.1 g) is added thereto, and again stirred under heat at 155° C. for 3 hours. After cooled, the reaction mixture is made acidic with water and 1 M HCl added thereto. Then, this is extracted with ethyl acetate. The organic layer is washed with a saturated saline solution, and dried with anhydrous sodium sulfate. Then, the drying agent is removed through filtration, and the filtrate is concentrated under reduced pressure. The resulting crystalline residue is washed with a mixed solution of ethyl acetate and hexane, and dried to obtain 6-carboxy-2-(2,4-dichlorobenzyl)-3-methylindole (86) (0.63 g).

$^1$H-NMR (DMSO-d6, δ ppm): 2.18 (3H, s), 4.17 (2H, s), 7.12 (1H, d, J=8.3 Hz), 7.35 (1H, dd, J=2.1 and 8.3 Hz), 7.47 (1H, d, J=8.3 Hz), 7.58 (1H, dd, J=1.0 and 8.2Hz), 7.62 (1H, d, J=2.1 Hz), 7.89 (1H, s), 11.02 (1H, brs).

EXAMPLE 58
Production of 6-carboxy-1-(2,4-dichlorobenzyl)-3-methylindole (87)

According to the method of Example 44, obtained is 6-carboxy-1-(2,4-dichlorobenzyl)-3-methylindole (87) (0.46 g) from 1-(2,4-dichlorobenzyl)-6-(methoxycarbonyl)-3-methylindole (0.50 g).

$^1$H-NMR (DMSO-d6, δ ppm): 12.55 (1H, brs), 7.95 (1H, s), 7.68 (1H, d, J=2.1 Hz), 7.65 (1H, dd, J=1.2 and 8.3 Hz), 7.59 (1H, d, J=8.3 Hz), 7.40 (1H, s), 7.32 (1H, dd, J=2.0 and 8.3 Hz), 6.61 (1H, d, J=8.3 Hz), 5.51 (2H, s), 2.27 (3H, s).

EXAMPLE 59
Production of 3-(2,4-dichlorobenzyl)-5-(1-pentanesulfonylcarbamoyl)indole (88)

N,N'-Carbonyldiimidazole (0.282 g) is added to an N,N-dimethylfornamide (4.3 ml) solution of 5-carboxy-3-(2,4-dichlorobenzyl)indole (0.429 g), and stirred at room temperature for 1 hour. Diazabicycloundecene (0.306 g) and 1-pentanesulfonamide (0.304 g) are added thereto, and stirred at 100° C. for 40 hours. The reaction mixture is cooled, and then made acidic with water and 1M HCl added thereto. Then, the gummy residue formed is collected. This is dissolved in ethyl acetate, washed with water, and dried. The solvent is evaporated away, and the resulting residue is crystallized from ether. The crystal formed is collected and dried to obtain 3-(2,4-dichlorobenzyl)-5-(1-pentanesulfonylcarbamoyl)indole (88) (0.258 g).

$^1$H-NMR (DMSO-d6, δ ppm): 0.83 (3H, t, J=6.0 Hz), 1.22–1.43 (4H, m), 1.70 (2H, m), 3.52 (2H, t, J=6.0Hz), 4.18 (2H, s), 7.21–7.28 (2H, m), 7.35 (1H, d, J=8.0 Hz), 7.46 (1H, d, J=8.0 Hz), 7.62 (1H, s), 7.72 (1H, d, J=8.0 Hz), 8.28 (1H, s), 11.38 (1H, s), 11.76 (1H, s).

m.p.: 157–158° C.

EXAMPLE 60
Production of 3-(2,4-dichlorobenzyl)-2-methyl-5-(1-pentanesulfonylcarbamoyl)indole (89)

According to the method of Example 59, obtained is 3-(2,4-dichlorobenzyl)-2-methyl-5-(1-pentanesulfonylcarbamoyl)indole (89) (0.907 g) from 5-carboxy-3-(2,4-dichlorobenzyl)-2-methylindole (1.00 g), N,N'-carbonyldiimidazole (0.631 g), 1-pentanesulfonamide (0.588 g) and diazabicycloundecene (0.592 g).

$^1$H-NMR (DMSO-d6, δ ppm): 0.80 (3H, t, J=7.3 Hz), 1.25 (2H, m), 1.34 (2H, m), 1.67 (2H, m), 2.30 (3H, s), 3.47 (2H, t, J=7.7 Hz), 4.08 (2H, s), 6.93 (1H, d, J=8.4 Hz), 7.25 (1H, dd, J=8.4 and 2.1 Hz), 7.35 (1H, d, J=8.5 Hz), 7.60 (1H, d, J=2.1 Hz), 7.63 (1H, dd, J=8.5 and 1.6 Hz), 8.03 (1H, s), 11.38 (1H, s), 11.67 (1H, s).

IR (Nujol): 1682 cm$^{-1}$.

m.p.: 177–178.5° C.

EXAMPLE 61
Production of 6-(1-butanesulfonylcarbamoyl)-3-(2,4-dichlorobenzyl)-2-methylindole (90)

According to the method of Example 59, obtained is 6-(1-butanesulfonylcarbamoyl)-3-(2,4-dichlorobenzyl)-2-methylindole (90) (0.133 g) from 6-carboxy-3-(2,4-dichlorobenzyl)-2-methylindole (0.300 g), N,N'-carbonyldiimidazole (0.292 g), diazabicycloundecene (0.274 g) and 1-butanesulfonamide (0.247 g).

$^1$H-NMR (DMSO-d6, δ ppm): 0.86 (3H, t, J=7.4 Hz), 1.41 (2H, m), 1.66 (2H, m), 2.37 (3H, s), 3.50 (2H, t, J=7.7 Hz), 4.07 (2H, s), 7.01 (1H, d, J=8.4 Hz), 7.27 (2H, m), 7.49 (1H, d, J=8.4 Hz), 7.59 (1H, d, J=2.0 Hz), 7.92 (1H, s), 11.43 (1H, s), 11.78 (1H, s).

IR (Nujol): 1688 cm$^{-1}$.

Mass (FD): m/e 452 (M).

m.p.: 249–250° C.

EXAMPLE 62
Production of 3-(2,4-dichlorobenzyl)-2-methyl-5-(1-propanesulfonylcarbamoyl)indole (91)

According to the method of Example 59, obtained is 3-(2,4-dichlorobenzyl)-2-methyl-5-(1-propanesulfonylcarbamoyl)indole (91) (0.233 g) from 5-carboxy-3-(2,4-dichlorobenzyl)-2-methylindole (0.267 g), N,N'-carbonyldiimidazole (0.195 g), diazabicycloundecene (0.183 g) and 1-propanesulfonamide (0.148 g).

$^1$H-NMR (DMSO-d6, δ ppm): 0.97 (3H, t, J=7.4 Hz), 1.70 (2H, m), 2.30 (3H, s), 3.46 (2H, t, J=7.6 Hz), 4.08 (2H, s), 6.93 (1H, d, J=8.3 Hz), 7.26 (1H, dd, J=8.3 and 2.1 Hz), 7.35 (1H, d, J=8.5 Hz), 7.63 (2H, m), 8.04 (1H, s), 11.39 (1H, s), 11.68 (1H, s).

IR (Nujol): 1673 cm$^{-1}$.
Mass (FD): m/e 438 (M).
m.p.: 161–163° C.

EXAMPLE 63
Production of 3-(2,4-dichlorobenzyl)-2-methyl-5-(1-octanesulfonylcarbamoyl)indole (92)

According to the method of Example 59, obtained is 3-(2,4-dichlorobenzyl)-2-methyl-5-(1-octanesulfonylcarbamoyl)indole (92) (0.280 g) from 5-carboxy-3-(2,4-dichlorobenzyl)-2-methylindole (0.300 g), N,N'-carbonyldiimidazole (0.218 g), 1-octanesulfonamide (0.260 g) and diazabicycloundecene (0.205 g).

$^1$H-NMR (DMSO-d6, δ ppm): 0.80 (3H, t), 1.12–1.27 (8H, m), 1.35 (2H, m), 1.65 (2H, m), 2.30 (3H, s), 3.46 (2H, m), 4.08 (2H, s), 6.92 (1H, d, J=8.4 Hz), 7.25 (1H, dd, J=8.4 and 2.1 Hz), 7.34 (1H, d, J=8.5 Hz), 7.59–7.65 (2H, m), 8.03 (1H, s), 11.38 (1H, s), 11.67 (1H, s).

IR (Nujol): 1673 cm$^{-1}$.
m.p.: 194.5–197.5° C.

EXAMPLE 64
Production of 5-(benzenesulfonylcarbamoyl)-3-(2,4-dichlorobenzyl)-2-methylindole (93)

According to the method of Example 59, obtained is 5-(benzenesulfonylcarbamoyl)-3-(2,4-dichlorobenzyl)-2-methylindole (93) (0.235 g) from 5-carboxy-3-(2,4-dichlorobenzyl)-2-methylindole (0.267 g), N,N'-carbonyldiimidazole (0.195 g), benzenesulfonamide (0.189 g) and diazabicycloundecene (0.183 g).

$^1$H-NMR (DMSO-d6, δ ppm): 2.28 (3H, s), 4.07 (2H, s), 6.90 (1H, d, J=8.4 Hz), 7.25 (1H, dd, J=8.4 and 2.2 Hz), 7.31 (1H, d, J=8.5 Hz), 7.54 (1H, dd, J=8.6 and 1.6 Hz), 7.59–7.63 (3H, m), 7.68 (1H, m), 7.97 (3H, m), 11.37 (1H, s), 12.19 (1H, brs).

IR (Nujol): 1682 cm$^{-1}$.
Mass (FD): m/e 472 (M)
m.p.: 244–245° C.

EXAMPLE 65
Production of 3-(2,4-dichlorobenzyl)-5-(1-hexanesulfonylcarbamoyl)-2-methylindole (94)

According to the method of Example 59, obtained is 3-(2,4-dichlorobenzyl)-5-(1-hexanesulfonylcarbamoyl)-2-methylindole (94) (0.188 g) from 5-carboxy-3-(2,4-dichlorobenzyl)-2-methylindole (0.267 g), N,N'-carbonyldiimidazole (0.195 g), diazabicycloundecene (0.183 g) and 1-hexanesulfonamide (0.198 g).

$^1$H-NMR (DMSO-d6, δ ppm): 0.80 (3H, d, J=7.0 Hz), 1.21 (4H, m), 1.36 (2H, m), 1.66 (2H, m), 2.30 (3H, s), 3.47 (2H, t, J=7.7 Hz), 4.08 (2H, s), 6.92 (1H, d, J=8.5 Hz), 7.25 (1H, dd, J=8.4 and 1.2 Hz), 7.35 (1H, d, J=8.5 Hz), 7.62 (2H, m), 8.03 (1H, s), 11.39 (1H, s), 11.67 (1H, s).

IR (Nujol): 1667 cm$^{-1}$.
Mass (FD): m/e 480 (M)
m.p.: 183–185° C.

EXAMPLE 66
Production of 3-(biphenyl-4-ylmethyl)-2-methyl-5-(1-pentanesulfonylcarbamoyl)indole (95)

According to the method of Example 59, obtained is 3-(biphenyl-4-ylmethyl)-2-methyl-5-(1-pentanesulfonylcarbamoyl)indole (95) (0.147 g) from 3-(biphenyl-4-ylmethyl)-5-carboxy-2-methylindole (0.355 g), N,N'-carbonyldiimidazole (0.253 g), diazabicycloundecene (0.237 g) and 1-pentanesulfonamide (0.236).

$^1$H-NMR (DMSO-d6, δ ppm): 0.80 (3H, t, J=7.3 Hz), 1.26 (2H, m). 1.35 (2H, m), 1.68 (2H, m), 2.39 (3H, s), 3.49 (2H, t, J=7.7 Hz), 4.07 (2H, s), 7.29–7.33 (4H, m), 7.41 (2H, t, J=7.7 Hz), 7.53 (2H, d, J=8.2 Hz), 7.59 (2H, m), 7.62 (1H, dd, J=8.6 and 1.6 Hz), 8.21 (1H, s), 11.29 (1H, s), 11.73 (1H, s).

IR (Nujol): 1664 cm$^{-1}$.
Mass (FD): m/e 474 (M)
m.p.: 189–190° C.

EXAMPLE 67
Production of 3-(2-chlorobenzyl)-2-methyl-5-(1-pentanesulfonylcarbamoyl)indole (96)

According to the method of Example 59, obtained is 3-(2-chlorobenzyl)-2-methyl-5-(1-pentanesulfonylcarbamoyl)indole (96) (0.115 g) from 5-carboxy-3-(2-chlorobenzyl)-2-methylindole (0.164 g), N,N'-carbonyldiimidazole (0.133 g), diazabicycloundecene (0.125 g) and 1-pentanesulfonamide (0.124).

$^1$H-NMR (DMSO-d6, δ ppm): 0.81 (3H, t, J=7.3 Hz), 1.26 (2H, m), 1.34 (2H, m), 1.66 (2H, m), 2.30 (3H, s), 3.47 (2H, t, J=7.8 Hz), 4.11 (2H, s), 6.95 (1H, dd, J=1.6 and 7.6 Hz), 7.15–7.21 (2H, m), 7.34 (1H, d, J=8.5 Hz), 7.45 (1H, dd, J=1.3 and 7.8 Hz), 7.62 (1H, dd, J1.6 and 8.5 Hz), 8.05 (1H, d, J=1.0 Hz), 11.36 (1H, s), 11.68 (1H, s).

IR(Nujol): 1671 cm$^{-1}$.
Mass (FD): m/e 432 (M)
m.p.: 175–177° C.

EXAMPLE 68
Production of 5-(1-butanesulfonylcarbamoyl)-3-(2,4-dichlorobenzoyl)-2-methylindole (97)

According to the method of Example 59, 5-carboxy-3-(2,4-dichlorobenzoyl)-2-methylindole (0.500 g) is suspended in N,N-dimethylformamide (10 ml), to which is added N,N'-carbonyldiimidazole (0.350 g), and stirred at room temperature for 2 hours. Next, 1-butanesulfonamide (0.296 g) and diazabicycloundecene (0.328 g) are added thereto, and stirred under heat at 100° C. for 6 hours. The reaction mixture is concentrated under reduced pressure, and the residue is made acidic with water and 3 M HCl added thereto, and then extracted with ethyl acetate. The organic layer is washed with a saturated saline solution, and dried with anhydrous sodium sulfate. The drying agent is removed through filtration, and the filtrate is concentrated under reduced pressure. The resulting oily residue is purified through silica gel column chromatography (eluent: chloroform/methanol=10/1), and recrystallized from ethanol-hexane to obtain a colorless crystal of 5-(1-butanesulfonylcarbamoyl)-3-(2,4-dichlorobenzoyl)-2-methylindole (97) (0.420 g).

$^1$H-NMR (DMSO-d6, δ ppm): 0.86 (3H, t, J=7.3 Hz), 1.41 (2H, sextet, J=7.4 Hz), 1.66 (2H, qunit, J=7.4 Hz), 2.13 (3H, s), 3.48 (2H, m), 7.47 (1H, d, J=8.6 Hz), 7.48 (1H, d, J=8.2 Hz), 7.58 (1H, dd, J=8.0 and 2.0 Hz), 7.75 (1H, dd, J=8.6 and 1.8 Hz), 7.80 (1H, d, J=2.0 Hz), 8.44 (1H, brs), 12.05 (1H, brs), 12.43 (1H, brs).

IR (Nujol): 1686, 1571 cm$^{-1}$.
Mass (FD): m/e 466 (M)
m.p.: 241–243° C.

EXAMPLE 69
Production of 3-(2,4-dichlorobenzyl)-2-methyl-5-(3-methyl-1-butanesulfonylcarbamoyl)indole (98)

According to the method of Example 59, obtained is 3-(2,4-dichlorobenzyl)-2-methyl-5-(3-methyl-1-butanesulfonylcarbamoyl)indole (98) (0.270 g) from 5-carboxy-3-(2,4-dichlorobenzyl)-2-methylindole (0.290 g), N,N'-carbonyldiimidazole (0.211 g), diazabicycloundecene (0.198 g) and 3-methyl-1-butanesulfonamide (0.197 g).

¹H-NMR (DMSO-d6, δ ppm): 0.84 (6H, d, J=6.6 Hz), 1.55 (2H, m), 1.65 (1H, m), 2.30 (2H, s), 3,48 (2H, t, J=7.9 Hz), 4.08 (2H, s), 6.93 (1H, d, J=8.4 Hz), 7.25 (1H, dd, J=2.2 and 8.4 Hz), 7.34 (1H, d, J=8.6 Hz), 7.60 (1H, d, J=2.1 Hz), 7.62 (1H, dd, J=1.6 and 8.6 Hz), 8.02 (1H, s), 11.38 (1H, s), 11.68 (1H, s).
IR (Nujol): 1682 cm⁻¹.
Mass (FD): m/e 466 (M)
m.p.: 167–169° C.

EXAMPLE 70
Production of 3-(2,4-dichlorobenzyl)-5-(2-methoxyethanesulfonylcarbamoyl)-2-methylindole (99)

According to the method of Example 59, obtained is 3-(2,4-dichlorobenzyl)-5-(2-methoxyethanesulfonylcarbamoyl)-2-methylindole (99) (0.056 g) from 5-carboxy-3-(2,4-dichlorobenzyl)-2-methylindole (0.290 g), N,N'-carbonyldiimidazole (0.211 g), diazabicycloundecene (0.198 g) and 2-methoxyethanesulfonamide (0.181 g).

¹H-NMR (DMSO-d6, δ ppm): 2.30 (3H, s), 3.13 (3H, s), 3.59 (4H, m), 4.08 (2H, s), 6.92 (1H, d, J=8.4 Hz), 7.25 (1H, dd, J=2.1 and 8.4 Hz), 7.34 (1H, d, J=8.5 Hz), 7.61 (2H, m), 8.01 (1H, s), 11.37 (1H, s), 11.72 (1H, s).
IR (Nujol): 1671 cm⁻¹.
m.p.: 166–168° C.

EXAMPLE 71
Production of 3-(4-benzyloxybenzyl)-2-methyl-5-(1-pentanesulfonylcarbamoyl)indole (100)

According to the method of Example 59, obtained is 3-(4-benzyloxybenzyl)-2-methyl-5-(1-pentanesulfonylcarbamoyl)indole (100) (0.270 g) from 3-(4-benzyloxybenzyl)-5-carboxy-2-methylindole (0.460 g), N,N'-carbonyldiimidazole (0.301 g), diazabicycloundecene (0.283 g) and 1-pentanesulfonamide (0.281 g).

¹H-NMR (DMSO-d6, δ ppm): 0.81 (3H, t, J=7.2 Hz), 1.26 (2H, m), 1.35 (2H, m), 1.67 (2H, m), 2.34 (3H, s), 3.43 (2H, t, J=7.6 Hz), 3.95 (2H, s), 5.01 (2H, s), 6.87 (2H, d, J=8.1Hz), 7.11 (2H, d, J=8.2 Hz), 7.25–7.41 (6H, m), 7.61 (1H, d, J=8.6 Hz), 8.13 (1H, s), 11.17 (1H, s), 11.76 (1H, brs).
IR (Nujol): 1652 cm⁻¹.
Mass (FD): m/e 504 (M).
m.p.: 180–184° C.

EXAMPLE 72
Production of 3-(2,4-dichlorobenzyl)-5-(1-pentanesulfonylcarbamoyl)-2-propylindole (101)

According to the method of Example 59, obtained is 3-(2,4-dichlorobenzyl)-5-(1-pentanesulfonylcarbamoyl)-2-propylindole (101) (0.167 g) from 5-carboxy-3-(2,4-dichlorobenzyl)-2-propylindole (0.185 g), N,N'-carbonyldiimidazole (0.125 g), diazabicycloundecene (0.117 g) and 1-pentanesulfonamide (0.116 g).

¹H-NMR (DMSO-d6, δ ppm): 0.81 (6H, m), 1.25 (2H, m), 1.34 (2H, m), 1.57 (2H, m), 1.66 (2H, m), 2.63 (2H, t, J=7.5 Hz), 3.47 (2H, t, J=7.7 Hz), 4.09 (2H, s), 6.87 (1H, d, J=8.4 Hz), 7.25 (1H, d, J=8.4 Hz), 7.36 (1H, d, J=8.5 Hz), 7.62 (2H, m), 8.04 (1H, s), 11.38 (1H, s), 11.68 (1H, s).
IR (Nujol): 1682 cm⁻¹.
Mass (FD): m/e 494 (M).
m.p.: 168–169° C.

EXAMPLE 73
Production of 3-(2,4-dichlorobenzyl)-2-ethyl-5-(1-pentanesulfonylcarbamoyl)indole (102)

According to the method of Example 59, obtained is 3-(2,4-dichlorobenzyl)-2-ethyl-5-(1-pentanesulfonylcarbamoyl)indole (102) (0.255 g) from 5-carboxy-3-(2,4-dichlorobenzyl)-2-ethylindole (0.370 g), N,N'-carbonyldiimidazole (0.259 g), diazabicycloundecene (0.243 g) and 1-pentanesulfonamide (0.242 g).

¹H-NMR (DMSO-d6, δ ppm): 0.80 (3H, t, J=7.3 Hz), 1.14 (3H, t, J=7.6 Hz), 1.25 (2H, m), 1.34 (2H, m), 1.66 (2H, m), 2.67 (2H, q, J=7.6 Hz), 3,47 (2H, t, J=7.8 Hz), 4.09 (2H, s), 6.87 (1H, d, J=8.4 Hz), 7.25 (1H, dd, J=1.9 and 8.4 Hz), 7.37 (1H, d, J=8.5 Hz), 7.63 (2H, m), 8.04 (1H, s), 11.40 (1H, s), 11.68 (1H, s).
IR (Nujol): 1671 cm⁻¹.
Mass (FD): m/e 480 (M).
m.p.: 164.5–165.0° C.

EXAMPLE 74
Production of 3-(1-bromonaphthalen-2-ylmethyl)-2-methyl-5-(1-pentanesulfonylcarbamoyl)indole (103)

According to the method of Example 59, obtained is 3-(1-bromonaphthalen-2-ylmethyl)-2-methyl-5-(1-pentanesulfonylcarbamoyl)indole (103) (0.238 g) from 3-(1-bromonaphthalen-2-ylmethyl)-5-carboxy-2-methylindole (0.300 g), N,N'-carbonyldiimidazole (0.247 g), 1-pentanesulfonamide (0.230 g) and diazabicycloundecene (0.232 g).

¹H-NMR (DMSO-d6, δ ppm): 0.79 (3H, t, J=7.3 Hz), 1.19–1.28 (2H, m), 1.29–1.37 (2H, m), 1.61–1.69 (2H, m), 2.33 (3H, s), 3,46 (2H, t, J=7.8 Hz), 4.39 (2H, s), 7.12 (1H, d, J=8.4 Hz), 7.36 (1H, d, J=8.5 Hz), 7.56 (1H, t, J=7.1 Hz), 7.64 (1H, dd, J=8.5 and 1.6 Hz), 7.68 (1H, t, J=7.3 Hz), 7.79 (1H, d, J=8.5 Hz), 7.91 (1H, d, J=7.9 Hz), 8.10 (1H, s), 8.27 (1H, d, J=8.6 Hz), 11.40 (1H, s), 11.69 (1H, s).
IR (Nujol): 1674 cm⁻¹.
m.p.: 188.5–190.5° C.

EXAMPLE 75
Production of 3-((3-chloropyridin-4-yl)methyl)-2-methyl-5-(1-pentanesulfonylcarbamoyl)indole (104)

According to the method of Example 59, obtained is 3-((3-chloropyridin-4-yl)methyl)-2-methyl-5-(1-pentanesulfonylcarbamoyl)indole (104) (0.263 g) from 5-carboxy-3-((3-chloropyridin-4-yl)methyl)-2-methylindole (0.370 g), N,N'-carbonyldiimidazole (0.309 g), 1-pentanesulfonamide (0.288 g) and diazabicycloundecene (0.290 g).

¹H-NMR (DMSO-d6, δ ppm): 0.81 (3H, t, J=7.3 Hz), 1.22–1.30 (2H, m), 1.31–1.39 (2H, m), 1.63–1.71 (2H, m), 2.33 (3H, s), 3.49 (2H, t, J=7.8 Hz), 4.15 (2H, s), 6.92 (1H, d, J=5.0 Hz), 7.37 (1H, d, J=8.6 Hz), 7.64 (1H, d, J=8.6 Hz), 8.06 (1H, s), 8.33 (1H, d, J=4.9 Hz), 8.60 (1H, s), 11,45 (1H, s), 11.69 (1H, s).
IR (Nujol): 1677 cm⁻¹.
m.p.: 217–219° C.

EXAMPLE 76
Production of 2-methyl-5-(1-pentanesulfonylcarbamoyl)-3-(4-(2-phenylethenyl)benzyl)indole (105)

According to the method of Example 59, obtained is 2-methyl-5-(1-pentanesulfonylcarbamoyl)-3-(4-(2-phenylethenyl)benzyl)indole (105) (0.080 g) from 5-carboxy-2-methyl-3-(4-(2-phenylethenyl)benzyl)indole (0.120 g), N,N'-carbonyldiimidazole (0.106 g), 1-pentanesulfonamide (0.099 g) and diazabicycloundecene (0.100 g).

¹H-NMR (CD3OD, δ ppm): 0.79 (3H, t, J=7.3 Hz), 1.20–1.38 (4H, m), 1.71 (2H, m), 2.32 (3H, s), 3.42 (2H, m), 4.02 (2H, s), 7.01 (2H, d, J=3.8 Hz), 7.09–7.14 (3H, m), 7.20–7.27 (3H, m), 7.34 (2H, d, J=8.1 Hz), 7.41 (2H, d, J=7.3 Hz), 7.53 (1H, d, J=10.2 Hz), 7.95 (1H, s).

EXAMPLE 77
Production of 3-(2,4-dichlorobenzyl)-5-(ethanesulfonylcarbamoyl)-2-propylindole (106)

According to the method of Example 59, obtained is 3-(2,4-dichlorobenzyl)-5-(ethanesulfonylcarbamoyl)-2-propylindole (106) (0.130 g) from 5-carboxy-3-(2,4-dichlorobenzyl)-2-propylindole (0.154 g), N,N'-carbonyldiimidazole (0.138 g), diazabicycloundecene (0.129 g) and ethanesulfonamide (0.0928 g).

$^1$H-NMR (DMSO-d6, δ ppm): 0.82 (3H, t, J=7.3 Hz), 1.22 (3H, t, J=7.3 Hz), 1.57 (2H, m), 2.62 (2H, t, J=7.5 Hz), 3.48 (2H, q, J=7.3 Hz), 4.10 (2H, s), 6.88 (1H, d, J=8.4 Hz), 7.25 (1H, dd, J=8.4 and 2.1 Hz), 7.37 (1H, d, J=7.4 Hz), 7.61 (1H, d, J=2.1 Hz)), 7.65 (1H, dd, J=8.5 and 1.6 Hz), 8.05 (1H, brs), 11.38 (1H, s), 11.66 (1H, s).

IR (Nujol): 1683 cm$^{-1}$.
m.p.: 204.5–205.5° C.

EXAMPLE 78
Production of 3-(2,4-dichlorobenzyl)-2-methyl-5-(2-thiophenesulfonylcarbamoyl)indole (107)

According to the method of Example 59, obtained is 3-(2,4-dichlorobenzyl)-2-methyl-5-(2-thiophenesulfonylcarbamoyl)indole (107) (0.226 g) from 5-carboxy-3-(2,4-dichlorobenzyl)-2-methylindole (0.334 g), N,N'-carbonyldiimidazole (0.275 g), diazabicycloundecene (0.258 g) and 2-thiophenesulfonamide (0.277 g).

$^1$H-NMR (DMSO-d6, δ ppm): 2.28 (3H, s), 4.07 (2H, s), 6.91 (1H, d, J=8.4 Hz), 7.18 (1H, t, J=4.2 Hz), 7.25 (1H, dd, J=2.2 and 8.4 Hz), 7.32 (1H, d, J=8.5 Hz), 7.58 (1H, dd, J=1.6 and 8.6 Hz), 7.61 (1H, d, J=2.1 Hz), 7.82 (1H, dd, J=1.0 and 3.8 Hz), 8.00 (2H, m), 11.39 (1H, brs), 12.31 (1H, brs).

IR (Nujol): 1690 cm$^{-1}$.
m.p.: 221–222° C.

EXAMPLE 79
Production of 3-(2,4-dichlorobenzyl)-5-((4-methoxybenzene)sulfonylcarbamoyl)-2-methylindole (108)

According to the method of Example 59, obtained is 3-(2,4-dichlorobenzyl)-5-((4-methoxybenzene)sulfonylcarbamoyl)-2-methylindole (108) (0.260 g) from 5-carboxy-3-(2,4-dichlorobenzyl)-2-methylindole (0.300 g), N,N'-carbonyldiimidazole (0.185 g), 4-methoxybenzenesulfonamide (0.214 g) and diazabicycloundecene (0.174 g).

$^1$H-NMR (DMSO-d6, δ ppm): 2.29 (3H, s), 3.83 (3H, s), 4.07 (2H, s), 6.92 (1H, d, J=8.4 Hz), 7.13 (2H, d, J=9.0 Hz), 7.26 (1H, dd, J=8.4 and 2.3 Hz), 7.31 (1H, d, J=8.6 Hz), 7.54 (1H, dd, J=8.5 and 1.8 Hz), 7.62 (1H, d, J=2.2 Hz), 7.91 (2H, d, J=8.9 Hz), 7.97 (1H, s), 11.37 (1H, s), 12.03 (1H, s).

IR (Nujol): 1684 cm$^{-1}$.
m.p.: 106.5–109° C.

EXAMPLE 80
Production of 5-(benzenesulfonylcarbamoyl)-3-(2,4-dichlorobenzyl)-2-ethylindole (109)

According to the method of Example 59, obtained is 5-(benzenesulfonylcarbamoyl)-3-(2,4-dichlorobenzyl)-2-ethylindole (109) (0.095 g) from 5-carboxy-3-(2,4-dichlorobenzyl)-2-ethylindole (0.313 g), N,N'-carbonyldiimidazole (0.212 g), diazabicycloundecene (0.206 g) and benzenesulfonamide (0.219 g).

$^1$H-NMR (DMSO-d6, δ ppm): 1.13 (3H, t, J=7.5 Hz), 2.65 (2H, q, J=7.5 Hz), 4.08 (2H, s), 6.85 (1H, d, J=8.4 Hz), 7.24 (1H, dd, J=8.4 and 2.1 Hz), 7.33 (1H, d, J=8.6 Hz), 7.54–7.64 (4H, m), 7.68 (1H, t), 7.95–8.00 (3H, m), 11.38 (1H, s), 12.18 (1H, s).

IR (Nujol): 1696 cm$^{-1}$.
m.p.: 229–231° C.

EXAMPLE 81
Production of 3-((4-chloroisoquinolin-3-yl)methyl)-2-methyl-5-(1-pentanesulfonylcarbamoyl)indole (110)

According to the method of Example 59, obtained is 3-((4-chloroisoquinolin-3-yl)methyl)-2-methyl-5-(1-pentanesulfonylcarbamoyl)indole (110) (0.020 g) from 5-carboxy-3-((4-chloroisoquinolin-3-yl)methyl)-2-methylindole (0.112 g), N,N'-carbonyldiimidazole (0.078 g), diazabicycloundecene (0.073 g) and 1-pentanesulfonamide (0.072 g).

$^1$H-NMR (DMSO-d6, δ ppm): 0.79 (3H, t, J=7.3 Hz), 1.25 (2H, m), 1.34 (2H, m), 1.66 (2H, m), 2.41 (3H, s), 3.43 (2H, t, J=6.5 Hz), 4.49 (2H, s), 7.26 (1H, d, J=8.5 Hz), 7.56 (1H, d, J=8.5 Hz), 7.72 (1H, t, J=7.6 Hz), 7.91 (1H, t, J=7.7 Hz), 8.16 (2H, m), 8.26 (1H, s), 9.22 (1H, s), 11.22 (1H, s), 11.71 (1H, brs).

IR (Nujol): 1673 cm$^{-1}$.
m.p.: 196–198° C.

EXAMPLE 82
Production of 3-((4-bromoisoquinolin-3-yl)methyl)-2-methyl-5-(1-pentanesulfonylcarbamoyl)indole (111)

According to the method of Example 59, obtained is 3-((4-bromoisoquinolin-3-yl)methyl)-2-methyl-5-(1-pentanesulfonylcarbamoyl)indole (111) (0.063 g) from 3-((4-bromoisoquinolin-3-yl)methyl)-5-carboxy-2-methylindole (0.121 g), N,N'-carbonyldiimidazole (0.099 g), diazabicycloundecene (0.093 g) and 1-pentanesulfonamide (0.093 g).

$^1$H-NMR (DMSO-d6, ppm): 0.97 (3H, t, J=7.3 Hz), 1.24 (2H, m), 1.34 (2H, m), 1.66 (2H, m), 2.39 (3H, s), 3,43 (2H, m), 4.54 (2H, s), 7.26 (1H, d, J=8.5 Hz), 7.56 (1H, dd, J=1.6 and 8.5 Hz), 7.72 (1H, t, J=7.7 Hz), 7.91 (1H, m), 8.14 (2H, m), 8.23 (1H, s), 9.22 (1H, s), 11.22 (1H, s), 11.69 (1H, brs).

IR (Nujol): 1676 cm$^{-1}$.
m.p.: 171–175° C.

EXAMPLE 83
Production of 3-(2,4-dichlorobenzyl)-2-methyl-5-(1-pent-1-enesulfonylcarbamoyl)indole (112)

According to the method of Example 59, obtained is 3-(2,4-dichlorobenzyl)-2-methyl-5-(1-pent-1-enesulfonylcarbamoyl)indole (112) (0.300 g) from 5-carboxy-3-(2,4-dichlorobenzyl)-2-methylindole (0.325 g), N,N'-carbonyldiimidazole (0.315 g), 1-pent-1-enesulfonamide (0.290 g) and diazabicycloundecene (0.290 g).

$^1$H-NMR (CDCl$_3$, δ ppm): 0.89 (3H, d, J=7.4 Hz), 1.46 (2H, m), 2.19 (2H, m), 2.32 (3H, s), 4.05 (2H, s), 6.62 (1H, d, J=15.2 Hz), 6.75 (1H, d, J=8.4 Hz), 6.97 (1H, dd, J=8.3 and 2.1 Hz), 7.03 (1H, m), 7.30 (1H, d, J=8.5 Hz), 7.37 (1H, d, J=2.1 Hz), 7.57 (1H, dd, J=8.5 and 1.6Hz), 7.87 (1H, s), 8.62 (1H, s).

IR (Nujol): 1667 cm$^{-1}$.

EXAMPLE 84
Production of 3-(2,4-dichlorobenzyl)-2-methyl-5-(trifluoromethanesulfonylcarbamoyl)indole (113)

According to the method of Example 59, obtained is 3-(2,4-dichlorobenzyl)-2-methyl-5-(trifluoromethanesulfonylcarbamoyl)indole (113) (0.088 g) from 5-carboxy-3-(2,4-dichlorobenzyl)-2-methylindole (0.414 g), N,N'-carbonyldiimidazole (0.40 g), diazabicycloundecene (0.378 g) and trifluoromethanesulfonamide (0.307 g).

$^1$H-NMR (DMSO-d6, δ ppm): 2.31 (3H, s), 4.05 (2H, s), 6.96 (1H, d, J=8.4 Hz), 7.24 (2H, m), 7.58 (1H, d, J=2.2 Hz), 7.65 (1H, dd, J=1.3 and 8.5 Hz), 7.89 (1H, s), 11.12 (1H, s).
IR (Nujol): 1722 cm$^{-1}$.
Mass (FD): m/e 464 (M).
m.p.: 201–205° C.

EXAMPLE 85
Production of 3-(2,4-dichlorobenzyl)-5-(2,2-dimethylpropanesulfonylcarbamoyl)-2-methylindole (114)

According to the method of Example 59, obtained is 3-(2,4-dichlorobenzyl)-5-(2,2-dimethylpropanesulfonylcarbamoyl)-2-methylindole (114) (0.287 g) from 5-carboxy-3-(2,4-dichlorobenzyl)-2-methylindole (0.368 g), N,N'-carbonyldiimidazole (0.268 g), diazabicycloundecene (0.251 g) and 2,2-dimethylpropanesulfonamide (0.250 g).

$^1$H-NMR (DMSO-d6, δ ppm): 1.09 (9H, s), 2.30 (3H, s), 3.48 (2H, s), 4.08 (2H, s), 6.93 (1H, d, J=8.4 Hz), 7.26 (1H, dd, J=1.9 and 8.3 Hz), 7.34 (1H, d, J=8.6 Hz), 7.61 (1H, d, J=2.0 Hz), 7.62 (1H, d, J=8.5 Hz), 8.02 (1H, s), 11.38 (1H, s), 11.70 (1H, brs).
IR (Nujol): 1656 cm$^{-1}$.
m.p.: 134–138° C.

EXAMPLE 86
Production of 3-(2,4-dichlorobenzyl)-2-methyl-5-(8-quinolinesulfonylcarbamoyl)indole (115)

According to the method of Example 59, obtained is 3-(2,4-dichlorobenzyl)-2-methyl-5-(8-quinolinesulfonylcarbamoyl)indole (115) (0.170 g) from 5-carboxy-3-(2,4-dichlorobenzyl)-2-methylindole (0.200 g), N,N'-carbonyldiimidazole (0.198 g), 8-quinolinesulfonamide (0.249 g) and diazabicycloundecene (0.182 g).

$^1$H-NMR (DMSO-d6, δ ppm): 2.27 (3H, s), 4.02 (2H, s), 6.81 (1H, d, J=8.4 Hz), 7.21–7.27 (2H, m), 7.47 (1H, d, J=9.6 Hz), 7.55 (1H, dd, J=8.2 and 4.2 Hz), 7.66 (1H, d, J=2.0 Hz), 7.81 (1H, t, J=7.8 Hz), 8.06 (1H, s), 8.32 (1H, d, J=8.0 Hz), 8.50 (2H, d, J=7.6 Hz), 8.76 (1H, d), 11.32 (1H, s).
IR (Nujol): 1678 cm$^{-1}$.
m.p.: 255–256° C.

EXAMPLE 87
Production of 3-(2,4-dichlorobenzyl)-2-methyl-5-((2-phenylethane)sulfonylcarbamoyl)indole (116)

According to the method of Example 59, obtained is 3-(2,4-dichlorobenzyl)-2-methyl-5-((2-phenylethane)sulfonylcarbamoyl)indole (116) (0.050 g) from 5-carboxy-3-(2,4-dichlorobenzyl)-2-methylindole (0.145 g), N,N'-carbonyldiimidazole (0.100 g), 8-quinolinesulfonamide (0.114 g) and diazabicycloundecene (0.094 g).

$^1$H-NMR (DMSO-d6, δ ppm): 2.30 (3H, s), 3.01 (2H, m), 3.80 (2H, m), 4.09 (2H, s), 6.93 (1H, d, J=8.4 Hz), 7.15 (1H, m), 7.21–7.28 (5H, m), 7.34 (1H, d, J=8.5 Hz), 7.60–7.64 (2H, m), 8.01 (1H, s), 11.39 (1H, s), 11.77 (1H, s).
IR (Nujol): 1674 cm$^{-1}$.
m.p.: 212–213° C.

EXAMPLE 88
Production of 3-(2,4-dichlorobenzyl)-2-methyl-5-(-toluenesulfonylcarbamoyl)indole (117)

According to the method of Example 59, obtained is 3-(2,4-dichlorobenzyl)-2-methyl-5-(-toluenesulfonylcarbamoyl)indole (117) (0.217 g) from 5-carboxy-3-(2,4-dichlorobenzyl)-2-methylindole (0.334 g), N,N'-carbonyldiimidazole (0.243 g), diazabicycloundecene (0.228 g) and -toluenesulfonamide (0.257 g).
[Physical Properties of Compound (117)]
$^1$H-NMR (DMSO-d6, ppm): 2.30 (3H, s), 4.05 (2H, s), 4.81 (2H, s), 6.90 (1H, d, J=8.4Hz), 7.26 (1H, dd, J=2.1 and 8.4 Hz), 7.29 (5H, m), 7.35 (1H, d, J=8.5Hz), 7.61 (1H, d, J=2.1 Hz), 7.63 (1H, dd, J=1.7 and 8.6 Hz), 7.97 (1H, d, J=1.0 Hz), 11.46 (1H, s), 11.62 (1H, s).
IR (Nujol): 1690 cm$^{-1}$.
m.p.: 224–225° C.

EXAMPLE 89
Production of 5-cyclohexanesulfonylcarbamoyl-3-(2,4-dichlorobenzyl)-2-methylindole (118)

According to the method of Example 59, obtained is 5-cyclohexanesulfonylcarbamoyl-3-(2,4-dichlorobenzyl)-2-methylindole (118) (0.032 g) from 5-carboxy-3-(2,4-dichlorobenzyl)-2-methylindole (0.217 g), N,N'-carbonyldiimidazole (0.126 g), diazabicycloundecene (0.119 g) and cyclohexanesulfonamide (0.127 g).

$^1$H-NMR (DMSO-d6, δ ppm): 1.14 (1H, m), 1.26 (2H, m), 1.46 (2H, m), 1.60 (1H, m), 1.79 (2H, d, J=11.6 Hz), 2.00 (2H, d, J=10.4 Hz), 2.29 (3H, s), 3.57 (1H, m), 4.08 (2H, s), 6.93 (1H, d, J=8.3 Hz), 7.26 (1H, d, J=8.2 Hz), 7.34 (1H, d, J=8.4 Hz), 7.62 (2H, m), 8.03 (1H, s), 11.39 (1H, s), 11.60 (1H, brs).
IR (Nujol): 1657 cm$^{-1}$.
m.p.: 176–181° C.

EXAMPLE 90
Production of 5-(3-chloro-1-propanesulfonylcarbamoyl)-3-(2,4-dichlorobenzyl)-2-methylindole (119) and 3-(2,4-dichlorobenzyl)-2-methyl-5-(propanesultam-1-ylcarbonyl)indole (120)

A mixture of 5-carboxy-3-(2,4-dichlorobenzyl)-2-methylindole (0.334 g), N,N'-carbonyldiimidazole (0.243 g) and N,N-dimethylformamide (5 ml) is stirred at room temperature for 40 minutes. Then, (3-chloro-1-propane) sulfonamide (0.236 g) and diazabicycloundecene (0.228 g) are added thereto, and stirred at room temperature for 14 days. This is made acidic with 0.5 M HCl (8 ml), and the solid formed is taken out through filtration. This solid is dissolved in ethyl acetate (60 ml), to which is added a saline solution (100 ml) for liquid-liquid separation. The organic layer is dried and concentrated, and the resulting residue is separated and purified through silica gel column chromatography (methanol/chloroforn=3/97). The resulting two components are separately recrystallized and purified from diethyl ether/hexane to obtain 5-(3-chloro-1-propanesulfonylcarbamoyl)-3-(2,4-dichlorobenzyl)-2-methylindole (119) (0.160 g) and 3-(2,4-dichlorobenzyl)-2-methyl-5-(propanesultam-1-ylcarbonyl)indole (120) (0.091 g).

$^1$H-NMR (DMSO-d6, δ ppm): 2.13 (2H, m), 2.30 (3H, s), 3.63 (2H, t, J=7.5 Hz), 3.75 (2H, t, J=6.5 Hz), 4.09 (2H, s), 6.93 (1H, d, J=8.4 Hz), 7.26 (1H, dd, J=2.1 and 8.4 Hz), 7.35 (1H, d, J=8.5 Hz), 7.61 (1H, d, J=2.1 Hz), 7.63 (1h, dd, J=1.6 and 8.6 Hz), 8.03 (1H, s), 11.40 (1H, s), 11.80 (1H, brs).
IR(Nujol): 1681 cm$^{-1}$.
m.p.: 95.5–96.2° C.
[Physical Properties of Compound (120)]
$^1$H-NMR (DMSO-d6, δ ppm): 2.29 (2H, m), 2.33 (3H, s), 3.49 (2H, t, J=7.0 Hz), 3.85 (2H, t, J=6.6 Hz), 4.06 (2H, s), 7.02 (1H, d, J=8.4 Hz), 7.25 (1H, m), 7.33 (1H, d, J=8.4 Hz), 7.39 (1H, dd, J=1.4 and 8.4 Hz), 7.58 (1H, m), 7.72 (1H, m), 11.33 (1H, s).

EXAMPLE 91
Production of 6-(1-butanesulfonylcarbamoyl)-2-(2,4-dichlorobenzyl)-3-methylindole (121)

From 6-carboxy-2-(2,4-dichlorobenzyl)-3-methylindole (0.550 g), N,N'-carbonyldiimidazole (0.400 g), 1-butanesulfonamide (0.340 g) and diazabicycloundecene (0.376 g), obtained is 6-(1-butanesulfonylcarbamoyl)-2-(2,4-dichlorobenzyl)-3-methylindole (121) (0.250 g).

$^1$H-NMR (DMSO-d6, δ ppm): 0.86 (3H, t, J=7.3 Hz), 1.40 (2H, sextet, J=7.4 Hz), 1.66 (2H, quint, J=7.4 Hz), 2.18 (3H, s), 3.50 (2H, m), 4.19 (2H, s), 7.09 (1H, d, J=8.4 Hz), 7.36 (1H, dd, J=2.2 and 8.4 Hz), 7.51 (1H, d, J=8.4 Hz), 7.57 (1H, dd, J=1.5 and 8.4 Hz), 7.62 (1H, d, J=2.2 Hz), 7.91 (1H, d, J=1.5 Hz), 11.16 (1H, brs), 11.77 (1H, brs).

IR (Nujol): 1666 cm$^{-1}$.
Mass (FD): m/e 452 (M).
m.p.: 215.5–216.1° C.

EXAMPLE 92
Production of 1-(2,4-dichlorobenzyl)-3-methyl-6-(1-pentanesulfonylcarbamoyl)indole (122)

According to the method of Example 59, obtained is a colorless crystal of 1-(2,4-dichlorobenzyl)-3-methyl-6-(1-pentanesulfonylcarbamoyl)indole (122) (0.370 g) from 6-carboxy-1-(2,4-dichlorobenzyl)-3-methylindole (0.46 g), N,N'-carbonyldiimidazole (0.335 g), I -pentanesulfonamide (0.312 g) and diazabicycloundecene (0.314 g).

$^1$H-NMR (DMSO-d6, δ ppm): 0.80 (3H, t, J=7.3 Hz), 1.25 (2H, sextet, J=7.6 Hz), 1.34 (2H, quint, J=7.5 Hz), 1.67 (2H, qunit, J=7.5 Hz), 2.28 (3H, s), 3.49 (2H, m), 5.50 (2H, s), 6.55 (1H, d, J=8.4 Hz), 7.32 (1H, dd, J=2.0 and 8.4 Hz), 7.42 (1H, s), 7.64 (2H, s), 7.70 (1H, d, J=2.0Hz), 8.10 (1H, s), 11.77 (1H, brs).

IR (Nujol): 1686 cm$^{-1}$.
m.p.: 116–117.5° C.

EXAMPLE 93
Production of 3-(2,4-dichlorobenzyl)-2-methyl-5-((4-methylbenzene)sulfonylcarbamoyl)indole (123)

According to the method of Example 59, obtained is 3-(2,4-dichlorobenzyl)-2-methyl-5-((4-methylbenzene)sulfonylcarbamoyl)indole (123) (0.356 g) from 5-carboxy-3-(2,4-dichlorobenzyl)-2-methylindole (0.334 g), N,N'-carbonyldiimidazole (0.243 g), (4-methylbenzene)sulfonamide (0.257 g) and diazabicycloundecene (0.228 g).

$^1$H-NMR (DMSO-d6, δ ppm): 2.28 (3H, s), 2.37 (3H, s), 4.06 (2H, s), 6.90 (1H, d, J=8.4 Hz), 7.25 (1H, dd, J=8.4 and 2.2 Hz), 7.30 (1H, d, J=8.6 Hz), 7.40 (2H, d, J=8.2 Hz), 7.53 (1H, dd, J=8.7 and 2.1 Hz), 7.60 (1H, d, J=2.2 Hz), 7.85 (2H, d, J=8.3 Hz), 7.96 (1H, s), 11.36 (1H, s), 12.09 (1H, s).

IR (Nujol): 1688 cm$^{-1}$.
m.p.: 243–246° C.

EXAMPLE 94
Production of 3-(2,4-dichlorobenzyl)-2-methyl-5-((4-nitrobenzene)sulfonylcarbamoyl)indole (124)

According to the method of Example 59, obtained is 3-(2,4-dichlorobenzyl)-2-methyl-5-((4-nitrobenzene)sulfonylcarbamoyl)indole (124) (0.350 g) from 5-carboxy-3-(2,4-dichlorobenzyl)-2-methylindole (0.334 g), N,N'-carbonyldiimidazole (0.243 g), (4-nitrobenzene)sulfonamide (0.303 g) and diazabicycloundecene (0.228 g).

$^1$H-NMR (DMSO-d6, δ ppm): 2.28 (3H, s), 4.07 (2H, s), 6.89 (1H, d, J=8.4 Hz), 7.25 (1H, dd, J=8.4 and 2.1 Hz), 7.32 (1H, d, J=8.5 Hz), 7.55 (1H, d, J=8.5 Hz), 7.60 (1H, d, J=2.0 Hz), 7.97 (1H, s), 8.21 (2H, d, J=8.8 Hz), 8.43 (2H, d, J=8.9 Hz), 11.41 (1H, s), 12.50 (1H, brs).

IR (Nujol): 1675 cm$^{-1}$.
m.p.: 216–221° C.

EXAMPLE 95
Production of 5-((4-chlorobenzene)sulfonylcarbamoyl)-3-(2,4-dichlorobenzyl)-2-methylindole (125)

According to the method of Example 59, obtained is 5-((4-chlorobenzene)sulfonylcarbamoyl)-3-(2,4-dichlorobenzyl)-2-methylindole (125) (0.195 g) from 5-carboxy-3-(2,4-dichlorobenzyl)-2-methylindole (0.334 g), N,N'-carbonyldiimidazole (0.243 g), (4-chlorobenzene)sulfonamide (0.287 g) and diazabicycloundecene (0.228 g).

$^1$H-NMR (DMSO-d6, δ ppm): 2.28 (3H, s), 4.07 (2H, s), 6.90 (1H, d, J=8.5 Hz), 7.25 (1H, dd, J=8.4 and 2.3 Hz), 7.32 (1H, d, J=8.6 Hz), 7.54 (1H, dd, J=8.7 and 1.5 Hz), 7.61 (1H, d, J=2.0 Hz), 7.69 (2H, d, J=8.6 Hz), 7.97 (3H, m), 11.39 (1H, s), 12.27 (1H, brs).

IR (Nujol): 1659 cm$^{-1}$.
m.p.: 133–136° C.

EXAMPLE 96
Production of 5-((3-chlorobenzene)sulfonylcarbamoyl)-3-(2,4-dichlorobenzyl)-2-methylindole (126)

According to the method of Example 59, obtained is 5-((3-chlorobenzene)sulfonylcarbamoyl)-3-(2,4-dichlorobenzyl)-2-methylindole (126) (0.107 g) from 5-carboxy-3-(2,4-dichlorobenzyl)-2-methylindole (0.334 g), N,N'-carbonyldiimidazole (0.243 g), (3-chlorobenzene)sulfonamide (0.287 g) and diazabicycloundecene (0.228 g).

$^1$H-NMR (DMSO-d6, δ ppm): 2.28 (3H, s), 4.07 (2H, s), 6.90 (1H, d, J=8.5 Hz), 7.25 (1H, dd, J=8.4 and 2.2 Hz), 7.32 (1H, d, J=8.5 Hz), 7.55 (1H, m), 7.60 (1H, d, J=2.1 Hz), 7.66 (1H, t, J=8.0 Hz), 7.79 (1H, d, J=7.8 Hz), 7.92 (1H, d, J=7.7 Hz), 7.95 (1H, s), 7.98 (1H, s), 11.40 (1H, s), 12.31 (1H, brs).

IR (Nujol): 1687 cm$^{-1}$.
m.p.: 206–207° C.

EXAMPLE 97
Production of 5-((2-chlorobenzene)sulfonylcarbamoyl)-3-(2,4-dichlorobenzyl)-2-methylindole (127)

According to the method of Example 59, obtained is 5-((2-chlorobenzene)sulfonylcarbamoyl)-3-(2,4-dichlorobenzyl)-2-methylindole (127) (0.240 g) from 5-carboxy-3-(2,4-dichlorobenzyl)-2-methylindole (0.334 g), N,N'-carbonyldiimidazole (0.243 g), (2-chlorobenzene)sulfonamide (0.287 g) and diazabicycloundecene (0.228 g).

$^1$H-NMR (DMSO-d6, δ ppm): 2.29 (3H, s), 4.07 (2H, s), 6.94 (1H, d, J=8.4 Hz), 7.26 (1H, dd, J=2.0 and 8.3 Hz), 7.31 (1H, d, J=8.6 Hz), 7.56 (1H, d, J=8.5 Hz), 7.61 (3H, m), 7.68 (1H, m), 8.06 (1H, s), 8.15 (1H, d, J=7.8 Hz), 11.38 (1H, s), 12.54 (1H, brs).

IR (Nujol): 1690 cm$^{-1}$.
m.p.: 224–226° C.

EXAMPLE 98
Production of 3-(2,4-dichlorobenzyl)-5-((4-fluorobenzene)sulfonylcarbamoyl)-2-methylindole (128)

According to the method of Example 59, obtained is 3-(2,4-dichlorobenzyl)-5-((4-fluorobenzene)sulfonylcarbamoyl)-2-methylindole (128) (0.130 g) from 5-carboxy-3-(2,4-dichlorobenzyl)-2-methylindole (0.334 g), N,N'-carbonyldiimidazole (0.243 g), (4-fluorobenzene)sulfonamide (0.263 g) and diazabicycloundecene (0.228 g).

$^1$H-NMR (DMSO-d6, δ ppm): 2.28 (3H, s), 4.07 (2H, s), 6.90 (1H, d, J=8.4 Hz), 7.25 (1H, dd, J=1.9 and 8.4Hz), 7.32

(1H, d, J=8.6 Hz), 7.45 (2H, t, J=8.7 Hz), 7.55 (1H, d, J=8.5 Hz), 7.60 (1H, d, J=2.0 Hz), 7.97 (1H, s), 8.03 (1H, d, J=8.6 Hz), 8.04 (1H, d, J=8.8 Hz), 11.38 (1H, s), 12.22 (1H, brs).
IR (Nujol): 1685 cm$^{-1}$.
m.p.: 222–225° C.

EXAMPLE 99
Production of 3-(2,4-dichlorobenzyl)-2-methyl-5-((2-naphthalene)sulfonylcarbamoyl)indole (129)

According to the method of Example 59, obtained is 3-(2,4-dichlorobenzyl)-2-methyl-5-(2-naphthalenesulfonylcarbamoyl)indole (129) (0.132 g) from 5-carboxy-3-(2,4-dichlorobenzyl)-2-methylindole (0.334 g), N,N'-carbonyldiimidazole (0.243 g), 2-naphthalenesulfonamide (0.331 g) and diazabicycloundecene (0.228 g).
$^{1}$H-NMR (DMSO-d6, δ ppm): 2.27 (3H, s), 4.06 (2H, s), 6.90 (1H, d, J=8.4 Hz), 7.24 (1H, dd, J=8.4 and 1.6 Hz), 7.30 (1H, d, J=8.5 Hz), 7.53 (1H, d, J=8.5 Hz), 7.59 (1H, d, J=2.2 Hz), 7.68 (1H, t, J=8.1 Hz), 7.73 (1H, t, J=7.9 Hz), 7.94 (1H, dd, J=8.7 and 1.7 Hz), 7.98 (1H, s), 8.04 (1H, d, J=8.1 Hz), 8.12 (1H, d, J=8.7 Hz), 8.22 (1H, d, J=8.1 Hz), 8.65 (1H, s), 11.36 (1H, s), 12.27 (1H, brs).
IR (Nujol): 1688 cm$^{-1}$.
m.p.: 219–224° C.

EXAMPLE 100
Production of 3-(2,4-dichlorobenzyl)-2-methyl-5-((1-naphthalene)sulfonylcarbamoyl)indole (130)

According to the method of Example 59, obtained is 3-(2,4-dichlorobenzyl)-2-methyl-5-(1-naphthalenesulfonylcarbamoyl)indole (130) (0.191 g) from 5-carboxy-3-(2,4-dichlorobenzyl)-2-methylindole (0.334 g), N,N'-carbonyldiimidazole (0.243 g), 1-naphthalenesulfonamide (0.331 g) and diazabicycloundecene (0.228 g).
$^{1}$H-NMR (DMSO-d6, δ ppm): 2.27 (3H, s), 4.06 (2H, s), 6.85 (1H, d, J=8.4 Hz), 7.21 (1H, dd, J=2.2 and 8.3 Hz), 7.27 (1H, d, J=8.6 Hz), 7.48 (1H, dd, J=1.7 and 8.6 Hz), 7.60 (2H, m), 7.63 (1H, d, J=2.2 Hz), 7.72 (1H, t, J=7.8 Hz), 7.94 (1H, s), 8.08 (1H, m), 8.28 (1H, d, J 8.3 Hz), 8.36 (1H, d, J=7.4 Hz), 8.69 (1H, m), 11.35 (1H, s), 12.50 (1H, brs).
IR (Nujol): 1693 cm$^{-1}$.
m.p.: 221–223° C.

EXAMPLE 101
Production of 3-(2,4-dichlorobenzyl)-2-methyl-5-((2-methylbenzene)sulfonylcarbamoyl)indole (131)

According to the method of Example 59, obtained is 3-(2,4-dichlorobenzyl)-2-methyl-5-((2-methylbenzene)sulfonylcarbamoyl)indole (131) (0.150 g) from 5-carboxy-3-(2,4-dichlorobenzyl)-2-methylindole (0.334 g), N,N'-carbonyldiimidazole (0.243 g), (2-methylbenzene)sulfonamide (0.257 g) and diazabicycloundecene (0.228 g).
$^{1}$H-NMR (DMSO-d6, δ ppm): 2.29 (3H, s), 2.57 (3H, s), 4.07 (2H, s), 6.94 (1H, d, J=8.4 Hz), 7.25 (1H, dd, J=2.1 and 8.4 Hz), 7.31 (1H, t, J=7.6 Hz), 7.36 (1H, d, J=7.4Hz), 7.43 (1H, t, J=7.6 Hz), 7.55 (2H, m), 7.60 (1H, d, J=2.1 Hz), 8.01 (2H, m), 11.37 (1H, s), 12.28 (1H, brs).
IR (Nujol): 1689 cm$^{-1}$.
m.p.: 194–196° C.

EXAMPLE 102
Production of 3-(2,4-dichlorobenzyl)-5-(2,5-dimethylbenzene)sulfonylcarbamoyl-2-methylindole (132)

According to the method of Example 59, obtained is 3-(2,4-dichlorobenzyl)-5-(2,5-dimethylbenzene)sulfonylcarbamoyl-2-methylindole (132) (0.285 g) from 5-carboxy-3-(2,4-dichlorobenzyl)-2-methylindole (0.334 g), N,N'-carbonyldiimidazole (0.243 g), (2,5-dimethylbenzene)sulfonamide (0.278 g) and diazabicycloundecene (0.228 g).
$^{1}$H-NMR (DMSO-d6, δ ppm): 2.29 (3H, s), 2.35 (3H, s), 2.51 (3H, s), 4.07 (2H, s), 6.93 (1H, d, J=8.4 Hz), 7.25 (2H, m), 7.31 (1H, d, J=8.5 Hz), 7.36 (1H, d, J=7.8 Hz), 7.55 (1H, dd, J=1.5 and 8.5 Hz), 7.60 (1H, d, J=2.1 Hz), 7.82 (1H, s), 8.01 (1H, s), 11.37 (1H, s), 12.24 (1H, s).
IR (Nujol): 1682 cm$^{-1}$.
m.p.: 228–238° C.

EXAMPLE 103
Production of 5-(4-bromobenzene)sulfonylcarbamoyl-3-(2,4-dichlorobenzyl)-2-methylindole (133)

According to the method of Example 59, obtained is 5-(4-bromobenzene)sulfonylcarbamoyl-3-(2,4-dichlorobenzyl)-2-methylindole (133) (0.295 g) from 5-carboxy-3-(2,4-dichlorobenzyl)-2-methylindole (0.334 g), N,N'-carbonyldiimidazole (0.243 g), (4-bromobenzene)sulfonamide (0.354 g) and diazabicycloundecene (0.228 g).
$^{1}$H-NMR (DMSO-d6, δ ppm): 2.28 (3H, s), 4.07 (2H, s), 6.90 (1H, d, J=8.4 Hz), 7.25 (1H, dd, J=1.7 and 8.3 Hz), 7.32 (1H, d, J=8.5 Hz), 7.54 (1H, d, J=8.5 Hz), 7.60 (1H, d, J=2.0 Hz), 7.84 (2H, d, J=8.2 Hz), 7.89 (2H, d, J=8.7 Hz), 7.97 (1H, s), 11.39 (1H, s), 12.28 (1H, brs).
IR (Nujol): 1660 cm$^{-1}$.
m.p.: 132–137° C.

EXAMPLE 104
Production of 3-(2,4-dichlorobenzyl)-2-methyl-5-((E)-styrenesulfonylcarbamoyl)indole (134)

According to the method of Example 59, obtained is 3-(2,4-dichlorobenzyl)-2-methyl-5-((E)-styrenesulfonylcarbamoyl)indole (134) (0.242 g) from 5-carboxy-3-(2,4-dichlorobenzyl)-2-methylindole (0.334 g), N,N'-carbonyldiimidazole (0.243 g), (E)-styrenesulfonamide (0.275 g) and diazabicycloundecene (0.228 g).
$^{1}$H-NMR (DMSO-d6, δ ppm): 2.29 (3H, s), 4.08 (2H, s), 6.90 (1H, d, J=8.4 Hz), 7.25 (1H, dd, J=8.4 and 2.0 Hz), 7.33 (1H, d, J=8.6 Hz), 7.45 (3H, m), 7.49 (1H, d, J=15.4 Hz), 7.61 (3H, m), 7.76 (2H, m), 8.05 (1H, s), 11.38 (1H, s), 11.79 (1H, brs).
IR (Nujol): 1674 cm$^{-1}$.
m.p.: 190–196° C.

EXAMPLE 105
Production of 3-(2,4-dichlorobenzyl)-2-methyl-5-(4-vinylbenzene)sulfonylcarbamoyl)indole (135)

According to the method of Example 59, obtained is 3-(2,4-dichlorobenzyl)-2-methyl-5-(4-vinylbenzene)sulfonylcarbamoyl)indole (135) (0.175 g) from 5-carboxy-3-(2,4-dichlorobenzyl)-2-methylindole (0.334 g), N,N'-carbonyldiimidazole (0.243 g), (4-vinylbenzene)sulfonamide (0.275 g) and diazabicycloundecene (0.228 g).
$^{1}$H-NMR (DMSO-d6, δ ppm): 2.28 (3H, s), 4.07 (2H, s), 5.45 (1H, d, J=10.9 Hz), 6.01 (1H, d, J=17.6 Hz), 6.81 (1H, dd, J=11.0 and 17.6 Hz), 6.90 (1H, d, J=8.4Hz), 7.25 (1H, m), 7.31 (1H, d, J=8.5 Hz), 7.54 (1H, d, J=8.4Hz), 7.60 (1H, s), 7.69 (2H, d, J=8.2 Hz), 7.93 (2H, d, J=8.2 Hz), 7.97 (1H, s), 11.37 (1H, s), 12.16 (1H, brs).
IR (Nujol): 1674 cm$^{-1}$.
m.p.: 143–146° C.

EXAMPLE 106
Production of 5-((4-phenylazobenzene)sulfonylcarbamoyl)-3-(2,4-dichlorobenzyl)-2-methylindole (136)

5-Carboxy-3-(2,4-dichlorobenzyl)-2-methylindole (0.334 g) and N,N'-carbonyldiimidazole (0.243 g) are dissolved in N,N-dimethylformamide (5 ml) and stirred at room temperature for 90 minutes. Next, (4-phenylazobenzene)sulfonamide (0.392 g) and diazabicycloundecene (0.228 g) are added thereto, and stirred at 100° C. for 7 hours. The reaction mixture is cooled to room temperature, to which are added chloroform (40 ml), water (40 ml) and 1 N HCl (3 ml) for liquid-liquid separation. The organic layer is concentrated under reduced pressure, and the resulting residue is again subjected to liquid-liquid separation with ethyl acetate (40 ml) and water (40 ml) added thereto. Then, the organic layer is dried with anhydrous sodium sulfate, and concentrated under reduced pressure. The resulting residue is recrystallized from chloroform (4 ml) and t-butyl methyl ether (2 ml) to obtain 5-((4-phenylazobenzene)sulfonylcarbamoyl)-3-(2,4-dichlorobenzyl)-2-methylindole (136) (0.150 g).

$^1$H-NMR (DMSO-d6, δ ppm): 2.28 (3H, s), 4.07 (2H, s), 6.91 (1H, d, J=8.4 Hz), 7.25 (1H, dd, J=2.1 and 8.3 Hz), 7.32 (1H, d, J=8.6 Hz), 7.56 (1H, dd, J=1.7 and 8.6 Hz), 7.60 (1H, d, J=2.3 Hz), 7.62 (3H, m), 7.93 (2H, m), 8.00 (1H, m), 8.06 (2H, d, J=8.7 Hz), 8.18 (2H, d, J=8.7 Hz), 11.39 (1H, s), 12.34 (1H, brs).

IR (Nujol): 1677 cm$^{-1}$.

m.p.: 207–223° C.

EXAMPLE 107

Production of 3-(2,4-dichlorobenzyl)-2-methyl-5-((4-trifluoromethylbenzene)sulfonylcarbamoyl)indole (137)

According to the method of Example 106, obtained is 3-(2,4-dichlorobenzyl)-2-methyl-5-((4-trifluoromethylbenzene)sulfonylcarbamoyl)indole (137) (0.360 g) from 5-carboxy-3-(2,4-dichlorobenzyl)-2-methylindole (0.334 g), N,N'-carbonyldiimidazole (0.243 g), (4-trifluoromethylbenzene)sulfonamide (0.338 g) and diazabicycloundecene (0.228 g).

$^1$H-NMR (DMSO-d6, δ ppm): 2.28 (3H, s), 4.07 (2H, s), 6.90 (1H, d, J=8.4 Hz), 7.25 (1H, dd, J=2.2 and 8.4 Hz), 7.32 (1H, d, J=8.6 Hz), 7.55 (1H, dd, J=1.6 and 8.6 Hz), 7.60 (1H, d, J=2.2 Hz), 7.98 (1H, s), 8.01 (2H, d, J=8.3 Hz), 8.17 (2H, d, J=8.3 Hz), 11.40 (1H, s), 12.41 (1H, brs).

IR (Nujol): 1622 cm$^{-1}$.

m.p.: 147–151° C.

EXAMPLE 108

Production of 3-(2,4-dichlorobenzyl)-2-methyl-5-((4-methyl-1-pent-1-ene)sulfonylcarbamoyl)indole (138)

According to the method of Example 106, obtained is 3-(2,4-dichlorobenzyl)-2-methyl-5-((4-methyl-1-pent-1-ene)sulfonylcarbamoyl)indole (138) (0.218 g) from 5-carboxy-3-(2,4-dichlorobenzyl)-2-methylindole (0.400 g), N,N'-carbonyldiimidazole (0.388 g), (4-methyl-1-pent-1-ene)sulfonamide (0.391 g) and diazabicycloundecene (0.364 g).

$^1$H-NMR (DMSO-d6, δ ppm): 0.86 (6H, d, J=6.6 Hz), 1.71–1.80 (1H, m), 2.14 (2H, t, J=6.7 Hz), 2.30 (3H, s), 4.08 (2H, s), 6.74–6.85 (2H, m), 6.92 (1H, d, J=8.4 Hz), 7.26 (1H, dd, J=2.1 and 8.4Hz), 7.34 (1H, d, J=8.5 Hz), 7.59 (1H, d, J=1.3 Hz), 7.61 (1H, d, J=1.3 Hz), 8.00 (1H, d, J=1.3 Hz), 11.38 (1H, s), 11.79 (1H, s).

IR (Nujol): 1682 cm$^{-1}$.

m.p.: 199.0–203.0° C.

EXAMPLE 109

Production of 3-(2,4-dichlorobenzyl)-5-((3,4-dimethoxybenzene)sulfonylcarbamoyl)-2-methylindole (139)

According to the method of Example 106, obtained is 3-(2,4-dichlorobenzyl)-5-((3,4-dimethoxybenzene)sulfonylcarbamoyl)-2-methylindole (139) (0.167 g) from 5-carboxy-3-(2,4-dichlorobenzyl)-2-methylindole (0.334 g), N,N'-carbonyldiimidazole (0.243 g), (3,4-dimethoxybenzene)sulfonamide (0.326 g) and diazabicycloundecene (0.228 g).

$^1$H-NMR (DMSO-d6, δ ppm): 2.28 (3H, s), 3.79 (3H, s), 3.83 (3H, s), 4.07 (2H, s), 6.90 (1H, d, J=8.4 Hz), 7.15 (1H, d, J=8.6 Hz), 7.25 (1H, dd, J=2.0 and 8.4 Hz), 7.31 (1H, d, J=8.6 Hz), 7.45 (1H, d, J=2.1 Hz), 7.54 (1H, dd, J=1.5 and 8.6 Hz), 7.57 (1H, dd, J=2.1 and 8.6 Hz), 7.60 (1H, d, J=2.1 Hz), 7.96 (1H, s), 11.36 (1H, s), 11.97 (1H, s).

IR (Nujol): 1673 cm$^{-1}$.

m.p.: 148–152° C.

EXAMPLE 110

Production of 5-((4-t-butylbenzene)sulfonylcarbamoyl)-3-(2,4-dichlorobenzyl)-2-methylindole (140)

According to the method of Example 106, obtained is 5-((4-t-butylbenzene)sulfonylcarbamoyl)-3-(2,4-dichlorobenzyl)-2-methylindole (140) (0.123 g) from 5-carboxy-3-(2,4-dichlorobenzyl)-2-methylindole (0.334 g), N,N'-carbonyldiimidazole (0.243 g), (4-t-butylbenzene)sulfonamide (0.320 g) and diazabicycloundecene (0.228 g).

$^1$H-NMR (DMSO-d6, δ ppm): 1.28 (9H, s), 2.28 (3H, s), 4.07 (2H, s), 6.91 (1H, d, J=7.9 Hz), 7.25 (1H, d, J=8.3 Hz), 7.31 (1H, d, J=8.1 Hz), 7.54 (1H, d, J=8.2 Hz), 7.61 (3H, m), 7.89 (2H, d, J=7.3 Hz), 7.98 (1H, s), 11.37 (1H, s), 12. 12 (1H, brs).

IR (Nujol): 1688 cm$^{-1}$.

m.p.: 203–207° C.

EXAMPLE 111

Production of 3-(2,4-dichlorobenzyl)-2-methyl-5-((3-methylbenzene)sulfonylcarbamoyl)indole (141)

According to the method of Example 106, obtained is 3-(2,4-dichlorobenzyl)-2-methyl-5-((3-methylbenzene)sulfonylcarbamoyl)indole (141) (0.200 g) from 5-carboxy-3-(2,4-dichlorobenzyl)-2-methylindole (0.250 g), N,N'-carbonyldiimidazole (0.182 g), (3-methylbenzene)sulfonamide (0.192 g) and diazabicycloundecene (0.171 g).

$^1$H-NMR (DMSO-d6, δ ppm): 2.28 (3H, s), 2.38 (3H, s), 4.07 (2H, s), 6.90 (1H, d, J=8.4 Hz), 7.25 (1H, dd, J=2.1 and 8.3 Hz), 7.30 (1H, d, J=8.5 Hz), 7.46–7.50 (2H, m), 7.55 (1H, d, J 8.5 Hz), 7.60 (H, d, J=2.1 Hz), 7.73–7.78 (2H, m), 7.97 (1H, s), 11.36 (1H, s), 12.14 (1H, brs).

IR (Nujol): 1683 cm$^{-1}$.

m.p.: 105–115° C. (foamy solid).

EXAMPLE 112

Production of 3-(2,4-dichlorobenzyl)-2-methyl-5-(2-octanesulfonylcarbamoyl)indole (142)

According to the method of Example 106, obtained is 3-(2,4-dichlorobenzyl)-2-methyl-5-(2-octanesulfonylcarbamoyl)indole (142) (0.032 g) from 5-carboxy-3-(2,4-dichlorobenzyl)-2-methylindole (0.107 g), N,N'-carbonyldiimidazole (0.063 g), 2-octanesulfonamide (0.075 g) and diazabicycloundecene (0.059 g).

$^1$H-NMR (DMSO-d6, δ ppm): 0.85 (3H, t, J=7.7 Hz), 1.2–1.5 (8H, m), 1.43 (3H, d, J=6.9 Hz), 1.64 (1H, m), 2.05 (1H, m), 2.38 (3H, s), 3.89 (1H, m), 4.11 (2H, s), 6.80 (1H, d, J=8.3 Hz), 7.04 (1H, dd, J=2.0 and 8.3 Hz), 7.36 (1H, d, J=8.5 Hz), 7.42 (1H, d, J=2.0 Hz), 7.60 (1H, dd, J=1.6 and 8.5 Hz), 7.84 (1H, brs), 8.21 (2H, brs).

IR (N jol): 1678 cm$^{-1}$.

m.p.: 181–182° C.

EXAMPLE 113
Production of 3-(2,4-dichlorobenzyl)-2-methyl-5-((4-phenylbenzene)sulfonylcarbamoyl)indole (143)

According to the method of Example 106, obtained is 3-(2,4-dichlorobenzyl)-2-methyl-5-((4-phenylbenzene)sulfonylcarbamoyl)indole (143) (0.109 g) from 5-carboxy-3-(2,4-dichlorobenzyl)-2-methylindole (0.334 g), N,N'-carbonyldiimidazole (0.243 g), (4-phenylbenzene)sulfonamide (0.350 g) and diazabicycloundecene (0.228 g).

$^1$H-NMR (DMSO-d6, δ ppm): 2.28 (3H, s), 4.07 (2H, s), 6.91 (1H, d, J=8.4 Hz), 7.25 (1H, dd, J=2.0 and 8.3 Hz), 7.32 (1H, d, J=8.6 Hz), 7.43 (1H, t, J=7.3 Hz), 7.50 (2H, t, J=7.5 Hz), 7.55 (1H, dd, J=1.3 and 8.6 Hz), 7.60 (1H, d, J=1.9 Hz), 7.73 (2H, d, J=8.6 Hz), 7.90 (2H, d, J=8.5 Hz), 7.99 (1H, s), 8.04 (2H, d, J=8.5 Hz), 11.38 (1H, s), 12.22 (1H, brs).

IR (Nujol): 1678 cm$^{-1}$.

m.p.: 206–207° C.

EXAMPLE 114
Production of 3-(2-chloro-4-phenylbenzyl)-5-methoxycarbonyl-2-methylindole (144)

A mixture of 5-methoxycarbonyl-2-methylindole (0.84 g), 2-chloro-4-phenylbenzyl bromide (2.0 g), L-tartaric acid (1.07 g), sodium hydroxide (0.37 g), sodium iodide (0.53 g), 1,4-dioxane (15 ml) and water (8 ml) is stirred at 90° C. for 4 hours. The reaction mixture is extracted with water and ethyl acetate added thereto, and the organic layer is washed with water, dried and concentrated. The resulting residue is purified through silica gel column chromatography (eluent: ethyl acetate/hexane=1/4 to 1/2), and crystallized from a mixed solution of hexane and ethyl acetate to obtain 3-(2-chloro-4-phenylbenzyl)-5-methoxycarbonyl-2-methylindole (144) (0.965).

$^1$H-NMR (DMSO-d6, δ ppm): 2.38 (3H, s), 3.77 (3H, s), 4.16 (2H, s), 7.04 (1H, d, J=8.1 Hz), 7.36 (2H, t, J=5.9 Hz), 7.44 (2H, t, J=7.2 Hz), 7.48 (1H, d, 8.0 Hz), 7.65 (3H, m), 7.74 (1H, s), 7.96 (1H, s), 11.36 (1H, s).

EXAMPLE 115
Production of 5-carboxy-3-(2-chloro-4-phenylbenzyl)-2-methylindole (145)

To 3-(2-chloro-4-phenylbenzyl)-5-methoxycarbonyl-2-methylindole (0.95 g), added are ethanol (5 ml), water (5 ml) and aqueous sodium hydroxide (0.29 g), and refluxed for 3 hours. The reaction mixture is cooled, and neutralized with HCl. This is extracted with ethyl acetate and water, and the organic layer is dried and concentrated. The resulting residue is crystallized from a small amount of a mixed solution of chloroform and ether. The crystal is taken out through filtration and dried to obtain 5-carboxy-3-(2-chloro-4-phenylbenzyl)-2-methylindole (145) (0.701 g).

$^1$H-NMR (DMSO-d6, δ ppm): 2.37 (3H, s), 4.13 (2H, s), 7.04 (1H, d, J=8.1 Hz), 7.28 (1H, d, J=8.5 Hz), 7.36 (1H, d, J=6.8 Hz), 7.44 (2H, d, J=7.6 Hz), 7.47 (1H, d, J=8.0 Hz), 7.64 (3H, m), 7.73 (1H, d, J=1.8 Hz), 7.92 (1H, s), 11.24 (1H, s).

EXAMPLE 116
Production of 3-((2-chloro-4-phenyl)benzyl)-2-methyl-5-((1-pent-1-ene)sulfonylcarbamoyl)indole (146)

According to the method of Example 106, obtained is 3-((2-chloro-4-phenyl)benzyl)-2-methyl-5-((1-pent-1-ene)sulfonylcarbamoyl)indole (146) (0.135 g) from 5-carboxy-3-((2-chloro-4-phenyl)benzyl)-2-methylindole (0.301 g), N,N'-carbonylduimidazole (0.195 g), (1-pent-1-ene)sulfonamide (0.179 g) and diazabicycloundecene (0.183 g).

$^1$H-NMR (DMSO-d6, δ ppm): 0.84 (3H, t, J=7.4 Hz), 1.42 (2H, m), 2.21 (2H, m), 2.33 (3H, s), 4.14 (2H, s), 6.75 (1H, d, J=15.2 Hz), 6.83 (1H, dt, J=6.4 and 15.1 Hz), 6.98 (1H, d, J=8.0 Hz), 7.35 (2H, m), 7.42–7.47 (3H, m), 7.60–7.47 3H, m), 7.74 (1H, d, J=1.7 Hz), 8.07 (1H, s), 11.38 (1H, s), 11.81 (1H, s).

IR (Nujol): 1654 cm$^{-1}$.

m.p.: 166–167° C.

EXAMPLE 117
Production of 3-(2-chloro-4-phenylbenzyl)-2-methyl-5-(1-pentanesulfonylcarbamoyl)indole (147)

According to the method of Example 106, obtained is 3-(2-chloro-4-phenylbenzyl)-2-methyl-5-((1-pent-1-ene)sulfonylcarbamoyl)indole (147) (0.122 g) from 5-carboxy-3-(2,4-dichlorobenzyl)-2-methylindole (0.200 g), N,N'-carbonyldiimidazole (0.173 g), 1-pentanesulfonamide (0.165 g) and diazabicycloundecene (0.162 g).

$^1$H-NMR (DMSO-d6, δ ppm): 0.79 (3H, t, J=7.3 Hz), 1.21–1.41 (4H, m), 1.65–1.72 (2H, m), 2.34 (3H, s), 3.48 (2H, t, J=7.7 Hz), 4.16 (2H, s), 7.01 (1H, d, J=8.1 Hz), 7.37 (2H, d, J=8.2 Hz), 7.42–7.49 (3H, m), 7.64 (3H, m), 7.75 (2H, d, J=1.8 Hz), 8.10 (1H, s), 11.40 (1H, s), 11.71 (1H, s).

IR (Nujol): 1684 cm$^{-1}$.

m.p.: 155.5–156.5° C.

EXAMPLE 118
Production of 5-(benzenesulfonylcarbamoyl)-3-((2-chloro-4-phenyl)benzyl)-2-methylindole (148)

According to the method of Example 106, obtained is 5-(benzenesulfonylcarbamoyl)-3-((2-chloro-4-phenyl)benzyl)-2-methylindole (148) (0.057 g) from 5-carboxy-3-((2-chloro-4-phenyl)benzyl)-2-methylindole (0.225 g), N,N'-carbonyldiimidazole (0.221 g), benzenesulfonamide (0.214 g) and diazabicycloundecene (0.207 g).

$^1$H-NMR (DMSO-d6, δ ppm): 2.32 (3H, s), 4.13 (2H, s), 6.97 (1H, d, J=8.0 Hz), 7.31–7.37 (2H, m), 7.42–7.47 (3H, m), 7.54–7.67 (6H, m), 7.73 (1H 7.96 (2H, d, J=8.0 Hz), 8.03 (1H, s), 11.38 (1H, s), 12.20 (1H, brs).

IR (Nujol): 1661 cm$^{-1}$.

m.p.: 134–137° C.

EXAMPLE 119
Production of 3-(2,4-dichlorobenzyl)-5-((4-ethylbenzene)sulfonylcarbamoyl)-2-methylindole (149)

According to the method of Example 106, obtained is 3-(2,4-dichlorobenzyl)-5-((4-ethylbenzene)sulfonylcarbamoyl)-2-methylindole (149) (0.108 g) from 5-carboxy-3-(2,4-dichlorobenzyl)-2-methylindole (0.334 g), N,N'-carbonyldiimidazole (0.243 g), (4-ethylbenzene)sulfonamide (0.278 g) and diazabicycloundecene (0.228 g).

$^1$H-NMR (DMSO-d6, δ ppm): 1.18 (3H, t, J=7.5 Hz), 2.28 (3H, s), 2.67 (2H, q, J=7.3 Hz), 4.07 (2H, s), 6.91 (1H, d, J=8.3 Hz), 7.25 (1H, d, J=7.5 Hz), 7.31 (1H, d, J=8.4 Hz), 7.44 (2H, d, J=7.9 Hz), 7.54 (1H, d, J=8.6 Hz), 7.60 (1H, s), 7.87 (2H, d, J=8.0 Hz), 7.97 (1H, s), 11.37 (1H, s), 12.10 (1H, brs).

IR (Nujol): 1682 cm$^{-1}$.

m.p.: 197–198° C.

EXAMPLE 120
Production of 5-((4-n-butylbenzene)sulfonylcarbamoyl)-3-(2,4-dichlorobenzyl)-2-methylindole (150)

According to the method of Example 106, obtained is 5-((4-n-butylbenzene)sulfonylcarbamoyl)-3-(2,4-dichlorobenzyl)-2-methylindole (150) (0.230 g) from 5-carboxy-3-(2,4-dichlorobenzyl)-2-methylindole (0.334 g), N,N'-carbonyldiimidazole (0.243 g), (4-n-butylbenzene)sulfonamide (0.320 g) and diazabicycloundecene (0.228 g).

$^1$H-NMR (DMSO-d6, δ ppm): 0.87 (3H, t, J=7.3 Hz), 1.28 (2H, m), 1.55 (2H, m), 2.28 (3H, s), 2.64 (2H, t, J=7.6 Hz), 4.07 (2H, s), 6.90 (1H, d, J=8.4 Hz), 7.25 (1H, dd, J=2.0 and 8.3 Hz), 7.31 (1H, d, J=8.6 Hz), 7.42 (1H, d, J=8.2 Hz), 7.54 (1H, dd, J=1.5 and 8.6 Hz), 7.60 (1H, d, J=2.0Hz), 7.87 (2H, d, J=8.3 Hz), 7.97 (1H, s), 11.37 (1H, s), 12.09 (1H, s).
IR (Nujol): 1659 cm$^{-1}$.
m.p.: 154–155° C.

EXAMPLE 121
Production of 5-((4-n-butoxybenzene)sulfonylcarbamoyl)-3-(2,4-dichlorobenzyl)-2-methylindole (151)

According to the method of Example 106, obtained is 5-((4-n-butoxybenzene)sulfonylcarbamoyl)-3-(2,4-dichlorobenzyl)-2-methylindole (151) (0.140 g) from 5-carboxy-3-(2,4-dichlorobenzyl)-2-methylindole (0.334 g), N,N'-carbonyldiimidazole (0.243 g), (4-n-butoxybenzene)sulfonamide (0.344 g) and diazabicycloundecene (0.228 g).

$^1$H-NMR (DMSO-d6, δ ppm): 0.91 (3H, t, J=7.1 Hz), 1.42 (2H, m), 1.69 (2H, m), 2.28 (3H, s), 4.04 (2H, t, J=6.5 Hz), 4.06 (2H, s), 6.90 (1H, d, J=8.3 Hz, 7.10 (2H, d, J=8.0 Hz), 7.24 (1H, d, J 8.0 Hz), 7.30 (1H, d, J=8.5 Hz), 7.54 (1H, d, J=8.5 Hz), 7.60 (1H, s), 7.88 (2H, d, J=7.9 Hz), 7.96 (1H, s), 11.36 (1H, s), 12.04 (1H, brs).
IR (Nujol): 1654 cm$^{-1}$.
m.p.: 185–189° C.

EXAMPLE 122
Production of 3-(2,4-dichlorobenzyl)-5-methoxycarbonyl-2-methylthioindole (152)

To a methylene chloride (10 ml) solution of trifluoroacetic acid (1.238 g) and triethylsilane (2.52 g), added is a methylene chloride (10 ml) solution of 5-methoxycarbonyl-2-methylthioindole (0.800 g), which had been prepared according to the method described in "Tetrahedron, 42 (16), 4511 (1986)", and 2,4-dichlorobenzaldehyde (0.760 g), in an ice-water bath. This is stirred for 3 hours in the ice-water bath. The crystal formed is taken out through filtration and dried to obtain 3-(2,4-dichlorobenzyl)-5-methoxycarbonyl-2-methylthioindole (152) (0.727 g).

$^1$H-NMR (CDCl$_3$, δ ppm): 2.33 (3H, s), 3.89 (3H, s), 4.29 (2H, s), 6.79 (1H, d, J=8.3 Hz), 7.02 (1H, d, J=8.3 Hz), 7.35 (1H, d, J=8.6 Hz), 7.42 (1H, d, J=1.9 Hz), 7.92 (1H, dd, J=1.3 and 8.7 Hz), 8.10 (1H, s), 8.32 (1H, brs).

EXAMPLE 123
Production of 5-carboxy-3-(2,4-dichlorobenzyl)-2-methylthioindole (153)

According to the method of Example 115, obtained is 5-carboxy-3-(2,4-dichlorobenzyl)-2-methylthioindole (153) (0.795 g) from 3-(2,4-dichlorobenzyl)-5-methoxycarbonyl-2-methylthioindole (0.950 g).

$^1$H-NMR (DMSO-d6, δ ppm): 2.44 (3H, s), 4.20 (2H, s), 6.94 (1H, d, J=8.3 Hz), 7.28 (1H, dd, J=2.2 and 8.4 Hz), 7.38 (1H, d, J=8.6 Hz), 7.62 (1H, d, J=2.2Hz), 7.72 (1H, d, J=8.7Hz), 7.92 (1H, s), 11.79 (1H, s), 12.44 (1H, brs).

EXAMPLE 124
Production of 3-(2,4-dichlorobenzyl)-2-methylthio-5-((1-pent-1-ene)sulfonylcarbamoyl)indole (154)

According to the method of Example 106, obtained is 3-(2,4-dichlorobenzyl)-2-methylthio-5-((1-pent-1-ene)sulfonylcarbamoyl)indole (154) (0.068 g) from 5-carboxy-3-(2,4-dichlorobenzyl)-2-methylthioindole (0.200 g), N,N'-carbonyldiimidazole (0.177 g), (1-pent-1-ene)sulfonamide (0.163 g) and diazabicycloundecene (0.166 g).

$^1$H-NMR (DMSO-d6, δ ppm): 0.86 (3H, t, J=7.4 Hz), 1.40–1.49 (2H, m), 2.23 (2H, q, J=7.2 Hz), 2.41 (3H, s), 4.18 (2H, s), 6.76 (1H, d, J=6.0 Hz), 6.82–6.89 (2H, m), 7.26 (1H, dd, J=1.9 and 8.4Hz), 7.40 (1H, d, J=8.7 Hz), 8.63 (1H, d, J=2.0 Hz), 7.70 (1H, d, J=8.8 Hz), 8.07 (1H, s), 11.86 (1H, brs), 11.88 (1H, brs).
IR (Nujol): 1682 cm$^{-1}$.
m.p.: 140.5–142.0° C.

EXAMPLE 125
Production of 5-(benzenesulfonylcarbamoyl)-3-(2,4-dichlorobenzyl)-2-methylthioindole (155)

According to the method of Example 106, obtained is 5-(benzenesulfonylcarbamoyl)-3-(2,4-dichlorobenzyl)-2-methylthioindole (155) (0.100 g) from 5-carboxy-3-(2,4-dichlorobenzyl)-2-methylthioindole (0.160 g), N,N'-carbonyldiimidazole (0.092 g), benzenesulfonamide (0.089 g) and diazabicycloundecene (0.086 g).

$^1$H-NMR (DMSO-d6, δ ppm): 2.41 (3H, s), 4.17 (2H, s), 6.82 (1H, d, J=8.4 Hz), 7.26 (1H, dd, J=2.1 and 8.3 Hz), 7.38 (1H, d, J=8.7 Hz), 7.60–7.66 (4H, m), 7.70 (1H, t, J=7.3 Hz), 7.98 (2H, d, J=7.5 Hz), 8.04 (1H, s), 11.88 (1H, brs), 12.26 (1H, brs).
IR (Nujol): 1698 cm$^{-1}$.
m.p.: 223.0–226.0° C.

EXAMPLE 126
Production of 3-(2,4-dichlorobenzyl)-2-methylthio-5-(1-pentanesulfonylcarbamoyl)indole (156)

According to the method of Example 106, obtained is 3-(2,4-dichlorobenzyl)-2-methylthio-5-(1-pentanesulfonylcarbamoyl)indole (156) (0.218 g) from 5-carboxy-3-(2,4-dichlorobenzyl)-2-methylthioindole (0.200 g), N,N'-carbonyldiimidazole (0.177 g), 1-pentanesulfonamide (0.165 g) and diazabicycloundecene (0.166 g).

$^1$H-NMR (DMSO-d6, δ ppm): 0.81 (3H, t, J=7.3 Hz), 1.22–1.31 (2H, m), 1.31–1.39 (2H, m), 1.63–1.70 (2H, m), 2.42 (3H, d, J=0.7 Hz), 3.49 (2H, t, J=7.5 Hz), 4.19 (2H, s), 6.85 (1H, d, J=8.4 Hz), 7.26 (1H, d, J=8.4 Hz), 7.42 (1H, d, J=8.7 Hz), 8.63 (1H, d, J=1.9 Hz), 7.72 (1H, d, J=8.6 Hz), 8.09 (1H, s), 11.76 (1H, s), 11.89 (1H, s).
IR (Nujol): 1682 cm$^{-1}$.
m.p.: 176.5–180.0° C.

EXAMPLE 127
Production of 3-(2,4-dichlorobenzyl)-2-methyl-5-((1-penta-1,3-diene)sulfonylcarbamoyl)indole (157)

According to the method of Example 106, obtained is 3-(2,4-dichlorobenzyl)-2-methyl-5-((1-penta-1,3-diene)sulfonylcarbarnoyl)indole (157) (0.174 g) from 5-carboxy-3-(2,4-dichlorobenzyl)-2-methylindole (0.300 g), N,N'-carbonyldiimidazole (0.291 g), (1-penta-1,3-diene)sulfonamide (0.264 g) and diazabicycloundecene (0.273 g).

$^1$H-NMR (DMSO-d6, δ ppm): 1.83 (3H, d, J=6.4 Hz), 2.30 (3H, s), 4.09 (2H, s), 6.25–6.42 (2H, m), 6.77 (1H, d, J14.8 Hz), 6.92 (1H, d, J=8.4 Hz), 7.18 (1H, dd, J=9.5 and 14.8 Hz), 7.26 (1H, dd, J=2.2 and 8.4 Hz), 7.34 (1H, d, J=8.5 Hz), 7.61 (2H, m), 8.02 (1H, s), 11.38 (1H, brs), 11.82 (1H, brs).
IR (Nujol): 1682 cm$^{-1}$.
m.p.: 174.0–177.0° C.

EXAMPLE 128
Production of 5-((2-cyclopropylethylene)sulfonylcarbamoyl)-3-(2,4-dichlorobenzyl)-2-methylindole (158)

According to the method of Example 106, obtained is 5-((2-cyclopropylethylene)sulfonylcarbamoyl)-3-(2,4-dichlorobenzyl)-2-methylindole (158) (0.180 g) from 5-carboxy-3-(2,4-dichlorobenzyl)-2-methylthioindole (0.300 g), N,N'- carbonyldiimidazole (0.291 g), (2-cyclopropylethylene)sulfonylcarbamoyl (0.264 g) and diazabicycloundecene (0.273 g).

$^1$H-NMR (DMSO-d6, δ ppm): 0.70–0.74 (2H, m), 0.94–0.98 (2H, m), 1.68–1.77 (1H, m), 2.30 (3H, s), 4.09 (2H, s), 6.34 (1H, dd, J=10.4 and 14.8 Hz), 6.84 (1H, d, J=14.8 Hz), 6.92 (1H, d, J=8.4 Hz), 7.27 (1H, dd, J=2.2 and Hz), 7.34 (1H, d, J=8.6 Hz), 7.62 (2H, m), 8.02 (1H, s), 11.38 (1H, brs), 11.73 (1H, brs).

IR (Nujol): 1684 cm$^{-1}$.

m.p.: 172.5–174.0° C.

EXAMPLE 129

Production of 3-(2,4-dichlorobenzyl)-2-methyl-5-((4-methyl-(E)-styrene)sulfonylcarbamoyl)indole (159)

According to the method of Example 106, obtained is 3-(2,4-dichlorobenzyl)-2-methyl-5-((4-methyl-(E)-styrene) sulfonylcarbamoyl)indole (159) (0.122 g) from 5-carboxy-3-(2,4-dichlorobenzyl)-2-methylthioindole (0.200 g), N,N'-1-carbonyldiimidazole (0.126 g), (4-methyl-(E)-styrene) sulfonamide (0.153 g) and diazabicycloundecene (0.118 g).

$^1$H-NMR (DMSO-d6, δppm): 2.29 (3H, s), 2.34 (3H, s), 4.08 (2H, s), 6.91 (1H, d, J=8.4 Hz), 7.26 (3H, m), 7.34 (1H, d, J=8.5 Hz), 7.42 (1H, d, J=15.4 Hz), 7.56–7.67 (5H, m), 8.05 (1H, s), 11.38 (1H, brs), 11.95 (1H, brs).

IR (Nujol): 1678 cm$^{-1}$.

m.p.: 253.5–255.0° C.

EXAMPLE 130

Production of 3-(2,4-dichlorobenzyl)-5-((4-methoxy-(E)-styrene)sulfonylcarbamoyl)-2-methylindole (160)

According to the method of Example 106, obtained is 3-(2,4-dichlorobenzyl)-5-((4-methoxy-(E)- -styrene) sulfonylcarbamoyl)-2-methylindole (160) (0.067 g) from 5-carboxy-3-(2,4-dichlorobenzyl)-2-methylthioindole (0.200 g), N,N'-carbonyldiimidazole (0.126 g), (4-methoxy-(E)- -styrene)sulfonamide (0.165 g) and diazabicycloundecene (0.118 g).

$^1$H-NMR (DMSO-d6, δ ppm): 2.29 (3H, s), 3.80 (3H, s), 4.08 (2H, s), 6.91 (1H, d, J=8.5 Hz), 6.99 (2H, d, J=8.8 Hz), 7.25 (1H, dd, J=8.4 and 2.1 Hz), 7.32 (1H, d, J=15.4 Hz), 7.33 (1H, d, J=8.4 Hz), 7.55 (1H, d, J=15.4 Hz), 7.60–7.64 (2H, m), 7.71 (2H, d, J=8.7 Hz), 8.05 (1H, s), 11.37 (1H, s), 11.89 (1H, brs).

IR (Nujol): 1674 cm$^{-1}$.

m.p.: 227.5–231.0° C.

EXAMPLE 131

Production of 3-(2,4-dichlorobenzyl)-5-methoxycarbonyl-2-(methoxymethyl)indole (161)

Trifluoroacetic acid (1.14 g) and triethylsilane (2.33 g) are dissolved in dichloromethane (10 ml), and the resulting solution is cooled at 0° C., to which is dropwise added a solution of 5-methoxycarbonyl-2-(methoxymethyl)indole (1.10 g) and 2,4-dichlorobenzaldehyde (0.96 g) dissolved in dichloromethane (20 ml). The reaction mixture is stirred at 0° C. for 3 hours, and thereafter an aqueous solution of 10% sodium hydroxide (5 ml), chloroform (40 ml) and a saturated saline solution (40 ml) are added thereto in that order for liquid-liquid separation. The organic layer is dried with anhydrous sodium sulfate, and concentrated under reduced pressure. The resulting residue is purified through silica gel column chromatography (ethyl acetate/hexane=3/7) to obtain 3-(2,4-dichlorobenzyl)-5-methoxycarbonyl-2-(methoxymethyl)indole (161) (0.61 g).

$^1$H-NMR (DMSO-d6, δ ppm): 3.37 (3H, s), 3.90 (3H, s), 4.16 (2H, s), 4.54 (2H, s), 6.86 (1H, d, J=8.4 Hz), 7.04 (1H, dd, J=2.2 and 8.4 Hz), 7.33 (1H, d, J=9.6 Hz), 7.41 (1H, d, J=2.2 Hz), 7.90 (1H, dd, J=1.5 and 8.5 Hz), 8.15 (1H, s) 8.53 (1H, brs).

EXAMPLE 132

Production of 5-carboxy-3-(2,4-dichlorobenzyl)-2-(methoxymethyl)indole (162)

According to the method of Example 115, obtained is 5-carboxy-3-(2,4-dichlorobenzyl)-2-(methoxymethyl) indole (162) (0.56 g) from 3-(2,4-dichlorobenzyl)-5-methoxycarbonyl-2-(methoxymethyl)indole (0.61 g).

EXAMPLE 133

Production of 3-(2,4-dichlorobenzyl)-2-methoxymethyl-5-(1-pentanesulfonylcarbamoyl)indole (163)

According to the method of Example 106, obtained is 3-(2,4-dichlorobenzyl)-2-methoxymethyl-5-(1-pentanesulfonylcarbamoyl)indole (163) (0.115 g) from 5-carboxy- 3-(2,4-dichlorobenzyl)-2-methoxymethylindole (0.364 g), N,N'-carbonyldiimidazole (0.243 g), 1-pentanesulfonamide (0.227 g) and diazabicycloundecene (0.228 g).

$^1$H-NMR (DMSO-d6, δ ppm): 0.80 (3H, t, J=7.3 Hz), 1.25 (2H, m), 1.34 (2H, m), 1.66 (2H, m), 3.32 (3H, s), 3.48 (2H, t, J=7.7 Hz), 4.17 (2H, s), 4.51 (2H, s), 6.92 (1H, d, J=8.4 Hz), 7.25 (1H, dd, J=2.1 and 8.3 Hz), 7.41 (1H, d, J=8.6 Hz), 7.62 (1H, d, J=2.1 Hz), 7.69 (1H, dd, J=1.5 and 8.6 Hz), 8.10 (1H, s), 11.64 (1H, s), 11.73 (1H, s).

IR (Nujol): 1685 cm$^{-1}$.

m.p.: 189–192° C.

EXAMPLE 134

Production of 3-((1-bromonaphthalen-2-yl)methyl)-2-methyl-5-((E)-styrene)sulfonylcarbamoyl)indole (164)

According to the method of Example 106, obtained is 3-((1-bromonaphthalen-2-yl)methyl)-2-methyl-5-((E)-- styrene)sulfonylcarbamoyl)indole (164) (0.080 g) from 3-((1-bromonaphthalen-2-yl)methyl)-5-carboxy-2-methylindole (0.237 g), N,N'-carbonyldiimidazole (0.162 g), (E)- -styrenesulfonamide (0.183 g) and diazabicycloundecene (0.152 g).

$^1$H-NMR (DMSO-d6, δ ppm): 2.31 (3H, s), 4.37 (2H, s), 7.10 (1H, d, J=8.5 Hz), 7.34 (1H, d, J=8.6 Hz), 7.43 (3H, m), 7.47 (1H, d, J=15.4 Hz), 7.55 (1H, t, J=7.7 Hz), 7.60 (1H, d, J=15.9 Hz), 7.62 (1H, m), 7.67 (1H, m), 7.74 (2H, m), 7.78 (1H, d, J=8.5 Hz), 7.88 (1H, d, J=8.0 Hz), 8.12 (1H, s), 8.26 (1H, d, J=8.6 Hz), 11.38 (1H, s), 11.97 (1H, s).

IR (Nujol): 1674 cm$^{-1}$.

m.p.: 235–238° C.

EXAMPLE 135

Production of 3-((1-bromonaphthalen-2-yl)methyl)-2-methyl-5-(4-vinylbenzene)sulfonylcarbamoyl)indole (165)

According to the method of Example 106, obtained is 3-((1-bromonaphthalen-2-yl)methyl)-2-methyl-5-(4-vinylbenzene)sulfonylcarbamoyl)indole (165) (0.130 g) from 3-((1-bromonaphthalen-2-yl)methyl)-5-carboxy-2-methylindole (0.237 g), N,N'-carbonyldiimidazole (0.162 g), (4-vinylbenzene)sulfonamide (0.183 g) and diazabicycloundecene (0.152 g).

$^1$H-NMR (DMSO-d6, δ ppm): 2.30 (3H, s), 4.36 (2H, s), 5.44 (1H, d, J=11.0 Hz), 5.99 (1H, d, J=17.6 Hz), 6.79 (1H, dd, J=11.1 and 17.7 Hz), 7.10 (1H, d, J=8.4 Hz), 7.32 (1H, d, J=8.6 Hz), 7.55 (2H, m), 7.67 (3H, m), 7.78 (1H, d, J=8.5 Hz), 7.90 (3H, m), 8.04 (1H, s), 8.26 (1H, d, J=8.4 Hz), 11.38 (1H, s), 12.16 (1H, s).

IR (Nujol): 1674 cm$^{-1}$.

m.p.: 222–224° C.

EXAMPLE 136
Production of 3-((1-bromonaphthalen-2-yl)methyl)-2-methyl-5-(p-toluenesulfonylcarbamoyl)indole (166)

According to the method of Example 106, obtained is 3-((1-bromonaphthalen-2-yl)methyl)-2-methyl-5-(p-toluenesulfonylcarbamoyl)indole (166) (0.145 g) from 3-((1-bromonaphthalen-2-yl)methyl)-5-carboxy-2-methylindole (0.237 g), N,N'-carbonyldiimidazole (0.162 g), p-toluenesulfonamide (0.171 g) and diazabicycloundecene (0.152 g).

$^1$H-NMR (DMSO-d6, δ ppm): 2.30 (3H, s), 2.35 (3H, s), 4.36 (2H, s), 7.09 (1H, d, J=8.5 Hz), 7.31 (1H, d, J=8.6 Hz), 7.37 (2H, d, J=8.1 Hz), 7.54 (2H, m), 7.67 (1H, t, J=7.9 Hz), 7.78 (1H, d, J=8.5 Hz), 7.83 (2H, d, J=8.2 Hz), 7.89 (1H, d, J=8.2 Hz), 8.03 (1H, s), 8.26 (1H, d, J=8.6 Hz), 11.37 (1H, s), 12.09 (1H, brs).

IR (Nujol): 1674 cm$^{-1}$.

m.p.: 260–262° C.

EXAMPLE 137
Production of 5-(benzenesulfonylcarbamoyl)-3-((1-bromonaphthalen-2-yl)methyl)-2-methylindole (167)

According to the method of Example 106, obtained is 5-(benzenesulfonylcarbamoyl)-3-((1-bromonaphthalen-2-yl)methyl)-2-methylindole (167) (0.120 g) from 3-((1-bromonaphthalen-2-yl)methyl)-5-carboxy-2-methylindole (0.237 g), N,N'-carbonyldiimidazole (0.162 g), benzenesulfonamide (0.157 g) and diazabicycloundecene (0.152 g).

$^1$H-NMR (DMSO-d6, δ ppm): 2.30 (3H, s), 4.36 (2H, s), 7.09 (1H, d, J=8.5 Hz), 7.32 (1H, d, J=8.5 Hz), 7.53–7.60 (4H, m), 7.67 (2H, m), 7.78 (H, d, J=8.5 Hz), 7.89 (1H, d, J=8.2 Hz), 7.95 (2H, m), 8.05 (1H, s), 8.26 (1H, d, J=8.5 Hz), 11.38 (1H, s), 12.18 (1H, brs).

IR(Nujol): 1674 cm$^{-1}$.

m.p.: 159–161° C.

EXAMPLE 138
Production of 3-((2-chloro-4-phenyl)benzyl)-2-methyl-5-((E)-styrenesulfonylcarbamoyl)indole (168)

According to the method of Example 106, obtained is 3-((2-chloro-4-phenyl)benzyl)-2-methyl-5-((E)-styrenesulfonylcarbamoyl)indole (168) (0.107 g) from 5-carboxy-3-((2-chloro-4-phenyl)benzyl)-2-methylindole (0.226 g), N,N'-carbonyldiimidazole (0.162 g), (E)-styrenesulfonamide (0.183 g) and diazabicycloundecene (0.152 g).

$^1$H-NMR (DMSO-d6, δ ppm): 2.32 (3H, s), 4.14 (2H, s), 6.98 (1H, d, J=8.1 Hz), 7.35 (2H, m), 7.43 (6H, m), 7.48 (1H, d, J=15.6 Hz), 7.63 (4H, m), 7.74 (3H, m), 8.11 (1H, s), 11.38 (1H, s), 11.99 (1H, brs).

IR (Nujol): 1670 cm$^{-1}$.

m.p.: 232–235° C.

EXAMPLE 139
Production of 3-((2-chloro-4-phenyl)benzyl)-2-methyl-5-((4-vinylbenzene)sulfonylcarbamoyl)indole (169)

According to the method of Example 106, obtained is 3-((2-chloro-4-phenyl)benzyl)-2-methyl-5-((4-vinylbenzene)sulfonylcarbamoyl)indole (169) (0.078 g) from 5-carboxy-3-((2-chloro-4-phenyl)benzyl)-2-methylindole (0.226 g), N,N'-carbonyldiimidazole (0.162 g), (4-vinylbenzene)sulfonamide (0.183 g) and diazabicycloundecene (0.152 g).

$^1$H-NMR (DMSO-d6, δ ppm): 2.32 (3H, s), 4.13 (2H, s), 5.44 (1H, d, J=11.0 Hz), 5.98 (1H, d, J=17.6 Hz), 6.79 (1H, dd, J=17.5 and 10.9 Hz), 6.98 (1H, d, J=8.1 Hz), 7.32 (1H, d, J=8.6 Hz), 7.36 (1H, d, J=7.4 Hz), 7.42–7.47 (3H, m), 7.54 (1H, dd, J=8.4 and 2.0 Hz), 7.63 (2H, m), 7.67 (2H, d, J=8.5 Hz), 7.73 (1H, d, J=1.8 Hz), 7.91 (2H, d, J=8.5 Hz), 8.03 (1H, s), 11.37 (1H, s), 12.21 (1H, brs).

IR (Nujol): 1670 cm$^{-1}$.

m.p.: 204–210° C.

EXAMPLE 140
Production of 3-((1-bromonaphthalen-2-yl)methyl)-2-methyl-5-((1-pent-2-ene)sulfonylcarbamoyl)indole (170)

According to the method of Example 106, obtained is 3-((1-bromonaphthalen-2-yl)methyl)- 5-((1-pent-2-ene)sulfonylcarbamoyl)indole (170) (0.058 g) from 3-((1-bromonaphthalen-2-yl)methyl)-5-carboxy-2-methylindole (0.237 g), N,N'-carbonyldiimidazole (0.162 g), (1-pent-1-ene)sulfonamide (0.149 g) and diazabicycloundecene (0.152 g).

$^1$H-NMR (DMSO-d6, δ ppm): 0.83 (3H, brs), 1.41 (2H, m), 2.19 (2H, m), 2.32 (3H, s), 4.37 (2H, s), 6.73 (1H, d, J=14.9 Hz), 6.80 (1H, m), 7.10 (1H, d, J=8.1 Hz), 7.34 (1H, d, J=8.3 Hz), 7.55 (1H, m), 7.60 (1H, d, J=8.2 Hz), 7.67 (1H, m), 7.78 (1H, d, J=8.2 Hz), 7.89 (1H, d, J=7.8 Hz), 8.07 (1H, s), 8.27 (1H, d, J=8.1 Hz), 11.38 (1H, s), 11.79 (1H, brs).

IR (Nujol): 1670 cm$^{-1}$.

m.p.: 104–113° C.

EXAMPLE 141
Production of 3-((2-chloro-4-phenyl)benzyl)-2-methyl-5-(p-toluenesulfonylcarbamoyl)indole (171)

According to the method of Example 106, obtained is 3-((2-chloro-4-phenyl)benzyl)-2-methyl-5-(p-toluenesulfonylcarbamoyl)indole (171) (0.063 g) from 5-carboxy-3-((2-chloro-4-phenyl)benzyl)-2-methylindole (0.226 g), N,N'-carbonyldiimidazole (0.162 g), p-toluenesulfonamide (0.171 g) and diazabicycloundecene (0.152 g).

$^1$H-NMR (DMSO-d6, δ ppm): 2.32 (3H, s), 2.35 (3H, s), 4.13 (2H, s), 6.98 (1H, d, J=8.2 Hz), 7.31 (1H, d, J=8.4 Hz), 7.37 (3H, m), 7.42–7.47 (3H, m), 7.54 (1H, d, J=8.4 Hz), 7.64 (2H, d, J=7.8 Hz), 7.73 (1H, brs), 7.84 (2H, d, J=8.1 Hz), 8.02 (1H, s), 11.36 (1H, s), 12.22 (1H, brs).

IR (Nujol): 1682 cm$^{-1}$.

m.p.: 150–154° C.

EXAMPLE 142
Production of 3-(4-bromo-2-chlorobenzyl)-2-methyl-5-(1-pentanesulfonylcarbamoyl)indole (172)

From 5-carboxy-3-(4-bromo-2-chlorobenzyl)-2-methylindole (0.15 g), N,N'-carbonyldiimidazole (0.128 g), diazabicycloundecene (0.12 g) and 1-pentanesulfonamide (0.12 g), obtained is 3-(4-bromo-2-chlorobenzyl)-2-methyl-5-(1-pentanesulfonylcarbamoyl)indole (172) (0.152 g).

$^1$H-NMR (DMSO-d6, δ ppm): 0.82 (3H, t, J=7.2 Hz), 1.24–1.32 (2H, m), 1.33–1.42 (2H, m), 1.67–1.72 (2H, m), 2.31 (3H, s), 3.48 (2H, t, J=7.7 Hz), 4.07 (2H, s), 6.87 (1H, d, J=8.3 Hz), 7.36 (1H, d, J=8.5 Hz), 7.39 (1H, dd, J=1.9 and 8.4 Hz), 7.64 (1H, dd, J=1.0 and 8.4 Hz), 7.72 (1H, d, J=1.9 Hz), 8.04 (1H, s), 11.39 (1H, s), 11.69 (1H, brs).

IR (Nujol): 1667 cm$^{-1}$.

m.p.: 168–172° C.

EXAMPLE 143
Production of 3-(4-bromo-2-chlorobenzyl)-2-methyl-5-(2-(5-chlorothienyl)sulfonylcarbamoyl)indole (173)

From 5-carboxy-3-(4-bromo-2-chlorobenzyl)-2-methylindole (0.15 g), N,N'-carbonyldiimidazole (0.128 g), diazabicycloundecene (0.12 g) and 2-(5-chlorothienyl)sulfonamide (0.156 g), obtained is 3-(4-bromo-2-chlorobenzyl)-2-methyl-5-(2-(5-chlorothienyl)sulfonylcarbamoyl)indole (173) (0.146 g).

¹H-NMR (DMSO-d6, δ ppm): 2.29 (3H, s), 4.07 (2H, s), 6.85 (1H, d, J=8.3 Hz), 7.26 (1H, d, J=4.2 Hz), 7.34 (1H, d, J=8.5 Hz), 7.39 (1H, d, J=8.3 Hz), 7.60 (1H, d, J=8.6 Hz), 7.70 (1H, d, J=3.9 Hz), 7.73 (1H, s), 8.00 (1H, s), 11.41 (1H, s), 12.51 (1H, brs).
IR (Nujol): 1689 cm⁻¹.
m.p.: 223–228° C.
(30)
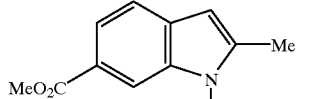
(31)
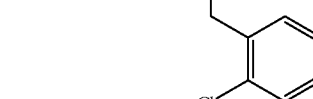
(32)
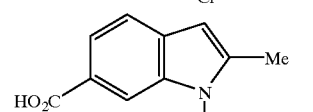
(33)
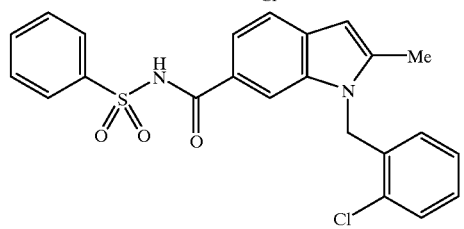
(34)
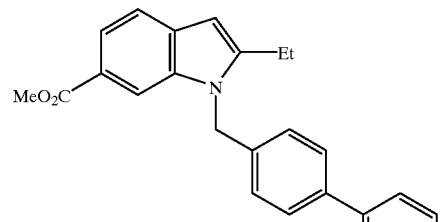
(35)
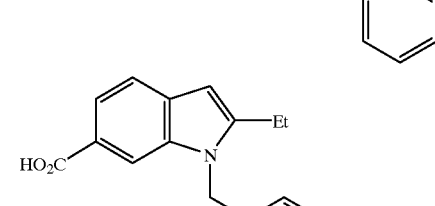
-continued
(36)
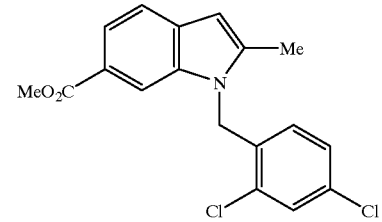
(37)
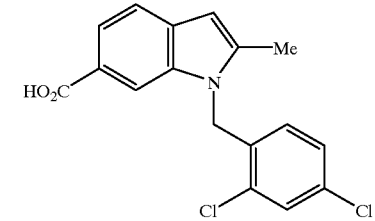
(38)
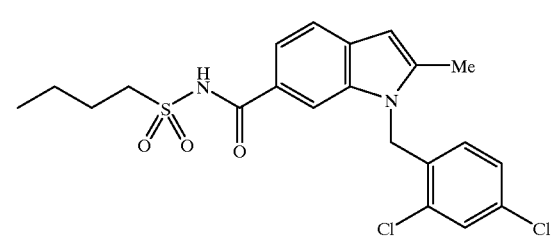
(39)
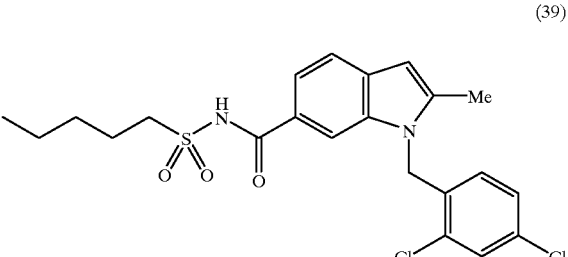
(40)
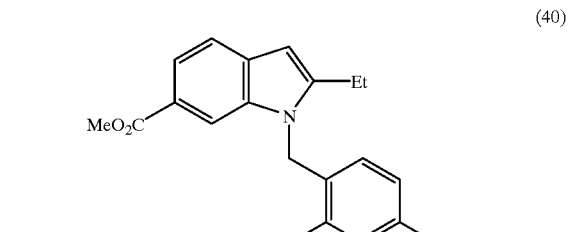
(41)
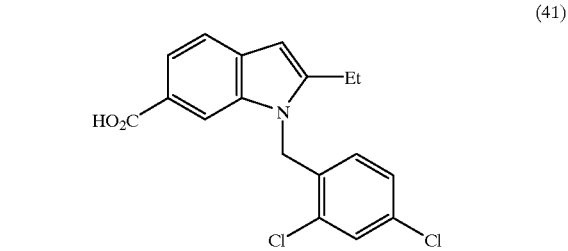

(42)
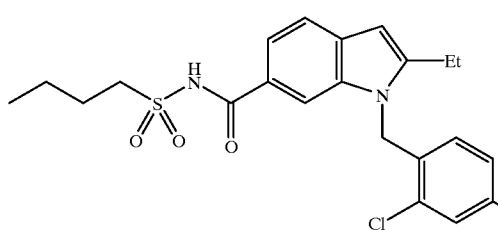
(43)
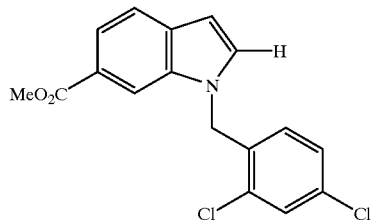
(44)
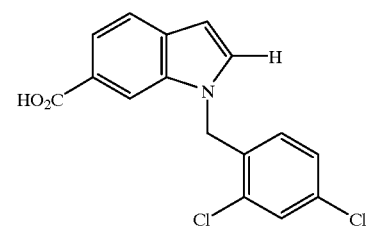
(45)
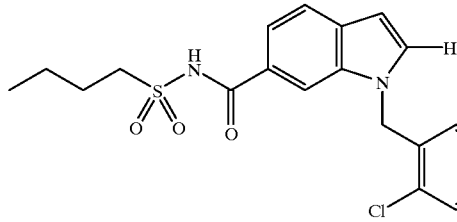
(46)
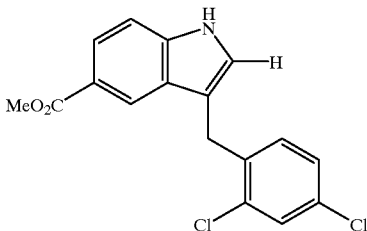
(47)
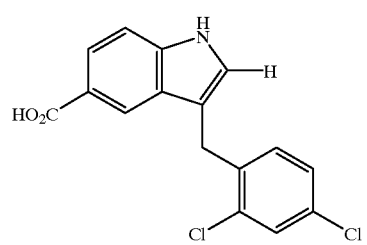
(48)
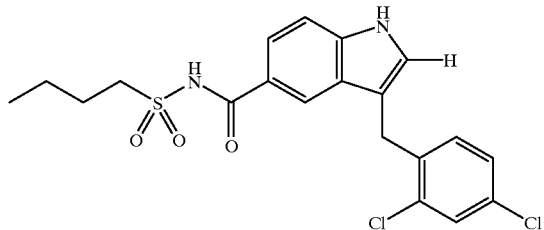
(49)
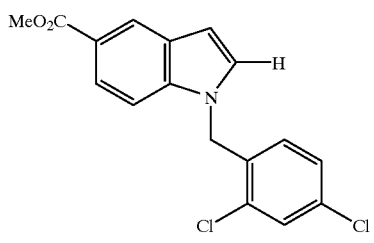
(50)
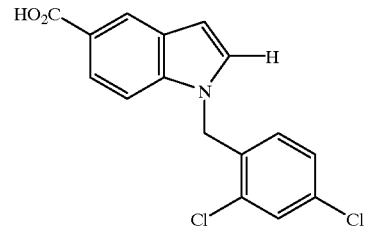
(51)
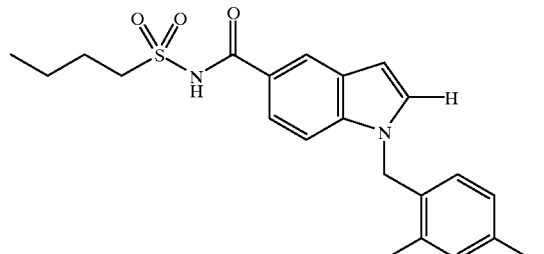
(52)
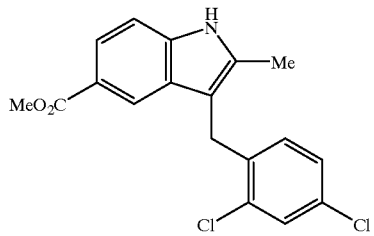
(53)
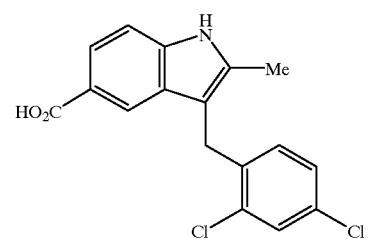

-continued
(54)
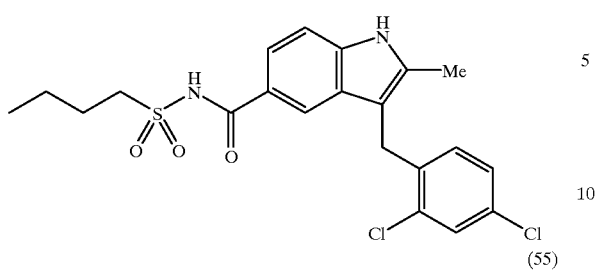
(55)
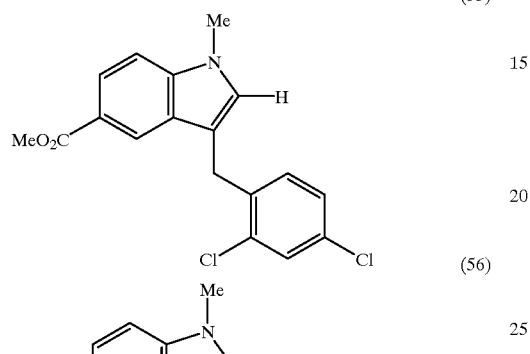
(56)
(57)
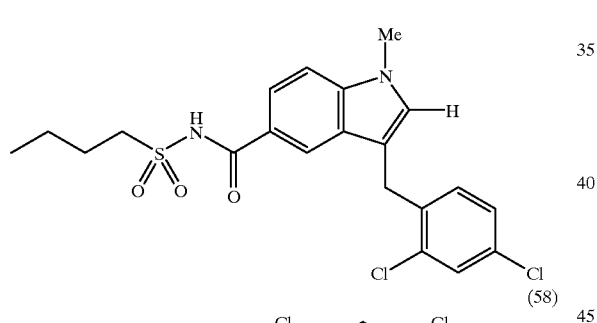
(58)
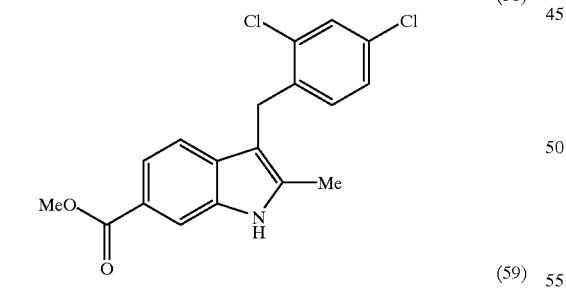
(59)
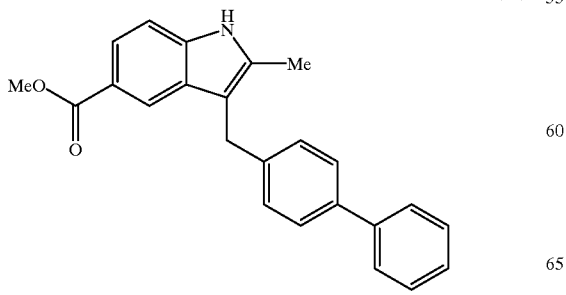
-continued
(60)
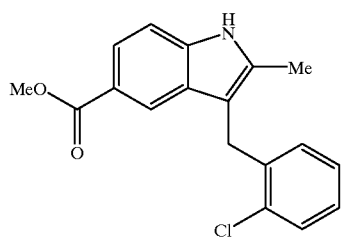
(61)
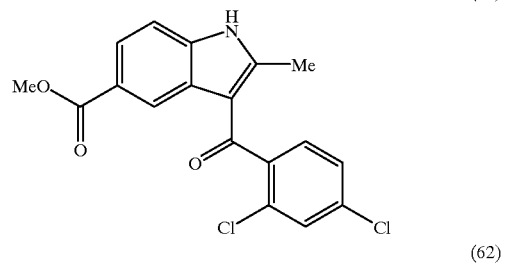
(62)
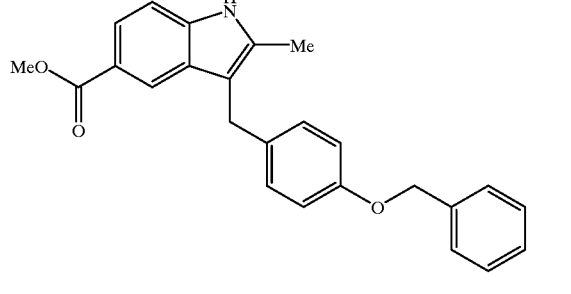
(63)
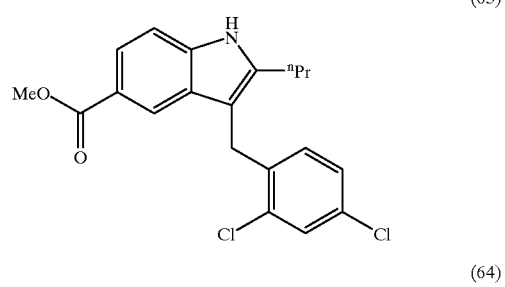
(64)
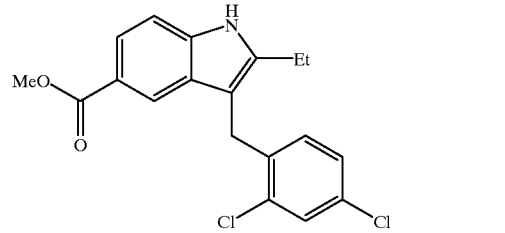
(65)

(66) 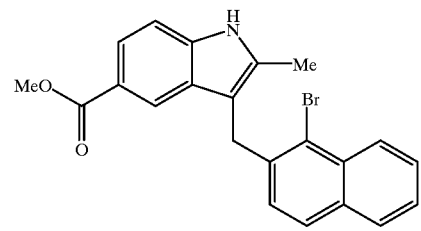
(67) 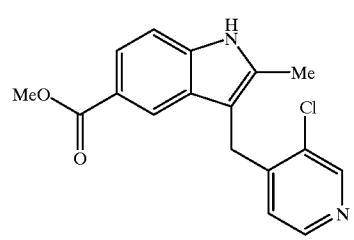
(68) 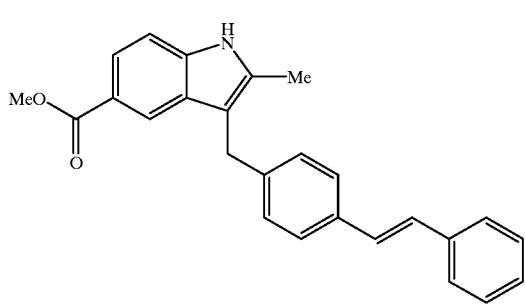
(69) 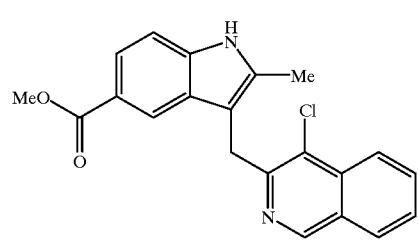
(70) 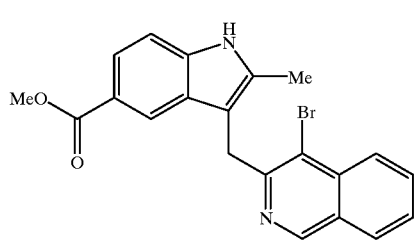
(71) 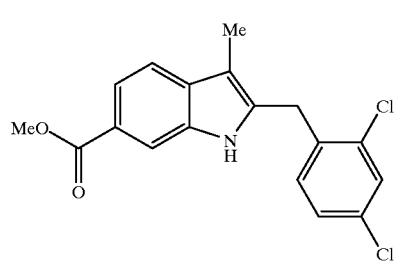
(72) 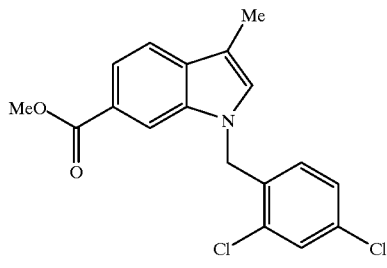
(73) 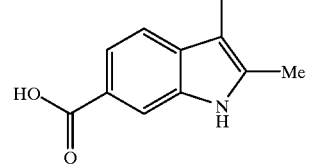
(74) 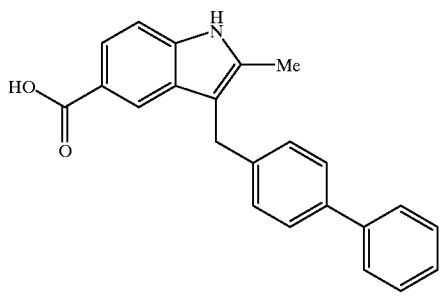
(75) 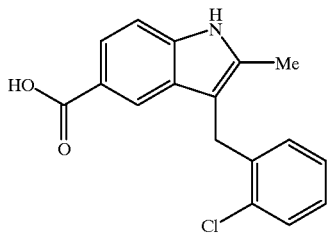
(76) 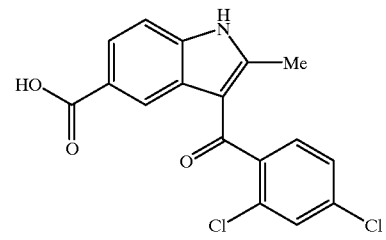
(77) 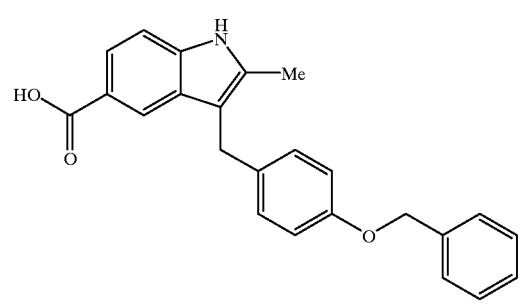

(78)
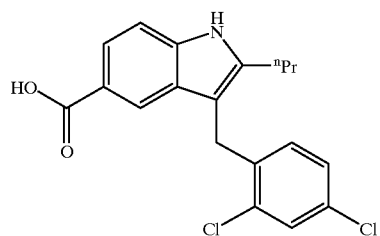
(79)
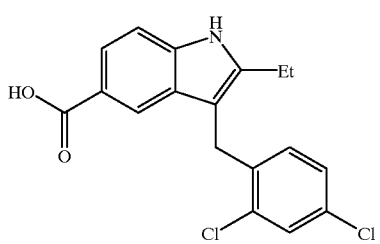
(80)
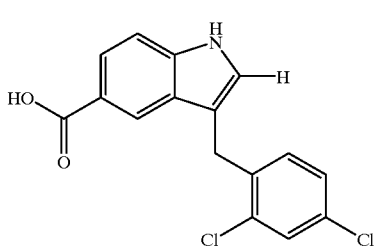
(81)
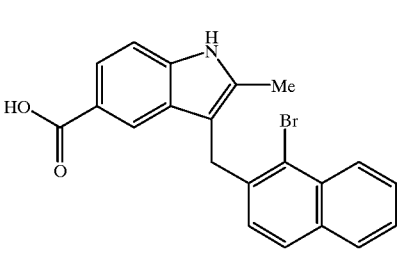
(82)
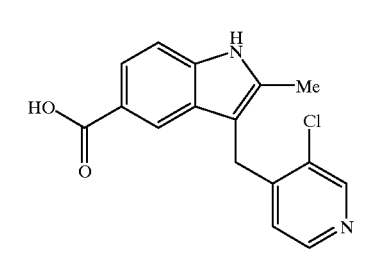
(83)
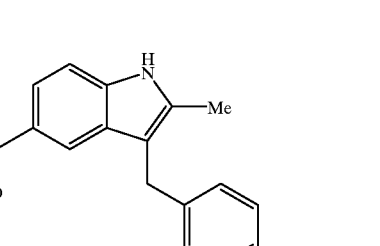
(84)
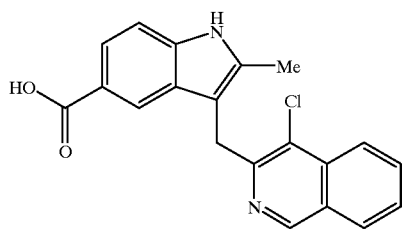
(85)
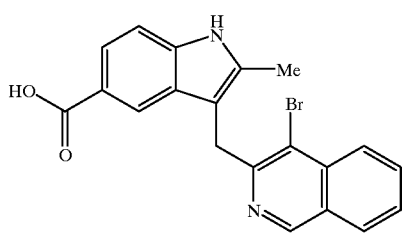
(86)
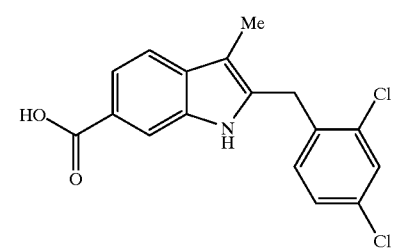
(87)
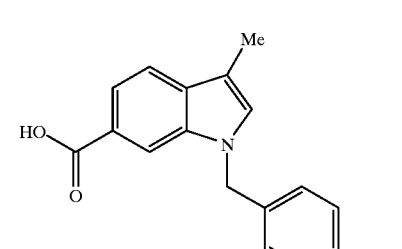
(88)
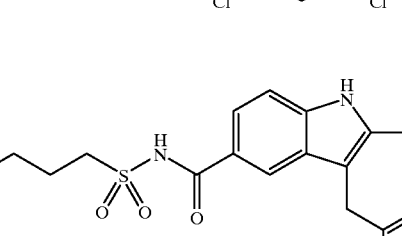
(89)
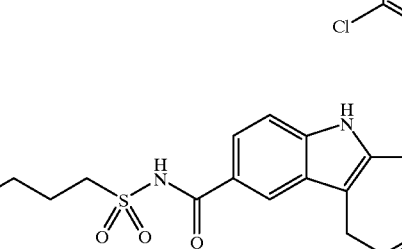

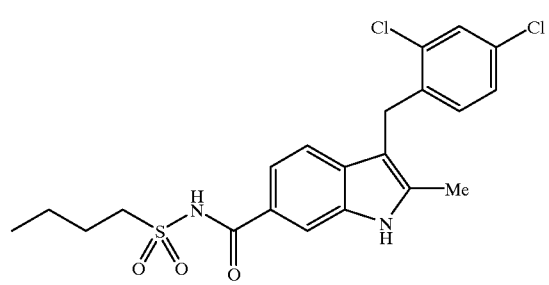
(90)
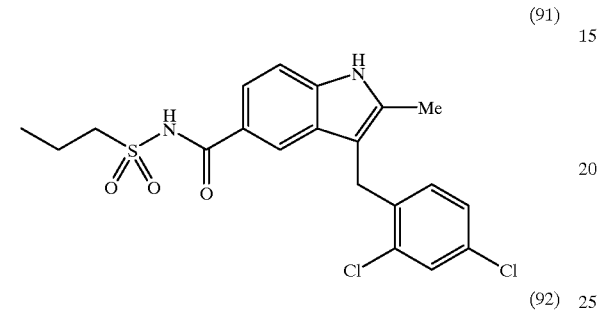
(91)
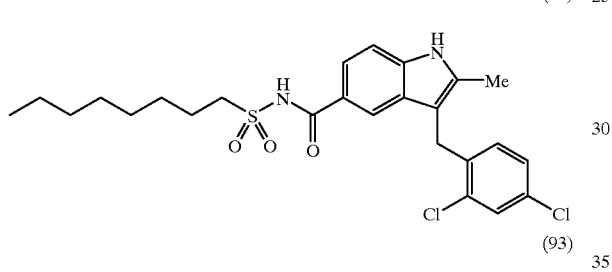
(92)
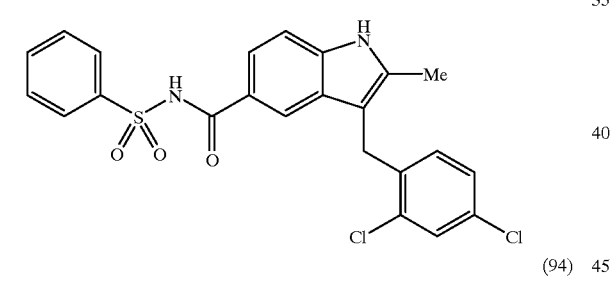
(93)
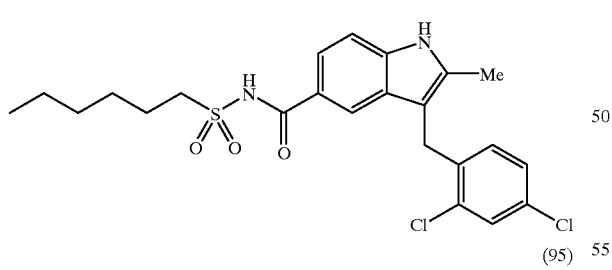
(94)
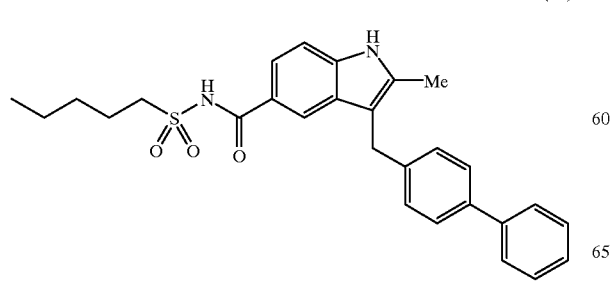
(95)
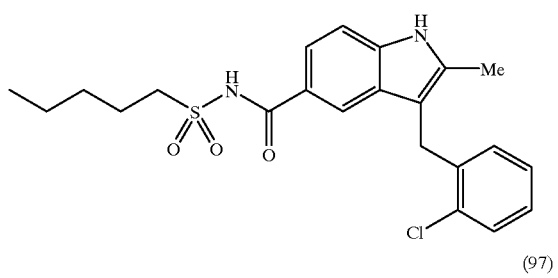
(96)
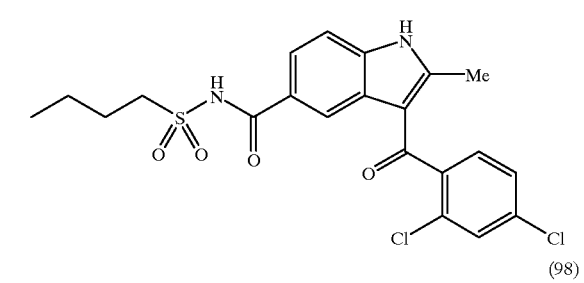
(97)
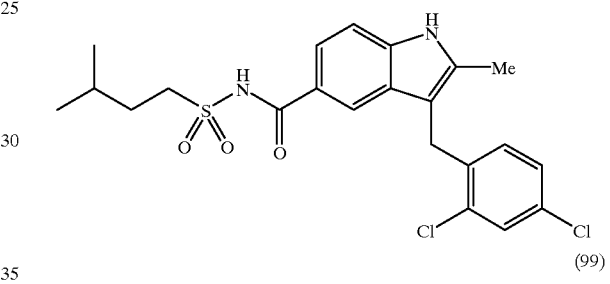
(98)
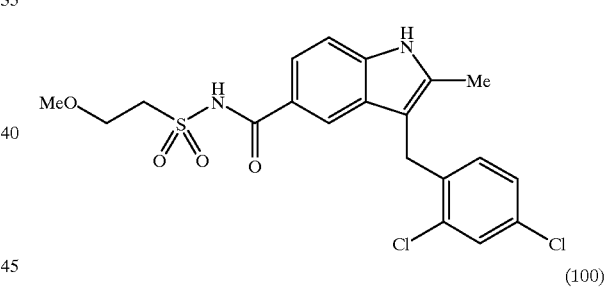
(99)
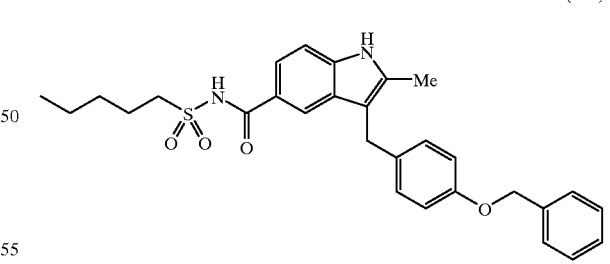
(100)
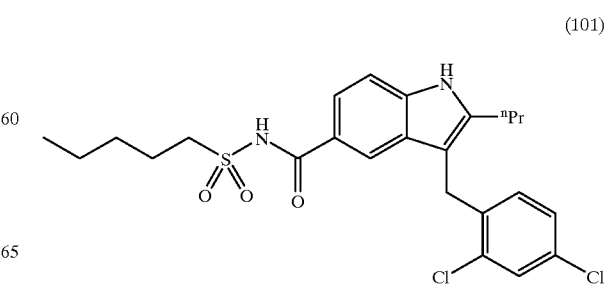
(101)

(102)
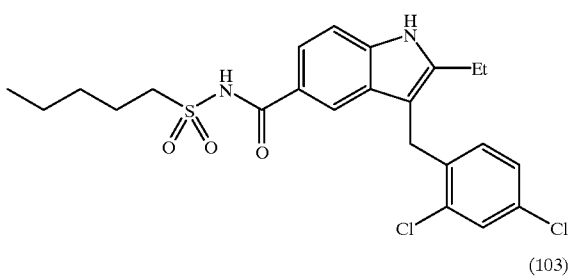
(103)
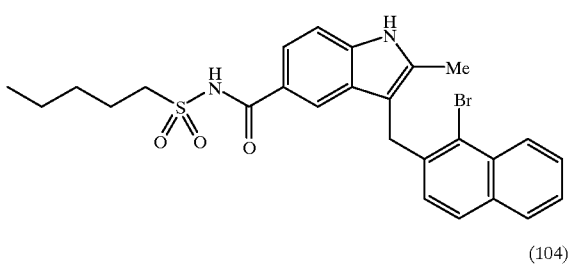
(104)
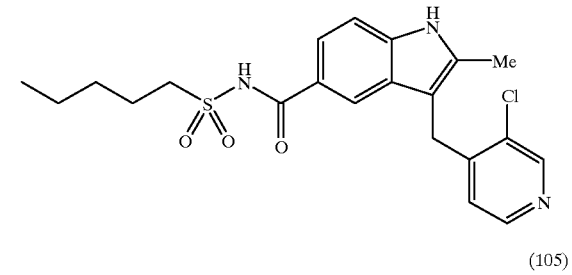
(105)
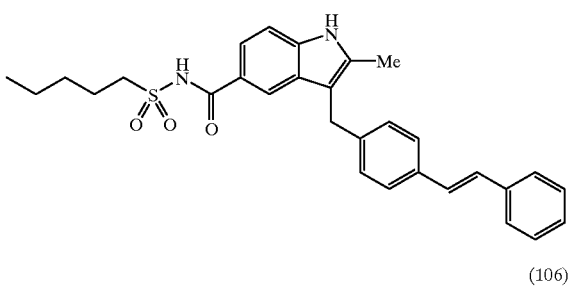
(106)
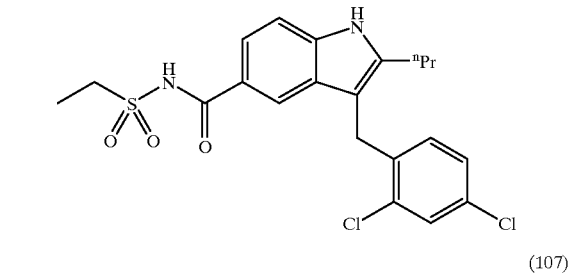
(107)
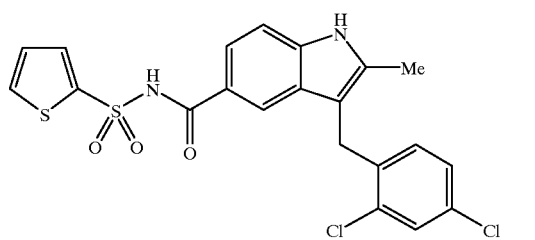
(108)
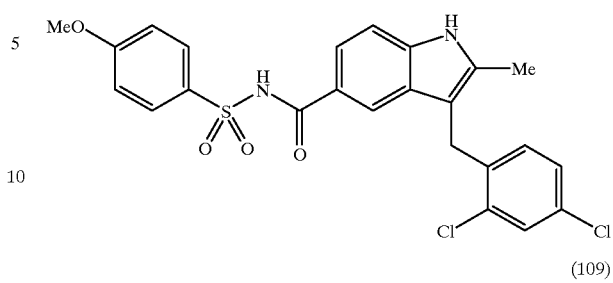
(109)
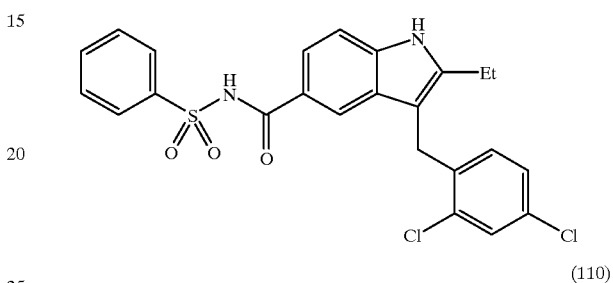
(110)
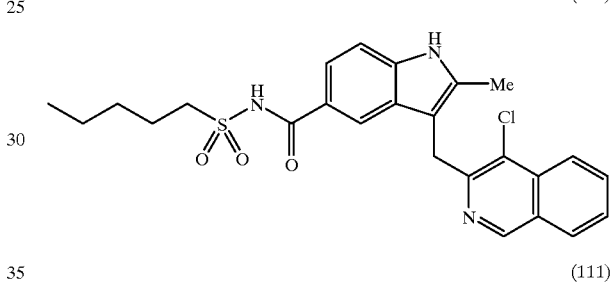
(111)
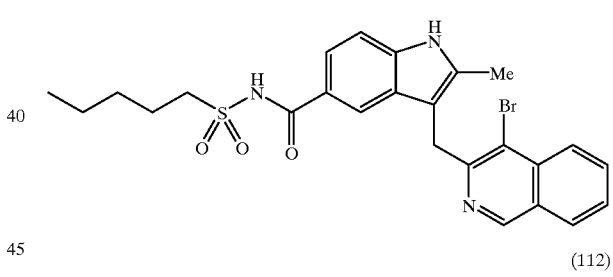
(112)
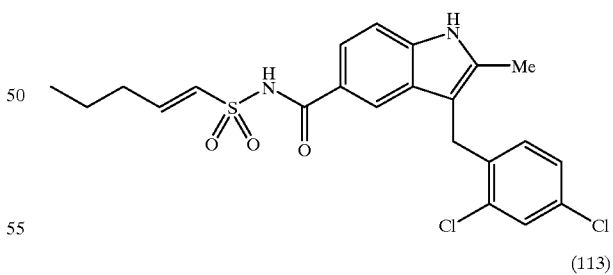
(113)
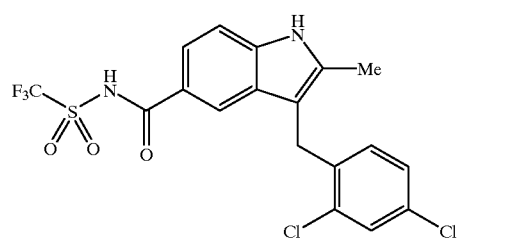

(114) 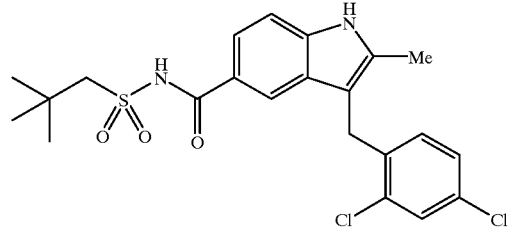
(115) 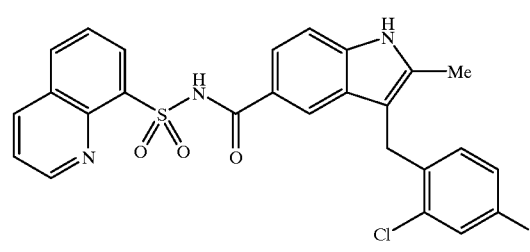
(116) 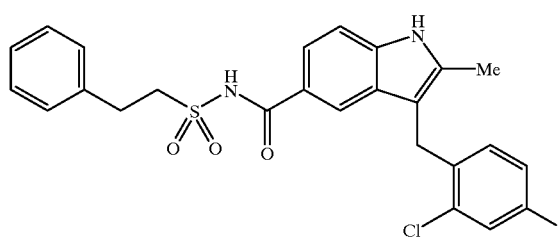
(117) 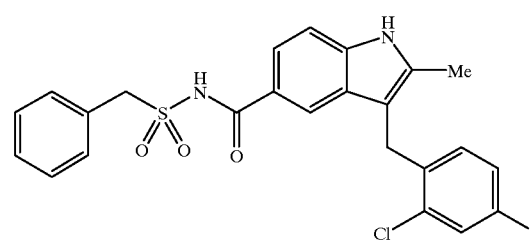
(118) 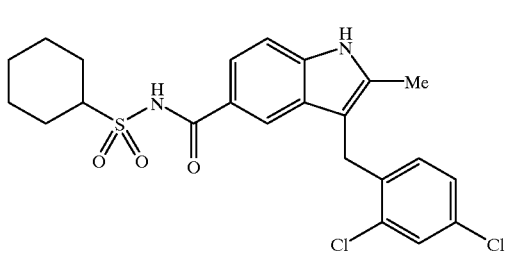
(119) 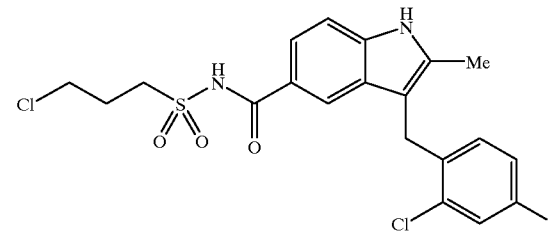
(120) 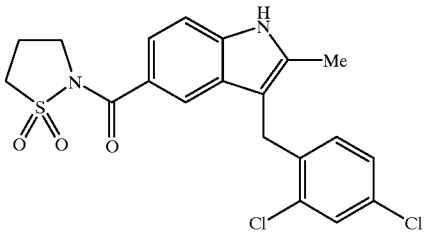
(121) 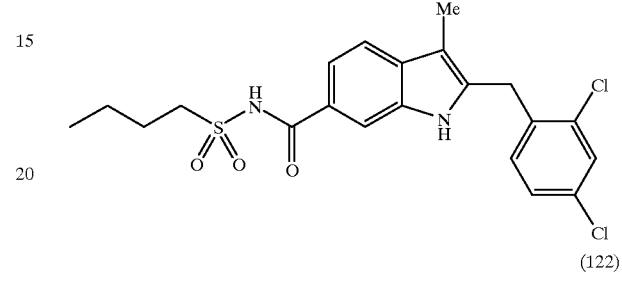
(122) 
(123) 
(124) 
(125) 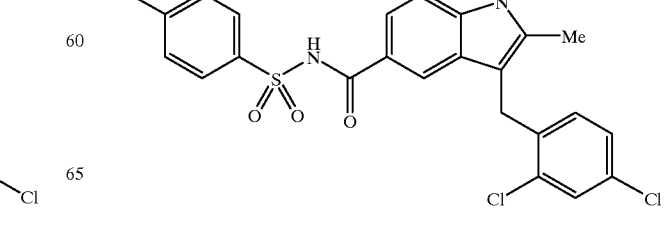

(126)
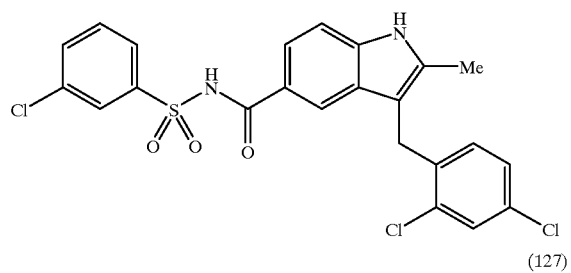
(127)
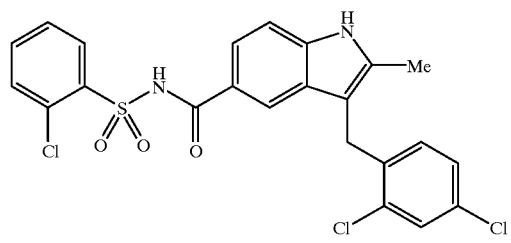
(128)
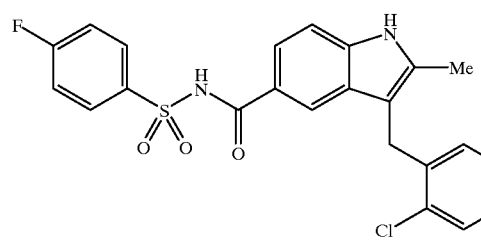
(129)
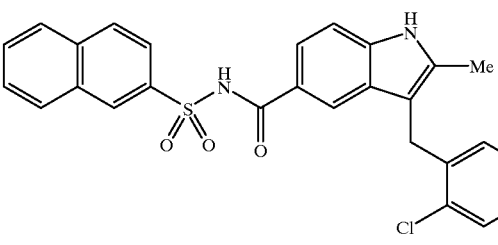
(130)
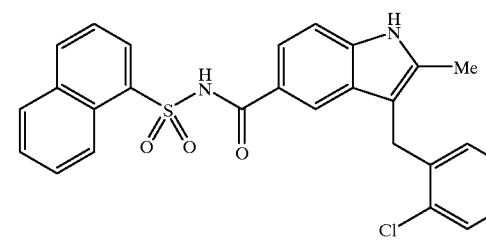
(131)
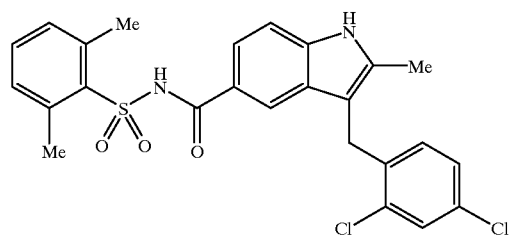
(132)
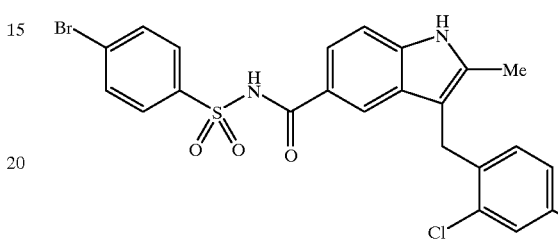
(133)
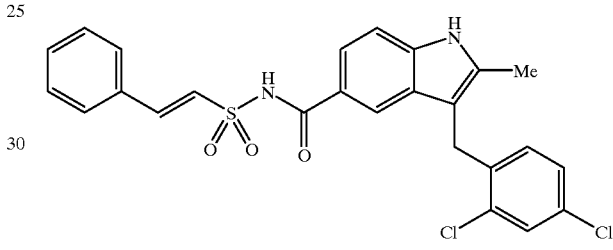
(134)
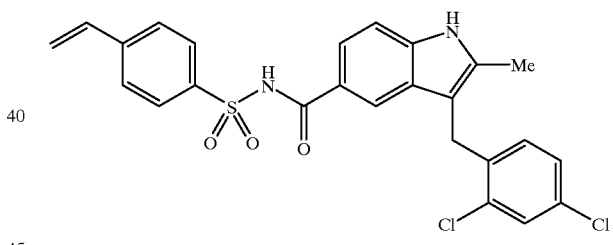
(135)
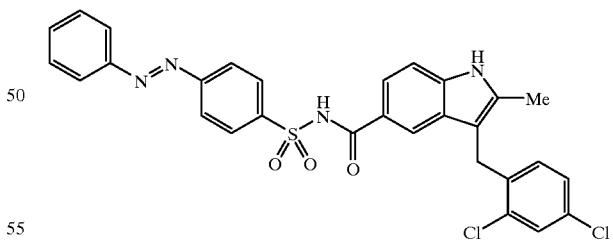
(136)
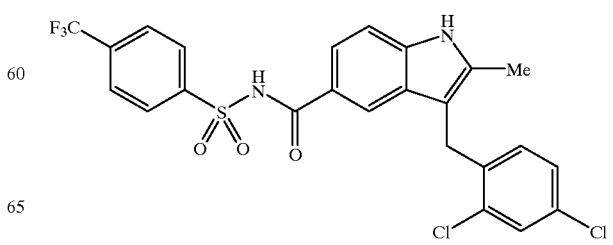
(137)

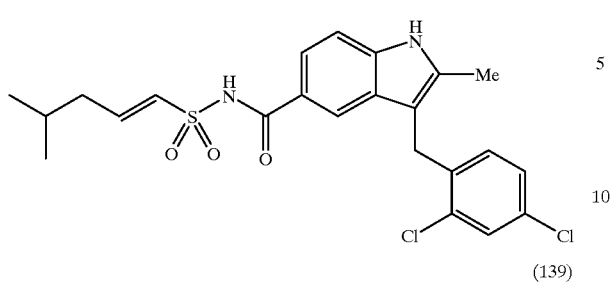
(138)
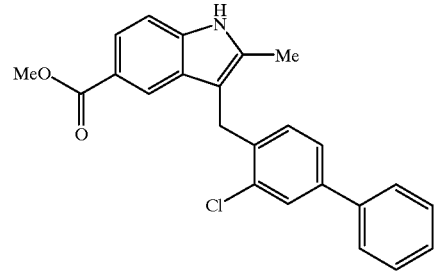
(144)
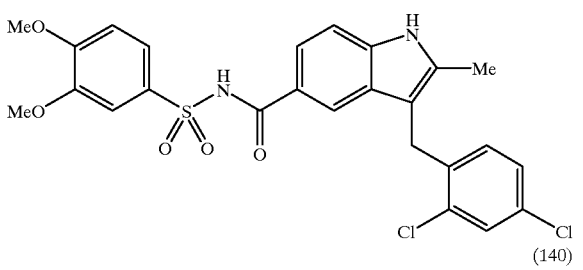
(139)
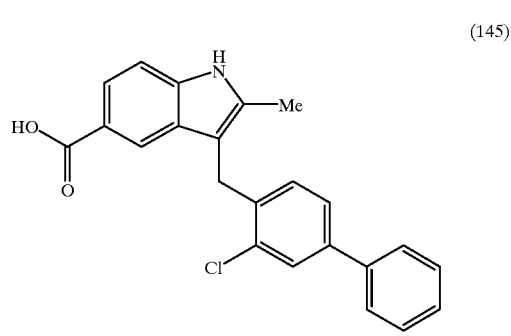
(145)
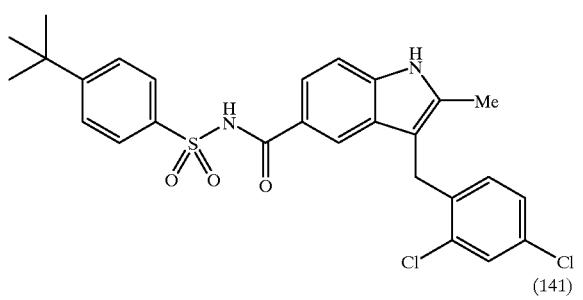
(140)
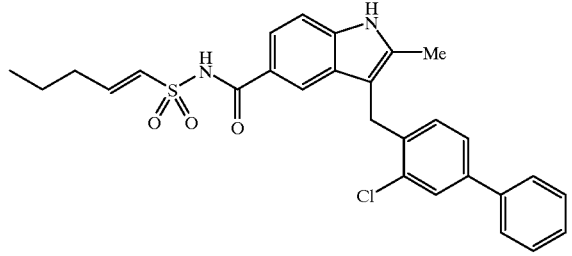
(146)
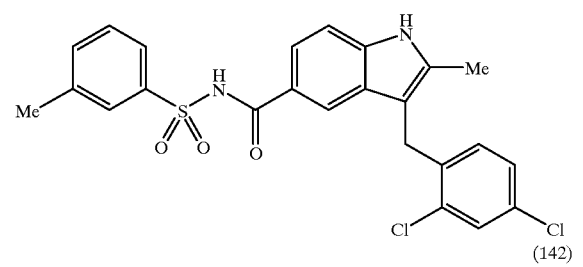
(141)
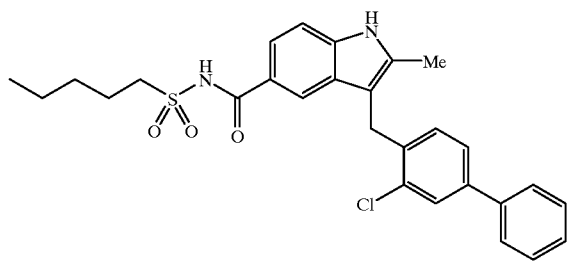
(147)
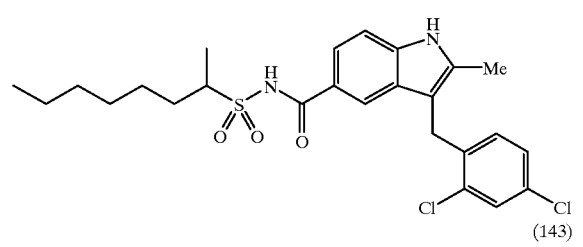
(142)
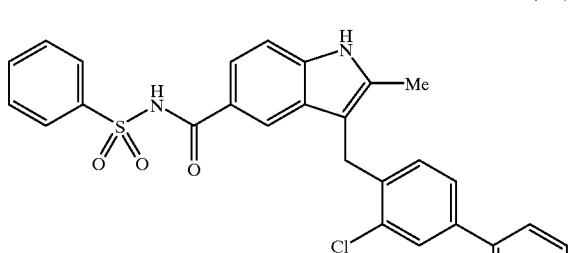
(148)
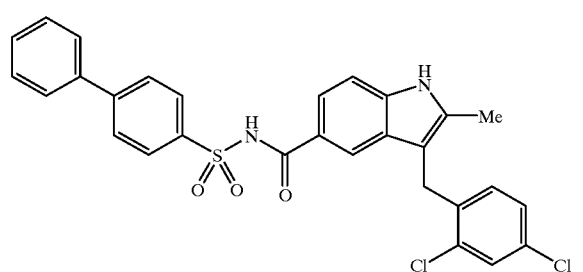
(143)

(149)
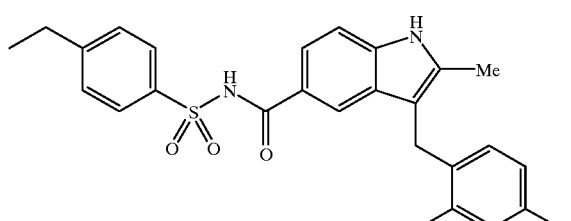
(150)
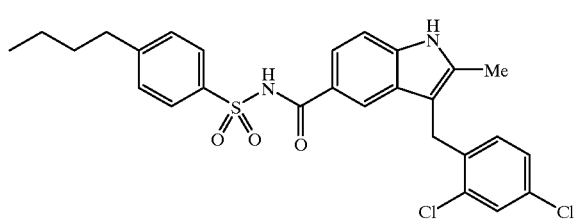
(151)
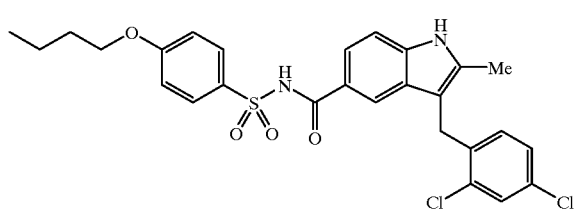
(152)
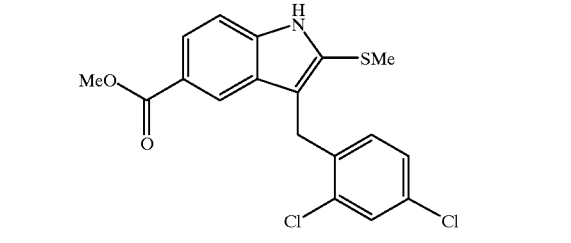
(153)
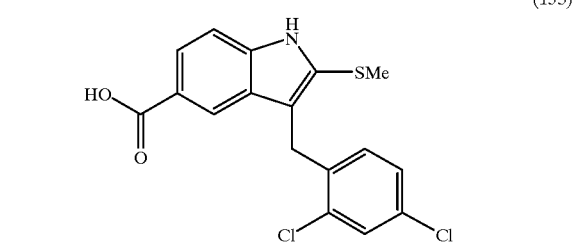
(154)
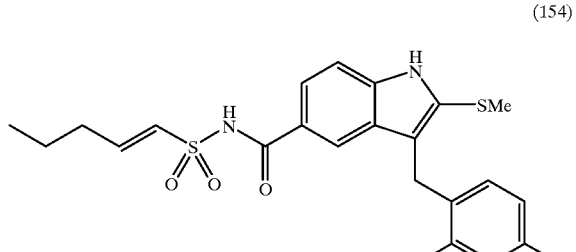
(155)
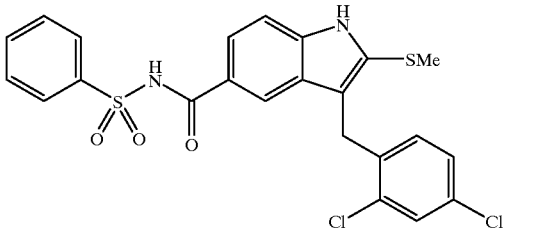
(156)
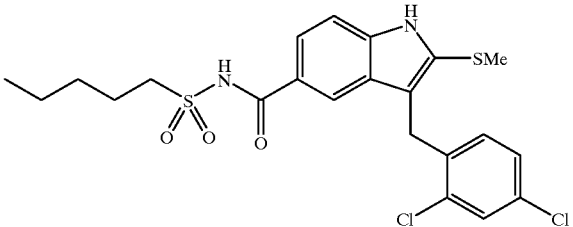
(157)
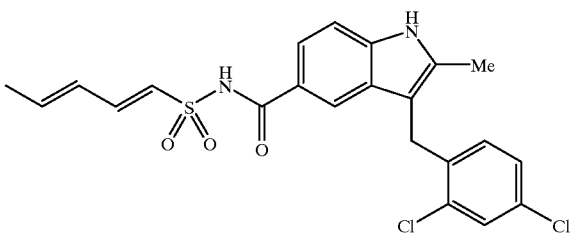
(158)
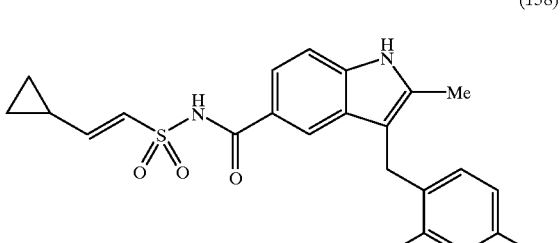
(159)
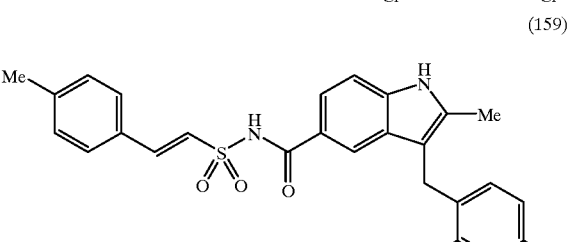
(160)

(161) 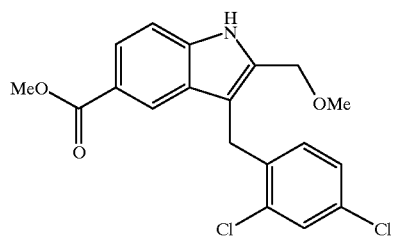
(162) 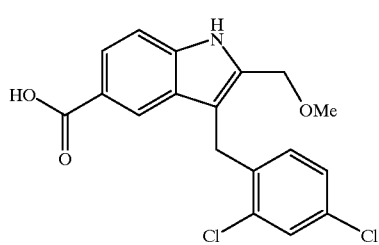
(163) 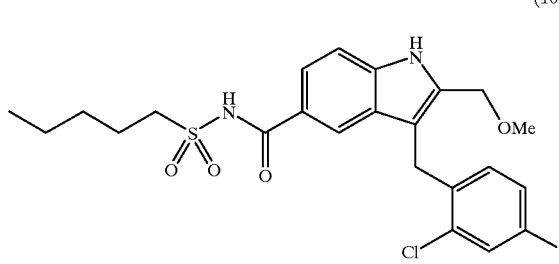
(164) 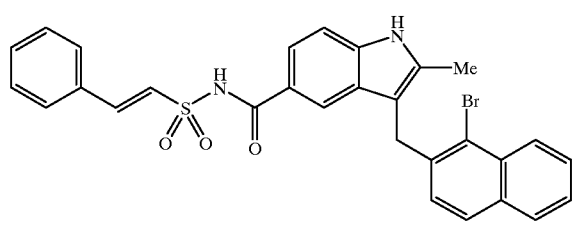
(165) 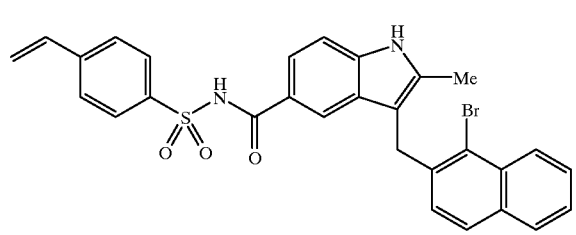
(166) 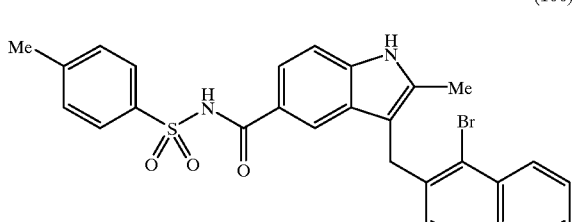
(167) 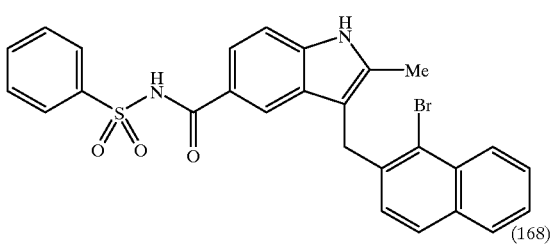
(168) 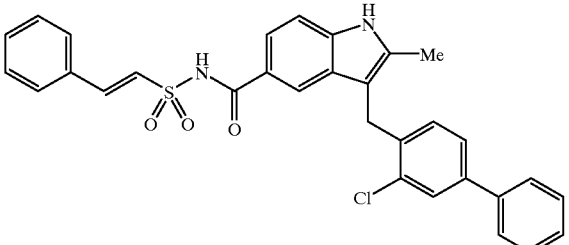
(169) 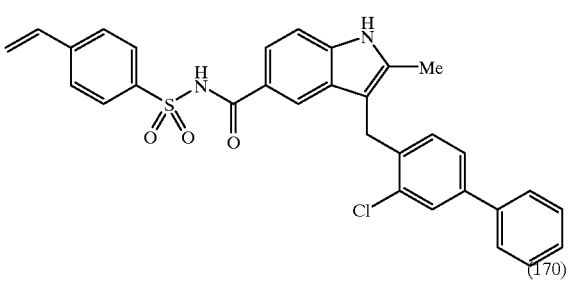
(170) 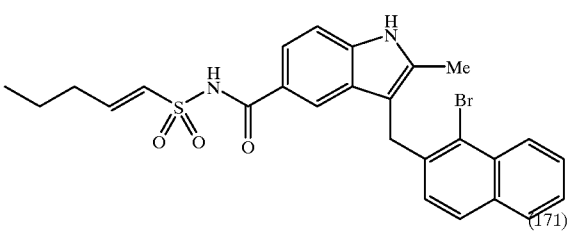
(171) 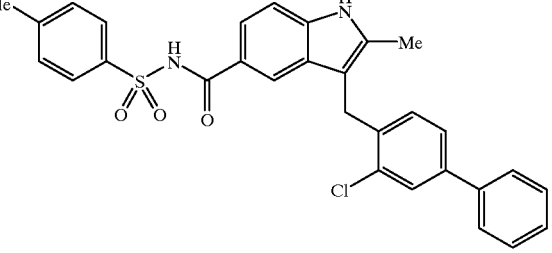
(172) 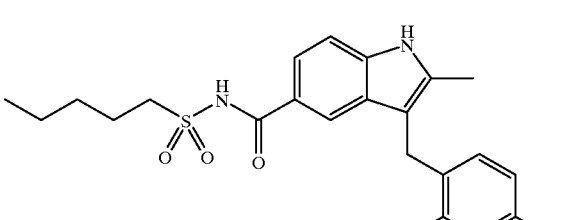

-continued (173)

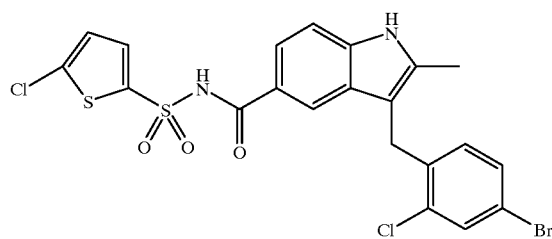

It will be understood that various changes and modifications can be made in the details of procedure, formulation and use without departing from the spirit of the invention, especially as defined in the following claims.

We claim:

1. A method for inhibiting the growth of neoplastic cells sensitive to the compounds of formula I comprising exposing the cells to a growth inhibiting effective amount of a compound of Formula I:

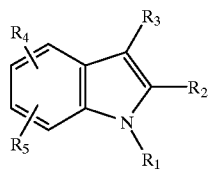
(I)

wherein $R_1$ to $R_3$ each represent;
(1) a hydrogen atom,
(2) a lower alkyl group, a lower alkylthio group, or a lower alkoxy-lower alkyl group, with the proviso that $R_1$ to $R_3$ are not simultaneously hydrogen atoms; or
$R_4$ is selected from the group consisting of hydrogen atom or lower alkyl;
$R_5$ is selected from the group consisting of carboxyl, an esterified carboxyl group, or an amidated carboxyl group.

2. A method of treating a mammal having precancerous lesions sensitive to the compounds of formula I comprising administering to said mammal a pharmacologically effective amount of a compound of Formula I:

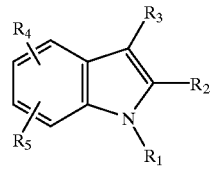
(I)

wherein $R_1$ to $R_3$ each represent;
(1) a hydrogen atom,
(2) a lower alkyl group, a lower alkylthio group, or a lower alkoxy-lower alkyl group, with the proviso that $R_1$ to $R_3$ are not simultaneously hydrogen atoms; or
$R_4$ is selected from the group consisting of hydrogen atom or lower alkyl;
$R_5$ is selected from the group consisting of carboxyl, an esterified carboxyl group, or an amidated carboxyl group.

* * * * *